(12) United States Patent
Crawford et al.

(10) Patent No.: US 8,507,638 B2
(45) Date of Patent: *Aug. 13, 2013

(54) POLYESTER COMPOSITIONS CONTAINING CYCLOBUTANEDIOL HAVING A CERTAIN COMBINATION OF INHERENT VISCOSITY AND MODERATE GLASS TRANSITION TEMPERATURE AND ARTICLES MADE THEREFROM

(75) Inventors: Emmett Dudley Crawford, Kingsport, TN (US); Thomas Joseph Pecorini, Kingsport, TN (US); Douglas Stephen McWilliams, Kingsport, TN (US); David Scott Porter, Blountville, TN (US); Gary Wayne Connell, Church Hill, TN (US); Ted Calvin Germroth, Kingsport, TN (US); Benjamin Fredrick Barton, Kingsport, TN (US); Damon Bryan Shackelford, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/215,511

(22) Filed: Aug. 23, 2011

(65) Prior Publication Data

US 2011/0306730 A1   Dec. 15, 2011

Related U.S. Application Data

(63) Continuation of application No. 12/784,193, filed on May 20, 2010, now Pat. No. 8,101,705, which is a continuation of application No. 11/391,565, filed on Mar. 28, 2006, now Pat. No. 7,781,562.

(60) Provisional application No. 60/738,869, filed on Nov. 22, 2005.

(51) Int. Cl.
*C08G 63/00* (2006.01)
*C08L 67/02* (2006.01)

(52) U.S. Cl.
USPC ........... 528/307; 528/302; 528/304; 528/305; 525/165; 525/173; 525/177; 525/390; 525/397; 525/425; 525/439; 525/444

(58) Field of Classification Search
USPC ................. 528/307, 302, 304, 305; 525/165, 525/173, 177, 390, 397, 425, 439, 444
See application file for complete search history.

(56) References Cited

U.S. PATENT DOCUMENTS

| | | | |
|---|---|---|---|
| 1,602,699 A | 10/1926 | Nightingale | |
| 2,160,841 A | 6/1939 | Dreyfus | |
| 2,202,046 A | 5/1940 | Dreyfus et al. | |
| 2,278,537 A | 4/1942 | Dreyfus et al. | |
| 2,720,507 A | 10/1955 | Caldwell | |
| 2,806,064 A | 9/1957 | McKlveen | |
| 2,901,466 A | 8/1959 | Kibler | |
| 2,936,324 A | 5/1960 | Hasek et al. | |
| 3,000,906 A | 9/1961 | Hasek et al. | |
| 3,030,335 A | 4/1962 | Goldberg | |
| 3,062,852 A | 11/1962 | Martin et al. | |
| 3,075,952 A | 1/1963 | Coover et al. | |
| 3,091,600 A | 5/1963 | Caldwell et al. | |
| 3,169,121 A | 2/1965 | Goldberg et al. | |
| 3,190,928 A | 6/1965 | Elam et al. | |
| 3,201,474 A | 8/1965 | Hasek et al. | |
| 3,207,814 A | 9/1965 | Goldberg et al. | |
| 3,218,372 A | 11/1965 | Okamura et al. | |
| 3,227,764 A | 1/1966 | Martin et al. | |
| 3,236,899 A | 2/1966 | Clark | |
| 3,249,652 A | 5/1966 | Quisenberry | |
| 3,259,469 A | 7/1966 | Painter et al. | |
| 3,287,390 A | 11/1966 | Poos et al. | |
| 3,288,854 A | 11/1966 | Martin | |
| 3,312,741 A | 4/1967 | Martin | |
| 3,313,777 A | 4/1967 | Elam et al. | |
| 3,317,466 A | 5/1967 | Caldwell et al. | |
| 3,329,722 A | 7/1967 | Rylander | |
| 3,360,547 A | 12/1967 | Wilson et al. | |
| 3,366,689 A | 1/1968 | Maeda et al. | |
| 3,386,935 A | 6/1968 | Jackson et al. | |
| 3,403,181 A | 9/1968 | Painter et al. | |
| T858012 I4 | 1/1969 | Caldwell et al. | |

(Continued)

FOREIGN PATENT DOCUMENTS

| BE | 615850 | 4/1962 |
|---|---|---|
| CA | 2035149 | 8/1991 |

(Continued)

OTHER PUBLICATIONS

USPTO Office Action dated Aug. 17, 2011 for copending U.S. Appl. No. 12/274,692.

(Continued)

*Primary Examiner* — Ling Choi
*Assistant Examiner* — Gennadiy Mesh
(74) *Attorney, Agent, or Firm* — Betty J. Boshears

(57) ABSTRACT

Described are polyesters comprising (a) a dicarboxylic acid component comprising terephthalic acid residues; optionally, aromatic dicarboxylic acid residues or aliphatic dicarboxylic acid residues; 2,2,4,4-tetramethyl-1,3-cyclobutanediol residues; and cyclohexanedimethanol residues. The polyesters have a desirable combination of inherent viscosity and glass transition temperature ("Tg"). The polyesters can have an inherent viscosity from 0.35 to 1.2 dL/g as determined in 60/40 (wt/wt) phenol/tetrachloroethane at a concentration of 0.5 g/100 ml at 25° C. and a Tg of 85 to 115° C. The polyesters may be manufactured into articles such as fibers, films, bottles or sheets.

32 Claims, 3 Drawing Sheets

(56) References Cited

U.S. PATENT DOCUMENTS

| | | |
|---|---|---|
| 3,484,339 A | 12/1969 | Caldwell |
| 3,502,620 A | 3/1970 | Caldwell, Jr. |
| T873016 I4 | 4/1970 | Gilkey et al. |
| 3,541,059 A | 11/1970 | Schaper |
| 3,546,177 A | 12/1970 | Kibler et al. |
| 3,629,202 A | 12/1971 | Gilkey et al. |
| RE27,682 E | 6/1973 | Schnell et al. |
| 3,772,405 A | 11/1973 | Hamb |
| 3,799,953 A | 3/1974 | Freitag et al. |
| 3,907,754 A | 9/1975 | Tershansy et al. |
| 3,915,913 A | 10/1975 | Jackson, Jr. et al. |
| 3,962,189 A | 6/1976 | Russin et al. |
| 4,001,184 A | 1/1977 | Scott |
| 4,010,145 A | 3/1977 | Russin et al. |
| 4,046,933 A | 9/1977 | Stefanik |
| 4,056,504 A | 11/1977 | Grundmeier et al. |
| 4,084,889 A | 4/1978 | Vischer, Jr. |
| 4,125,572 A | 11/1978 | Scott |
| 4,156,069 A | 5/1979 | Prevorsek et al. |
| 4,160,383 A | 7/1979 | Rauschenberger |
| 4,185,009 A | 1/1980 | Idel et al. |
| 4,188,314 A | 2/1980 | Fox et al. |
| 4,194,038 A | 3/1980 | Baker et al. |
| 4,263,364 A | 4/1981 | Seymour et al. |
| 4,356,299 A | 10/1982 | Cholod et al. |
| 4,367,186 A | 1/1983 | Adelmann et al. |
| 4,379,802 A | 4/1983 | Weaver et al. |
| 4,384,106 A | 5/1983 | Go et al. |
| 4,391,954 A | 7/1983 | Scott |
| 4,424,140 A | 1/1984 | Weinberg et al. |
| 4,426,512 A | 1/1984 | Barbee et al. |
| 4,427,614 A | 1/1984 | Barham et al. |
| 4,430,484 A | 2/1984 | Quinn |
| 4,431,793 A | 2/1984 | Rosenquist |
| 4,452,933 A | 6/1984 | McCready |
| 4,465,820 A | 8/1984 | Miller et al. |
| 4,469,861 A | 9/1984 | Mark et al. |
| 4,480,086 A | 10/1984 | O'Neill |
| 4,525,504 A | 6/1985 | Morris et al. |
| 4,578,295 A | 3/1986 | Jabarin |
| 4,578,437 A | 3/1986 | Light et al. |
| 4,642,959 A | 2/1987 | Swiech, Jr. et al. |
| 4,738,880 A | 4/1988 | Asada et al. |
| 4,749,773 A | 6/1988 | Weaver et al. |
| 4,786,692 A | 11/1988 | Allen et al. |
| 4,816,308 A | 3/1989 | Shimizu et al. |
| 4,826,903 A | 5/1989 | Weaver et al. |
| 4,845,188 A | 7/1989 | Weaver et al. |
| 4,880,592 A | 11/1989 | Martini et al. |
| 4,882,412 A | 11/1989 | Weaver et al. |
| 4,892,922 A | 1/1990 | Weaver et al. |
| 4,892,923 A | 1/1990 | Weaver et al. |
| 4,937,134 A | 6/1990 | Schrenk et al. |
| 4,939,186 A | 7/1990 | Nelson et al. |
| 4,976,057 A | 12/1990 | Bianchi |
| 4,981,898 A | 1/1991 | Bassett |
| 4,985,342 A | 1/1991 | Muramoto et al. |
| 5,017,679 A | 5/1991 | Chang et al. |
| 5,017,680 A | 5/1991 | Sublett |
| 5,034,252 A | 7/1991 | Nilsson et al. |
| 5,104,450 A | 4/1992 | Sand et al. |
| 5,118,760 A | 6/1992 | Blakely et al. |
| 5,118,847 A | 6/1992 | Jackson et al. |
| 5,142,088 A | 8/1992 | Phelps et al. |
| 5,169,994 A | 12/1992 | Sumner, Jr. et al. |
| 5,183,863 A | 2/1993 | Nakamura et al. |
| 5,191,038 A | 3/1993 | Krabbenhoft et al. |
| 5,207,967 A | 5/1993 | Small et al. |
| 5,219,510 A | 6/1993 | Machell et al. |
| 5,224,958 A | 7/1993 | Warunek et al. |
| 5,239,020 A | 8/1993 | Morris |
| 5,256,761 A | 10/1993 | Blount, Jr. |
| 5,258,556 A | 11/1993 | Sumner, Jr. et al. |
| 5,268,219 A | 12/1993 | Harada et al. |
| 5,288,715 A | 2/1994 | Machell et al. |
| 5,288,764 A | 2/1994 | Rotter et al. |
| 5,292,783 A | 3/1994 | Buchanan et al. |
| 5,310,611 A | 5/1994 | Okabe et al. |
| 5,310,787 A | 5/1994 | Kutsuwa et al. |
| 5,326,584 A | 7/1994 | Kamel et al. |
| 5,331,034 A | 7/1994 | Pfahler et al. |
| 5,333,073 A | 7/1994 | Suzuki |
| 5,354,791 A | 10/1994 | Gallucci |
| 5,372,864 A | 12/1994 | Weaver et al. |
| 5,372,879 A | 12/1994 | Handa et al. |
| 5,378,796 A | 1/1995 | George et al. |
| 5,382,292 A | 1/1995 | Conroy et al. |
| 5,384,377 A | 1/1995 | Weaver et al. |
| 5,475,144 A | 12/1995 | Watson et al. |
| 5,480,926 A | 1/1996 | Fagerburg et al. |
| 5,486,562 A | 1/1996 | Borman et al. |
| 5,489,665 A | 2/1996 | Yamato et al. |
| 5,494,992 A | 2/1996 | Kanno et al. |
| 5,498,668 A | 3/1996 | Scott |
| 5,498,688 A | 3/1996 | Oshino et al. |
| 5,506,014 A | 4/1996 | Minnick |
| 5,523,382 A | 6/1996 | Beavers et al. |
| 5,534,609 A | 7/1996 | Lewis et al. |
| 5,552,512 A | 9/1996 | Sublett |
| 5,591,530 A | 1/1997 | Warner et al. |
| 5,633,340 A | 5/1997 | Hoffman et al. |
| 5,650,453 A | 7/1997 | Eckberg et al. |
| 5,654,347 A | 8/1997 | Khemani et al. |
| 5,656,715 A | 8/1997 | Dickerson et al. |
| 5,668,243 A | 9/1997 | Yau et al. |
| 5,681,918 A | 10/1997 | Adams et al. |
| 5,688,874 A | 11/1997 | Hoffman |
| 5,696,176 A | 12/1997 | Khemani et al. |
| 5,705,575 A | 1/1998 | Kelsey |
| 5,783,307 A | 7/1998 | Fagerburg et al. |
| 5,804,617 A | 9/1998 | Hoffman et al. |
| 5,814,679 A | 9/1998 | Eckberg et al. |
| 5,859,116 A | 1/1999 | Shih |
| 5,863,622 A | 1/1999 | Jester |
| 5,902,631 A | 5/1999 | Wang et al. |
| 5,907,026 A | 5/1999 | Factor et al. |
| 5,942,585 A | 8/1999 | Scott et al. |
| 5,955,565 A | 9/1999 | Morris et al. |
| 5,958,539 A | 9/1999 | Eckart et al. |
| 5,958,581 A | 9/1999 | Khanarian et al. |
| 5,959,066 A | 9/1999 | Charbonneau et al. |
| 5,962,625 A | 10/1999 | Yau |
| 5,977,347 A | 11/1999 | Shuto et al. |
| 5,989,663 A | 11/1999 | Morris et al. |
| 6,001,910 A | 12/1999 | Blumenthal et al. |
| 6,005,059 A | 12/1999 | Scott et al. |
| 6,011,124 A | 1/2000 | Scott et al. |
| 6,012,597 A | 1/2000 | Nishihara et al. |
| 6,022,603 A | 2/2000 | Umeda et al. |
| 6,025,061 A | 2/2000 | Khanarian et al. |
| 6,030,671 A | 2/2000 | Yang et al. |
| 6,037,424 A | 3/2000 | Scott et al. |
| 6,043,322 A | 3/2000 | Scott et al. |
| 6,044,996 A | 4/2000 | Carew et al. |
| 6,063,464 A | 5/2000 | Charbonneau et al. |
| 6,063,465 A | 5/2000 | Charbonneau et al. |
| 6,063,495 A | 5/2000 | Charbonneau et al. |
| 6,084,019 A | 7/2000 | Matayabas et al. |
| 6,096,854 A | 8/2000 | Morris et al. |
| 6,114,575 A | 9/2000 | McMahon et al. |
| 6,120,477 A | 9/2000 | Campbell et al. |
| 6,120,889 A | 9/2000 | Turner et al. |
| 6,126,992 A | 10/2000 | Khanarian et al. |
| 6,127,492 A | 10/2000 | Nagashima et al. |
| 6,146,228 A | 11/2000 | Mougin et al. |
| 6,150,494 A | 11/2000 | Wang et al. |
| 6,183,848 B1 | 2/2001 | Turner et al. |
| 6,191,209 B1 | 2/2001 | Andrews et al. |
| 6,211,309 B1 | 4/2001 | McIntosh et al. |
| 6,221,556 B1 | 4/2001 | Gallucci et al. |
| 6,225,436 B1 | 5/2001 | Eiffler et al. |
| 6,232,504 B1 | 5/2001 | Barteau et al. |
| 6,239,210 B1 | 5/2001 | Kim et al. |
| 6,255,523 B1 | 7/2001 | Panandiker et al. |

| | | |
|---|---|---|
| 6,287,656 B1 | 9/2001 | Turner et al. |
| 6,307,006 B1 | 10/2001 | Konig et al. |
| 6,309,718 B1 | 10/2001 | Sprayberry |
| 6,320,042 B1 | 11/2001 | Michihata et al. |
| 6,323,291 B1 | 11/2001 | Mason et al. |
| 6,323,304 B1 | 11/2001 | Lemmon et al. |
| 6,342,304 B1 | 1/2002 | Buchanan et al. |
| 6,352,783 B1 | 3/2002 | Fagerburg |
| 6,354,986 B1 | 3/2002 | Hlavinka et al. |
| 6,359,070 B1 | 3/2002 | Khanarian et al. |
| 6,406,792 B1 | 6/2002 | Briquet et al. |
| 6,437,083 B1 | 8/2002 | Brack et al. |
| 6,448,334 B1 | 9/2002 | Verhoogt et al. |
| 6,458,468 B1 | 10/2002 | Moskala et al. |
| 6,504,002 B1 | 1/2003 | Karlik et al. |
| 6,559,272 B1 | 5/2003 | Jeon et al. |
| 6,573,328 B2 | 6/2003 | Kropp et al. |
| 6,599,994 B2 | 7/2003 | Shelby et al. |
| 6,639,067 B1 | 10/2003 | Brinegar et al. |
| 6,656,577 B1 | 12/2003 | Adelman et al. |
| 6,669,980 B2 | 12/2003 | Hansen |
| 6,723,768 B2 | 4/2004 | Adams et al. |
| 6,733,716 B2 | 5/2004 | Belcher |
| 6,740,377 B2 | 5/2004 | Pecorini et al. |
| 6,773,653 B2 | 8/2004 | Miller et al. |
| 6,818,293 B1 | 11/2004 | Keep et al. |
| 6,818,730 B2 | 11/2004 | Brandenburg et al. |
| 6,846,440 B2 | 1/2005 | Flynn et al. |
| 6,846,508 B1 | 1/2005 | Colas et al. |
| 6,896,966 B2 | 5/2005 | Crawford et al. |
| 6,908,650 B2 | 6/2005 | Odorisio et al. |
| 6,914,120 B2 | 7/2005 | Germroth et al. |
| 7,037,576 B2 | 5/2006 | Willham et al. |
| 7,048,978 B2 | 5/2006 | Tanaka et al. |
| 7,053,143 B2 | 5/2006 | Mori et al. |
| 7,122,661 B2 | 10/2006 | Fleche et al. |
| 7,169,880 B2 | 1/2007 | Shelby et al. |
| 7,297,755 B2 | 11/2007 | Shelby et al. |
| 7,354,628 B2 | 4/2008 | Steube |
| 7,375,154 B2 | 5/2008 | Stafford et al. |
| 7,427,430 B2 | 9/2008 | Rhee et al. |
| 7,468,409 B2 | 12/2008 | Pearson et al. |
| 7,482,397 B2 | 1/2009 | Pearson et al. |
| 2001/0029324 A1 | 10/2001 | Walker et al. |
| 2001/0031805 A1 | 10/2001 | Buhler |
| 2001/0034419 A1 | 10/2001 | Kanayama et al. |
| 2001/0044003 A1 | 11/2001 | Galluci et al. |
| 2002/0055586 A1 | 5/2002 | Dalgewicz, III et al. |
| 2002/0128357 A1 | 9/2002 | Goossens et al. |
| 2002/0132963 A1 | 9/2002 | Quillen |
| 2002/0137856 A1 | 9/2002 | Andrews et al. |
| 2002/0188092 A1 | 12/2002 | Moskala et al. |
| 2002/0198297 A1 | 12/2002 | Odorisio et al. |
| 2003/0032737 A1 | 2/2003 | Andrews et al. |
| 2003/0060546 A1 | 3/2003 | Moskala et al. |
| 2003/0075516 A1 | 4/2003 | Rothman et al. |
| 2003/0077546 A1 | 4/2003 | Donovan et al. |
| 2003/0135015 A1 | 7/2003 | Fujimaki et al. |
| 2003/0139497 A1 | 7/2003 | Odorisio et al. |
| 2003/0149177 A1 | 8/2003 | Andrews et al. |
| 2003/0169514 A1 | 9/2003 | Bourdelais et al. |
| 2003/0187151 A1 | 10/2003 | Adams et al. |
| 2003/0195295 A1 | 10/2003 | Mahood et al. |
| 2003/0221716 A1 | 12/2003 | Olson |
| 2003/0229181 A1 | 12/2003 | Hariharan et al. |
| 2004/0022526 A1 | 2/2004 | Kuno et al. |
| 2004/0063864 A1 | 4/2004 | Adams et al. |
| 2004/0101687 A1 | 5/2004 | Crawford et al. |
| 2004/0106707 A1 | 6/2004 | Su et al. |
| 2004/0106767 A1 | 6/2004 | Simon et al. |
| 2004/0108623 A1 | 6/2004 | Deeter et al. |
| 2004/0138381 A1 | 7/2004 | Blasius et al. |
| 2004/0145700 A1 | 7/2004 | Miniutti et al. |
| 2004/0164279 A1 | 8/2004 | Stevenson et al. |
| 2004/0202822 A1 | 10/2004 | Bourdelais et al. |
| 2004/0214984 A1 | 10/2004 | Keep et al. |
| 2005/0008885 A1 | 1/2005 | Blakely et al. |
| 2005/0072060 A1 | 4/2005 | Moncho et al. |
| 2005/0096453 A1 | 5/2005 | Flynn et al. |
| 2005/0101759 A1 | 5/2005 | Odorisio et al. |
| 2005/0113556 A1 | 5/2005 | Strand et al. |
| 2005/0119359 A1 | 6/2005 | Shelby et al. |
| 2005/0124779 A1 | 6/2005 | Shelby et al. |
| 2005/0181155 A1 | 8/2005 | Share et al. |
| 2006/0004151 A1 | 1/2006 | Shaikh et al. |
| 2006/0036012 A1 | 2/2006 | Hayes et al. |
| 2006/0094858 A1 | 5/2006 | Turner et al. |
| 2006/0111481 A1 | 5/2006 | Pearson et al. |
| 2006/0111519 A1 | 5/2006 | Strand et al. |
| 2006/0135668 A1 | 6/2006 | Hayes |
| 2006/0146228 A1 | 7/2006 | Sogo et al. |
| 2006/0180560 A1 | 8/2006 | Robinson |
| 2006/0197246 A1 | 9/2006 | Hale et al. |
| 2006/0199904 A1 | 9/2006 | Hale et al. |
| 2006/0199919 A1 | 9/2006 | Hale et al. |
| 2006/0228507 A1 | 10/2006 | Hale et al. |
| 2006/0234073 A1 | 10/2006 | Hale et al. |
| 2006/0235167 A1 | 10/2006 | Hale et al. |
| 2006/0247388 A1 | 11/2006 | Hale et al. |
| 2006/0270773 A1 | 11/2006 | Hale et al. |
| 2006/0270806 A1 | 11/2006 | Hale |
| 2007/0071930 A1 | 3/2007 | Shelby et al. |

FOREIGN PATENT DOCUMENTS

| | | |
|---|---|---|
| DE | 29 21 868 A1 | 12/1980 |
| DE | 197 27 709 | 6/1997 |
| DE | 198 11 773 A1 | 9/1999 |
| EP | 0 039 838 A1 | 11/1981 |
| EP | 0 273 144 | 5/1987 |
| EP | 0 282 277 | 9/1988 |
| EP | 0 372 846 | 6/1990 |
| EP | 0 544 008 A1 | 6/1993 |
| EP | 0 595 413 A1 | 5/1994 |
| EP | 0 698 631 | 2/1996 |
| EP | 0 714 764 A2 | 6/1996 |
| EP | 0 902 052 A1 | 3/1999 |
| EP | 0 930 531 A1 | 7/1999 |
| EP | 1 066 825 A1 | 1/2001 |
| EP | 1 674 496 A1 | 6/2006 |
| FR | 1278284 | 12/1961 |
| FR | 1291273 | 5/1965 |
| FR | 1432471 | 2/1966 |
| FR | 1434658 | 2/1966 |
| FR | 2112400 | 6/1972 |
| GB | 962913 | 7/1964 |
| GB | 1041651 | 9/1966 |
| GB | 1044015 | 9/1966 |
| GB | 1047043 | 11/1966 |
| GB | 1090241 | 11/1967 |
| GB | 1130558 | 10/1968 |
| GB | 1 278 284 | 6/1972 |
| GB | 1364732 | 8/1974 |
| GB | 2216919 A | 10/1989 |
| JP | 56-88440 A | 12/1979 |
| JP | 03207743 | 9/1991 |
| JP | 65-01040 | 2/1994 |
| JP | 9-59371 A | 4/1997 |
| JP | 11-222516 | 8/1999 |
| JP | 2001-066701 | 8/1999 |
| JP | 2000-352620 A | 12/2000 |
| JP | 2001-098086 | 4/2001 |
| JP | 2001-214049 | 8/2001 |
| JP | 2004-244497 A | 9/2004 |
| JP | 2004-292558 A | 10/2004 |
| KR | 2001/089942 | 10/2001 |
| KR | 2003/054611 | 7/2003 |
| WO | WO 97/01118 | 1/1997 |
| WO | WO 01/06981 | 2/2001 |
| WO | WO 01/85824 A2 | 11/2001 |
| WO | WO 02/055570 A1 | 7/2002 |
| WO | WO 02/059207 | 8/2002 |
| WO | WO 2004/009146 A1 | 1/2004 |
| WO | WO 2004/039860 | 5/2004 |
| WO | WO 2004/104077 A1 | 12/2004 |
| WO | WO 2004/106988 A2 | 12/2004 |
| WO | WO 2005/007735 A2 | 1/2005 |
| WO | WO 2005/026241 A1 | 3/2005 |
| WO | WO 2006/025827 | 3/2006 |

| | | | |
|---|---|---|---|
| WO | WO 2006/127755 A2 | 11/2006 | |
| WO | WO 2006/127831 A1 | 11/2006 | |
| WO | WO 2007/053434 A1 | 5/2007 | |
| WO | WO 2007/053548 A2 | 5/2007 | |
| WO | WO 2007/053549 A1 | 5/2007 | |
| WO | WO 2007/053550 | 5/2007 | |

OTHER PUBLICATIONS

USPTO Office Action dated Sep. 14, 2011 for copending U.S. Appl. No. 13/017,069.
USPTO Supplemental Notice of Allowability dated Sep. 16, 2011 for copending U.S. Appl. No. 11/390,671.
USPTO Notice of Allowance dated Sep. 16, 2011 for copending U.S. Appl. No. 12/784,193.
USPTO Office Action dated Oct. 17, 2011 for copending U.S. Appl. No. 12/853,717.
USPTO Notice of Allowance dated Oct. 25, 2011 for copending U.S. Appl. No. 12/900,060.
USPTO Office Action dated Nov. 2, 2011 for copending U.S. Appl. No. 12/479,893.
USPTO Notice of Allowance dated Nov. 10, 2011 for copending U.S. Appl. No. 12/943,217.
USPTO Office Action dated Oct. 31, 2011 for copending U.S. Appl. No. 12/639,324.
USPTO Notice of Allowance dated Nov. 2, 2011 for copending U.S. Appl. No. 12/390,694.
USPTO Notice of Allowance dated Nov. 28, 2011 for copending U.S. Appl. No. 12/274,692.
USPTO Notice of Allowance dated Dec. 16, 2011 for copending U.S. Appl. No. 12/390,694.
USPTO Office Action dated Dec. 21, 2011 for copending U.S. Appl. No. 12/091,570.
USPTO Notice of Allowance dated Oct. 17, 2011 for copending U.S. Appl. No. 11/390,794.
Abstract of U.S. Defense Publication T869,015, 869 O.G. 714, Dec. 16, 1969.
Abstract of U.S. Defense Publication T875,010, 875 O.G. 342, Jun. 9, 1970.
Chen et al., "The molecular basis for the relationship between the secondary relaxation and mechanical properties of a series of polyester copolymer glasses," Marcromolecules, 32:5944-5955 (1999).
Coover, H. et al., "Copolyester Molding Compositions," Chemical Abstracts Service, XP002391844.
Kelsey, E. et al., "High Impact, Amorphous Terephthalate Copolyesters of Rigid 2,2,4,4-Tetramethyl-1,3-cyclobutanediol with Flexible Diols," Macromolecules, vol. 33, 2000, pp. 5810-5818, American Chemical Society.
"Plastic Additives Handbook," 5th Edition, 2001, pp. 98-108 and pp. 109-112 (Hanser Gardner Publications, Inc., Cincinnati, OH.
Bergen, R. L., Jr., "Stress Cracking of Rigid Thermoplastics," SPE Journal, Jun. 1962.
Scheirs, John, et al., "Modern Polyesters: Chemistry and Technology of Polyesters and Copolyesters," Technology & Engineering, 2003, p. 287.
English language Abstract of JP 02-305816 from Patent Abstracts of Japan, Dec. 19, 1990.
English language translation of Belgian Patent No. BE 615,850, Apr. 13, 1962.
English language translation of French Patent No. FR 1,432,471, Feb. 7, 1966.
English language translation of French Patent No. FR 1,434,658, Feb. 28, 1966.
U.S. Appl. No. 11/390,555, filed Mar. 28, 2006, Emmett Dudley Crawford, et al.
U.S. Appl. No. 11/390,563, filed Mar. 28, 2006, Emmett Dudley Crawford, et al.
U.S. Appl. No. 11/390,629, filed Mar. 28, 2006, Emmett Dudley Crawford, et al.
U.S. Appl. No. 11/390,630, filed Mar. 28, 2006, Emmett Dudley Crawford, et al.
U.S. Appl. No. 11/390,631, filed Mar. 28, 2006, Emmett Dudley Crawford, et al.
U.S. Appl. No. 11/390,654, filed Mar. 28, 2006, Emmett Dudley Crawford, et al.
U.S. Appl. No. 11/390,655, filed Mar. 28, 2006, Emmett Dudley Crawford, et al.
U.S. Appl. No. 11/390,671, filed Mar. 28, 2006, Emmett Dudley Crawford, et al.
U.S. Appl. No. 11/390,672, filed Mar. 28, 2006, Emmett Dudley Crawford, et al.
U.S. Appl. No. 11/390,722, filed Mar. 28, 2006, Emmett Dudley Crawford, et al.
U.S. Appl. No. 11/390,750, filed Mar. 28, 2006, Emmett Dudley Crawford, et al.
U.S. Appl. No. 11/390,751, filed Mar. 28, 2006, Emmett Dudley Crawford, et al.
U.S. Appl. No. 11/390,752, filed Mar. 28, 2006, Emmett Dudley Crawford, et al.
U.S. Appl. No. 11/390,773, filed Mar. 28, 2006, Emmett Dudley Crawford, et al.
U.S. Appl. No. 11/390,793, filed Mar. 28, 2006, Emmett Dudley Crawford, et al.
U.S. Appl. No. 11/390,794, filed Mar. 28, 2006, Emmett Dudley Crawford, et al.
U.S. Appl. No. 11/390,809, filed Mar. 28, 2006, Wesley Raymond Hale, et al.
U.S. Appl. No. 11/390,811, filed Mar. 28, 2006, Emmett Dudley Crawford, et al.
U.S. Appl. No. 11/390,812, filed Mar. 28, 2006, Wesley Raymond Hale, et al.
U.S. Appl. No. 11/390,814, filed Mar. 28, 2006, Emmett Dudley Crawford, et al.
U.S. Appl. No. 11/390,826, filed Mar. 28, 2006, Emmett Dudley Crawford, et al.
U.S. Appl. No. 11/390,827, filed Mar. 28, 2006, Emmett Dudley Crawford, et al.
U.S. Appl. No. 11/390,836, filed Mar. 28, 2006, Emmett Dudley Crawford, et al.
U.S. Appl. No. 11/390,846, filed Mar. 28, 2006, Wesley Raymond Hale, et al.
U.S. Appl. No. 11/390,847, filed Mar. 28, 2006, Emmett Dudley Crawford, et al.
U.S. Appl. No. 11/390,853, filed Mar. 28, 2006, Emmett Dudley Crawford, et al.
U.S. Appl. No. 11/390,858, filed Mar. 28, 2006, Emmett Dudley Crawford, et al.
U.S. Appl. No. 11/390,864, filed Mar. 28, 2006, Wesley Raymond Hale, et al.
U.S. Appl. No. 11/390,865, filed Mar. 28, 2006, Emmett Dudley Crawford, et al.
U.S. Appl. No. 11/390,882, filed Mar. 28, 2006, Emmett Dudley Crawford, et al.
U.S. Appl. No. 11/390,883, filed Mar. 28, 2006, Thomas Joseph Pecorini, et al.
U.S. Appl. No. 11/390,908, filed Mar. 28, 2006, Wesley Raymond Hale, et al.
U.S. Appl. No. 11/391,063, filed Mar. 28, 2006, Emmett Dudley Crawford, et al.
U.S. Appl. No. 11/391,124, filed Mar. 28, 2006, Wesley Raymond Hale, et al.
U.S. Appl. No. 11/391,125, filed Mar. 28, 2006, Emmett Dudley Crawford, et al.
U.S. Appl. No. 11/391,137, filed Mar. 28, 2006, Emmett Dudley Crawford, et al.
U.S. Appl. No. 11/391,156, filed Mar. 28, 2006, Emmett Dudley Crawford, et al.
U.S. Appl. No. 11/391,485, filed Mar. 28, 2006, Emmett Dudley Crawford, et al.
U.S. Appl. No. 11/391,495, filed Mar. 28, 2006, Emmett Dudley Crawford, et al.
U.S. Appl. No. 11/391,505, filed Mar. 28, 2006, Emmett Dudley Crawford, et al.
U.S. Appl. No. 11/391,565, filed Mar. 28, 2006, Emmett Dudley Crawford, et al.

U.S. Appl. No. 11/391,571, filed Mar. 28, 2006, Emmett Dudley Crawford, et al.
U.S. Appl. No. 11/391,576, filed Mar. 28, 2006, Emmett Dudley Crawford, et al.
U.S. Appl. No. 11/391,642, filed Mar. 28, 2006, Emmett Dudley Crawford, et al.
U.S. Appl. No. 11/391,659, filed Mar. 28, 2006, Emmett Dudley Crawford, et al.
U.S. Appl. No. 11/588,524, filed Oct. 27, 2006, Emmett Dudley Crawford, et al.
U.S. Appl. No. 11/588,458, filed Oct. 27, 2006, Emmett Dudley Crawford, et al.
U.S. Appl. No. 11/588,907, filed Oct. 27, 2006, Emmett Dudley Crawford, et al.
U.S. Appl. No. 11/588,527, filed Oct. 27, 2006, Emmett Dudley Crawford, et al.
U.S. Appl. No. 11/588,906, filed Oct. 27, 2006, Ted Calvin Germroth, et al.
U.S. Appl. No. 11/588,883, filed Oct. 27, 2006, Ted Calvin Germroth, et al.
U.S. Appl. No. 11/588,554, filed Oct. 27, 2006, Emmett Dudley Crawford, et al.
U.S. Appl. No. 11/635,434, filed Dec. 7, 2006, Emmett Dudley Crawford.
U.S. Appl. No. 11/635,433, filed Dec. 7, 2006, Emmett Dudley Crawford.
U.S. Appl. No. 11/439,062, filed May 23, 2006, Wesley Raymond Hale, et al.
U.S. Appl. No. 11/439,340, filed May 23, 2006, Wesley Raymond Hale.
U.S. Appl. No. 11/706,476, filed Feb. 14, 2007, Leslie Shane Moody, et al.
U.S. Appl. No. 11/706,791, filed Feb. 14, 2007, Leslie Shane Moody, et al.
U.S. Appl. No. 12/091,568, filed Apr. 25, 2008, Emmett Dudley Crawford, et al.
U.S. Appl. No. 12/091,566, filed Apr. 25, 2008, Emmett Dudley Crawford, et al.
U.S. Appl. No. 12/091,570, filed Apr. 25, 2008, Ted Calvin Germroth, et al.
U.S. Appl. No. 12/091,572, filed Apr. 25, 2008, Ted Calvin Germroth, et al.
U.S. Appl. No. 12/294,690, filed Sep. 26, 2008, Ted Calvin Germroth et al.
U.S. Appl. No. 12/294,686, filed Sep. 26, 2008, Ted Calvin Germroth et al.
U.S. Appl. No. 12/274,692, filed Nov. 20, 2008, Thomas Joseph Pecorini et al.
U.S. Appl. No. 12/338,453, filed Dec. 18, 2008, Emmett Dudley Crawford, et al.
U.S. Appl. No. 12/361,779, filed Jan. 29, 2009, Emmett Dudley Crawford.
U.S. Appl. No. 12/365,515, filed Feb. 4, 2009, Emmett Dudley Crawford.
Chapter 4—Processing of Plastics in "Plastics Engineering, 3rd ed", R.J. Crawford, Butterworth-Heinemann Publisher, 1998, Oxford, England, pp. 245-342.
Fox equation (T.G. Fox, Session J, Bull. Am. Phys. Soc., 1, 123 (1956)).
The Technology of Plasticizers, by J. Kern Sears and Joseph R Darby, published by Society of Plastic Engineers/Wiley and Sons, New York, 1982; pp. 136-139.
Coleman et al., "Polymer Reviews—A Practical Guide to Polymer Miscibility," *Polymer 31*, pp. 1187-1203 (1990).
"*Hansen Solubility Parameters, a Users Handbook*", by Charles M. Hansen, Chapter 1, CRC Press, 2000, pp. 1-24.
Martinez et al., "*Phase Behavior and Mechanical Properties of Injection Molded Poly (Ethylene Terephthalate) / Polyatylate Blends*"; Journal of Applied Polymer Science, John Wiley and Sons Inc. New York, US, vol. 45, No. 7, Jul. 5, 1992, p. 1135-1143.
Won Ho Jo et al. : :*Miscibility of poly(ether imide)/poly(ethylene terephthalate) blends*; Polymer Bulletin, Springer, Heidelberg, DE, vol. 33, No. 1, Jun. 1, 1994, p. 113-118 (1994).

Anonymous: "*Poly (ethylene naphthalenedicarboxylate)/polyetherimide blends*" Research Disclosure, Mason Publications, Hampshire, GB, vol. 283, No. 38, Nov. 1987.
ASTM D1525-06, *Standard Test Method for Vicat Softening Temperature of Plastics*, Mar. 15, 2006.
ASTM D648-06, *Standard Test Method for Deflection Temperature of Plastics Under Flexural Load in the Edgewise Position*, Mar. 15, 2006.
ASTM D256-06, *Standard Test Methods for Determining the Izod Pendulum Impact Resistance of Plastics*, Mar. 15, 2006.
ASTM D790-03, *Standard Test Methods for Flexural Properties of Unreinforced and Reinforced Plastics and Electrical Insulating Materials*, Mar. 10, 2003.
ASTM D638-03, *Standard Test Method for Tensile Properties of Plastics*, Dec. 1, 2003.
ASTM D3418-03, *Transition Temperatures and Enthalpies of Fusion and Crystallization of Polymers by Differential Scanning Calorimetry*, Dec. 1, 2003.
Database WPI, Section Ch, Week 200536, Derwent Publications Ltd., London, GB; Class A23, AN 2005-355258, XP002396922 & WO 2005-030833 A1 (KANEBO LTD) Apr. 7, 2005 abstract.
Shearer, N. H., "T18-Type 1 Polyesters," Mar. 1966, SPE Annual Technical Conference and Exhibition, XP009080224.
Gachter, Muller, "Taschenbuch der Kunststoff-Additive," 1990, Carl Hanser Verlag Munchen Wien, XP02450422, pp. 96-97.
Gachter, Muller, "Kunstoff-Additive," 1990, Carl Hanser Verlag Munchen Wien, XP 02449987, pp. 96-99.
Brown, R., "Taschenbuch Kunstoff-Additive", 1990, Carl Hanswer Verlag Munchen Wiel, XP002455247, pp. 361-363.
Chang, S. et al., "Effect of Stabilizers on the Preparation of Poly(ethylene Terephthalate)", Journal of Polymer Science, Polymer Chemistry Edition, 1982, vol. 20, pp. 2053-2061, John Wiley & Sons, Inc.
USPTO Office Action dated Mar. 11, 2008 for copending U.S. Appl. No. 11/391,642.
USPTO Office Action dated Mar. 24, 2008 for copending U.S. Appl. No. 11/390,908.
USPTO Office Action dated Apr. 15, 2008 for copending U.S. Appl. No. 11/390,629.
USPTO Office Action dated Apr. 16, 2008 for copending U.S. Appl. No. 11/390,751.
USPTO Office Action dated Apr. 17, 2008 for copending U.S. Appl. No. 11/390,814.
USPTO Office Action dated Jun. 3, 2008 for copending U.S. Appl. No. 11/391,063.
USPTO Office Action dated Sep. 10, 2008 for copending U.S. Appl. No. 11/390,752.
USPTO Office Action dated Sep. 10, 2008 for copending U.S. Appl. No. 11/390,794.
USPTO Office Action dated Sep. 19, 2008 for copending U.S. Appl. No. 11/391,565.
USPTO Office Action dated Oct. 2, 2008 for copending U.S. Appl. No. 11/390,671.
USPTO Office Action dated Sep. 24, 2008 for copending U.S. Appl. No. 11/390,631.
USPTO Office Action dated Oct. 1, 2008 for copending U.S. Appl. No. 11/390,655.
USPTO Office Action dated Sep. 29, 2008, for copending U.S. Appl. No. 11/391,137.
USPTO Office Action dated Sep. 9, 2008 for copending U.S. Appl. No. 11/391,571.
USPTO Office Action dated Oct. 22, 2008 for copending U.S. Appl. No. 11/391,125.
USPTO Office Action dated Oct. 20, 2008 for copending U.S. Appl. No. 11/390,672.
USPTO Office Action dated Oct. 8, 2008 for copending U.S. Appl. No. 11/390,853.
USPTO Office Action dated Oct. 9, 2008 for copending U.S. Appl. No. 11/391,505.
USPTO Notice of Allowance dated Oct. 7, 2008 for copending U.S. Appl. No. 11/390,908.
USPTO Office Action dated Oct. 14, 2008 for copending U.S. Appl. No. 11/390,811.

USPTO Office Action dated Oct. 22, 2008 for copending U.S. Appl. No. 11/390,750.
USPTO Office Action dated Oct. 22, 2008 for copending U.S. Appl. No. 11/390,865.
USPTO Office Action dated Oct. 14, 2008 for copending U.S. Appl. No. 11/390,654.
USPTO Office Action dated Oct. 20, 2008 for copending U.S. Appl. No. 11/390,836.
Copending application, U.S. Appl. No. 12/254,894, filed Oct. 21, 2008, Gary Michael Stack, et al.
Copending U.S. Appl. No. 12/390,694, filed Feb. 23, 2009, Gary Michael Stack.
USPTO Office Action dated Oct. 29, 2008 for copending U.S. Appl. No. 11/390,955.
USPTO Notice of Allowance dated Nov. 3, 2008 for copending U.S. Appl. No. 11/391,642.
USPTO Office Action dated Nov. 3, 2008 for copending U.S. Appl. No. 11/391,485.
USPTO Office Action dated Oct. 29, 2008 for copending U.S. Appl. No. 11/390,864.
USPTO Office Action dated Oct. 30, 2008 for copending U.S. Appl. No. 11/391,495.
USPTO Office Action dated Oct. 31, 2008 for copending U.S. Appl. No. 11/391,156.
USPTO Office Action dated Nov. 3, 2008 for copending U.S. Appl. No. 11/390,883.
USPTO Office Action dated Dec. 19, 2008 for copending U.S. Appl. No. 11/390,751.
USPTO Office Action dated Dec. 31, 2008 for copending U.S. Appl. No. 11/390,827.
USPTO Office Action dated Dec. 31, 2008 for copending U.S. Appl. No. 11/390,826.
USPTO Office Action dated Nov. 14, 2008 for copending U.S. Appl. No. 11/390,630.
USPTO Office Action dated Dec. 19, 2008 for copending U.S. Appl. No. 11/391,576.
USPTO Office Action dated Dec. 19, 2008 for copending U.S. Appl. No. 11/390,629.
USPTO Office Action dated Dec. 31, 2008 for copending U.S. Appl. No. 11/390,773.
USPTO Office Action dated Dec. 12, 2008 for copending U.S. Appl. No. 11/391,063.
USPTO Office Action dated Dec. 19, 2008 for copending U.S. Appl. No. 11/390,814.
USPTO Office Action dated Dec. 31, 2008 for copending U.S. Appl. No. 11/390,722.
USPTO Office Action dated Nov. 14, 2008 for copending U.S. Appl. No. 11/390,882.
USPTO Office Action dated Jan. 29, 2009 for copending U.S. Appl. No. 11/588,524.
USPTO Office Action dated Jan. 30, 2009 for copending U.S. Appl. No. 11/588,458.
USPTO Office Action dated Feb. 2, 2009 for copending U.S. Appl. No. 11/390,853.
USPTO Office Action dated Jan. 21, 2009 for copending U.S. Appl. No. 11/390,847.
USPTO Office Action dated Jan. 12, 2009 for copending U.S. Appl. No. 11/390,858.
USPTO Office Action dated Jan. 26, 2009 for copending U.S. Appl. No. 11/391,659.
USPTO Office Action dated Jan. 26, 2009 for copending U.S. Appl. No. 11/588,554.
USPTO Office Action dated Feb. 3, 2009 for copending U.S. Appl. No. 11/391,505.
USPTO Office Action dated Feb. 10, 2009 for copending U.S. Appl. No. 11/390,865.
USPTO Office Action dated Feb. 12, 2009 for copending U.S. Appl. No. 11/439,062.
USPTO Office Action dated Feb. 13, 2009 for copending U.S. Appl. No. 11/439,340.
USPTO Office Action dated Feb. 25, 2009 for copending U.S. Appl. No. 11/588,907.
USPTO Office Action dated Feb. 25, 2009 for copending U.S. Appl. No. 11/588,527.
USPTO Office Action dated Feb. 27, 2009 for copending U.S. Appl. No. 11/390,955.
USPTO Office Action dated Feb. 25, 2009 for copending U.S. Appl. No. 11/588,906.
USPTO Office Action dated Feb. 25, 2009 for copending U.S. Appl. No. 11/588,883.
USPTO Office Action dated Mar. 5, 2009 for copending U.S. Appl. No. 11/390,864.
USPTO Office Action dated Mar. 6, 2009 for copending U.S. Appl. No. 11/391,156.
USPTO Office Action dated Feb. 25, 2009 for copending U.S. Appl. No. 11/390,811.
USPTO Office Action dated Feb. 27, 2009 for copending U.S. Appl. No. 11/390,654.
USPTO Office Action dated Feb. 27, 2009 for copending U.S. Appl. No. 11/390,836.
USPTO Office Action dated Mar. 13, 2009 for copending U.S. Appl. No. 11/390,883.
USPTO Office Action dated Mar. 11, 2009 for copending U.S. Appl. No. 11/390,630.
USPTO Office Action dated Mar. 9, 2009 for copending U.S. Appl. No. 11/391,495.
USPTO Office Action dated Mar. 9, 2009 for copending U.S. Appl. No. 11/390,750.
USTPO Office Action dated Mar. 16, 2009 for copending U.S. Appl. No. 11/390,882.
USPTO Office Action dated Apr. 27, 2009 for copending U.S. Appl. No. 11/390,655.
USPTO Office Action dated Apr. 27, 2009 for copending U.S. Appl. No. 11/391,137.
USPTO Office Action dated Mar. 16, 2009 for copending U.S. Appl. No. 11/391,485.
USPTO Office Action dated Apr. 15, 2009 for copending U.S. Appl. No. 12/091,566.
USPTO Notice of Allowance dated Apr. 13, 2009 for copending U.S. Appl. No. 11/391,063.
USPTO Office Action dated Apr. 16, 2009 for copending U.S. Appl. No. 12/091,570.
USPTO Office Action dated Apr. 17, 2009 for copending U.S. Appl. No. 11/390,671.
USPTO Office Action dated Apr. 17, 2009 for copending U.S. Appl. No. 11/391,565.
USPTO Office Action dated Apr. 20, 2009 for copending U.S. Appl. No. 11/390,631.
USPTO Office Action dated Mar. 31, 2009 for copending U.S. Appl. No. 11/390,563.
USPTO Office Action dated Apr. 2, 2009 for copending U.S. Appl. No. 11/390,793.
USPTO Office Action dated Mar. 23, 2009 for copending U.S. Appl. No. 11/390,752.
USPTO Office Action dated Mar. 23, 2009 for copending U.S. Appl. No. 11/390,794.
USPTO Office Action dated May 13, 2009 for copending U.S. Appl. No. 12/361,779.
USPTO Office Action dated May 13, 2009 for copending U.S. Appl. No. 12/365,515.
USPTO Office Action dated May 21, 2009 for copending U.S. Appl. No. 11/706,476.
USPTO Office Action dated May 22, 2009 for copending U.S. Appl. No. 11/706,791.
USPTO Office Action dated May 18, 2009 for copending U.S. Appl. No. 11/391,505.
USPTO Office Action dated Apr. 14, 2009 for copending U.S. Appl. No. 11/635,434.
USPTO Office Action dated Apr. 14, 2009 for copending U.S. Appl. No. 11/635,433.
USPTO Office Action dated May 18, 2009 for copending U.S. Appl. No. 11/390,846.
USPTO Office Action dated Jun. 11, 2009 for copending U.S. Appl. No. 11/390,809.

USPTO Office Action dated Jul. 2, 2009 for copending U.S. Appl. No. 11/390,827.
USPTO Office Action dated Aug. 7, 2009 for copending U.S. Appl. No. 11/390,773.
USPTO Office Action dated Aug. 27, 2009 for copending U.S. Appl. No. 11/390,826.
USPTO Office Action dated Aug. 10, 2009 for copending U.S. Appl. No. 11/390,722.
Dixon, E.R. et al., "The Inter-Relation of Some Mechanical Properties with Molecular Weight and Crystallinity in Poly(ethylene terephthalate)", 1968, pp. 464-470, Journal of Materials Science, vol. 3.
USPTO Office Action dated Sep. 4, 2009, for copending U.S. Appl. No. 11/391,124.
USPTO Office Action dated Sep. 10, 2009, for copending U.S. Appl. No. 11/390,812.
New Copending U.S. Appl. No. 12/479,893, filed Jun. 8, 2009, Emmett Dudley Crawford, et al.
USPTO Office Action dated Sep. 14, 2009 for copending U.S. Appl. No. 11/391,576.
Ellis, Thomas S., "Miscibility of Polyamide Blends: Effects of Configuration," 1995, Polymer, vol. 36, Issue 20, pp. 3919-3926.
Buschow, K.H.J., et al., "Packaging: Papers for Sacks and Bags," 2001, Encyclopedia of Materials: Science and Technology, vol. 8, Elsevier, pp. 6646-6652.
Coles, Richard, et al., "Food Packaging Technology," 2003, pp. 194-195 and 224-229, Blackwell Publishing.
Sajiki, Junko, et al., "Leaching of Bisphenol A (BPA) to Seawater from Polycarbonate Plastic and its Degradation by Reactive Oxygen Species," 2003, Chemosphere, 51, pp. 55-62.
USPTO Office Action dated Oct. 2, 2009 for copending U.S. Appl. No. 11/588,524.
USPTO Office Action dated Oct. 7, 2009 for copending U.S. Appl. No. 11/588,458.
USPTO Office Action dated Sep. 29, 2009 for copending U.S. Appl. No. 11/390,751.
USPTO Office Action dated Sep. 24, 2009 for copending U.S. Appl. No. 11/588,883.
USPTO Office Action dated Sep. 28, 2009 for copending U.S. Appl. No. 11/390,847.
USPTO Office Action dated Sep. 24, 2009 for copending U.S. Appl. No. 11/390,858.
USPTO Office Action dated Sep. 29, 2009 for copending U.S. Appl. No. 11/390,629.
USPTO Office Action dated Sep. 29, 2009 for copending U.S. Appl. No. 11/390,814.
USPTO Office Action dated Oct. 19, 2009 for copending U.S. Appl. No. 11/390,563.
USPTO Office Action dated Oct. 21, 2009 for copending U.S. Appl. No. 11/391,156.
Gupta, V.B. et al., "PET Fibers, Films, and Bottles: Section 5-7", Handbook of Thermoplastic Polyesters: Homopolymers, Copolymers, Blends, and Composites, 2005, pp. 362-388, Wiley InterScience.
USPTO Office Action dated Oct. 22, 2009 for copending U.S. Appl. No. 11/588,906.
USPTO Office Action dated Nov. 3, 2009 for copending U.S. Appl. No. 11/390,883.
USPTO Office Action dated Nov. 4, 2009 for copending U.S. Appl. No. 11/390,750.
USPTO Office Action dated Nov. 4, 2009 for copending U.S. Appl. No. 11/390,864.
USPTO Office Action dated Nov. 17, 2009 for copending U.S. Appl. No. 12/254,894.
USPTO Office Action dated Nov. 18, 2009 for copending U.S. Appl. No. 11/390,630.
USPTO Office Action dated Nov. 30, 2009 for copending U.S. Appl. No. 11/391,495.
Turner, S.R., et al., "Amorphous and Crystalline Polyesters based on 1,4-Cyclohexanedimethanol", Chapter 7, Modern Polyesters: Chemistry and Technology of Polyesters and Copolyesters, Edited by J. Sheirs and T.E. Long, 2003 John Wiley & Sons, Ltd., pp. 267-292.
USPTO Office Action dated Nov. 18, 2009 for copending U.S. Appl. No. 11/390,794.
USPTO Office Action dated Nov. 20, 2009 for copending U.S. Appl. No. 11/391,485.
USPTO Office Action dated Nov. 20, 2009 for copending U.S. Appl. No. 11/390,882.
USPTO Office Action dated Dec. 1, 2009 for copending U.S. Appl. No. 12/091,570.
USPTO Office Action dated Dec. 3, 2009 for copending U.S. Appl. No. 11/395,505.
USPTO Office Action dated Dec. 4, 2009 for copending U.S. Appl. No. 12/091,566.
Zipper, Marcus D.,et al., "A Free Volume Study of Miscible Polyester Blends," 1995, pp. 127-136, Polymer International, vol. 36.
"APEC High-Heat Polycarbonate Resin," 2004, Bayer Material Science Product Information *NOT PRIOR ART; SUBMITTED FOR STATE OF THE ART.*
Lobo, Hubert et al, "Handbook of Plastics Analysis," 2003, pp. 20 and 21, Marcel Dekker, Inc.
Turner, S.R., et al. "Amorphous and Crystalline Polyesters based on 1,4-Cyclohexanedimethanol," 2003, *Modern Polyesters: Chemistry and Technology of Polyesters and Copolyesters*, pp. 268, 284-285, J. Sheirs and T.E. Long, ed., John Wiley and Sons, Ltd.
USPTO Notice of Allowance dated Dec. 11, 2009 for copending U.S. Appl. No. 12/365,515.
USPTO Office Action dated Dec. 18, 2009 for copending U.S. Appl. No. 11/390,846.
Copending U.S. Appl. No. 12/639,324, filed Dec. 16, 2009.
USPTO Notice of Allowance dated Dec. 22, 2009 for copending U.S. Appl. No. 12/361,779.
USPTO Office Action dated Jan. 7, 2010 for copending U.S. Appl. No. 12/091,568.
USPTO Office Action dated Jan. 13, 2010 for copending U.S. Appl. No. 11/635,433.
USPTO Office Action dated Jan. 14, 2010 for copending U.S. Appl. No. 11/390,809.
USPTO Notice of Allowance dated Jan. 27, 2010 for copending U.S. Appl. No. 11/635,434.
USPTO Office Action dated Mar. 11, 2010, for copending U.S. Appl. No. 11/391,812.
Copending U.S. Appl. No. 12/724,492, filed Mar. 16, 2010.
Copending U.S. Appl. No. 12/724,480, filed Mar. 16, 2010.
Copending U.S. Appl. No. 12/724,468, filed Mar. 16, 2010.
USPTO Office Action dated Mar. 19, 2010, for copending U.S. Appl. No. 11/588,527.
USPTO Notice of Allowance dated Mar. 24, 2010 for copending U.S. Appl. No. 11/391,565.
USPTO Office Action dated Mar. 29, 2010 for copending U.S. Appl. No. 11/390,812.
USPTO Notice of Allowance dated Apr. 15, 2010 for copending U.S. Appl. No. 11/391,505.
USPTO Office Action dated Apr. 19, 2010 for copending U.S. Appl. No. 12/724,480.
USPTO Office Action dated Apr. 21, 2010 for copending U.S. Appl. No. 12/724,468.
USPTO Office Action dated Apr. 21, 2010 for copending U.S. Appl. No. 12/724,492.
USPTO Office Action dated May 6, 2010 for copending U.S. Appl. No. 12/254,894.
New copending U.S. Appl. No. 12/784,193, filed May 20, 2010, Emmett Dudley Crawford, et al.
USPTO Notice of Allowance dated May 13, 2010 for copending U.S. Appl. No. 11/390,629.
USPTO Notice of Allowance dated May 13, 2010 for copending U.S. Appl. No. 11/390,751.
USPTO Notice of Allowance dated May 21, 2010 for copending U.S. Appl. No. 11/391,156.
USPTO Notice of Allowance dated May 26, 2010 for copending U.S. Appl. No. 11/391,495.
USPTO Notice of Allowance dated Jun. 24, 2010 for copending U.S. Appl. No. 11/391,576.
USPTO Office Action dated Jun. 24, 2010 for copending U.S. Appl. No. 11/390,846.

USPTO Office Action dated Jul. 8, 2010 for copending U.S. Appl. No. 11/390,809.
USPTO Notice of Allowance dated Jul. 8, 2010 for copending U.S. Appl. No. 11/390,630.
USPTO Notice of Allowance dated Jul. 8, 2010 for copending U.S. Appl. No. 11/390,883.
USPTO Office Action dated Jul. 12, 2010 for copending U.S. Appl. No. 11/390,794.
Notice of Allowance dated Jul. 13, 2010 for copending U.S. Appl. No. 11/391,505.
USPTO Office Action dated Jul. 22, 2010 for copending U.S. Appl. No. 12/479,893.
USPTO Notice of Allowance dated Jul. 22, 2010 for copending U.S. Appl. No. 11/391,485.
USPTO Notice of Allowance dated Aug. 3, 2010 for copending U.S. Appl. No. 11/390,864.
New copending U.S. Appl. No. 12/853,717, filed Aug. 10, 2010, Emmett Dudley Crawford, et al.
USPTO Notice of Allowance dated Aug. 11, 2010 for copending U.S. Appl. No. 11/390,631.
USPTO Notice of Allowance dated Sep. 2, 2010 for copending U.S. Appl. No. 11/390,811.
USPTO Office Action dated Sep. 2, 2010 for copending U.S. Appl. No. 11/391,124.
New copending U.S. Appl. No. 12/888,648, filed Sep. 23, 2010, Thomas Joseph Pecorini et al.
USPTO Office Action dated Oct. 5, 2010 for copending U.S. Appl. No. 11/390,655.
New copending U.S. Appl. No. 12/900,060, filed Oct. 7, 2010, Thomas Joseph Pecorini, et al.
USPTO Office Action dated Oct. 8, 2010 for copending U.S. Appl. No. 11/390,812.
USPTO Notice of Allowance dated Oct. 28, 2010 for copending U.S. Appl. No. 11/390,827.
USPTO Office Action dated Oct. 27, 2010 for copending U.S. Appl. No. 12/294,690.
New Copending U.S. Appl. No. 12/900,060, filed Oct. 7, 2010, Joseph Thomas Pecorini.
USPTO Notice of Allowance dated Oct. 14, 2010 for copending U.S. Appl. No. 11/390,722.
USPTO Notice of Allowance dated Nov. 2, 2010 for copending U.S. Appl. No. 12/724,480.
USPTO Notice of Allowance dated Nov. 4, 2010 for copending U.S. Appl. No. 12/724,468.
USPTO Notice of Allowance dated Nov. 4, 2010 for copending U.S. Appl. No. 11/390,955.
USPTO Office Action dated Nov. 4, 2010 for copending U.S. Appl. No. 12/294,686.
USPTO Notice of Allowance dated Nov. 4, 2010 for copending U.S. Appl. No. 11/390,826.
USPTO Office Action dated Oct. 27, 2010 for copending U.S. Appl. No. 11/390,836.
USPTO Notice of Allowance dated Nov. 23, 2010 for copending U.S. Appl. No. 11/390,563.
New copending U.S. Appl. No. 12/943,217, filed Nov. 10, 2010, Emmett Dudley Crawford et al.
New copending U.S. Appl. No. 13/007,838, filed Jan. 17, 2011, Emmett Dudley Crawford et al.
New copending U.S. Appl. No. 13/016,147, filed Jan. 28, 2011, Emmett Dudley Crawford, et al.
New copending U.S. Appl. No. 13/017,069, filed Jan. 31, 2011, Emmett Dudley Crawford, et al.
New Copending U.S. Appl. No. 13/017,352, filed Jan. 31, 2011, Emmett Dudley Crawford, et al.
USPTO Office Action dated Jan. 25, 2011 for copending U.S. Appl. No. 12/853,717.
Al-Malaika, S., "Stabilization", Encyclopedia of Polymer Science and Technology, vol. 4, 2001, pp. 179-229, John Wiley & Sons, Inc.
USPTO Notice of Allowance dated Jan. 26, 2011 for copending U.S. Appl. No. 11/390,858.
USPTO Office Action dated Feb. 2, 2011 for copending U.S. Appl. No. 11/390,655.
USPTO Office Action dated Mar. 17, 2011 for copending U.S. Appl. No. 12/479,893.
USPTO Notice of Allowance dated Mar. 17, 2011 for copending U.S. Appl. No. 11/391,137.
USPTO Office Action dated Feb. 14, 2011 for copending U.S. Appl. No. 12/294,690.
USPTO Notice of Allowance dated Feb. 18, 2011 for copending U.S. Appl. No. 11/390,809.
USPTO Notice of Allowance dated Feb. 17, 2011 for copending U.S. Appl. No. 11/390,812.
USPTO Office Action dated Jun. 8, 2011 for copending U.S. Appl. No. 11/588,883.
USPTO Notice of Allowance dated Aug. 12, 2011 for copending U.S. Appl. No. 11/390,752.
USPTO Office Action dated Jul. 7, 2011 for copending U.S. Appl. No. 11/588,906.
USPTO Notice of Allowance dated Jul. 21, 2011 for copending U.S. Appl. No. 11/390,671.
USPTO Office Action dated Jun. 22, 2011 for copending U.S. Appl. No. 12/091,570.
USPTO Notice of Allowance dated Aug. 3, 2011 for copending U.S. Appl. No. 11/390,655.
USPTO Office Action dated Jul. 19, 2011 for copending U.S. Appl. No. 11/390,794.
New Copending U.S. Appl. No. 13/162,870, filed Jun. 17, 2011, Emmett Dudley Crawford, et al.
USPTO Notice of Allowance dated Mar. 8, 2012 for copending U.S. Appl. No. 12/274,692.
USPTO Notice of Allowance dated Feb. 14, 2012 for copending U.S. Appl. No. 11/588,906.
New copending U.S. Appl. No. 13/348,677, filed Jan. 12, 2012, Emmett Dudley Crawford et al.
New copending U.S. Appl. No. 13/398,262, filed Feb. 16, 2012, Emmett Dudley Crawford et al.
USPTO Notice of Allowance dated Mar. 21, 2012 for copending U.S. Appl. No. 12/390,694.
New co-pending U.S. Appl. No. 13/596,754, filed Aug. 28, 2012; Thomas Joseph Pecorini et al.
New co-pending U.S. Appl. No. 13/596,805, filed Aug. 28, 2012; Ted Calvin Germroth et al.
Notice of Allowance received in co-pending U.S. Appl. No. 13/016,147 received on Sep. 28, 2012.
USPTO Non-Final Office Action received in co-pending U.S. Appl. No. 13/596,754 received Oct. 2, 2012.
USPTO Non-Final Office Action received in co-pending U.S. Appl. No. 13/162,870 received Oct. 18, 2012.
New co-pending U.S. Appl. No. 13/658,249, filed Oct. 23, 2012; Emmett Dudley Crawford et al.
Notice of Allowance and Fee(s) Due mailing date Jul. 18, 2012 received in co-pending U.S. Appl. No. 13/348,677.
Notice of Allowance and Fee(s) Due mailing date Jun. 21, 2012 received in co-pending U.S. Appl. No. 12/091,570.
Notice of Allowance and Fee(s) Due mailing date Jun. 11, 2012 received in co-pending U.S. Appl. No. 12/274,692.
C.I. Constitution No. 515240, Nov. 6, 2006.
C.I. Constitution No. 515245, Nov. 6, 2006.
USPTO Office Action dated Dec. 7, 2012 for co-pending U.S. Appl. No. 13/398,262.
Notice of Allowance and Fee(s) Due mailing date Nov. 23, 2012 received in co-pending U.S. Appl. No. 13/348,677.

THE EFFECT OF COMONOMER ON
THE FASTEST CRYSTALLIZATION
HALFTIMES OF MODIFIED PCT COPOLYESTERS

THE EFFECT OF COMONOMER ON
THE BRITTLE-TO-DUCTILE TRANSITION
TEMPERATURE ($T_{bd}$) IN A NOTCHED IZOD TEST
(ASTM D256, 1/8 IN THICK, 10 MIL NOTCH)

THE EFFECT OF 2,2,4,4-TETRAMETHYL-1,3-CYCLOBUTANEDIOL COMPOSITION ON THE GLASS TRANSITION TEMPERATURE ($T_g$) OF THE COPOLYESTER

US 8,507,638 B2

POLYESTER COMPOSITIONS CONTAINING CYCLOBUTANEDIOL HAVING A CERTAIN COMBINATION OF INHERENT VISCOSITY AND MODERATE GLASS TRANSITION TEMPERATURE AND ARTICLES MADE THEREFROM

CROSS-REFERENCES TO RELATED APPLICATIONS

This application is a continuation of application Ser. No. 12/784,193 filed on May 20, 2010, which application is a continuation of application Ser. No. 11/391,565, filed on Mar. 28, 2006, now U.S. Pat. No. 7,781,562 issued on Aug. 24, 2010, which claims the benefit of U.S. Provisional Application Ser. No. 60/738,869, filed on Nov. 22, 2005, all of which are hereby incorporated by this reference in their entireties.

FIELD OF THE INVENTION

The present invention generally relates to polyester compositions made from terephthalic acid or an ester thereof or mixtures thereof; 2,2,4,4-tetramethyl-1,3-cyclobutanediol; and cyclohexanedimethanol, the polyester having a certain combination of inherent viscosity and glass transition temperature (Tg). These compositions have a certain combination of at least two of high impact strengths, moderate glass transition temperature ($T_g$), toughness, certain inherent viscosities, low ductile-to-brittle transition temperatures, good color and clarity, low densities, chemical resistance, and long crystallization half-times, which allow them to be easily formed into articles.

BACKGROUND OF THE INVENTION

Poly(1,4-cyclohexylenedimethylene terephthalate) (PCT), a polyester based solely on terephthalic acid or an ester thereof and 1,4-cyclohexanedimethanol, is known in the art and is commercially available. This polyester crystallizes rapidly upon cooling from the melt, making it very difficult to form amorphous articles by methods known in the art such as extrusion, injection molding, and the like. In order to slow down the crystallization rate of PCT, copolyesters can be prepared containing additional dicarboxylic acids or glycols such as isophthalic acid or ethylene glycol. These ethylene glycol- or isophthalic acid-modified PCTs are also known in the art and are commercially available.

One common copolyester used to produce films, sheeting, and molded articles is made from terephthalic acid, 1,4-cyclohexanedimethanol, and ethylene glycol. While these copolyesters are useful in many end-use applications, they exhibit deficiencies in properties such as glass transition temperature and impact strength when sufficient modifying ethylene glycol is included in the formulation to provide for long crystallization half-times. For example, copolyesters made from terephthalic acid, 1,4-cyclohexanedimethanol, and ethylene glycol with sufficiently long crystallization half-times can provide amorphous products that exhibit what is believed to be undesirably higher ductile-to-brittle transition temperatures and lower glass transition temperatures than the compositions revealed herein.

The polycarbonate of 4,4'-isopropylidenediphenol (bisphenol A polycarbonate) has been used as an alternative for polyesters known in the art and is a well known engineering molding plastic. Bisphenol A polycarbonate is a clear, high-performance plastic having good physical properties such as dimensional stability, high heat resistance, and good impact strength. Although bisphenol-A polycarbonate has many good physical properties, its relatively high melt viscosity leads to poor melt processability and the polycarbonate exhibits poor chemical resistance. It is also difficult to thermoform.

Polymers containing 2,2,4,4-tetramethyl-1,3-cyclobutanediol have also been generally described in the art. Generally, however, these polymers exhibit high inherent viscosities, high melt viscosities, and high glass transition temperatures such that the equipment used in industry can be insufficient to manufacture or post polymerization process these materials.

Thus, there is a need in the art for a polymer having a combination of two or more properties, chosen from at least one of the following: toughness, moderate glass transition temperatures (Tg), good impact strength, hydrolytic stability, chemical resistance, long crystallization half-times, low ductile to brittle transition temperatures, good color and clarity, lower density and/or thermoformability of polyesters while retaining processability on the standard equipment used in the industry.

SUMMARY OF THE INVENTION

It is believed that certain compositions made from terephthalic acid residues, an ester thereof, or mixtures thereof; cyclohexanedimethanol, an ester thereof, and mixtures thereof; and 2,2,4,4-tetramethyl-1,3-cyclobutanediol with a certain combination of inherent viscosities and/or glass transition temperatures are superior to polyesters known in the art and to polycarbonate with respect to at least one of the following: of high impact strengths, hydrolytic stability, toughness, chemical resistance, good color and clarity, long crystallization half-times, low ductile to brittle transition temperatures, lower specific gravity and thermoformability. These compositions are believed to be similar to polycarbonate in heat resistance and are still processable on the standard industry equipment.

In one aspect, the invention relates to a polyester composition comprising at least one polyester which comprises:
(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 1 to 99 mole % of 2,2,4,4-tetramethyl-1,3-cyclobutanediol residues; and
  ii) 1 to 99 mole % of cyclohexanedimethanol residues,
wherein the total mole % of the dicarboxylic acid component is 100 mole %, and the total mole % of the glycol component is 100 mole %; and
wherein the inherent viscosity is 0.10 to less than 1.0 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 1 to 99 mole % of 2,2,4,4-tetramethyl-1,3-cyclobutanediol residues; and ii) 1 to 99 mole % of cyclohexanedimethanol residues,
wherein the total mole % of the dicarboxylic acid component is 100 mole %, and the total mole % of the glycol component is 100 mole %; and
wherein the inherent viscosity is 0.35 to less than 1.0 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 5 to less than 50 mole % of 2,2,4,4-tetramethyl-1,3-cyclobutanediol residues; and
ii) greater than 50 to 95 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 1.2 dL/g as determined in 60/40 (wt/wt) phenol/tetrachloroethane at a concentration of 0.25 g/50 ml at 25° C.; and
wherein the polyester has a Tg of 85 to 125° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 5 to less than 50 mole % of 2,2,4,4-tetramethyl-1,3-cyclobutanediol residues; and
ii) greater than 50 to 95 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 1.2 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 10 to 30 mole % of 2,2,4,4-tetramethyl-1,3-cyclobutanediol residues; and
ii) 70 to 90 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 1.2 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 15 to 25 mole % of 2,2,4,4-tetramethyl-1,3-cyclobutanediol residues; and
ii) 75 to 85 mole % of cyclohexanedimethanol residues,
wherein the total mole % of the dicarboxylic acid component is 100 mole %, and the total mole % of the glycol component is 100 mole %; and
wherein the inherent viscosity is from 0.50 to 1.2 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 15 to 25 mole % of 2,2,4,4-tetramethyl-1,3-cyclobutanediol residues; and
ii) 75 to 85 mole % of cyclohexanedimethanol residues,
wherein the total mole % of the dicarboxylic acid component is 100 mole %, and the total mole % of the glycol component is 100 mole %; and
wherein the inherent viscosity is from 0.50 to 0.8 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 15 to 25 mole % of 2,2,4,4-tetramethyl-1,3-cyclobutanediol residues; and
ii) 75 to 85 mole % of cyclohexanedimethanol residues,
wherein the total mole % of the dicarboxylic acid component is 100 mole %, and the total mole % of the glycol component is 100 mole %; and
wherein the inherent viscosity is from 0.50 to 0.75 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and (b) a glycol component comprising:
  i) 1 to 99 mole % of 2,2,4,4-tetramethyl-1,3-cyclobutane-diol residues; and
  ii) 1 to 99 mole % of cyclohexanedimethanol residues,
wherein the total mole % of the dicarboxylic acid component is 100 mole %, and the total mole % of the glycol component is 100 mole %; and
wherein the inherent viscosity is from 0.35 to 1.2 dL/g as determined in 60/40 (wt/wt) phenol/tetrachloroethane at a concentration of 0.25 g/50 ml at 25° C.; and
wherein the polyester has a Tg of 100 to 120° C.

In one aspect, the invention relates to a polyester composition comprising at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 15 to 25 mole % of 2,2,4,4-tetramethyl-1,3-cyclobutane-diol residues; and
    ii) 75 to 85 mole % of cyclohexanedimethanol residues,
wherein the total mole % of the dicarboxylic acid component is 100 mole %, and the total mole % of the glycol component is 100 mole %; and
wherein the inherent viscosity is from 0.50 to 1.2 dL/g as determined in 60/40 (wt/wt) phenol/tetrachloroethane at a concentration of 0.25 g/50 ml at 25° C.; and
wherein the polyester has a Tg of 100 to 120° C.

In one aspect, the invention relates to a polyester composition comprising at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 15 to 25 mole % of 2,2,4,4-tetramethyl-1,3-cyclobutane-diol residues; and
    ii) 75 to 85 mole % of cyclohexanedimethanol residues,
wherein the total mole % of the dicarboxylic acid component is 100 mole %, and the total mole % of the glycol component is 100 mole %; and
wherein the inherent viscosity is from 0.50 to 0.8 dL/g as determined in 60/40 (wt/wt) phenol/tetrachloroethane at a concentration of 0.25 g/50 ml at 25° C.; and
wherein the polyester has a Tg of 100 to 120° C.

In one aspect, this invention relates to a polyester composition comprising at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 5 to less than 50 mole % of 2,2,4,4-tetramethyl-1,3-cyclobutanediol residues; and
    ii) greater than 50 to 95 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 1.2 dL/g as determined in 60/40 (wt/wt) phenol/tetrachloroethane at a concentration of 0.25 g/50 ml at 25° C.; and
wherein the polyester has a Tg of 95 to 115° C.

In one aspect, the invention relates to a polyester composition comprising at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 10 to 30 mole % of 2,2,4,4-tetramethyl-1,3-cyclobutane-diol residues; and
    ii) 70 to 90 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 1.2 dL/g as determined in 60/40 (wt/wt) phenol/tetrachloroethane at a concentration of 0.25 g/50 ml at 25° C.; and
wherein the polyester has a Tg of 95 to 115° C.

In one aspect, the invention relates to a polyester composition comprising at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 15 to 25 mole % of 2,2,4,4-tetramethyl-1,3-cyclobutane-diol residues; and
    ii) 75 to 85 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 1.2 dL/g as determined in 60/40 (wt/wt) phenol/tetrachloroethane at a concentration of 0.25 g/50 ml at 25° C.; and
wherein the polyester has a Tg of 95 to 115° C.

In one aspect, this invention relates to a polyester composition comprising at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and
    iii) 0 to 10 mole % of aliphatic dicarboxylic acid residues having up to 16 carbon atoms; and
  (b) a glycol component comprising:
    i) 5 to less than 50 mole % of 2,2,4,4-tetramethyl-1,3-cyclobutanediol residues; and
    ii) greater than 50 to 95 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 0.75 dL/g as determined in 60/40 (wt/wt) phenol/tetrachloroethane at a concentration of 0.25 g/50 ml at 25° C.; and
wherein the polyester has a Tg of 85 to 125° C.

In one aspect, this invention relates to a polyester composition comprising at least one polyester which comprises:
  (a) a dicarboxylic acid component comprising:
    i) 70 to 100 mole % of terephthalic acid residues;
    ii) 0 to 30 mole % of aromatic dicarboxylic acid residues having up to 20 carbon atoms; and iii) 0 to 10 mole % of aliphatic dicarboxylic acid residues having up to 16 carbon atoms; and
(b) a glycol component comprising:
 i) 5 to less than 50 mole % of 2,2,4,4-tetramethyl-1,3-cyclobutanediol residues; and
 ii) greater than 50 to 95 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.50 to less than 0.75 dL/g as determined in 60/40 (wt/wt) phenol/tetrachloroethane at a concentration of 0.25 g/50 ml at 25° C.; and wherein the polyester has a Tg of 85 to 120° C.

In one aspect, this invention relates to a polyester composition comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 5 to less than 50 mole % of 2,2,4,4-tetramethyl-1,3-cyclobutanediol residues; and
 ii) greater than 50 to 95 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.50 to 0.75 dL/g as determined in 60/40 (wt/wt) phenol/tetrachloroethane at a concentration of 0.25 g/50 ml at 25° C.; and wherein the polyester has a Tg of 85 to 120° C.

In one aspect, this invention relates to a polyester composition comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 5 to less than 50 mole % of 2,2,4,4-tetramethyl-1,3-cyclobutanediol residues; and
 ii) greater than 50 to 95 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.6 to 0.75 dL/g as determined in 60/40 (wt/wt) phenol/tetrachloroethane at a concentration of 0.25 g/50 ml at 25° C.; and wherein the polyester has a Tg of 85 to 120° C.

In one aspect, this invention relates to a polyester composition comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 5 to less than 50 mole % of 2,2,4,4-tetramethyl-1,3-cyclobutanediol residues; and
 ii) greater than 50 to 95 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.65 to 0.75 dL/g as determined in 60/40 (wt/wt) phenol/tetrachloroethane at a concentration of 0.25 g/50 ml at 25° C.; and wherein the polyester has a Tg of 85 to 120° C.

In one aspect, this invention relates to a polyester composition comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 5 to less than 50 mole % of 2,2,4,4-tetramethyl-1,3-cyclobutanediol residues; and
 ii) greater than 50 to 95 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.68 to 0.78 dL/g as determined in 60/40 (wt/wt) phenol/tetrachloroethane at a concentration of 0.25 g/50 ml at 25° C.; and wherein the polyester has a Tg of 85 to 120° C.

In one aspect, this invention relates to a polyester composition comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 10 to 30 mole % of 2,2,4,4-tetramethyl-1,3-cyclobutanediol residues; and
 ii) 70 to 90 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.50 to less than 0.75 dL/g as determined in 60/40 (wt/wt) phenol/tetrachloroethane at a concentration of 0.25 g/50 ml at 25° C.; and wherein the polyester has a Tg of 85 to 120° C.

In one aspect, this invention relates to a polyester composition comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 10 to 30 mole % of 2,2,4,4-tetramethyl-1,3-cyclobutanediol residues; and
 ii) 70 to 90 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.50 to 0.75 dL/g as determined in 60/40 (wt/wt) phenol/tetrachloroethane at a concentration of 0.25 g/50 ml at 25° C.; and wherein the polyester has a Tg of 85 to 120° C.

In one aspect, this invention relates to a polyester composition comprising at least one polyester which comprises:

(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 15 to 25 mole % of 2,2,4,4-tetramethyl-1,3-cyclobutanediol residues; and
ii) 75 to 85 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.50 to 0.75 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 15 to 25 mole % of 2,2,4,4-tetramethyl-1,3-cyclobutanediol residues; and
ii) 75 to 85 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.50 to less than 0.75 dL/g as determined in 60/40 (wt/wt) phenol/tetrachloroethane at a concentration of 0.25 g/50 ml at 25° C.; and wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 17 to 28 mole % of 2,2,4,4-tetramethyl-1,3-cyclobutanediol residues; and
ii) 72 to 83 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.65 to 0.75 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 15 to 25 mole % of 2,2,4,4-tetramethyl-1,3-cyclobutanediol residues; and
ii) 75 to 85 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.65 to 0.75 dL/g as determined in 60/40 (wt/wt) phenol/tetrachloroethane at a concentration of 0.25 g/50 ml at 25° C.; and
wherein the polyester has a Tg of 100 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 17 to 28 mole % of 2,2,4,4-tetramethyl-1,3-cyclobutanediol residues; and
ii) 72 to 83 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.7 to 0.8 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 17 to 28 mole % of 2,2,4,4-tetramethyl-1,3-cyclobutanediol residues; and
ii) 72 to 83 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.7 to 0.8 dL/g as determined in 60/40 (wt/wt) phenol/tetrachloroethane at a concentration of 0.25 g/50 ml at 25° C.; and
wherein the polyester has a Tg of 100 to 120° C.

In one aspect, the invention relates to a polyester composition comprising at least one polyester which comprises:
(a) a dicarboxylic acid component comprising:
i) 70 to 100 mole % of terephthalic acid residues;
ii) 0 to 30 mole % of aromatic dicarboxylic acid residues having up to 20 carbon atoms; and
iii) 0 to 10 mole % of aliphatic dicarboxylic acid residues having up to 16 carbon atoms; and
(b) a glycol component comprising:
i) 17 to 28 mole % of 2,2,4,4-tetramethyl-1,3-cyclobutanediol residues; and
ii) 75 to 85 mole % of cyclohexanedimethanol residues, wherein the total mole % of the dicarboxylic acid component is 100 mole %, and the total mole % of the glycol component is 100 mole %; and
wherein the inherent viscosity of the polyester is from 0.65 to 0.75 dL/g as determined in 60/40 (wt/wt) phenol/tetrachloroethane at a concentration of 0.25 g/50 ml at 25° C.; and wherein the polyester has a Tg of 100 to 115° C.

In one aspect, the invention relates to a polyester composition comprising at least one polyester which comprises:

(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 5 to less than 50 mole % of 2,2,4,4-tetramethyl-1,3-cyclobutanediol residues; and
   ii) greater than 50 to 95 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 0.75 dL/g as determined in 60/40 (wt/wt) phenol/tetrachloroethane at a concentration of 0.25 g/50 ml at 25° C.; and wherein the polyester has a Tg of 95 to 115° C.

In one aspect, the invention relates to a polyester composition comprising at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 5 to less than 50 mole % of 2,2,4,4-tetramethyl-1,3-cyclobutanediol residues; and
   ii) greater than 50 to 95 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to less than 0.75 dL/g as determined in 60/40 (wt/wt) phenol/tetrachloroethane at a concentration of 0.25 g/50 ml at 25° C.; and wherein the polyester has a Tg of 95 to 115° C.

In one aspect, this invention relates to a polyester composition comprising at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 10 to 30 mole % of 2,2,4,4-tetramethyl-1,3-cyclobutanediol residues; and
   ii) 70 to 90 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 0.75 dL/g as determined in 60/40 (wt/wt) phenol/tetrachloroethane at a concentration of 0.25 g/50 ml at 25° C.; and wherein the polyester has a Tg of 95 to 115° C.

In one aspect, this invention relates to a polyester composition comprising at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 10 to 30 mole % of 2,2,4,4-tetramethyl-1,3-cyclobutanediol residues; and
   ii) 70 to 90 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to less than 0.75 dL/g as determined in 60/40 (wt/wt) phenol/tetrachloroethane at a concentration of 0.25 g/50 ml at 25° C.; and wherein the polyester has a Tg of 95 to 115° C.

In one aspect, this invention relates to a polyester composition comprising at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 15 to 25 mole % of 2,2,4,4-tetramethyl-1,3-cyclobutanediol residues; and
   ii) 75 to 85 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to 0.75 dL/g as determined in 60/40 (wt/wt) phenol/tetrachloroethane at a concentration of 0.25 g/50 ml at 25° C.; and wherein the polyester has a Tg of 95 to 115° C.

In one aspect, this invention relates to a polyester composition comprising at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 15 to 25 mole % of 2,2,4,4-tetramethyl-1,3-cyclobutanediol residues; and
   ii) 75 to 85 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.50 to less than 0.75 dL/g as determined in 60/40 (wt/wt) phenol/tetrachloroethane at a concentration of 0.25 g/50 ml at 25° C.; and wherein the polyester has a Tg of 95 to 115° C.

In one aspect, the invention relates to a polyester composition comprising at least one polyester which comprises:
(a) a dicarboxylic acid component comprising:
   i) 70 to 100 mole % of terephthalic acid residues;
   ii) 0 to 30 mole % of aromatic dicarboxylic acid residues having up to 20 carbon atoms; and
   iii) 0 to 10 mole % of aliphatic dicarboxylic acid residues having up to 16 carbon atoms; and
(b) a glycol component comprising:
   i) 15 to 25 mole % of 2,2,4,4-tetramethyl-1,3-cyclobutanediol residues; and
   ii) 75 to 85 mole % of cyclohexanedimethanol residues,
wherein the total mole % of the dicarboxylic acid component is 100 mole %, and the total mole % of the glycol component is 100 mole %; and
wherein the inherent viscosity of the polyester is from 0.60 to 0.72 dL/g as determined in 60/40 (wt/wt) phenol/tetrachloroethane at a concentration of 0.25 g/50 ml at 25° C.; and wherein the polyester has a Tg of 95 to 115° C.

In one aspect, the invention relates to a polyester composition comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 1 to 99 mole % of 2,2,4,4-tetramethyl-1,3-cyclobutanediol residues; and
 ii) 1 to 98.99 mole % of cyclohexanedimethanol residues,
 iii) 0.01 to less than 15 mole % ethylene glycol;
wherein the total mole % of the dicarboxylic acid component is 100 mole %, and the total mole % of the glycol component is 100 mole %; and
wherein the inherent viscosity is 0.35 to 1.2 dL/g as determined in 60/40 (wt/wt) phenol/tetrachloroethane at a concentration of 0.25 g/50 ml at 25° C.; and
wherein the polyester has a Tg of 85 to 120° C.

In one aspect, the invention relates to a polyester composition comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 1 to 99 mole % of 2,2,4,4-tetramethyl-1,3-cyclobutanediol residues; and
 ii) 1 to 99 mole % of cyclohexanedimethanol residues,
wherein the total mole % of the dicarboxylic acid component is 100 mole %, and the total mole % of the glycol component is 100 mole %; and
wherein the inherent viscosity is 0.35 to 1.2 dL/g as determined in 60/40 (wt/wt) phenol/tetrachloroethane at a concentration of 0.25 g/50 ml at 25° C.; and
wherein the polyester has a Tg of 85 to 120° C.; and optionally, wherein one or more branching agents is added prior to or during the polymerization of the polyester.

In one aspect, the invention relates to a polyester composition comprising at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms;
(b) a glycol component comprising:
 i) 1 to 99 mole % of 2,2,4,4-tetramethyl-1,3-cyclobutanediol residues; and
 ii) 1 to 99 mole % of cyclohexanedimethanol residues; and
(c) residues from at least one branching agent;
wherein the total mole % of the dicarboxylic acid component is 100 mole %, and the total mole % of the glycol component is 100 mole %; and
wherein the inherent viscosity is 0.35 to 1.2 dL/g as determined in 60/40 (wt/wt) phenol/tetrachloroethane at a concentration of 0.25 g/50 ml at 25° C.; and
wherein the polyester has a Tg of 85 to 120° C.

In one aspect, this invention relates to a polyester composition comprising:

at least one polyester which comprises:
(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 1 to 99 mole % of 2,2,4,4-tetramethyl-1,3-cyclobutanediol residues; and
 ii) 1 to 99 mole % of cyclohexanedimethanol residues; and
at least one thermal stabilizer or reaction products thereof;
wherein the total mole % of the dicarboxylic acid component is 100 mole %, and the total mole % of the glycol component is 100 mole %; and
wherein the inherent viscosity of the polyester is 0.35 to 1.2 dL/g as determined in 60/40 (wt/wt) phenol/tetrachloroethane at a concentration of 0.25 g/50 ml at 25° C.; and wherein the polyester has a Tg of 85 to 120° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
 (a) a dicarboxylic acid component comprising:
  (i) 70 to 100 mole % of terephthalic acid residues;
  (ii) 0 to 30 mole % of aromatic dicarboxylic acid residues having up to 20 carbon atoms; and
  (iii) 0 to 10 mole % of aliphatic dicarboxylic acid residues having up to 16 carbon atoms; and
 (b) a glycol component comprising:
  (i) 2,2,4,4-tetramethyl-1,3-cyclobutanediol residues; and
  (ii) cyclohexanedimethanol residues;
 wherein the molar ratio of glycol component/dicarboxylic acid component added in Step (I) is 1.0-1.5/1.0;
 wherein the mixture in Step (I) is heated in the presence of:
  (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one phosphorus compound, reaction products thereof, and mixtures thereof;
(II) heating the product of Step (I) at a temperature of 230° C. to 320° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters of the invention comprising the following steps:

(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;
  wherein the molar ratio of glycol component/dicarboxylic acid component added in Step (I) is 1.05-1.15/1.0;
  wherein the mixture in Step (I) is heated in the presence of:
    (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one phosphorus compound, reaction products thereof, and mixtures thereof;
(II) heating the product of Step (I) at a temperature of 230° C. to 320° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters of the invention comprising the following steps:
  (I) heating a mixture at least one temperature chosen from 150° C. to 200° C., under at least one pressure chosen from the range of 0 psig to 75 psig wherein said mixture comprises:
    (a) a dicarboxylic acid component comprising:
      (i) 70 to 100 mole % of terephthalic acid residues;
      (ii) 0 to 30 mole % of aromatic dicarboxylic acid residues having up to 20 carbon atoms; and
      (iii) 0 to 10 mole % of aliphatic dicarboxylic acid residues having up to 16 carbon atoms; and
    (b) a glycol component comprising:
      (i) 2,2,4,4-tetramethyl-1,3-cyclobutanediol residues; and
      (ii) cyclohexanedimethanol residues;
    wherein the molar ratio of glycol component/dicarboxylic acid component added in Step (I) is 1.0-1.5/1.0;
    wherein the mixture in Step (I) is heated in the presence of: (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;
  (II) heating the product of Step (I) at a temperature of 230° C. to 320° C. for 1 to 6 hours under at least one pressure chosen from the range of the final pressure of Step (I) to 0.02 torr absolute, in the presence of at least one thermal stabilizer chosen from at least one phosphorus compound, reaction products thereof, and mixtures thereof;
wherein the total mole % of the dicarboxylic acid component of the final polyester is 100 mole %; wherein the total mole % of the glycol component of the final polyester is 100 mole %; wherein the inherent viscosity of a final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters of the invention comprising the following steps:
  (I) heating a mixture at least one temperature chosen from 150° C. to 200° C., under at least one pressure chosen from the range of 0 psig to 75 psig wherein said mixture comprises:
    (a) a dicarboxylic acid component comprising:
      (i) 70 to 100 mole % of terephthalic acid residues;
      (ii) 0 to 30 mole % of aromatic dicarboxylic acid residues having up to 20 carbon atoms; and
      (iii) 0 to 10 mole % of aliphatic dicarboxylic acid residues having up to 16 carbon atoms; and
    (b) a glycol component comprising:
      (i) 2,2,4,4-tetramethyl-1,3-cyclobutanediol residues; and
      (ii) cyclohexanedimethanol residues;
    wherein the molar ratio of glycol component/dicarboxylic acid component added in Step (I) is 1.05-1.15/1.0;
    wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;
  (II) heating the product of Step (I) at a temperature of 230° C. to 320° C. for 1 to 6 hours under at least one pressure chosen from the range of the final pressure of Step (I) to 0.02 torr absolute, in the presence of at least one thermal stabilizer chosen from at least one phosphorus compound, reaction products thereof, and mixtures thereof;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters of the invention comprising the following steps:
  (I) heating a mixture at least one temperature chosen from 150° C. to 200° C., under at least one pressure chosen from the range of 0 psig to 75 psig wherein said mixture comprises:
    (a) a dicarboxylic acid component comprising:
      (i) 70 to 100 mole % of terephthalic acid residues;
      (ii) 0 to 30 mole % of aromatic dicarboxylic acid residues having up to 20 carbon atoms; and
      (iii) 0 to 10 mole % of aliphatic dicarboxylic acid residues having up to 16 carbon atoms; and
    (b) a glycol component comprising:
      (i) 2,2,4,4-tetramethyl-1,3-cyclobutanediol residues; and
      (ii) cyclohexanedimethanol residues;
    wherein the molar ratio of glycol component/dicarboxylic acid component added in Step (I) is 1.0-1.5/1.0;

wherein the mixture in Step (I) is heated in the presence of:
(i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one phosphorus compound, reaction products thereof, and mixtures thereof;

(II) heating the product of Step (I) at a temperature of 250° C. to 305° C. for 1 to 6 hours, under at least one pressure chosen from the range of the final pressure of Step (I) to 0.02 torr absolute, to form a final polyester;

wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters of the invention comprising the following steps:

(I) heating a mixture at least one temperature chosen from 150° C. to 200° C., under at least one pressure chosen from the range of 0 psig to 75 psig wherein said mixture comprises:
(a) a dicarboxylic acid component comprising:
(i) 70 to 100 mole % of terephthalic acid residues;
(ii) 0 to 30 mole % of aromatic dicarboxylic acid residues having up to 20 carbon atoms; and
(iii) 0 to 10 mole % of aliphatic dicarboxylic acid residues having up to 16 carbon atoms; and
(b) a glycol component comprising:
(i) 2,2,4,4-tetramethyl-1,3-cyclobutanediol residues; and
(ii) cyclohexanedimethanol residues;
wherein the molar ratio of glycol component/dicarboxylic acid component added in Step (I) is 1.05-1.15/1.0;
wherein the mixture in Step (I) is heated in the presence of:
(i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one phosphorus compound, reaction products thereof, and mixtures thereof;

(II) heating the product of Step (I) at a temperature of 250° C. to 305° C. for 1 to 6 hours, under at least one pressure chosen from the range of the final pressure of Step (I) to 0.02 torr absolute, to form a final polyester;

wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters of the invention comprising the following steps:

(I) heating a mixture at least one temperature chosen from 150° C. to 200° C., under at least one pressure chosen from the range of 0 psig to 75 psig wherein said mixture comprises:
(a) a dicarboxylic acid component comprising:
(i) 70 to 100 mole % of terephthalic acid residues;
(ii) 0 to 30 mole % of aromatic dicarboxylic acid residues having up to 20 carbon atoms; and
(iii) 0 to 10 mole % of aliphatic dicarboxylic acid residues having up to 16 carbon atoms; and
(b) a glycol component comprising:
(i) 2,2,4,4-tetramethyl-1,3-cyclobutanediol residues; and
(ii) cyclohexanedimethanol residues;
wherein the molar ratio of glycol component/dicarboxylic acid component added in Step (I) is 1.0-1.5/1.0;
wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;

(II) heating the product of Step (I) at a temperature of 250° C. to 305° C. for 1 to 6 hours under at least one pressure chosen from the range of the final pressure of Step (I) to 0.02 torr absolute, in the presence of at least one thermal stabilizer chosen from at least one phosphorus compound, reaction products thereof, and mixtures thereof;

wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters of the invention comprising the following steps:

(I) heating a mixture at least one temperature chosen from 150° C. to 200° C., under at least one pressure chosen from the range of 0 psig to 75 psig wherein said mixture comprises:
(a) a dicarboxylic acid component comprising:
(i) 70 to 100 mole % of terephthalic acid residues;
(ii) 0 to 30 mole % of aromatic dicarboxylic acid residues having up to 20 carbon atoms; and
(iii) 0 to 10 mole % of aliphatic dicarboxylic acid residues having up to 16 carbon atoms; and
(b) a glycol component comprising:
(i) 2,2,4,4-tetramethyl-1,3-cyclobutanediol residues; and
(ii) cyclohexanedimethanol residues;
wherein the molar ratio of glycol component/dicarboxylic acid component added in Step (I) is 1.05-1.15/1.0;
wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;

(II) heating the product of Step (I) at a temperature of 250° C. to 305° C. for 1 to 6 hours under at least one pressure chosen from the range of the final pressure of Step (I) to 0.02 torr absolute, in the presence of at least one thermal stabilizer chosen from at least one phosphorus compound, reaction products thereof, and mixtures thereof; wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters of the invention comprising the following steps:
(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;
  wherein the molar ratio of glycol component/dicarboxylic acid component added in Step (I) is 1.0-1.5/1.0;
  wherein the mixture in Step (I) is heated in the presence of: (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one of alkyl phosphate esters, aryl phosphate esters, mixed alkyl aryl phosphate esters, reaction products thereof, and mixtures thereof;
(II) heating the product of Step (I) at a temperature of 230° C. to 320° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;
  wherein the molar ratio of glycol component/dicarboxylic acid component added in Step (I) is 1.05-1.15/1.0;
  wherein the mixture in Step (I) is heated in the presence of:
    (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one of alkyl phosphate esters, aryl phosphate esters, mixed alkyl aryl phosphate esters, reaction products thereof, and mixtures thereof; to form a polyester; and
(II) heating the product of Step (I) at a temperature of 230° C. to 320° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;
  wherein the molar ratio of glycol component/dicarboxylic acid component added in Step (I) is 1.0-1.5/1.0;
  wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;
(II) heating the product of Step (I) at a temperature of 230° C. to 320° C. for 1 to 6 hours under at least one pressure chosen from the range of the final pressure of Step (I) to 0.02 torr absolute, in the presence of at least one thermal stabilizer chosen from at least one of alkyl phosphate esters, aryl phosphate esters, mixed alkyl aryl phosphate esters, reaction products thereof, and mixtures thereof; to form a polyester; and
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
(a) a dicarboxylic acid component comprising:
(i) 70 to 100 mole % of terephthalic acid residues;
(ii) 0 to 30 mole % of aromatic dicarboxylic acid residues having up to 20 carbon atoms; and
(iii) 0 to 10 mole % of aliphatic dicarboxylic acid residues having up to 16 carbon atoms; and
(b) a glycol component comprising:
(i) 2,2,4,4-tetramethyl-1,3-cyclobutanediol residues; and
(ii) cyclohexanedimethanol residues;
wherein the molar ratio of glycol component/dicarboxylic acid component added in Step (I) is 1.05-1.15/1.0;
wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;
(II) heating the product of Step (I) at a temperature of 230° C. to 320° C. for 1 to 6 hours under at least one pressure chosen from the range of the final pressure of Step (I) to 0.02 torr absolute, in the presence of at least one thermal stabilizer chosen from at least one of alkyl phosphate esters, aryl phosphate esters, mixed alkyl aryl phosphate esters, reaction products thereof, and mixtures thereof; to form a polyester;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
(a) a dicarboxylic acid component comprising:
(i) 70 to 100 mole % of terephthalic acid residues;
(ii) 0 to 30 mole % of aromatic dicarboxylic acid residues having up to 20 carbon atoms; and
(iii) 0 to 10 mole % of aliphatic dicarboxylic acid residues having up to 16 carbon atoms; and
(b) a glycol component comprising:
(i) 2,2,4,4-tetramethyl-1,3-cyclobutanediol residues; and
(ii) cyclohexanedimethanol residues;
wherein the molar ratio of glycol component/dicarboxylic acid component added in Step (I) is 1.0-1.5/1.0;
wherein the mixture in Step (I) is heated in the presence of:
(i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one of alkyl phosphate esters, aryl phosphate esters, mixed alkyl aryl phosphate esters, reaction products thereof, and mixtures thereof;
(II) heating the product of Step (I) at a temperature of 230° C. to 320° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
(a) a dicarboxylic acid component comprising:
(i) 70 to 100 mole % of terephthalic acid residues;
(ii) 0 to 30 mole % of aromatic dicarboxylic acid residues having up to 20 carbon atoms; and
(iii) 0 to 10 mole % of aliphatic dicarboxylic acid residues having up to 16 carbon atoms; and
(b) a glycol component comprising:
(i) 2,2,4,4-tetramethyl-1,3-cyclobutanediol residues; and
(ii) cyclohexanedimethanol residues;
wherein the molar ratio of glycol component/dicarboxylic acid component added in Step (I) is 1.05-1.15/1.0;
wherein the mixture in Step (I) is heated in the presence of: (i) at least one catalyst comprising at least one tin compound, and, optionally, at least one titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one of alkyl phosphate esters, aryl phosphate esters, mixed alkyl aryl phosphate esters, reaction products thereof, and mixtures thereof;
(II) heating the product of Step (I) at a temperature of 230° C. to 320° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:

(a) a dicarboxylic acid component comprising:
  (i) 70 to 100 mole % of terephthalic acid residues;
  (ii) 0 to 30 mole % of aromatic dicarboxylic acid residues having up to 20 carbon atoms; and
  (iii) 0 to 10 mole % of aliphatic dicarboxylic acid residues having up to 16 carbon atoms; and
(b) a glycol component comprising:
  (i) 2,2,4,4-tetramethyl-1,3-cyclobutanediol residues; and
  (ii) cyclohexanedimethanol residues;
wherein the molar ratio of glycol component/dicarboxylic acid component added in Step (I) is 1.0-1.5/1.0;
wherein the mixture in Step (I) is heated in the presence of: (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;
(II) heating the product of Step (I) at a temperature of 230° C. to 320° C. for 1 to 6 hours under at least one pressure chosen from the range of the final pressure of Step (I) to 0.02 torr absolute, in the presence of at least one thermal stabilizer chosen from at least one of alkyl phosphate esters, aryl phosphate esters, mixed alkyl aryl phosphate esters, reaction products thereof, and mixtures thereof;
wherein the total mole % of the dicarboxylic acid component of the final polyester is 100 mole %; wherein the total mole % of the glycol component of the final polyester is 100 mole %; wherein the inherent viscosity of a final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;
  wherein the molar ratio of glycol component/dicarboxylic acid component added in Step (I) is 1.05-1.15/1.0;
  wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;
(II) heating the product of Step (I) at a temperature of 230° C. to 320° C. for 1 to 6 hours under at least one pressure chosen from the range of the final pressure of Step (I) to 0.02 torr absolute, in the presence of at least one thermal stabilizer chosen from at least one of alkyl phosphate esters, aryl phosphate esters, mixed alkyl aryl phosphate esters, reaction products thereof, and mixtures thereof;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;
  wherein the molar ratio of glycol component/dicarboxylic acid component added in Step (I) is 1.0-1.5/1.0;
  wherein the mixture in Step (I) is heated in the presence of:
    (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one of alkyl phosphate esters, aryl phosphate esters, mixed alkyl aryl phosphate esters, reaction products thereof, and mixtures thereof;
(II) heating the product of Step (I) at a temperature of 250° C. to 305° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;

wherein the molar ratio of glycol component/dicarboxylic acid component added in Step (I) is 1.05-1.15/1.0;
wherein the mixture in Step (I) is heated in the presence of:
(i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one of alkyl phosphate esters, aryl phosphate esters, mixed alkyl aryl phosphate esters, reaction products thereof, and mixtures thereof;
(II) heating the product of Step (I) at a temperature of 250° C. to 305° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
(a) a dicarboxylic acid component comprising:
(i) 70 to 100 mole % of terephthalic acid residues;
(ii) 0 to 30 mole % of aromatic dicarboxylic acid residues having up to 20 carbon atoms; and
(iii) 0 to 10 mole % of aliphatic dicarboxylic acid residues having up to 16 carbon atoms; and
(b) a glycol component comprising:
(i) 2,2,4,4-tetramethyl-1,3-cyclobutanediol residues; and
(ii) cyclohexanedimethanol residues;
wherein the molar ratio of glycol component/dicarboxylic acid component added in Step (I) is 1.0-1.5/1.0;
wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;
(II) heating the product of Step (I) at a temperature of 250° C. to 305° C. for 1 to 6 hours under at least one pressure chosen from the range of the final pressure of Step (I) to 0.02 torr absolute, in the presence of at least one thermal stabilizer chosen from at least one of alkyl phosphate esters, aryl phosphate esters, mixed alkyl aryl phosphate esters, reaction products thereof, and mixtures thereof;
wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
(a) a dicarboxylic acid component comprising:
(i) 70 to 100 mole % of terephthalic acid residues;
(ii) 0 to 30 mole % of aromatic dicarboxylic acid residues having up to 20 carbon atoms; and
(iii) 0 to 10 mole % of aliphatic dicarboxylic acid residues having up to 16 carbon atoms; and
(b) a glycol component comprising:
(i) 2,2,4,4-tetramethyl-1,3-cyclobutanediol residues; and
(ii) cyclohexanedimethanol residues;
wherein the molar ratio of glycol component/dicarboxylic acid component added in Step (I) is 1.0-1.5/1.0;
wherein the mixture in Step (I) is heated in the presence of: (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one of alkyl phosphate esters, aryl phosphate esters, mixed alkyl aryl phosphate esters, reaction products thereof, and mixtures thereof;

(II) heating the product of Step (I) at a temperature of 230° C. to 320° C. for 1 to 6 hours, under at least one pressure chosen from the range of the final pressure of Step (I) to 0.02 torr absolute, to form a final polyester;

wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:

(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;
  wherein the molar ratio of glycol component/dicarboxylic acid component added in Step (I) is 1.05-1.15/1.0;
  wherein the mixture in Step (I) is heated in the presence of:
    (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and (ii) at least one thermal stabilizer chosen from at least one of alkyl phosphate esters, aryl phosphate esters, mixed alkyl aryl phosphate esters, reaction products thereof, and mixtures thereof; to form a polyester; and (II) heating the product of Step (I) at a temperature of 230° C. to 320° C. for 1 to 6 hours, under at least one pressure chosen from the range of the final pressure of Step (I) to 0.02 torr absolute, to form a final polyester;

wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:

(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;
  wherein the molar ratio of glycol component/dicarboxylic acid component added in Step (I) is 1.0-1.5/1.0;
  wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;

(II) heating the product of Step (I) at a temperature of 230° C. to 320° C. for 1 to 6 hours under at least one pressure chosen from the range of the final pressure of Step (I) to 0.02 torr absolute, in the presence of at least one thermal stabilizer chosen from at least one of alkyl phosphate esters, aryl phosphate esters, mixed alkyl aryl phosphate esters, reaction products thereof, and mixtures thereof; to form a polyester; and wherein the total mole % of the dicarboxylic acid component of the final polyester is 100 mole %; wherein the total mole % of the glycol component of the final polyester is 100 mole %; wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the invention comprises a process for making any of the polyesters useful in the invention comprising the following steps:

(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 2,2,4,4-tetramethyl-1,3-cyclobutanediol residues; and
    (ii) cyclohexanedimethanol residues;
  wherein the molar ratio of glycol component/dicarboxylic acid component added in Step (I) is 1.05-1.15/1.0;
  wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;

(II) heating the product of Step (I) at a temperature of 230° C. to 320° C. for 1 to 6 hours under at least one pressure chosen from the range of the final pressure of Step (I) to 0.02 torr absolute, in the presence of at least one thermal stabilizer chosen from at least one of alkyl phosphate esters, aryl phosphate esters, mixed alkyl aryl phosphate esters, reaction products thereof, and mixtures thereof; to form a polyester;

wherein the total mole % of the dicarboxylic acid component of the final polyester is 100 mole %; wherein the total mole % of the glycol component of the final polyester is 100 mole %;

wherein the inherent viscosity of the final polyester is from 0.35 to 1.2 dL/g as determined in 60/40 (wt/wt) phenol/tetrachloroethane at a concentration of 0.25 g/50 ml at 25° C.; and wherein the final polyester has a Tg of from 85 to 200° C.

In one aspect, the polyester compositions of the invention contain at least one polycarbonate.

In one aspect, the polyester compositions of the invention contain no polycarbonate.

In one aspect, the polyesters useful in the invention contain less than 15 mole % ethylene glycol residues, such as, for example, 0.01 to less than 15 mole % ethylene glycol residues.

In one aspect, the polyesters useful in the invention contain no ethylene glycol residues.

In one aspect, the polyesters useful in the invention contain 50 to 99.99 mole % ethylene glycol residues.

In one aspect, the polyesters useful in the invention contain no branching agent, or alternatively, at least one branching agent is added either prior to or during polymerization of the polyester.

In one aspect, the polyesters useful in the invention contain at least one branching agent without regard to the method or sequence in which it is added.

In one aspect, the polyesters useful in the invention are made from no 1,3-propanediol, or, 1,4-butanediol, either singly or in combination. In other aspects, 1,3-propanediol or 1,4-butanediol, either singly or in combination, may be used in the making of the polyesters useful in this invention.

In one aspect of the invention, the mole % of cis-2,2,4,4-tetramethyl-1,3-cyclobutanediol useful in certain polyesters useful in the invention is greater than 50 mole % or greater than 55 mole % of cis-2,2,4,4-tetramethyl-1,3-cyclobutanediol or greater than 70 mole % of cis-2,2,4,4-tetramethyl-1,3-cyclobutanediol; wherein the total mole percentage of cis-2,2,4,4-tetramethyl-1,3-cyclobutanediol and trans-2,2,4,4-tetramethyl-1,3-cyclobutanediol is equal to a total of 100 mole %.

In one aspect of the invention, the mole % of the isomers of 2,2,4,4-tetramethyl-1,3-cyclobutanediol useful in certain polyesters useful in the invention is from 30 to 70 mole % of cis-2,2,4,4-tetramethyl-1,3-cyclobutanediol or from 30 to 70 mole % of trans-2,2,4,4-tetramethyl-1,3-cyclobutanediol, or from 40 to 60 mole % of cis-2,2,4,4-tetramethyl-1,3-cyclobutanediol or from 40 to 60 mole % of trans-2,2,4,4-tetramethyl-1,3-cyclobutanediol, wherein the total mole percentage of cis-2,2,4,4-tetramethyl-1,3-cyclobutanediol and trans-2,2,4,4-tetramethyl-1,3-cyclobutanediol is equal to a total of 100 mole %.

In one aspect, certain polyesters useful in the invention may be amorphous or semicrystalline. In one aspect, certain polyesters useful in the invention can have a relatively low crystallinity. Certain polyesters useful in the invention can thus have a substantially amorphous morphology, meaning that the polyesters comprise substantially unordered regions of polymer.

In one aspect, the polyesters useful in the invention can comprise at least one phosphorus compound whether or not present as a thermal stabilizer.

In one aspect, the polyesters useful in the invention can comprise at least one thermal stabilizer which comprises at least one phosphorus compound.

In one aspect, the polyesters and/or polyester compositions useful in the invention can comprise phosphorus atoms.

In one aspect, the polyesters and/or polyester compositions useful in the invention can comprise tin atoms.

In one embodiment, the polyesters useful in the invention can comprise phosphorus atoms and tin atoms.

In one aspect, the phosphorus compounds useful in the invention comprise phosphoric acid, phosphorous acid, phosphonic acid, phosphinic acid, phosphonous acid, and various esters and salts thereof. The esters can be alkyl, branched alkyl, substituted alkyl, difunctional alkyl, alkyl ethers, aryl, and substituted aryl.

In one aspect, the phosphorus compounds useful in the invention comprise at least one thermal stabilizer chosen from at least one of substituted or unsubstituted alkyl phosphate esters, substituted or unsubstituted aryl phosphate esters, substituted or unsubstituted mixed alkyl aryl phosphate esters, diphosphites, salts of phosphoric acid, phosphine oxides, and mixed aryl alkyl phosphites, reaction products thereof, and mixtures thereof. The phosphate esters include esters in which the phosphoric acid is fully esterified or only partially esterified.

In one aspect, the phosphorus compounds useful in the invention at least one thermal stabilizer chosen from at least one of substituted or unsubstituted alkyl phosphate esters, substituted or unsubstituted aryl phosphate esters, mixed substituted or unsubstituted alkyl aryl phosphate esters, reaction products thereof, and mixtures thereof. The phosphate esters include esters in which the phosphoric acid is fully esterified or only partially esterified.

In one aspect, the phosphorus compounds useful in the invention are chosen from at least one of alkyl phosphate esters, aryl phosphate esters, mixed alkyl aryl phosphate esters, reaction products, thereof, and mixtures thereof.

In one aspect, any of the polyester compositions of the invention may comprise at least one aryl phosphate ester.

In one aspect, any of the polyester compositions of the invention may comprise at least one unsubstituted aryl phosphate ester.

In one aspect, any of the polyester compositions of the invention may comprise at least one aryl phosphate ester which is not substituted with benzyl groups.

In one aspect, any of the polyester compositions of the invention may comprise at least one triaryl phosphate ester.

In one aspect, any of the polyester compositions of the invention may comprise at least one triaryl phosphate ester which is not substituted with benzyl groups.

In one aspect, any of the polyester compositions of the invention may comprise at least one alkyl phosphate ester.

In one aspect, any of the polyester compositions of the invention may comprise triphenyl phosphate and/or Merpol A. In one embodiment, any of the polyester compositions of the invention may comprise triphenyl phosphate.

In one aspect, the phosphorus compounds useful in the invention can be chosen from at least one of the following: diphosphites, salts of phosphoric acid, phosphine oxides, and mixed aryl alkyl phosphites.

In one embodiment, the phosphorus compounds useful in the invention comprise, but are not limited to, at least one diphosphite.

In one embodiment, the phosphorus compounds useful in the invention comprise, but are not limited to, at least one diphosphite which contains a 2,4,8,10-tetraoxa-3,9-diphosphaspiro[5.5]undecane structure, such as, for example, Weston 619 (GE Specialty Chemicals, CAS#3806-34-6) and/or Doverphos S-9228 (Dover Chemicals, CAS#154862-43-8).

In one aspect, the phosphorus compounds useful in the invention comprise at least one mixed alkyl aryl phosphite, such as, for example, bis(2,4-dicumylphenyl)pentaerythritol diphosphite also known as Doverphos S-9228 (Dover Chemicals, CAS#154862-43-8).

In one embodiment, the phosphorus compounds useful in the invention comprise at least one phosphine oxide.

In one embodiment, the phosphorus compounds useful in the invention comprise at least one salt of phosphoric acid such as, for example, $KH_2PO_4$ and $Zn_3(PO_4)_2$.

In one aspect, any of processes described herein for making the polyester compositions and/or polyesters comprise at least one of the phosphorus compounds described herein.

In one aspect, any of processes described herein for making any of the polyester compositions and/or polyesters can comprise at least one diphosphite. In one aspect, any of the processes described herein for making any of the polyester compositions and/or polyesters can comprise, at least one diphosphite which contains a 2,4,8,10-tetraoxa-3,9-diphosphaspiro[5.5]undecane structure, such as, for example, Weston 619 (GE Specialty Chemicals, CAS#3806-34-6) and/or Doverphos S-9228 (Dover Chemicals, CAS#154862-43-8).

It is believed that any of the processes of making the polyesters useful in the invention may be used to make any of the polyesters useful in the invention.

In one aspect, the pressure used in Step (I) of any of the processes of the invention consists of at least one pressure chosen from 0 psig to 75 psig. In one embodiment, the pressure used I Step (I) of any of the processes of the invention consists of at least one pressure chosen from 0 psig to 50 psig.

In one aspect, the pressure used in Step (II) of any of the processes of the invention consists of at least one pressure chosen from 20 torr absolute to 0.02 torr absolute; in one embodiment, the pressure used in Step (II) of any of the processes of the invention consists of at least one pressure chosen from 10 torr absolute to 0.02 torr absolute; in one embodiment, the pressure used in Step (II) of any of the processes of the invention consists of at least one pressure chosen from 5 torr absolute to 0.02 torr absolute; in one embodiment, the pressure used in Step (II) of any of the processes of the invention consists of at least one pressure chosen from 3 torr absolute to 0.02 torr absolute; in one embodiment, the pressure used in Step (II) of any of the processes of the invention consists of at least one pressure chosen from 20 torr absolute to 0.1 torr absolute; in one embodiment, the pressure used in Step (II) of any of the processes of the invention consists of at least one pressure chosen from 10 torr absolute to 0.1 torr absolute; in one embodiment, the pressure used in Step (II) of any of the processes of the invention consists of at least one pressure chosen from 5 torr absolute to 0.1 torr absolute; in one embodiment, the pressure used in Step (II) of any of the processes of the invention consists of at least one pressure chosen from 3 torr absolute to 0.1 torr absolute.

In one aspect, the molar ratio of glycol component/dicarboxylic acid component added in Step (I) of any of the processes of the invention is 1.0-1.5/1.0; in one aspect, the molar ratio of glycol component/dicarboxylic acid component added in Step (I) of any of the processes of the invention is 1.01-1.5/1.0; in one aspect, the molar ratio of glycol component/dicarboxylic acid component added in Step (I) of any of the processes of the invention is 1.01-1.3/1.0; in one aspect, the molar ratio of glycol component/dicarboxylic acid component added in Step (I) of any of the processes of the invention is 1.01-1.2/1.0; in one aspect, the molar ratio of glycol component/dicarboxylic acid component added in Step (I) of any of the processes of the invention is 1.01-1.15/1.0; in one aspect, the molar ratio of glycol component/dicarboxylic acid component added in Step (I) of any of the processes of the invention is 1.01-1.10/1.0; in one aspect, the molar ratio of glycol component/dicarboxylic acid component added in Step (I) of any of the processes of the invention is 1.03-1.5/1.0; in one aspect, the molar ratio of glycol component/dicarboxylic acid component added in Step (I) of any of the processes of the invention is 1.03-1.3/1.0; in one aspect, the molar ratio of glycol component/dicarboxylic acid component added in Step (I) of any of the processes of the invention is 1.03-1.2/1.0; in one aspect, the molar ratio of glycol component/dicarboxylic acid component added in Step (I) of any of the processes of the invention is 1.03-1.15/1.0; in one aspect, the molar ratio of glycol component/dicarboxylic acid component added in Step (I) of any of the processes of the invention is 1.03-1.10/1.0; in one aspect, the molar ratio of glycol component/dicarboxylic acid component added in Step (I) of any of the processes of the invention is 1.05-1.5/1.0; in one aspect, the molar ratio of glycol component/dicarboxylic acid component added in Step (I) of any of the processes of the invention is 1.05-1.3/1.0; in one aspect, the molar ratio of glycol component/dicarboxylic acid component added in Step (I) of any of the processes of the invention is 1.05-1.2/1.0; in one aspect, the molar ratio of glycol component/dicarboxylic acid component added in Step (I) of any of the processes of the invention is 1.05-1.15/1.0; and in one aspect, the molar ratio of glycol component/dicarboxylic acid component added in Step (I) of any of the processes of the invention is 1.01-1.10/1.0.

In any of the process embodiments for making the polyesters useful in the invention, the heating time of Step (II) may be from 1 to 5 hours. In any of the process embodiments for making the polyesters useful in the invention, the heating time of Step (II) may be from 1 to 4 hours. In any of the process embodiments for making the polyesters useful in the invention, the heating time of Step (II) may be from 1 to 3 hours. In any of the process embodiments for making the polyesters useful in the invention, the heating time of Step (II) may be from 1.5 to 3 hours. In any of the process embodiments for making the polyesters useful in the invention, the heating time of Step (II) may be from 1 to 2 hours.

In another aspect, any of the polyester compositions and/or processes of the invention may comprise at least one tin compound as described herein.

In one aspect, any of the polyester compositions and/or processes of the invention may comprise at least one tin compound and, optionally, at least one catalyst chosen from titanium, gallium, zinc, antimony, cobalt, manganese, magnesium, germanium, lithium, aluminum compounds and an aluminum compound with lithium hydroxide or sodium hydroxide.

In one embodiment, any of the polyester compositions and/or processes of making the polyesters useful in the invention may be prepared using at least one tin compound and at least one titanium compound as catalysts.

In one embodiment, the addition of the phosphorus compound(s) in the process(es) of the invention can result in a weight ratio of total tin atoms to total phosphorus atoms in the final polyester of 2-10:1. In one embodiment, the addition of the phosphorus compound(s) in the process(es) can result in a weight ratio of total tin atoms to total phosphorus atoms in the final polyester of 5-9:1. In one embodiment, the addition of the phosphorus compound(s) in the process(es) can result in a weight ratio of total tin atoms to total phosphorus atoms in the final polyester of 6-8:1. In one embodiment, the addition of the phosphorus compound(s) in the process(es) can result in a weight ratio of total tin atoms to total phosphorus atoms in the final polyester of 7:1.

In one embodiment, the amount of tin atoms in the final polyester useful in the invention can be from 15 to 400 ppm tin atoms based on the weight of the final polyester.

In one embodiment, the amount of tin atoms in the final polyester useful in the invention can be from 25 to 400 ppm tin atoms based on the weight of the final polyester.

In one embodiment, the amount of tin atoms in the final polyester useful in the invention can be from 40 to 200 ppm tin atoms based on the weight of the final polyester.

In one embodiment, the amount of tin atoms in the final polyester useful in the invention can be from 50 to 125 ppm tin atoms based on the weight of the final polyester.

In one embodiment, the amount of phosphorus atoms in the final polyester useful in the invention can be from 1 to 100 ppm phosphorus atoms based on the weight of the final polyester.

In one embodiment, the amount of phosphorus atoms in the final polyester useful in the invention can be from 4 to 60 ppm phosphorus atoms based on the weight of the final polyester.

In one embodiment, the amount of phosphorus atoms in the final polyester useful in the invention can be from 6 to 20 ppm phosphorus atoms based on the weight of the final polyester.

In one embodiment, the amount of phosphorus atoms in the final polyester useful in the invention can be from 1 to 100 ppm phosphorus atoms based on the weight of the final polyester and the amount of tin atoms in the final polyester can be from 15 to 400 ppm tin atoms based on the weight of the final polyester.

In one embodiment, the amount of phosphorus atoms in the final polyester useful in the invention can be from 1 to 100 ppm phosphorus atoms based on the weight of the final polyester and the amount of tin atoms in the final polyester can be from 25 to 400 ppm tin atoms based on the weight of the final polyester.

In one embodiment, the amount of phosphorus atoms in the final polyester useful in the invention can be from 4 to 60 ppm phosphorus atoms based on the weight of the final polyester and the amount of tin atoms in the final polyester can be from 40 to 200 ppm tin atoms based on the weight of the final polyester.

In one embodiment, the amount of phosphorus atoms in the final polyester useful in the invention can be from 6 to 20 ppm phosphorus atoms based on the weight of the final polyester and the amount of tin atoms in the final polyester can be from 50 to 125 ppm tin atoms based on the weight of the final polyester.

In one aspect, any of the processes described herein for making any of the polyester compositions and/or polyesters can comprise at least one mixed alkyl aryl phosphites, such as, for example, bis(2,4-dicumylphenyl)pentaerythritol diphosphite also known as Doverphos S-9228 (Dover Chemicals, CAS#154862-43-8).

In one aspect, any of the processes described herein for making any of the polyester compositions and/or polyesters can comprise, at least one phosphine oxide.

In one aspect, any of the processes described herein for making any of the polyester compositions and/or polyesters can comprise, at least one salt of phosphoric acid such as, for example, $KH_2PO_4$ and $Zn_3(PO_4)_2$.

In one aspect, the polyester compositions are useful in articles of manufacture including, but not limited to, extruded, calendered, and/or molded articles including, but not limited to, injection molded articles, extruded articles, cast extrusion articles, profile extrusion articles, melt spun articles, thermoformed articles, extrusion molded articles, injection blow molded articles, injection stretch blow molded articles, extrusion blow molded articles and extrusion stretch blow molded articles. These articles can include, but are not limited to, films, bottles, containers, sheet and/or fibers.

In one aspect, the polyester compositions useful in the invention may be used in various types of film and/or sheet, including but not limited to extruded film(s) and/or sheet(s), calendered film(s) and/or sheet(s), compression molded film(s) and/or sheet(s), solution casted film(s) and/or sheet(s). Methods of making film and/or sheet include but are not limited to extrusion, calendering, compression molding, and solution casting.

Also, in one aspect, use of these particular polyester compositions minimizes and/or eliminates the drying step prior to melt processing and/or thermoforming.

DETAILED DESCRIPTION OF THE INVENTION

Figure 1:
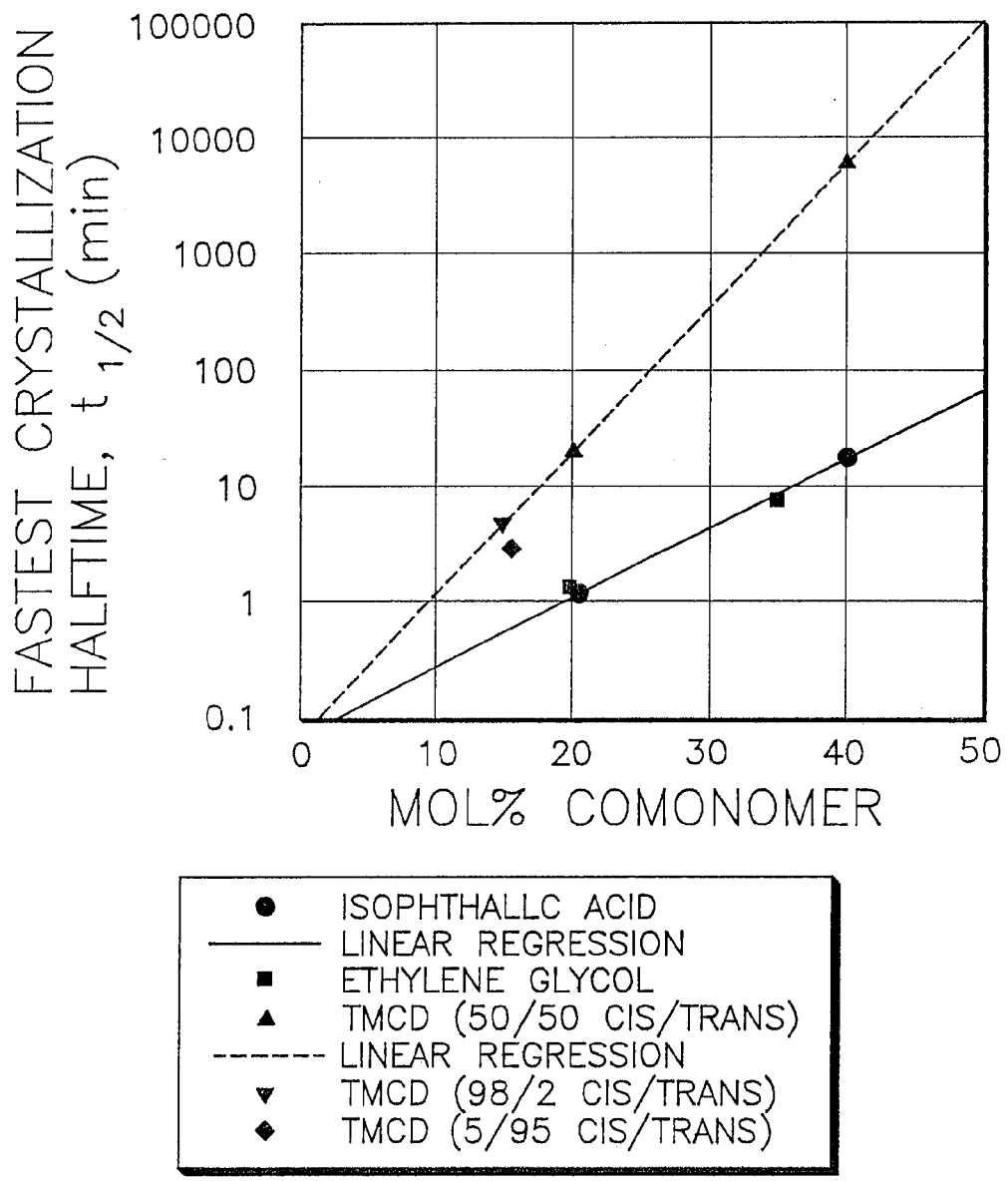
FIG. 1 is a graph showing the effect of comonomer on the fastest crystallization half-times of modified PCT copolyesters.

The present invention may be understood more readily by reference to the following detailed description of certain embodiments of the invention and the working examples. In accordance with the purpose(s) of this invention, certain embodiments of the invention are described in the Summary of the Invention and are further described herein below. Also, other embodiments of the invention are described herein.

It is believed that polyesters useful in the invention described herein can have a combination of two or more physical properties such as high impact strengths, moderate glass transition temperatures (Tg or $T_g$), chemical resistance, hydrolytic stability, toughness, low ductile-to-brittle transition temperatures, good color and clarity, low densities, long crystallization half-times, and good processability thereby easily permitting them to be formed into articles. In some of the embodiments of the invention, the polyesters have a unique combination of the properties of good impact strength, heat resistance, chemical resistance, density and/or the combination of the properties of good impact strength, heat resistance, and processability and/or the combination of two or more of the described properties, that have never before been believed to be present in a polyester.

The term "polyester", as used herein, is intended to include "copolyesters" and is understood to mean a synthetic polymer prepared by the reaction of one or more difunctional carboxylic acids and/or multifunctional carboxylic acids with one or more difunctional hydroxyl compounds and/or multifunctional hydroxyl compounds. Typically the difunctional carboxylic acid can be a dicarboxylic acid and the difunctional hydroxyl compound can be a dihydric alcohol such as, for example, glycols and diols. The term "glycol" as used in this application includes, but is not limited to, diols, glycols, and/or multifunctional hydroxyl compounds, for example, branching agents. Alternatively, the difunctional carboxylic acid may be a hydroxy carboxylic acid such as, for example, p-hydroxybenzoic acid, and the difunctional hydroxyl compound may be an aromatic nucleus bearing 2 hydroxyl substituents such as, for example, hydroquinone. The term "residue", as used herein, means any organic structure incorporated into a polymer through a polycondensation and/ or an esterification reaction from the corresponding monomer. The term "repeating unit", as used herein, means an organic structure having a dicarboxylic acid residue and a diol residue bonded through a carbonyloxy group. Thus, for example, the dicarboxylic acid residues may be derived from a dicarboxylic acid monomer or its associated acid halides, esters, salts, anhydrides, or mixtures thereof. As used herein, therefore, the term dicarboxylic acid is intended to include dicarboxylic acids and any derivative of a dicarboxylic acid, including its associated acid halides, esters, half-esters, salts, half-salts, anhydrides, mixed anhydrides, or mixtures thereof, useful in a reaction process with a diol to make polyester. Furthermore, as used in this application, the term "diacid" includes multifunctional acids, for example, branching agents. As used herein, the term "terephthalic acid" is intended to include terephthalic acid itself and residues thereof as well as any derivative of terephthalic acid, including its associated acid halides, esters, half-esters, salts, half-salts, anhydrides, mixed anhydrides, or mixtures thereof or residues thereof useful in a reaction process with a diol to make polyester.

In one embodiment, terephthalic acid may be used as the starting material. In another embodiment, dimethyl terephthalate may be used as the starting material. In yet another embodiment, mixtures of terephthalic acid and dimethyl terephthalate may be used as the starting material and/or as an intermediate material.

The polyesters used in the present invention typically can be prepared from dicarboxylic acids and diols which react in substantially equal proportions and are incorporated into the polyester polymer as their corresponding residues. The polyesters of the present invention, therefore, can contain substantially equal molar proportions of acid residues (100 mole %) and diol (and/or multifunctional hydroxyl compounds) residues (100 mole %) such that the total moles of repeating units is equal to 100 mole %. The mole percentages provided in the present disclosure, therefore, may be based on the total moles of acid residues, the total moles of diol residues, or the total moles of repeating units. For example, a polyester containing 30 mole % isophthalic acid, based on the total acid residues, means the polyester contains 30 mole % isophthalic acid residues out of a total of 100 mole % acid residues. Thus, there are 30 moles of isophthalic acid residues among every 100 moles of acid residues. In another example, a polyester containing 30 mole % 2,2,4,4-tetramethyl-1,3-cyclobutanediol, based on the total diol residues, means the polyester contains 30 mole % 2,2,4,4-tetramethyl-1,3-cyclobutanediol residues out of a total of 100 mole % diol residues. Thus, there are 30 moles of 2,2,4,4-tetramethyl-1,3-cyclobutanediol residues among every 100 moles of diol residues.

In other aspects of the invention, the Tg of the polyesters useful in the invention can be at least one of the following ranges: 85 to 130° C.; 85 to 125° C.; 85 to 120° C.; 85 to 115° C.; 85 to 110° C.; 85 to 105° C.; 85 to 100° C.; 85 to 95° C.; 85 to 90° C.; 90 to 130° C.; 90 to 125° C.; 90 to 120° C.; 90 to 115° C.; 90 to 110° C.; 90 to 105° C.; 90 to 100° C.; 90 to 95° C.; 95 to 130° C.; 95 to 125° C.; 95 to 120° C.; 95 to 115° C.; 95 to 110° C.; 95 to 105° C.; 95 to 100° C.; 100 to 130° C.; 100 to 125° C.; 100 to 120° C.; 100 to 115° C.; 100 to 110° C.; 100 to 105° C.; 105 to 130° C.; 105 to 125° C.; 105 to 120° C.; 105 to 115° C.; 105 to 110° C.; greater than 105 to 130° C.; greater than 105 to 125° C.; greater than 105 to 120° C.; greater than 105 to 115° C.; greater than 105 to 110° C.; 110 to 130° C.; 110 to 125° C.; 110 to 120° C.; 110 to 115° C.; 115 to 130° C.; 115 to 125° C.; 115 to 120° C.; 115 to 130° C.; 115 to 125° C.; 115 to 120° C.; 120 to 130° C.; and 125 to 130° C.

In other aspects of the invention, the glycol component for the polyesters useful in the invention include but are not limited to at least one of the following combinations of ranges: 1 to 99 mole % 2,2,4,4-tetramethyl-1,3-cyclobutanediol and 1 to 99 mole % cyclohexanedimethanol; 1 to 95 mole % 2,2,4,4-tetramethyl-1,3-cyclobutanediol and 5 to 99 mole % cyclohexanedimethanol; 1 to 90 mole % 2,2,4,4-tetramethyl-1,3-cyclobutanediol and 10 to 99 mole % cyclohexanedimethanol; 1 to 85 mole % 2,2,4,4-tetramethyl-1,3-cyclobutanediol and 15 to 99 mole % cyclohexanedimethanol; 1 to 80 mole % 2,2,4,4-tetramethyl-1,3-cyclobutanediol and 20 to 99 mole % cyclohexanedimethanol, 1 to 75 mole % 2,2,4,4-tetramethyl-1,3-cyclobutanediol and 25 to 99 mole % cyclohexanedimethanol; 1 to 70 mole % 2,2,4,4-tetramethyl-1,3-cyclobutanediol and 30 to 99 mole % cyclohexanedimethanol; 1 to 65 mole % 2,2,4,4-tetramethyl-1,3-cyclobutanediol and 35 to 99 mole % cyclohexanedimethanol; 1 to 60 mole % 2,2,4,4-tetramethyl-1,3-cyclobutanediol and 40 to 99 mole % cyclohexanedimethanol; 1 to 55 mole % 2,2,4,4-tetramethyl-1,3-cyclobutanediol and 45 to 99 mole % cyclohexanedimethanol; 1 to 50 mole % 2,2,4,4-tetramethyl-1,3-cyclobutanediol and 50 to 99 mole % cyclohexanedimethanol; 1 to 45 mole % 2,2,4,4-tetramethyl-1,3-cyclobutanediol and 55 to 99 mole % cyclohexanedimethanol; 1 to 40 mole % 2,2,4,4-tetramethyl-1,3-cyclobutanediol and 60 to 99 mole % cyclohexanedimethanol; 1 to 35 mole % 2,2,4,4-tetramethyl-1,3-cyclobutanediol and 65 to 99 mole % cyclohexanedimethanol; 1 to 30 mole % 2,2,4,4-tetramethyl-1,3-cyclobutanediol and 70 to 99 mole % cyclohexanedimethanol; 1 to 25 mole % 2,2,4,4-tetramethyl-1,3-cyclobutanediol and 75 to 99 mole % cyclohexanedimethanol; 1 to 20 mole % 2,2,4,4-tetramethyl-1,3-cyclobutanediol and 80 to 99 mole % cyclohexanedimethanol; 1 to 15 mole % 2,2,4,4-tetramethyl-1,3-cyclobutanediol and 85 to 99 mole % cyclohexanedimethanol; 1 to 10 mole % 2,2,4,4-tetramethyl-1,3-cyclobutanediol and 90 to 99 mole % cyclohexanedimethanol; and 1 to 5 mole % 2,2,4,4-tetramethyl-1,3-cyclobutanediol and 95 to 99 mole % cyclohexanedimethanol; greater than 0.01 to 10 mole % 2,2,4,4-tetramethyl-1,3-cyclobutanediol and 90 to less than 99.99 mole % cyclohexanedimethanol; and greater than 0.01 to 5 mole % 2,2,4,4-tetramethyl-1,3-cyclobutanediol and 95 to less than 99.99 mole % cyclohexanedimethanol.

In other aspects of the invention, the glycol component for the polyesters useful in the film or sheet of the invention include but are not limited to at least one of the following combinations of ranges: 5 to 99 mole % 2,2,4,4-tetramethyl-1,3-cyclobutanediol and 1 to 95 mole % cyclohexanedimethanol; 5 to 95 mole % 2,2,4,4-tetramethyl-1,3-cyclobutanediol and 5 to 95 mole % cyclohexanedimethanol; 5 to 90 mole % 2,2,4,4-tetramethyl-1,3-cyclobutanediol and 10 to 95 mole % cyclohexanedimethanol; 5 to 85 mole % 2,2,4,4-tetramethyl-1,3-cyclobutanediol and 15 to 95 mole % cyclohexanedimethanol; 5 to 80 mole % 2,2,4,4-tetramethyl-1,3-cyclobutanediol and 20 to 95 mole % cyclohexanedimethanol, 5 to 75 mole % 2,2,4,4-tetramethyl-1,3-cyclobutanediol and 25 to 95 mole % cyclohexanedimethanol; 5 to 70 mole % 2,2,4,4-tetramethyl-1,3-cyclobutanediol and 30 to 95 mole % cyclohexanedimethanol; 5 to 65 mole % 2,2,4,4-tetramethyl-1,3-cyclobutanediol and 35 to 95 mole % cyclohexanedimethanol; 5 to 60 mole % 2,2,4,4-tetramethyl-1,3-cyclobutanediol and 40 to 95 mole % cyclohexanedimethanol; 5 to 55 mole % 2,2,4,4-tetramethyl-1,3-cyclobutanediol and 45 to 95 mole % cyclohexanedimethanol; and 5 to 50 mole % 2,2,4,4-tetramethyl-1,3-cyclobutanediol and 50 to 95 mole % cyclohexanedimethanol.

In other aspects of the invention, the glycol component for the polyesters useful in the invention include but are not limited to at least one of the following combinations of ranges: 5 to less than 50 mole % 2,2,4,4-tetramethyl-1,3-cyclobutanediol and greater than 50 to 95 mole % cyclohexanedimethanol; 5 to 45 mole % 2,2,4,4-tetramethyl-1,3-cyclobutanediol and 55 to 95 mole % cyclohexanedimethanol; 5 to 40 mole % 2,2,4,4-tetramethyl-1,3-cyclobutanediol and 60 to 95 mole % cyclohexanedimethanol; 5 to 35 mole % 2,2,4,4-tetramethyl-1,3-cyclobutanediol and 65 to 95 mole % cyclohexanedimethanol; 5 to less than 35 mole % 2,2,4,4-tetramethyl-1,3-cyclobutanediol and greater than 65 to 95 mole % cyclohexanedimethanol; 5 to 30 mole % 2,2,4,4-tetramethyl-1,3-cyclobutanediol and 70 to 95 mole % cyclohexanedimethanol; 5 to 25 mole % 2,2,4,4-tetramethyl-1,3-cyclobutanediol and 75 to 95 mole % cyclohexanedimethanol; 5 to 20 mole % 2,2,4,4-tetramethyl-1,3-cyclobutanediol and 80 to 95 mole % cyclohexanedimethanol; 5 to 15 mole % 2,2,4,4-tetramethyl-1,3-cyclobutanediol and 85 to 95 mole % cyclohexanedimethanol; and 5 to 10 mole % 2,2,4,4-tetramethyl-1,3-cyclobutanediol and 75 to 90 mole % cyclohexanedimethanol.

In other aspects of the invention, the glycol component for the polyesters useful in the film or sheet of the invention include but are not limited to at least one of the following combinations of ranges: 10 to 99 mole % 2,2,4,4-tetramethyl-1,3-cyclobutanediol and 1 to 90 mole % cyclohexanedimethanol; 10 to 95 mole % 2,2,4,4-tetramethyl-1,3-cyclobutanediol and 5 to 90 mole % cyclohexanedimethanol; 10 to 90 mole % 2,2,4,4-tetramethyl-1,3-cyclobutanediol and 10 to 90 mole % cyclohexanedimethanol; 10 to 85 mole % 2,2,4,4-tetramethyl-1,3-cyclobutanediol and 15 to 90 mole % cyclohexanedimethanol; 10 to 80 mole % 2,2,4,4-tetramethyl-1,3-cyclobutanediol and 20 to 90 mole % cyclohexanedimethanol, 10 to 75 mole % 2,2,4,4-tetramethyl-1,3-cyclobutanediol and 25 to 90 mole % cyclohexanedimethanol; 10 to 70 mole % 2,2,4,4-tetramethyl-1,3-cyclobutanediol and 30 to 90 mole % cyclohexanedimethanol; 10 to 65 mole % 2,2,4,4-tetramethyl-1,3-cyclobutanediol and 35 to 90 mole % cyclohexanedimethanol; 10 to 60 mole % 2,2,4,4-tetramethyl-1,3-cyclobutanediol and 40 to 90 mole % cyclohexanedimethanol; 10 to 55 mole % 2,2,4,4-tetramethyl-1,3-cyclobutanediol and 45 to 90 mole % cyclohexanedimethanol; and 10 to 50 mole % 2,2,4,4-tetramethyl-1,3-cyclobutanediol and 50 to 90 mole % cyclohexanedimethanol.

In other aspects of the invention, the glycol component for the polyesters useful in the invention include but are not limited to at least one of the following combinations of ranges: 10 to less than 50 mole % 2,2,4,4-tetramethyl-1,3-cyclobutanediol and greater than 50 to 90 mole % cyclohexanedimethanol; 10 to 45 mole % 2,2,4,4-tetramethyl-1,3-cyclobutanediol and 55 to 90 mole % cyclohexanedimethanol; 10 to 40 mole % 2,2,4,4-tetramethyl-1,3-cyclobutanediol and 60 to 90 mole % cyclohexanedimethanol; 10 to 35 mole % 2,2,4,4-tetramethyl-1,3-cyclobutanediol and 65 to 90 mole % cyclohexanedimethanol; 10 to less than 35 mole % 2,2,4,4-tetramethyl-1,3-cyclobutanediol and greater than 65 up to 90 mole % cyclohexanedimethanol; 10 to 30 mole % 2,2,4,4-tetramethyl-1,3-cyclobutanediol and 70 to 90 mole % cyclohexanedimethanol; 10 to 25 mole % 2,2,4,4-tetramethyl-1,3-cyclobutanediol and greater than 75 to 90 mole % cyclohexanedimethanol. 10 to 20 mole % 2,2,4,4-tetramethyl-1,3-cyclobutanediol and greater than 80 to 90 mole % cyclohexanedimethanol; and 10 to 15 mole % 2,2,4,4-tetramethyl-1,3-cyclobutanediol and greater than 85 to 90 mole % cyclohexanedimethanol.

In other aspects of the invention, the glycol component for the polyesters useful in the invention include but are not limited to at least one of the following combinations of ranges: 11 to 99 mole % 2,2,4,4-tetramethyl-1,3-cyclobutanediol and 1 to 89 mole % cyclohexanedimethanol; 11 to 95 mole % 2,2,4,4-tetramethyl-1,3-cyclobutanediol and 5 to 89 mole % cyclohexanedimethanol; 11 to 90 mole % 2,2,4,4-tetramethyl-1,3-cyclobutanediol and 10 to 89 mole % cyclohexanedimethanol; 11 to 85 mole % 2,2,4,4-tetramethyl-1,3-cyclobutanediol and 15 to 89 mole % cyclohexanedimethanol; 11 to 80 mole % 2,2,4,4-tetramethyl-1,3-cyclobutanediol and 20 to 89 mole % cyclohexanedimethanol, 11 to 75 mole % 2,2,4,4-tetramethyl-1,3-cyclobutanediol and 25 to 89 mole % cyclohexanedimethanol; 11 to 70 mole % 2,2,4,4-tetramethyl-1,3-cyclobutanediol and 30 to 89 mole % cyclohexanedimethanol; 11 to 65 mole % 2,2,4,4-tetramethyl-1,3-cyclobutanediol and 35 to 89 mole % cyclohexanedimethanol; 11 to 60 mole % 2,2,4,4-tetramethyl-1,3-cyclobutanediol and 40 to 89 mole % cyclohexanedimethanol; 11 to 55 mole % 2,2,4,4-tetramethyl-1,3-cyclobutanediol and 45 to 89 mole % cyclohexanedimethanol; and 11 to 50 mole % 2,2,4,4-tetramethyl-1,3-cyclobutanediol and 50 to 89 mole % cyclohexanedimethanol.

In other aspects of the invention, the glycol component for the polyesters useful in the invention include but are not limited to at least one of the following combinations of ranges: 11 to less than 50 mole % 2,2,4,4-tetramethyl-1,3-cyclobutanediol and greater than 50 up to 89 mole % cyclohexanedimethanol; 11 to 45 mole % 2,2,4,4-tetramethyl-1,3-cyclobutanediol and 55 to 89 mole % cyclohexanedimethanol; 11 to 40 mole % 2,2,4,4-tetramethyl-1,3-cyclobutanediol and 60 to 89 mole % cyclohexanedimethanol; 11 to 35 mole % 2,2,4,4-tetramethyl-1,3-cyclobutanediol and 65 to 89 mole % cyclohexanedimethanol; 11 to 30 mole % 2,2,4,4-tetramethyl-1,3-cyclobutanediol and 70 to 89 mole % cyclohexanedimethanol; 11 to 25 mole % 2,2,4,4-tetramethyl-1,3-cyclobutanediol and 75 to 89 mole % cyclohexanedimethanol; 11 to 20 mole % 2,2,4,4-tetramethyl-1,3-cyclobutanediol and 80 to 89 mole % cyclohexanedimethanol, and 11 to 15 mole % 2,2,4,4-tetramethyl-1,3-cyclobutanediol and 80 to 85 mole % cyclohexanedimethanol.

In other aspects of the invention, the glycol component for the polyesters useful in the invention include but are not limited to at least one of the following combinations of ranges: 12 to 99 mole % 2,2,4,4-tetramethyl-1,3-cyclobutanediol and 1 to 86 mole % cyclohexanedimethanol; 12 to 95 mole % 2,2,4,4-tetramethyl-1,3-cyclobutanediol and 5 to 88 mole % cyclohexanedimethanol; 12 to 90 mole % 2,2,4,4-tetramethyl-1,3-cyclobutanediol and 10 to 88 mole % cyclohexanedimethanol; 12 to 85 mole % 2,2,4,4-tetramethyl-1,3-cyclobutanediol and 15 to 88 mole % cyclohexanedimethanol; 12 to 86 mole % 2,2,4,4-tetramethyl-1,3-cyclobutanediol and 14 to 88 mole % cyclohexanedimethanol, 12 to 75 mole % 2,2,4,4-tetramethyl-1,3-cyclobutanediol and 25 to 88 mole % cyclohexanedimethanol; 12 to 70 mole % 2,2,4,4-tetramethyl-1,3-cyclobutanediol and 30 to 88 mole % cyclohexanedimethanol; 12 to 65 mole % 2,2,4,4-tetramethyl-1,3-cyclobutanediol and 35 to 88 mole % cyclohexanedimethanol; 12 to 60 mole % 2,2,4,4-tetramethyl-1,3-cyclobutanediol and 40 to 88 mole % cyclohexanedimethanol; 12 to 55 mole % 2,2,4,4-tetramethyl-1,3- cyclobutanediol and 45 to 88 mole % cyclohexanedimethanol; and 12 to 50 mole % 2,2,4,4-tetramethyl-1,3-cyclobutanediol and 50 to 88 mole % cyclohexanedimethanol;

In other aspects of the invention, the glycol component for the polyesters useful in the invention include but are not limited to at least one of the following combinations of ranges: 12 to less than 50 mole % 2,2,4,4-tetramethyl-1,3-cyclobutanediol and greater than 50 up to 88 mole % cyclohexanedimethanol; 12 to 45 mole % 2,2,4,4-tetramethyl-1,3-cyclobutanediol and 55 to 88 mole % cyclohexanedimethanol; 12 to 40 mole % 2,2,4,4-tetramethyl-1,3-cyclobutanediol and 60 to 88 mole % cyclohexanedimethanol; 12 to 35 mole % 2,2,4,4-tetramethyl-1,3-cyclobutanediol and 65 to 88 mole % cyclohexanedimethanol; 12 to 30 mole % 2,2,4,4-tetramethyl-1,3-cyclobutanediol and 70 to 88 mole % cyclohexanedimethanol; 12 to 25 mole % 2,2,4,4-tetramethyl-1,3-cyclobutanediol and 75 to 88 mole % cyclohexanedimethanol; 12 to 20 mole % 2,2,4,4-tetramethyl-1,3-cyclobutanediol and 80 to 88 mole % cyclohexanedimethanol, and 12 to 15 mole % 2,2,4,4-tetramethyl-1,3-cyclobutanediol; and 85 to 88 mole % cyclohexanedimethanol.

In other aspects of the invention, the glycol component for the polyesters useful in the invention include but are not limited to at least one of the following combinations of ranges: 13 to 99 mole % 2,2,4,4-tetramethyl-1,3-cyclobutanediol and 1 to 87 mole % cyclohexanedimethanol; 13 to 95 mole % 2,2,4,4-tetramethyl-1,3-cyclobutanediol and 5 to 87 mole % cyclohexanedimethanol; 13 to 90 mole % 2,2,4,4-tetramethyl-1,3-cyclobutanediol and 10 to 87 mole % cyclohexanedimethanol; 13 to 85 mole % 2,2,4,4-tetramethyl-1,3-cyclobutanediol and 15 to 87 mole % cyclohexanedimethanol; 13 to 80 mole % 2,2,4,4-tetramethyl-1,3-cyclobutanediol and 20 to 87 mole % cyclohexanedimethanol, 13 to 75 mole % 2,2,4,4-tetramethyl-1,3-cyclobutanediol and 25 to 87 mole % cyclohexanedimethanol; 13 to 70 mole % 2,2,4,4-tetramethyl-1,3-cyclobutanediol and 30 to 87 mole % cyclohexanedimethanol; 13 to 65 mole % 2,2,4,4-tetramethyl-1,3-cyclobutanediol and 35 to 87 mole % cyclohexanedimethanol; 13 to 60 mole % 2,2,4,4-tetramethyl-1,3-cyclobutanediol and 40 to 87 mole % cyclohexanedimethanol; 13 to 55 mole % 2,2,4,4-tetramethyl-1,3-cyclobutanediol and 45 to 87 mole % cyclohexanedimethanol; and 13 to 50 mole % 2,2,4,4-tetramethyl-1,3-cyclobutanediol and 50 to 87 mole % cyclohexanedimethanol.

In other aspects of the invention, the glycol component for the polyesters useful in the invention include but are not limited to at least one of the following combinations of ranges: 13 to less than 50 mole % 2,2,4,4-tetramethyl-1,3-cyclobutanediol and greater than 50 up to 87 mole % cyclohexanedimethanol; 13 to 45 mole % 2,2,4,4-tetramethyl-1,3-cyclobutanediol and 55 to 87 mole % cyclohexanedimethanol; 13 to 40 mole % 2,2,4,4-tetramethyl-1,3-cyclobutanediol and 60 to 87 mole % cyclohexanedimethanol; 13 to 35 mole % 2,2,4,4-tetramethyl-1,3-cyclobutanediol and 65 to 87 mole % cyclohexanedimethanol; 13 to 30 mole % 2,2,4,4-tetramethyl-1,3-cyclobutanediol and 70 to 87 mole % cyclohexanedimethanol; 13 to 25 mole % 2,2,4,4-tetramethyl-1,3-cyclobutanediol and 75 to 87 mole % cyclohexanedimethanol; 13 to 20 mole % 2,2,4,4-tetramethyl-1,3-cyclobutanediol and 80 to 87 mole % cyclohexanedimethanol, and 13 to 15 mole % 2,2,4,4-tetramethyl-1,3-cyclobutanediol; and 85 to 87 mole % cyclohexanedimethanol.

In other aspects of the invention, the glycol component for the polyesters useful in the invention include but are not limited to at least one of the following combinations of ranges: 14 to 99 mole % 2,2,4,4-tetramethyl-1,3-cyclobutanediol and 1 to 86 mole % cyclohexanedimethanol; 14 to 95 mole % 2,2,4,4-tetramethyl-1,3-cyclobutanediol and 5 to 86 mole % cyclohexanedimethanol; 14 to 90 mole % 2,2,4,4-tetramethyl-1,3-cyclobutanediol and 10 to 86 mole % cyclohexanedimethanol; 14 to 85 mole % 2,2,4,4-tetramethyl-1,3-cyclobutanediol and 15 to 86 mole % cyclohexanedimethanol; 14 to 86 mole % 2,2,4,4-tetramethyl-1,3-cyclobutanediol and 14 to 86 mole % cyclohexanedimethanol, 14 to 75 mole % 2,2,4,4-tetramethyl-1,3-cyclobutanediol and 25 to 86 mole % cyclohexanedimethanol; 14 to 70 mole % 2,2,4,4-tetramethyl-1,3-cyclobutanediol and 30 to 86 mole % cyclohexanedimethanol; 14 to 65 mole % 2,2,4,4-tetramethyl-1,3-cyclobutanediol and 35 to 86 mole % cyclohexanedimethanol; 14 to 60 mole % 2,2,4,4-tetramethyl-1,3-cyclobutanediol and 40 to 86 mole % cyclohexanedimethanol; 14 to 55 mole % 2,2,4,4-tetramethyl-1,3-cyclobutanediol and 45 to 86 mole % cyclohexanedimethanol; and 14 to 50 mole % 2,2,4,4-tetramethyl-1,3-cyclobutanediol and 50 to 86 mole % cyclohexanedimethanol;

In other aspects of the invention, the glycol component for the polyesters useful in the invention include but are not limited to at least one of the following combinations of ranges: 14 to less than 50 mole % 2,2,4,4-tetramethyl-1,3-cyclobutanediol and greater than 50 up to 86 mole % cyclohexanedimethanol; 14 to 45 mole % 2,2,4,4-tetramethyl-1,3-cyclobutanediol and 55 to 86 mole % cyclohexanedimethanol; 14 to 40 mole % 2,2,4,4-tetramethyl-1,3-cyclobutanediol and 60 to 86 mole % cyclohexanedimethanol; 14 to 35 mole % 2,2,4,4-tetramethyl-1,3-cyclobutanediol and 65 to 86 mole % cyclohexanedimethanol; 14 to 30 mole % 2,2,4,4-tetramethyl-1,3-cyclobutanediol and 70 to 86 mole % cyclohexanedimethanol; 14 to 25 mole % 2,2,4,4-tetramethyl-1,3-cyclobutanediol and 75 to 86 mole % cyclohexanedimethanol; and 14 to 20 mole % 2,2,4,4-tetramethyl-1,3-cyclobutanediol and 80 to 86 mole % cyclohexanedimethanol.

In other aspects of the invention, the glycol component for the polyesters useful in the invention include but are not limited to at least one of the following combinations of ranges: 15 to 99 mole % 2,2,4,4-tetramethyl-1,3-cyclobutanediol and 1 to 85 mole % cyclohexanedimethanol; 15 to 95 mole % 2,2,4,4-tetramethyl-1,3-cyclobutanediol and 5 to 85 mole % cyclohexanedimethanol; 15 to 90 mole % 2,2,4,4-tetramethyl-1,3-cyclobutanediol and 10 to 85 mole % cyclohexanedimethanol; 15 to 85 mole % 2,2,4,4-tetramethyl-1,3-cyclobutanediol and 15 to 85 mole % cyclohexanedimethanol; 15 to 85 mole % 2,2,4,4-tetramethyl-1,3-cyclobutanediol and 15 to 85 mole % cyclohexanedimethanol, 15 to 75 mole % 2,2,4,4-tetramethyl-1,3-cyclobutanediol and 25 to 85 mole % cyclohexanedimethanol; 15 to 70 mole % 2,2,4,4-tetramethyl-1,3-cyclobutanediol and 30 to 85 mole % 1,4-cyclohexanedimethanol; 15 to 65 mole % 2,2,4,4-tetramethyl-1,3-cyclobutanediol and 35 to 85 mole % cyclohexanedimethanol; 15 to 60 mole % 2,2,4,4-tetramethyl-1,3-cyclobutanediol and 40 to 85 mole % cyclohexanedimethanol; 15 to 55 mole % 2,2,4,4-tetramethyl-1,3-cyclobutanediol and 45 to 85 mole % cyclohexanedimethanol; and 15 to 50 mole % 2,2,4,4-tetramethyl-1,3-cyclobutanediol and 50 to 85 mole % cyclohexanedimethanol.

In other aspects of the invention, the glycol component for the polyesters useful in the invention include but are not limited to at least one of the following combinations of ranges: 15 to less than 50 mole % 2,2,4,4-tetramethyl-1,3-cyclobutanediol and greater than 50 up to 85 mole % cyclohexanedimethanol; 15 to 45 mole % 2,2,4,4-tetramethyl-1,3-cyclobutanediol and 55 to 85 mole % cyclohexanedimethanol; 15 to 40 mole % 2,2,4,4-tetramethyl-1,3-cyclobutanediol and 60 to 85 mole % cyclohexanedimethanol; 15 to 35 mole % 2,2,4,4-tetramethyl-1,3-cyclobutanediol and 65 to 85 mole % cyclohexanedimethanol; 15 to 30 mole % 2,2,4,4-tetramethyl-1,3-cyclobutanediol and 70 to 85 mole % cyclohexanedimethanol; 15 to 25 mole % 2,2,4,4-tetramethyl-1,3-cyclobutanediol and 75 to 85 mole % cyclohexanedimethanol; 15 to 20 mole % 2,2,4,4-tetramethyl-1,3-cyclobutanediol and 80 to 85 mole % cyclohexanedimethanol; and 17 to 23 mole % 2,2,4,4-tetramethyl-1,3-cyclobutanediol and 77 to 83 mole % cyclohexanedimethanol.

In other aspects of the invention, the glycol component for the polyesters useful in the invention include but are not limited to at least one of the following combinations of ranges: 20 to 99 mole % 2,2,4,4-tetramethyl-1,3-cyclobutanediol and 1 to 80 mole % cyclohexanedimethanol; 20 to 95 mole % 2,2,4,4-tetramethyl-1,3-cyclobutanediol and 5 to 80 mole % cyclohexanedimethanol; 20 to 90 mole % 2,2,4,4-tetramethyl-1,3-cyclobutanediol and 10 to 80 mole % cyclohexanedimethanol; 20 to 85 mole % 2,2,4,4-tetramethyl-1,3-cyclobutanediol and 15 to 80 mole % cyclohexanedimethanol; 20 to 80 mole % 2,2,4,4-tetramethyl-1,3-cyclobutanediol and 20 to 80 mole % cyclohexanedimethanol, 20 to 75 mole % 2,2,4,4-tetramethyl-1,3-cyclobutanediol and 25 to 80 mole % cyclohexanedimethanol; 20 to 70 mole % 2,2,4,4-tetramethyl-1,3-cyclobutanediol and 30 to 80 mole % cyclohexanedimethanol; 20 to 65 mole % 2,2,4,4-tetramethyl-1,3-cyclobutanediol and 35 to 80 mole % cyclohexanedimethanol; 20 to 60 mole % 2,2,4,4-tetramethyl-1,3-cyclobutanediol and 40 to 80 mole % cyclohexanedimethanol; 20 to 55 mole % 2,2,4,4-tetramethyl-1,3-cyclobutanediol and 45 to 80 mole % cyclohexanedimethanol; 20 to 50 mole % 2,2,4,4-tetramethyl-1,3-cyclobutanediol and 50 to 80 mole % cyclohexanedimethanol; 20 to 45 mole % 2,2,4,4-tetramethyl-1,3-cyclobutanediol and 55 to 80 mole % cyclohexanedimethanol; 20 to 40 mole % 2,2,4,4-tetramethyl-1,3-cyclobutanediol and 60 to 80 mole % cyclohexanedimethanol; 20 to 35 mole % 2,2,4,4-tetramethyl-1,3-cyclobutanediol and 65 to 80 mole % cyclohexanedimethanol; 20 to 30 mole % 2,2,4,4-tetramethyl-1,3-cyclobutanediol and 70 to 80 mole % cyclohexanedimethanol; and 20 to 25 mole % 2,2,4,4-tetramethyl-1,3-cyclobutanediol and 75 to 80 mole % cyclohexanedimethanol.

In other aspects of the invention, the glycol component for the polyesters useful in the invention include but are not limited to at least one of the following combinations of ranges: 25 to 99 mole % 2,2,4,4-tetramethyl-1,3-cyclobutanediol and 1 to 75 mole % cyclohexanedimethanol; 25 to 90 mole % 2,2,4,4-tetramethyl-1,3-cyclobutanediol and 10 to 75 mole % cyclohexanedimethanol; 25 to 85 mole % 2,2,4,4-tetramethyl-1,3-cyclobutanediol and 15 to 75 mole % cyclohexanedimethanol; 25 to 80 mole % 2,2,4,4-tetramethyl-1,3-cyclobutanediol and 20 to 75 mole % cyclohexanedimethanol, 25 to 75 mole % 2,2,4,4-tetramethyl-1,3-cyclobutanediol and 25 to 75 mole % cyclohexanedimethanol; 25 to 70 mole % 2,2,4,4-tetramethyl-1,3-cyclobutanediol and 30 to 75 mole % cyclohexanedimethanol; 25 to 65 mole % 2,2,4,4-tetramethyl-1,3-cyclobutanediol and 35 to 75 mole % cyclohexanedimethanol; 25 to 60 mole % 2,2,4,4-tetramethyl-1,3-cyclobutanediol and 40 to 75 mole % cyclohexanedimethanol; 25 to 55 mole % 2,2,4,4-tetramethyl-1,3-cyclobutanediol and 45 to 75 mole % cyclohexanedimethanol; 25 to 50 mole % 2,2,4,4-tetramethyl-1,3-cyclobutanediol and 50 to 75 mole % cyclohexanedimethanol; 25 to 45 mole % 2,2,4,4-tetramethyl-1,3-cyclobutanediol and 55 to 75 mole % cyclohexanedimethanol; 25 to 40 mole % 2,2,4,4-tetramethyl-1,3-cyclobutanediol and 60 to 75 mole % cyclohexanedimethanol; 25 to 35 mole % 2,2,4,4-tetramethyl-1,3-cyclobutanediol and 65 to 75 mole % cyclohexanedimethanol; 25 to 30 mole % 2,2,4,4-tetramethyl-1,3-cyclobutanediol and 70 to 75 mole % cyclohexanedimethanol.

In other aspects of the invention, the glycol component for the polyesters useful in the invention include but are not limited to at least one of the following combinations of ranges: 35 to 80 mole % 2,2,4,4-tetramethyl-1,3-cyclobutanediol and 20 to 65 mole % cyclohexanedimethanol; 37 to 80 mole % 2,2,4,4-tetramethyl-1,3-cyclobutanediol and 20 to 63 mole % cyclohexanedimethanol; 40 to 80 mole % 2,2,4,4-tetramethyl-1,3-cyclobutanediol and 20 to 60 mole % cyclohexanedimethanol; 45 to 80 mole % 2,2,4,4-tetramethyl-1,3-cyclobutanediol and 20 to 55 mole % cyclohexanedimethanol; 50 to 80 mole % 2,2,4,4-tetramethyl-1,3-cyclobutanediol and 20 to 50 mole % cyclohexanedimethanol; greater than 50 to 80 mole % 2,2,4,4-tetramethyl-1,3-cyclobutanediol and 20 to less than 50 mole % cyclohexanedimethanol; 55 to 80 mole % 2,2,4,4-tetramethyl-1,3-cyclobutanediol and 20 to 45 mole % cyclohexanedimethanol; 60 to 80 mole % 2,2,4,4-tetramethyl-1,3-cyclobutanediol and 20 to 40 mole % cyclohexanedimethanol; 65 to 80 mole % 2,2,4,4-tetramethyl-1,3-cyclobutanediol and 20 to 35 mole % cyclohexanedimethanol; 70 to 80 mole % 2,2,4,4-tetramethyl-1,3-cyclobutanediol and 20 to 30 mole % cyclohexanedimethanol; 40 to 75 mole % 2,2,4,4-tetramethyl-1,3-cyclobutanediol and 25 to 60 mole % cyclohexanedimethanol; 45 to 75 mole % 2,2,4,4-tetramethyl-1,3-cyclobutanediol and 25 to 55 mole % cyclohexanedimethanol; 50 to 75 mole % 2,2,4,4-tetramethyl-1,3-cyclobutanediol and 25 to 50 mole % cyclohexanedimethanol; 55 to 75 mole % 2,2,4,4-tetramethyl-1,3-cyclobutanediol and 25 to 45 mole % cyclohexanedimethanol; 60 to 75 mole % 2,2,4,4-tetramethyl-1,3-cyclobutanediol and 25 to 40 mole % cyclohexanedimethanol; 65 to 75 mole % 2,2,4,4-tetramethyl-1,3-cyclobutanediol and 25 to 35 mole % cyclohexanedimethanol; 40 to 70 mole % 2,2,4,4-tetramethyl-1,3-cyclobutanediol and 30 to 60 mole % cyclohexanedimethanol; 45 to 70 mole % 2,2,4,4-tetramethyl-1,3-cyclobutanediol and 30 to 55 mole % cyclohexanedimethanol; 50 to 70 mole % 2,2,4,4-tetramethyl-1,3-cyclobutanediol and 30 to 50 mole % cyclohexanedimethanol; greater than 50 to 99 mole % 2,2,4,4-tetramethyl-1,3-cyclobutanediol and 1 to less than 50 mole % cyclohexanedimethanol; greater than 50 to 80 mole % 2,2,4,4-tetramethyl-1,3-cyclobutanediol and 20 to less than 50 mole % cyclohexanedimethanol; greater than 50 to 75 mole % 2,2,4,4-tetramethyl-1,3-cyclobutanediol and 25 to less than 50 mole % cyclohexanedimethanol; greater than 50 to 70 mole % 2,2,4,4-tetramethyl-1,3-cyclobutanediol and 30 to less than 50 mole % cyclohexanedimethanol; 55 to 70 mole % 2,2,4,4-tetramethyl-1,3-cyclobutanediol and 30 to 45 mole % cyclohexanedimethanol; 60 to 70 mole % 2,2,4,4-tetramethyl-1,3-cyclobutanediol and 30 to 40 mole % cyclohexanedimethanol; 40 to 65 mole % 2,2,4,4-tetramethyl-1,3-cyclobutanediol and 35 to 60 mole % cyclohexanedimethanol; 40 to 55 mole % 2,2,4,4-tetramethyl-1,3-cyclobutanediol and 45 to 60 mole % cyclohexanedimethanol; 40 to less than 45 mole % 2,2,4,4-tetramethyl-1,3-cyclobutanediol and greater than 55 to 60 mole % cyclohexanedimethanol; 45 to 65 mole % 2,2,4,4-tetramethyl-1,3-cyclobutanediol and 35 to 55 mole % cyclohexanedimethanol; greater than 50 to 65 mole % 2,2,4,4-tetramethyl-1,3-cyclobutanediol and 35 to less than 50 mole % cyclohexanedimethanol; 50 to 65 mole % 2,2,4,4-tetramethyl-1,3-cyclobutanediol and 35 to 50 mole % cyclohexanedimethanol; 55 to 65 mole % 2,2,4,4-tetramethyl-1,3-cyclobutanediol and 35 to 45 mole % cyclohexanedimethanol; 40 to 60 mole % 2,2,4,4-tetramethyl-1,3-cyclobutanediol and 40 to 60 mole % cyclohexanedimethanol; 45 to 60 mole % 2,2,4,4-tetramethyl-1,3-cyclobutanediol and 40 to 55 mole % cyclohexanedimethanol; 45 to 55 mole % 2,2,4,4-tetramethyl-1,3-cyclobutanediol and 45 to 55 mole % cyclohexanedimethanol; greater than 45 to 55 mole % 2,2,4,4-tetramethyl-1,3-cyclobutanediol; 45 to less than 55 mole % cyclohexanedimethanol; and 46 to 55 mole % 2,2,4,4-tetramethyl-1,3-cyclobutanediol and 45 to 54 mole % cyclohexanedimethanol; and 46 to 65 mole % 2,2,4,4-tetramethyl-1,3-cyclobutanediol and 35 to 54 mole % cyclohexanedimethanol.

In addition to the diols set forth above, the polyesters useful in the polyester compositions of the invention may also be made from 1,3-propanediol, 1,4-butanediol, or mixtures thereof.

In addition to the diols set forth above, the polyesters useful in the polyester compositions of the invention may also be made from 1,3-propanediol, 1,4-butanediol, or mixtures thereof can possess at least one of the Tg ranges described herein, at least one of the inherent viscosity ranges described herein, and/or at least one of the glycol or diacid ranges described herein. In addition or in the alternative, the polyesters useful in the invention can be made from 1,3-propanediol or 1,4-butanediol or mixtures thereof may also be made from 1,4-cyclohexanedimethanol in at least one of the following amounts: from 0.1 to 99 mole %; from 0.1 to 95 mole %; from 0.1 to 90 mole %; from 0.1 to 85 mole %; from 0.1 to 80 mole %; from 0.1 to 70 mole %; from 0.1 to 60 mole %; from 0.1 to 50 mole %; from 0.1 to 40 mole %; from 0.1 to 35 mole %; from 0.1 to 30 mole %; from 0.1 to 25 mole %; from 0.1 to 20 mole %; from 0.1 to 15 mole %; from 0.1 to 10 mole %; from 0.1 to 5 mole %; from 1 to 99 mole %; 1 to 95 mole %; from 1 to 90 mole %; from 1 to 85 mole %; from 1 to 80 mole %; from 1 to 70 mole %; from 1 to 60 mole %; from 1 to 50 mole %; from 1 to 40 mole %; from 1 to 35 mole %; from 1 to 30 mole %; from 1 to 25 mole %; from 1 to 20 mole %; from 1 to 15 mole %; from 1 to 10 mole %; from 1 to 5 mole %; 5 to 99 mole %; 5 to 95 mole %; from 5 to 90 mole %; from 5 to 85 mole %; from 5 to 80 mole %; 5 to 70 mole %; from 5 to 60 mole %; from 5 to 50 mole %; from 5 to 40 mole %; from 5 to 35 mole %; from 5 to 30 mole %; from 5 to 25 mole %; from 5 to 20 mole %; and from 5 to 15 mole %; from 5 to 10 mole %; from 10 to 99 mole %; 10 to 95 mole %; from 10 to 90 mole %; from 10 to 85 mole %; from 10 to 80 mole %; from 10 to 70 mole %; from 10 to 60 mole %; from 10 to 50 mole %; from 10 to 40 mole %; from 10 to 35 mole %; from 10 to 30 mole %; from 10 to 25 mole %; from 10 to 20 mole %; from 10 to 15 mole %; from 20 to 99 mole %; 20 to 95 mole %; from 20 to 90 mole %; from 20 to 85 mole %; from 20 to 80 mole %; from 20 to 70 mole %; from 20 to 60 mole %; from 20 to 50 mole %; from 20 to 40 mole %; from 20 to 35 mole %; from 20 to 30 mole %; and from 20 to 25 mole %.

For certain embodiments of the invention, the polyesters useful in the invention may exhibit at least one of the following inherent viscosities as determined in 60/40 (wt/wt) phenol/tetrachloroethane at a concentration of 0.25 g/50 ml at 25° C.: 0.10 to 1.2 dL/g; 0.10 to 1.1 dL/g; 0.10 to 1 dL/g; 0.10 to less than 1 dL/g; 0.10 to 0.98 dL/g; 0.10 to 0.95 dL/g; 0.10 to 0.90 dL/g; 0.10 to 0.85 dL/g; 0.10 to 0.80 dL/g; 0.10 to 0.75 dL/g; 0.10 to less than 0.75 dL/g; 0.10 to 0.72 dL/g; 0.10 to 0.70 dL/g; 0.10 to less than 0.70 dL/g; 0.10 to 0.68 dL/g; 0.10 to less than 0.68 dL/g; 0.10 to 0.65 dL/g; 0.20 to 1.2 dL/g; 0.20 to 1.1 dL/g; 0.20 to 1 dL/g; 0.20 to less than 1 dL/g; 0.20 to 0.98 dL/g; 0.20 to 0.95 dL/g; 0.20 to 0.90 dL/g; 0.20 to 0.85 dL/g; 0.20 to 0.80 dL/g; 0.20 to 0.75 dL/g; 0.20 to less than 0.75 dL/g; 0.20 to 0.72 dL/g; 0.20 to 0.70 dL/g; 0.20 to less than 0.70 dL/g; 0.20 to 0.68 dL/g; 0.20 to less than 0.68 dL/g; 0.20 to 0.65 dL/g; 0.35 to 1.2 dL/g; 0.35 to 1.1 dL/g; 0.35 to 1 dL/g; 0.35 to less than 1 dL/g; 0.35 to 0.98 dL/g; 0.35 to 0.95 dL/g; 0.35 to 0.90 dL/g; 0.35 to 0.85 dL/g; 0.35 to 0.80 dL/g; 0.35 to 0.75 dL/g; 0.35 to less than 0.75 dL/g; 0.35 to 0.72 dL/g; 0.35 to 0.70 dL/g; 0.35 to less than 0.70 dL/g; 0.35 to 0.68 dL/g; 0.35 to less than 0.68 dL/g; 0.35 to 0.65 dL/g; 0.40 to 1.2 dL/g; 0.40 to 1.1 dL/g; 0.40 to 1 dL/g; 0.40 to less than 1 dL/g; 0.40 to 0.98 dL/g; 0.40 to 0.95 dL/g; 0.40 to 0.90 dL/g; 0.40 to 0.85 dL/g; 0.40 to 0.80 dL/g; 0.40 to 0.75 dL/g; 0.40 to less than 0.75 dL/g; 0.40 to 0.72 dL/g; 0.40 to 0.70 dL/g; 0.40 to less than 0.70 dL/g; 0.40 to 0.68 dL/g; 0.40 to less than 0.68 dL/g; 0.40 to 0.65 dL/g; greater than 0.42 to 1.2 dL/g; greater than 0.42 to 1.1 dL/g; greater than 0.42 to 1 dL/g; greater than 0.42 to less than 1 dL/g; greater than 0.42 to 0.98 dL/g; greater than 0.42 to 0.95 dL/g; greater than 0.42 to 0.90 dL/g; greater than 0.42 to 0.85 dL/g; greater than 0.42 to 0.80 dL/g; greater than 0.42 to 0.75 dL/g; greater than 0.42 to less than 0.75 dL/g; greater than 0.42 to 0.72 dL/g; greater than 0.42 to less than 0.70 dL/g; greater than 0.42 to 0.68 dL/g; greater than 0.42 to less than 0.68 dL/g; and greater than 0.42 to 0.65 dL/g.

For certain embodiments of the invention, the polyesters useful in the invention may exhibit at least one of the following inherent viscosities as determined in 60/40 (wt/wt) phenol/tetrachloroethane at a concentration of 0.25 g/50 ml at 25° C.: 0.45 to 1.2 dL/g; 0.45 to 1.1 dL/g; 0.45 to 1 dL/g; 0.45 to 0.98 dL/g; 0.45 to 0.95 dL/g; 0.45 to 0.90 dL/g; 0.45 to 0.85 dL/g; 0.45 to 0.80 dL/g; 0.45 to 0.75 dL/g; 0.45 to less than 0.75 dL/g; 0.45 to 0.72 dL/g; 0.45 to 0.70 dL/g; 0.45 to less than 0.70 dL/g; 0.45 to 0.68 dL/g; 0.45 to less than 0.68 dL/g; 0.45 to 0.65 dL/g; 0.50 to 1.2 dL/g; 0.50 to 1.1 dL/g; 0.50 to 1 dL/g; 0.50 to less than 1 dL/g; 0.50 to 0.98 dL/g; 0.50 to 0.95 dL/g; 0.50 to 0.90 dL/g; 0.50 to 0.85 dL/g; 0.50 to 0.80 dL/g; 0.50 to 0.75 dL/g; 0.50 to less than 0.75 dL/g; 0.50 to 0.72 dL/g; 0.50 to 0.70 dL/g; 0.50 to less than 0.70 dL/g; 0.50 to 0.68 dL/g; 0.50 to less than 0.68 dL/g; 0.50 to 0.65 dL/g; 0.55 to 1.2 dL/g; 0.55 to 1.1 dL/g; 0.55 to 1 dL/g; 0.55 to less than 1 dL/g; 0.55 to 0.98 dL/g; 0.55 to 0.95 dL/g; 0.55 to 0.90 dL/g; 0.55 to 0.85 dL/g; 0.55 to 0.80 dL/g; 0.55 to 0.75 dL/g; 0.55 to less than 0.75 dL/g; 0.55 to 0.72 dL/g; 0.55 to 0.70 dL/g; 0.55 to less than 0.70 dL/g; 0.55 to 0.68 dL/g; 0.55 to less than 0.68 dL/g; 0.55 to 0.65 dL/g; 0.58 to 1.2 dL/g; 0.58 to 1.1 dL/g; 0.58 to 1 dL/g; 0.58 to less than 1 dL/g; 0.58 to 0.98 dL/g; 0.58 to 0.95 dL/g; 0.58 to 0.90 dL/g; 0.58 to 0.85 dL/g; 0.58 to 0.80 dL/g; 0.58 to 0.75 dL/g; 0.58 to less than 0.75 dL/g; 0.58 to 0.72 dL/g; 0.58 to 0.70 dL/g; 0.58 to less than 0.70 dL/g; 0.58 to 0.68 dL/g; 0.58 to less than 0.68 dL/g; 0.58 to 0.65 dL/g; 0.60 to 1.2 dL/g; 0.60 to 1.1 dL/g; 0.60 to 1 dL/g; 0.60 to less than 1 dL/g; 0.60 to 0.98 dL/g; 0.60 to 0.95 dL/g; 0.60 to 0.90 dL/g; 0.60 to 0.85 dL/g; 0.60 to 0.80 dL/g; 0.60 to 0.75 dL/g; 0.60 to less than 0.75 dL/g; 0.60 to 0.72 dL/g; 0.60 to 0.70 dL/g; 0.60 to less than 0.70 dL/g; 0.60 to 0.68 dL/g; 0.60 to less than 0.68 dL/g; 0.60 to 0.65 dL/g; 0.65 to 1.2 dL/g; 0.65 to 1.1 dL/g; 0.65 to 1 dL/g; 0.65 to less than 1 dL/g; 0.65 to 0.98 dL/g; 0.65 to 0.95 dL/g; 0.65 to 0.90 dL/g; 0.65 to 0.85 dL/g; 0.65 to 0.80 dL/g; 0.65 to 0.75 dL/g; 0.65 to less than 0.75 dL/g; 0.65 to 0.72 dL/g; 0.65 to 0.70 dL/g; 0.65 to less than 0.70 dL/g; 0.68 to 1.2 dL/g; 0.68 to 1.1 dL/g; 0.68 to 1 dL/g; 0.68 to less than 1 dL/g; 0.68 to 0.98 dL/g; 0.68 to 0.95 dL/g; 0.68 to 0.90 dL/g; 0.68 to 0.85 dL/g; 0.68 to 0.80 dL/g; 0.68 to 0.75 dL/g; 0.68 to less than 0.75 dL/g; 0.68 to 0.72 dL/g; greater than 0.76 dL/g to 1.2 dL/g; greater than 0.76 dL/g to 1.1 dL/g; greater than 0.76 dL/g to 1 dL/g; greater than 0.76 dL/g to less than 1 dL/g; greater than 0.76 dL/g to 0.98 dL/g; greater than 0.76 dL/g to 0.95 dL/g; greater than 0.76 dL/g to 0.90 dL/g; greater than 0.80 dL/g to 1.2 dL/g; greater than 0.80 dL/g to 1.1 dL/g; greater than 0.80 dL/g to 1 dL/g; greater than 0.80 dL/g to less than 1 dL/g; greater than 0.80 dL/g to 1.2 dL/g; greater than 0.80 dL/g to 0.98 dL/g; greater than 0.80 dL/g to 0.95 dL/g; greater than 0.80 dL/g to 0.90 dL/g.

It is contemplated that the polyesters useful in the invention can possess at least one of the inherent viscosity ranges described herein and at least one of the monomer ranges for the polyesters described herein unless otherwise stated. It is also contemplated that the polyester useful in the invention can possess at least one of the Tg ranges described herein and at least one of the monomer ranges for the polyesters described herein unless otherwise stated. It is also contemplated that the polyesters useful in the invention can posses at least one of the Tg ranges described herein, at least one of the inherent viscosity ranges described herein, and at least one of the monomer ranges for the compositions described herein unless otherwise stated.

For the desired polyester, the molar ratio of cis/trans 2,2,4,4-tetramethyl-1,3-cyclobutanediol can vary from the pure form of each or mixtures thereof. In certain embodiments, the molar percentages for cis and/or trans 2,2,4,4-tetramethyl-1,3-cyclobutanediol are greater than 50 mole % cis and less than 50 mole % trans; or greater than 55 mole % cis and less than 45 mole % trans; or 30 to 70 mole % cis and 70 to 30% trans; or 40 to 60 mole % cis and 60 to 40 mole % trans; or 50 to 70 mole % trans and 50 to 30 mole % cis; or 50 to 70 mole % cis and 50 to 30% trans or 60 to 70 mole % cis and 30 to 40 mole % trans; or greater than 70 mole % cis and less than 30 mole % trans; wherein the total sum of the mole percentages for cis- and trans-2,2,4,4-tetramethyl-1,3-cyclobutanediol is equal to 100 mole %. The molar ratio of cis/trans 1,4-cyclohexanedimethanol can vary within the range of 50/50 to 0/100, for example, between 40/60 to 20/80.

In certain embodiments, terephthalic acid, or an ester thereof, such as, for example, dimethyl terephthalate, or a mixture of terephthalic acid and an ester thereof, makes up most or all of the dicarboxylic acid component used to form the polyesters useful in the invention. In certain embodiments, terephthalic acid residues can make up a portion or all of the dicarboxylic acid component used to form the present polyester at a concentration of at least 70 mole %, such as at least 80 mole %, at least 90 mole %, at least 95 mole %, at least 99 mole %, or 100 mole %. In certain embodiments, polyesters with higher amounts of terephthalic acid can be used in order to produce higher impact strength properties. For purposes of this disclosure, the terms "terephthalic acid" and "dimethyl terephthalate are used interchangeably herein. In one embodiment, dimethyl terephthalate is part or all of the dicarboxylic acid component used to make the polyesters useful in the present invention. In all embodiments, ranges of from 70 to 100 mole %; or 80 to 100 mole %; or 90 to 100 mole %; or 99 to 100 mole %; or 100 mole % terephthalic acid and/or dimethyl terephthalate and/or mixtures thereof may be used.

In addition to terephthalic acid residues, the dicarboxylic acid component of the polyesters useful in the invention can comprise up to 30 mole %, up to 20 mole %, up to 10 mole %, up to 5 mole %, or up to 1 mole % of one or more modifying aromatic dicarboxylic acids. Yet another embodiment contains 0 mole % modifying aromatic dicarboxylic acids. Thus, if present, it is contemplated that the amount of one or more modifying aromatic dicarboxylic acids can range from any of these preceding endpoint values including, for example, from 0.01 to 30 mole %, from 0.01 to 20 mole %, from 0.01 to 10 mole %, from 0.01 to 5 mole %, or from 0.01 to 1 mole % of one or more modifying aromatic dicarboxylic acids. In one embodiment, modifying aromatic dicarboxylic acids that may be used in the present invention include but are not limited to those having up to 20 carbon atoms, and that can be linear, para-oriented, or symmetrical. Examples of modifying aromatic dicarboxylic acids which may be used in this invention include, but are not limited to, isophthalic acid, 4,4'-biphenyldicarboxylic acid, 1,4-, 1,5-, 2,6-, 2,7-naphthalenedicarboxylic acid, and trans-4,4'-stilbenedicarboxylic acid, and esters thereof. In one embodiment, isophthalic acid is the modifying aromatic dicarboxylic acid.

The carboxylic acid component of the polyesters useful in the invention can be further modified with up to 10 mole %, such as up to 5 mole % or up to 1 mole % of one or more aliphatic dicarboxylic acids containing 2-16 carbon atoms, such as, for example, cyclohexanedicarboxylic, malonic, succinic, glutaric, adipic, pimelic, suberic, azelaic and dodecanedioic dicarboxylic acids. Certain embodiments can also comprise 0.01 or more mole %, such as 0.1 or more mole %, 1 or more mole %, 5 or more mole %, or 10 or more mole % of one or more modifying aliphatic dicarboxylic acids. Yet another embodiment contains 0 mole % modifying aliphatic dicarboxylic acids. Thus, if present, it is contemplated that the amount of one or more modifying aliphatic dicarboxylic acids can range from any of these preceding endpoint values including, for example, from 0.01 to 10 mole % and from 0.1 to 10 mole %. The total mole % of the dicarboxylic acid component is 100 mole %.

The modifying dicarboxylic acids of the invention can include indan dicarboxylic acids, for example, indan-1,3-dicarboxylic acids and/or phenylindan dicarboxylic acids. In one embodiment, the dicarboxylic acid may be chosen from at least one of 1,2,3-trimethyl-3-phenylindan-4',5-dicarboxylic acid and 1,1,3-trimethyl-5-carboxy-3-(4-carboxyphenyl) indan dicarboxylic acid. For the purposes of this invention, any of the indan dicarboxylic acids described in United States Patent Application Publication No. 2006/0004151A1 entitled "Copolymers Containing Indan Moieties and Blends Thereof" by Shaikh et al., assigned to General Electric Company may be used as at least one modifying dicarboxylic acid within the scope of this invention; United States Patent Application Publication No. 2006/0004151A1 is incorporated herein by reference with respect to any of the indan dicarboxylic acids described therein.

Esters of terephthalic acid and the other modifying dicarboxylic acids or their corresponding esters and/or salts may be used instead of the dicarboxylic acids. Suitable examples of dicarboxylic acid esters include, but are not limited to, the dimethyl, diethyl, dipropyl, diisopropyl, dibutyl, and diphenyl esters. In one embodiment, the esters are chosen from at least one of the following: methyl, ethyl, propyl, isopropyl, and phenyl esters.

The cyclohexanedimethanol may be cis, trans, or a mixture thereof, for example, a cis/trans ratio of 60:40 to 40:60 or a cis/trans ratio of 70:30 to 30:70. In another embodiment, the trans-cyclohexanedimethanol can be present in an amount of 60 to 80 mole % and the cis-cyclohexanedimethanol can be present in an amount of 20 to 40 mole % wherein the total ratio of cis and trans cyclohexanedimethanol is equal to 100 mole %. In particular embodiments, the trans-cyclohexanedimethanol can be present in an amount of 60 mole % and the cis-cyclohexanedimethanol can be present in an amount of 40 mole %. In particular embodiments, the trans-cyclohexanedimethanol can be present in an amount of 70 mole % and the cis-cyclohexanedimethanol can be present in an amount of 30 mole %. Any of 1,1-, 1,2-, 1,3-, 1,4-isomers of cyclohexanedimethanol or mixtures thereof may be present in the glycol component of this invention. In one embodiment, the polyesters useful in the invention comprise 1,4-cyclohexanedimethanol. In another embodiment, the polyesters useful in the invention comprise 1,4-cyclohexanedimethanol and 1,3-cyclohexanedimethanol.

The glycol component of the polyester portion of the polyester compositions useful in the invention can contain 25 mole % or less of one or more modifying glycols which are not 2,2,4,4-tetramethyl-1,3-cyclobutanediol or cyclohexanedimethanol; in one embodiment, the polyesters useful in the invention can contain less than 15 mole % of one or more modifying glycols. In another embodiment, the polyesters useful in the invention can contain 10 mole % or less of one or more modifying glycols. In another embodiment, the polyesters useful in the invention can contain 5 mole % or less of one or more modifying glycols. In another embodiment, the polyesters useful in the invention can contain 3 mole % or less of one or more modifying glycols. In another embodiment, the polyesters useful in the invention may contain 0 mole % modifying glycols. Certain embodiments can also contain 0.01 or more mole %, such as 0.1 or more mole %, 1 or more mole %, 5 or more mole %, or 10 or more mole % of one or more modifying glycols. Thus, if present, it is contemplated that the amount of one or more modifying glycols can range from any of these preceding endpoint values including, for example, from 0.01 to 15 mole % and from 0.1 to 10 mole %.

Modifying glycols useful in the polyesters useful in the invention refer to diols other than 2,2,4,4,-tetramethyl-1,3-cyclobutanediol and cyclohexanedimethanol and may contain 2 to 16 carbon atoms. Examples of suitable modifying glycols include, but are not limited to, ethylene glycol, diethylene glycol, 1,2-propanediol, 1,3-propanediol, neopentyl glycol, 1,4-butanediol, 1,5-pentanediol, 1,6-hexanediol, p-xylene glycol, polytetramethylene glycol, or mixtures thereof. In one embodiment, the modifying glycol is ethylene glycol. In another embodiment, the modifying glycols include but are not limited to 1,3-propanediol and/or 1,4-butanediol. In another embodiment, ethylene glycol is excluded as a modifying diol. In another embodiment, 1,3-propanediol and 1,4-butanediol are excluded as modifying diols. In another embodiment, 2,2-dimethyl-1,3-propanediol is excluded as a modifying diol. The polyesters and/or the polycarbonates useful in the polyesters compositions of the invention can comprise from 0 to 10 mole percent, for example, from 0.01 to 5 mole percent, from 0.01 to 1 mole percent, from 0.05 to 5 mole percent, from 0.05 to 1 mole percent, or from 0.1 to 0.7 mole percent, or 0.1 to 0.5 mole percent, based the total mole percentages of either the diol or diacid residues; respectively, of one or more residues of a branching monomer, also referred to herein as a branching agent, having 3 or more carboxyl substituents, hydroxyl substituents, or a combination thereof. In certain embodiments, the branching monomer or agent may be added prior to and/or during and/or after the polymerization of the polyester. The polyester(s) useful in the invention can thus be linear or branched. The polycarbonate can also be linear or branched. In certain embodiments, the branching monomer or agent may be added prior to and/or during and/or after the polymerization of the polycarbonate.

Examples of branching monomers include, but are not limited to, multifunctional acids or multifunctional alcohols such as trimellitic acid, trimellitic anhydride, pyromellitic dianhydride, trimethylolpropane, glycerol, pentaerythritol, citric acid, tartaric acid, 3-hydroxyglutaric acid and the like. In one embodiment, the branching monomer residues can comprise 0.1 to 0.7 mole percent of one or more residues chosen from at least one of the following: trimellitic anhydride, pyromellitic dianhydride, glycerol, sorbitol, 1,2,6-hexanetriol, pentaerythritol, trimethylolethane, and/or trimesic acid. The branching monomer may be added to the polyester reaction mixture or blended with the polyester in the form of a concentrate as described, for example, in U.S. Pat. Nos. 5,654,347 and 5,696,176, whose disclosure regarding branching monomers is incorporated herein by reference.

The glass transition temperature (Tg) of the polyesters useful in the invention was determined using a TA DSC 2920 from Thermal Analyst Instrument at a scan rate of 20° C./min.

Because of the long crystallization half-times (e.g., greater than 5 minutes) at 170° C. exhibited by certain polyesters useful in the present invention, it can be possible to produce articles, including but not limited to, injection molded parts, injection blow molded articles, injection stretch blow molded articles, extruded film, extruded sheet, extrusion blow molded articles, extrusion stretch blow molded articles, and fibers. A thermoformable sheet is an example of an article of manufacture provided by this invention. The polyesters of the invention can be amorphous or semicrystalline. In one aspect, certain polyesters useful in the invention can have relatively low crystallinity. Certain polyesters useful in the invention can thus have a substantially amorphous morphology, meaning that the polyesters comprise substantially unordered regions of polymer.

In one embodiment, an "amorphous" polyester can have a crystallization half-time of greater than 5 minutes at 170° C. or greater than 10 minutes at 170° C. or greater than 50 minutes at 170° C. or greater than 100 minutes at 170° C. In one embodiment, of the invention, the crystallization half-times are greater than 1,000 minutes at 170° C. In another embodiment of the invention, the crystallization half-times of the polyesters useful in the invention are greater than 10,000 minutes at 170° C. The crystallization half time of the polyesters, as used herein, may be measured using methods well-known to persons of skill in the art. For example, the crystallization half time of the polyester, $t_{1/2}$, can be determined by measuring the light transmission of a sample via a laser and photo detector as a function of time on a temperature controlled hot stage. This measurement can be done by exposing the polymers to a temperature, $T_{max}$, and then cooling it to the desired temperature. The sample can then be held at the desired temperature by a hot stage while transmission measurements were made as a function of time. Initially, the sample can be visually clear with high light transmission, and becomes opaque as the sample crystallizes. The crystallization half-time is the time at which the light transmission is halfway between the initial transmission and the final transmission. $T_{max}$ is defined as the temperature required to melt the crystalline domains of the sample (if crystalline domains are present). The sample can be heated to $T_{max}$ to condition the sample prior to crystallization half time measurement. The absolute $T_{max}$ temperature is different for each composition. For example PCT can be heated to some temperature greater than 290° C. to melt the crystalline domains.

As shown in Table 1 and FIG. 1 of the Examples, 2,2,4,4-tetramethyl-1,3-cyclobutanediol is more effective than other comonomers such ethylene glycol and isophthalic acid at increasing the crystallization half-time, i.e., the time required for a polymer to reach half of its maximum crystallinity. By decreasing the crystallization rate of PCT, i.e. increasing the crystallization half-time, amorphous articles based on modified PCT may be fabricated by methods known in the art such as extrusion, injection molding, and the like. As shown in Table 1, these materials can exhibit higher glass transition temperatures and lower densities than other modified PCT copolyesters.

The polyesters of the invention can exhibit an improvement in toughness combined with processability for some of the embodiments of the invention. For example, it is unexpected that lowering the inherent viscosity slightly of the polyesters useful in the invention results in a more processable melt viscosity while retaining good physical properties of the polyesters such as toughness and heat resistance.

Figure 2:
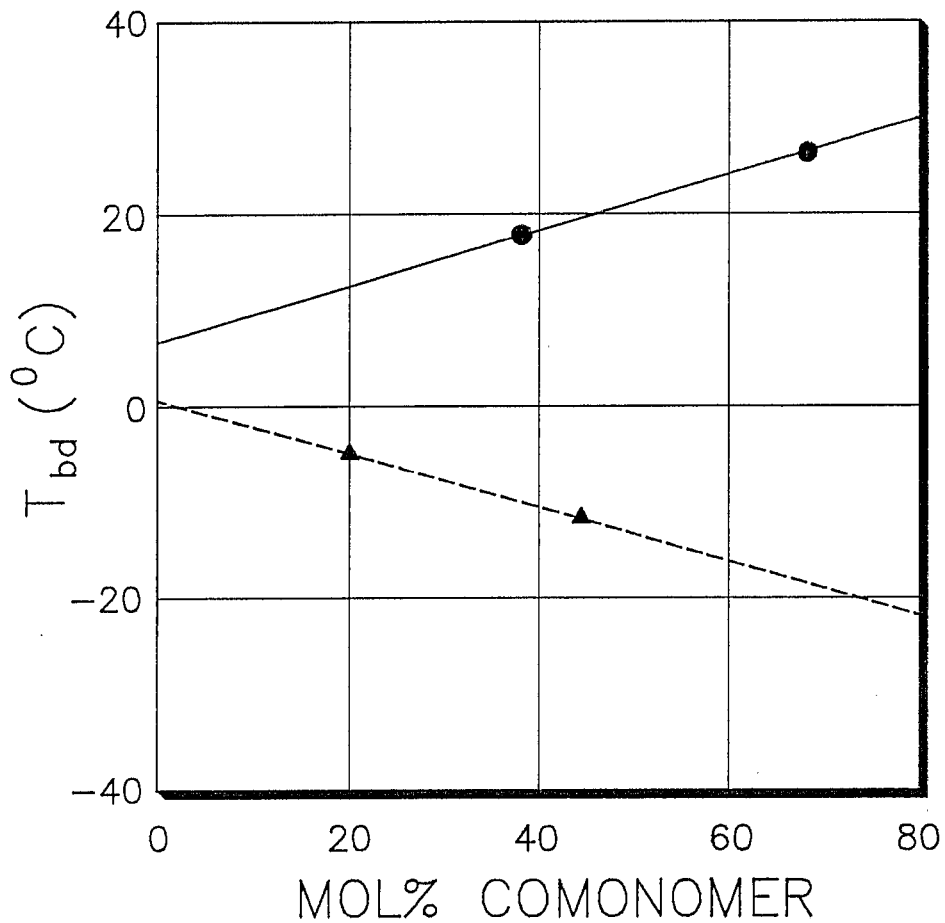
FIG. 2 is a graph showing the effect of comonomer on the brittle-to-ductile transition temperature ($T_{bd}$) in a notched Izod impact strength test ASTM D256, ⅛-in thick, 10-mil notch).

Increasing the content of cyclohexanedimethanol in a copolyester based on terephthalic acid, ethylene glycol, and cyclohexanedimethanol can improve toughness can be determined by the brittle-to-ductile transition temperature in a notched Izod impact strength test as measured by ASTM D256. This toughness improvement, by lowering of the brittle-to-ductile transition temperature with cyclohexanedimethanol, is believed to occur due to the flexibility and conformational behavior of cyclohexanedimethanol in the copolyester. Incorporating 2,2,4,4-tetramethyl-1,3-cyclobutanediol into PCT is believed to improve toughness, by lowering the brittle-to-ductile transition temperature, as shown in Table 2 and FIG. 2 of the Examples. This is unexpected given the rigidity of 2,2,4,4-tetramethyl-1,3-cyclobutanediol.

In one embodiment, the melt viscosity of the polyester(s) useful in the invention is less than 30,000 poise as measured a 1 radian/second on a rotary melt rheometer at 290° C. In another embodiment, the melt viscosity of the polyester(s) useful in the invention is less than 20,000 poise as measured a 1 radian/second on a rotary melt rheometer at 290° C.

In one embodiment, the melt viscosity of the polyester(s) useful in the invention is less than 15,000 poise as measured at 1 radian/second (rad/sec) on a rotary melt rheometer at 290° C. In one embodiment, the melt viscosity of the polyester(s) useful in the invention is less than 10,000 poise as measured at 1 radian/second (rad/sec) on a rotary melt rheometer at 290° C. In another embodiment, the melt viscosity of the polyester(s) useful in the invention is less than 6,000 poise as measured at 1 radian/second on a rotary melt rheometer at 290° C. Viscosity at rad/sec is related to processability. Typical polymers have viscosities of less than 10,000 poise as measured at 1 radian/second when measured at their processing temperature. Polyesters are typically not processed above 290° C. Polycarbonate is typically processed at 290° C. The viscosity at 1 rad/sec of a typical 12 melt flow rate polycarbonate is 7000 poise at 290° C.

In one embodiment, polyesters of this invention exhibit superior notched toughness in thick sections. Notched Izod impact strength, as described in ASTM D256, is a common method of measuring toughness. The present polyesters useful in this invention can possess one or more of the following properties. In one embodiment, the polyesters useful in the invention exhibit a impact strength of at least 150 J/m (3 ft-lb/in) at 23° C. with a 10-mil notch in a 3.2 mm (⅛-inch) thick bar determined according to ASTM D256; in one embodiment, the polyesters useful in the invention exhibit a notched Izod impact strength of at least (400 J/m) 7.5 ft-lb/in at 23° C. with a 10-mil notch in a 3.2 mm (⅛-inch) thick bar determined according to ASTM D256; in one embodiment, the polyesters useful in the invention exhibit a notched Izod impact strength of at least 1000 J/m (18 ft-lb/in) at 23° C. with a 10-mil notch in a 3.2 mm (⅛-inch) thick bar determined according to ASTM D256. In one embodiment, the polyesters useful in the invention exhibit a notched Izod impact strength of at least 150 J/m (3 ft-lb/in) at 23° C. with a 10-mil notch in a 6.4 mm (¼-inch) thick bar determined according to ASTM D256; in one embodiment, the polyesters useful in the invention exhibit a notched Izod impact strength of at least (400 J/m) 7.5 ft-lb/in at 23° C. with a 10-mil notch in a 6.4 mm (¼-inch) thick bar determined according to ASTM D256; in one embodiment, the polyesters useful in the invention exhibit a notched Izod impact strength of at least 1000 J/m (18 ft-lb/in) at 23° C. with a 10-mil notch in a 6.4 mm (¼-inch) thick bar determined according to ASTM D256.

In another embodiment, certain polyesters useful in the invention can exhibit an increase in notched Izod impact strength when measured at 0° C. of at least 3% or at least 5% or at least 10% or at least 15% as compared to the notched Izod impact strength when measured at −5° C. with a 10-mil notch in a ⅛-inch thick bar determined according to ASTM D256. In addition, certain other polyesters can also exhibit a retention of notched Izod impact strength within plus or minus 5% when measured at 0° C. through 30° C. with a 10-mil notch in a ⅛-inch thick bar determined according to ASTM D256.

In yet another embodiment, certain polyesters useful in the invention can exhibit a retention in notched Izod impact strength with a loss of no more than 70% when measured at 23° C. with a 10-mil notch in a ¼-inch thick bar determined according to ASTM D256 as compared to notched Izod impact strength for the same polyester when measured at the same temperature with a 10-mil notch in a ⅛-inch thick bar determined according to ASTM D256.

In one embodiment, the polyesters useful in the invention can exhibit a ductile-to-brittle transition temperature of less than 0° C. based on a 10-mil notch in a ⅛-inch thick bar as defined by ASTM D256.

In one embodiment, the polyesters useful in this invention can be visually clear. The term "visually clear" is defined herein as an appreciable absence of cloudiness, haziness, and/or muddiness, when inspected visually. In another embodiment, when the polyesters are blended with polycarbonate, including, but not limited to, bisphenol A polycarbonates, the blends can be visually clear.

The present polyesters possess one or more of the following properties. In other embodiments, the polyesters useful in the invention may have a yellowness index (ASTM D-1925) of less than 50 or less than 20.

In one embodiment, the polyesters useful in the invention and/or the polyester compositions of the invention, with or without toners, can have color values L*, a* and b* which can be determined using a Hunter Lab Ultrascan Spectra Colorimeter manufactured by Hunter Associates Lab Inc., Reston, Va. The color determinations are averages of values measured on either pellets of the polyesters or plaques or other items injection molded or extruded from them. They are determined by the L*a*b* color system of the CIE (International Commission on Illumination) (translated), wherein L* represents the lightness coordinate, a* represents the red/green coordinate, and b* represents the yellow/blue coordinate. In certain embodiments, the b* values for the polyesters useful in the invention can be from −10 to less than 10 and the L* values can be from 50 to 90. In other embodiments, the b* values for the polyesters useful in the invention can be present in one of the following ranges: −10 to 9; −10 to 8; −10 to 7; −10 to 6; −10 to 5; −10 to 4; −10 to 3; −10 to 2; from −5 to 9; −5 to 8; −5 to 7; −5 to 6; −5 to 5; −5 to 4; −5 to 3; −5 to 2; 0 to 9; 0 to 8; 0 to 7; 0 to 6; 0 to 5; 0 to 4; 0 to 3; 0 to 2; 1 to 10; 1 to 9; 1 to 8; 1 to 7; 1 to 6; 1 to 5; 1 to 4; 1 to 3; and 1 to 2. In other embodiments, the L* value for the polyesters useful in the invention can be present in one of the following ranges: 50 to 60; 50 to 70; 50 to 80; 50 to 90; 60 to 70; 60 to 80; 60 to 90; 70 to 80; 79 to 90.

In one embodiment, the polyesters useful in the invention can exhibit at least one of the following densities: a density of less than 1.3 g/ml at 23° C.; a density of less than 1.2 g/ml at 23° C.; a density of less than 1.18 g/ml at 23° C.; a density of 0.70 to 1.2 g/ml at 23° C.; a density of 0.70 to 1.3 g/ml at 23° C.; a density of 0.70 to less than 1.2 g/ml at 23° C.; a density of 0.75 to 1.2 at 23° C.; a density of 0.75 g/ml to less than 1.2 at 23° C.; a density of 0.80 g/ml to 1.2 at 23° C.; a density of 0.80 to less than 1.2 g/ml at 23° C.; a density of 0.90 to 1.2 g/ml at 23° C.; a density of 1.0 to 1.2 g/ml at 23° C.; a density of 1.0 to 1.3 g/ml at 23° C. a density of 1.1 to 1.2 g/ml at 23° C.; a density of 1.13 to 1.3 g/ml at 23° C. a density of 1.13 to 1.2 g/ml at 23° C.; a density of 0.80 to 1.18 g/ml at 23° C.; a density of 0.80 to less than 1.18 g/ml at 23° C.; a density of 1.0 to less than 1.18 g/ml at 23° C.; a density of 1.1 to less than 1.18 g/ml at 23° C.

In some embodiments, use of the polyester compositions useful in the invention minimizes and/or eliminates the drying step prior to melt processing and/or thermoforming.

Although the polyesters useful in this invention can have any moisture content, in one embodiment, they may have a moisture content of 0.02 to 1.0 weight percent of the total weight of the polyester prior to melt processing.

In certain embodiments, the polyesters are dried by conventional methods for less than 2 hours at 60° C. to 100° C. prior to melt processing.

The polyesters and/or polyester compositions and/or processes either useful in the invention or of the invention can comprise at least one thermal stabilizer.

Thermal stabilizers are compounds that stabilize polyesters during polyester manufacture and/or post polymerization, including but not limited to phosphorous compounds including but not limited to phosphoric acid, phosphorous acid, phosphonic acid, phosphinic acid, phosphonous acid, and various esters and salts thereof. These can be present in the polyester compositions useful in the invention. The esters can be alkyl, branched alkyl, substituted alkyl, difunctional alkyl, alkyl ethers, aryl, and substituted aryl. In one embodiment, the number of ester groups present in the particular phosphorous compound can vary from zero up to the maximum allowable based on the number of hydroxyl groups present on the thermal stabilizer used.

The term "thermal stabilizer" is intended to include the reaction product(s) thereof. The term "reaction product" as used in connection with the thermal stabilizers of the invention refers to any product of a polycondensation or esterification reaction between the thermal stabilizer and any of the monomers used in making the polyester as well as the product of a polycondensation or esterification reaction between the catalyst and any other type of additive.

In one embodiment, the thermal stabilizer(s) useful in the invention can be an organic compound such as, for example, a phosphorus acid ester containing halogenated or non-halogenated organic substituents. The thermal stabilizer can comprise a wide range of phosphorus compounds well-known in the art such as, for example, phosphines, phosphites, phosphinites, phosphonites, phosphinates, phosphonates, phosphine oxides, and phosphates. Examples of thermal stabilizers include tributyl phosphate, triethyl phosphate, tributoxyethyl phosphate, t-butylphenyl diphenyl phosphate, 2-ethylhexyl diphenyl phosphate, ethyl dimethyl phosphate, isodecyl diphenyl phosphate, trilauryl phosphate, triphenyl phosphate, tricresyl phosphate, trixylenyl phosphate, t-butylphenyl diphenylphosphate, resorcinol bis(diphenyl phosphate), tribenzyl phosphate, phenyl ethyl phosphate, trimethyl thionophosphate, phenyl ethyl thionophosphate, dimethyl methylphosphonate, diethyl methylphosphonate, diethyl pentylphosphonate, dilauryl methylphosphonate, diphenyl methylphosphonate, dibenzyl methylphosphonate, diphenyl cresylphosphonate, dimethyl cresylphosphonate, dimethyl methylthionophosphonate, phenyl diphenylphosphinate, benzyl diphenylphosphinate, methyl diphenylphosphinate, trimethyl phosphine oxide, triphenyl phosphine oxide, tribenzyl phosphine oxide, 4-methyl diphenyl phosphine oxide, triethyl phosphite, tributyl phosphite, trilauryl phosphite, triphenyl phosphite, tribenzyl phosphite, phenyl diethyl phosphite, phenyl dimethyl phosphite, benzyl dimethyl phosphite, dimethyl methylphosphonite, diethyl pentylphosphonite, diphenyl methylphosphonite, dibenzyl methylphosphonite, dimethyl cresylphosphonite, methyl dimethylphosphinite, methyl diethylphosphinite, phenyl diphenylphosphinite, methyl diphenylphosphinite, benzyl diphenylphosphinite, triphenyl phosphine, tribenzyl phosphine, and methyl diphenyl phosphine. In one embodiment, triphenyl phosphine oxide is excluded as a thermal stabilizer in the process(es) of making the polyesters useful in the invention and in the polyester composition(s) of the invention.

In one embodiment, thermal stabilizers useful in the invention can be any of the previously described phosphorus-based acids wherein one or more of the hydrogen atoms of the acid compound (bonded to either oxygen or phosphorus atoms) are replaced with alkyl, branched alkyl, substituted alkyl, alkyl ethers, substituted alkyl ethers, alkyl-aryl, alkyl-substituted aryl, aryl, substituted aryl, and mixtures thereof. In another embodiment, thermal stabilizers useful in the invention, include but are not limited to, the above described compounds wherein at least one of the hydrogen atoms bonded to an oxygen atom of the compound is replaced with a metallic ion or an ammonium ion.

The esters can contain alkyl, branched alkyl, substituted alkyl, alkyl ethers, aryl, and/or substituted aryl groups. The esters can also have at least one alkyl group and at least one aryl group. The number of ester groups present in the particular phosphorus compound can vary from zero up to the maximum allowable based on the number of hydroxyl groups present on the phosphorus compound used. For example, an alkyl phosphate ester can include one or more of the mono-, di-, and tri alkyl phosphate esters; an aryl phosphate ester includes one or more of the mono-, di-, and tri aryl phosphate esters; and an alkyl phosphate ester and/or an aryl phosphate ester also include, but are not limited to, mixed alkyl aryl phosphate esters having at least one alkyl and one aryl group.

In one embodiment, the thermal stabilizers useful in the invention include but are not limited to alkyl, aryl or mixed alkyl aryl esters or partial esters of phosphoric acid, phosphorus acid, phosphinic acid, phosphonic acid, or phosphonous acid. The alkyl or aryl groups can contain one or more substituents.

In one aspect, the phosphorus compounds useful in the invention comprise at least one thermal stabilizer chosen from at least one of substituted or unsubstituted alkyl phosphate esters, substituted or unsubstituted aryl phosphate esters, substituted or unsubstituted mixed alkyl aryl phosphate esters, diphosphites, salts of phosphoric acid, phosphine oxides, and mixed aryl alkyl phosphites, reaction products thereof, and mixtures thereof. The phosphate esters include esters in which the phosphoric acid is fully esterified or only partially esterified.

In one embodiment, for example, the thermal stabilizers useful in the invention can include at least one phosphate ester.

In one aspect, the phosphorus compounds useful in the invention comprise at least one thermal stabilizer chosen from at least one of substituted or unsubstituted alkyl phosphate esters, substituted or unsubstituted aryl phosphate esters, mixed substituted or unsubstituted alkyl aryl phosphate esters, reaction products thereof, and mixtures thereof. The phosphate esters include esters in which the phosphoric acid is fully esterified or only partially esterified.

In one embodiment, for example, the thermal stabilizers useful in the invention can include at least one phosphate ester.

In another embodiment, the phosphate esters useful in the invention can include but are not limited to alkyl phosphate esters, aryl phosphate esters, mixed alkyl aryl phosphate esters, and/or mixtures thereof.

In certain embodiments, the phosphate esters useful in the invention are those where the groups on the phosphate ester include are alkyl, alkoxy-alkyl, phenyl, or substituted phenyl groups. These phosphate esters are generally referred to herein as alkyl and/or aryl phosphate esters. Certain preferred embodiments include trialkyl phosphates, triaryl phosphates, alkyl diaryl phosphates, dialkyl aryl phosphates, and mixtures of such phosphates, wherein the alkyl groups are preferably those containing from 2 to 12 carbon atoms, and the aryl groups are preferably phenyl.

Representative alkyl and branched alkyl groups are preferably those containing from 1-12 carbon atoms, including, but not limited to, ethyl, propyl, isopropyl, butyl, hexyl, cyclohexyl, 2-ethylhexyl, octyl, decyl and dodecyl. Substituted alkyl groups include, but are not limited to, those containing at least one of carboxylic acid groups and esters thereof, hydroxyl groups, amino groups, keto groups, and the like.

Representative of alkyl-aryl and substituted alkyl-aryl groups are those wherein the alkyl portion contains from 1-12 carbon atoms, and the aryl group is phenyl or substituted phenyl wherein groups such as alkyl, branched alkyl, aryl, hydroxyl, and the like are substituted for hydrogen at any carbon position on the phenyl ring. Preferred aryl groups include phenyl or substituted phenyl wherein groups such as alkyl, branched alkyl, aryl, hydroxyl and the like are substituted for hydrogen at any position on the phenyl ring.

In one embodiment, the phosphate esters useful as thermal stabilizers in the invention include but are not limited to dibutylphenyl phosphate, triphenyl phosphate, tricresyl phosphate, tributyl phosphate, tri-2-ethylhexyl phosphate, trioctyl phosphate, and/or mixtures thereof, including particularly mixtures of tributyl phosphate and tricresyl phosphate, and mixtures of isocetyl diphenyl phosphate and 2-ethylhexyl diphenyl phosphate.

In one embodiment, the phosphate esters useful as thermal stabilizers in the invention include but are not limited to, at least one of the following: trialkyl phosphates, triaryl phosphates, alkyl diaryl phosphates, and mixed alkyl aryl phosphates.

In one embodiment, the phosphate esters useful as thermal stabilizers in the invention include but are not limited to, at least one of the following: triaryl phosphates, alkyl diaryl phosphates, and mixed alkyl aryl phosphates.

In one embodiment, the phosphate esters useful as thermal stabilizers in the invention include but are not limited to, at least one of the following: triaryl phosphates and mixed alkyl aryl phosphates. In one embodiment, at least one thermal stabilizer comprises, but is not limited to, triaryl phosphates, such as, for example, triphenyl phosphate. In one embodiment, at least one thermal stabilizer comprises, but is not limited to Merpol A.

In one embodiment, at least one thermal stabilizer useful in the invention comprises, but is not limited to, triaryl phosphates, such as, for example, triphenyl phosphate. In one embodiment, at least one thermal stabilizer comprises, but is not limited to Merpol A. In one embodiment, at least one thermal stabilizer useful in the invention comprises, but is not limited to, at least one of triphenyl phosphate and Merpol A. Merpol A is a phosphate ester commercially available from Stepan Chemical Co and/or E.I. duPont de Nemours & Co. The CAS Registry number for Merpol A is believed to be CAS Registry #37208-27-8.

In one embodiment, the polyester compositions and/or processes of the invention may comprise 2-ethylhexyl diphenyl phosphate.

In one embodiment, the polyester compositions and/or processes of the invention may comprise 2-ethylhexyl diphenyl phosphate.

In one embodiment, the phosphorus compounds useful in the invention comprise, but are not limited to, at least one diphosphite.

In one embodiment, the phosphorus compounds useful in the invention comprise, but are not limited to, at least one diphosphite which contains a 2,4,8,10-tetraoxa-3,9-diphosphaspiro[5.5]undecane structure, such as, for example, Weston 619 (GE Specialty Chemicals, CAS#3806-34-6) and/or Doverphos S-9228 (Dover Chemicals, CAS#154862-43-8).

In one embodiment, the phosphorus compounds useful in the invention comprise at least one phosphine oxide, such as, for example, triphenylphosphine oxide.

In one embodiment, the phosphorus compounds useful in the invention comprise at least one mixed alkyl aryl phosphites, such as, for example, bis(2,4-dicumylphenyl)pentaerythritol diphosphite also known as Doverphos S-9228 (Dover Chemicals, CAS#154862-43-8).

In one embodiment, any of processes described herein for making the polyester compositions and/or polyesters comprise at least one of the phosphorus compounds described herein.

In one embodiment, any of processes described herein for making any of the polyester compositions and/or polyesters can comprise at least one diphosphite.

In one embodiment, any of the processes described herein for making any of the polyester compositions and/or polyesters can comprise, at least one diphosphite which contains a 2,4,8,10-tetraoxa-3,9-diphosphaspiro[5.5]undecane structure, such as, for example, Weston 619 (GE Specialty Chemicals, CAS#3806-34-6) and/or Doverphos S-9228 (Dover Chemicals, CAS#154862-43-8).

In one embodiment, any of the processes described herein for making any of the polyester compositions and/or polyesters can comprise at least one phosphine oxide, such as, for example, triphenylphosphine oxide.

In one embodiment, any of the processes described herein for making any of the polyester compositions and/or polyesters can comprise at least one mixed alkyl aryl phosphites, such as, for example, bis(2,4-dicumylphenyl)pentaerythritol diphosphite also known as Doverphos S-9228 (Dover Chemicals, CAS#154862-43-8).

When phosphorus is added to the polyesters and/or polyester compositions and/or process of making the polyesters of the invention, it is added in the form of a phosphorus compound as described herein, for example, at least one phosphate ester, at least one diphosphite, at least one salt of phosphoric acid. The amount of phosphorus compound(s), (for example, at least one diphosphite), is added to the polyesters of the invention and/or polyester compositions of the invention and/or processes of the invention can be measured in the form of phosphorus atoms present in the final polyester, for example, by weight measured in ppm.

Amounts of thermal stabilizer added during polymerization or post manufacturing can include but are not limited to: 1 to 5000 ppm; 1 to 1000 ppm, 1 to 900 ppm, 1 to 800 ppm, 1 to 700 ppm. 1 to 600 ppm, 1 to 500 ppm, 1 to 400 ppm, 1 to 350 ppm, 1 to 300 ppm, 1 to 250 ppm, 1 to 200 ppm, 1 to 150 ppm, 1 to 100 ppm; 10 to 5000 ppm; 10 to 1000 ppm, 10 to 900 ppm, 10 to 800 ppm, 10 to 700 ppm. 10 to 600 ppm, 10 to 500 ppm, 10 to 400 ppm, 10 to 350 ppm, 10 to 300 ppm, 10 to 250 ppm, 10 to 200 ppm, 10 to 150 ppm, 10 to 100 ppm; based on the total weight of the polyester composition.

In one embodiment, amounts of the phosphorus compound (for example, diphosphite, phosphate ester, etc.) of the invention added during polymerization are chosen from the following: 1 to 5000 ppm; 1 to 1000 ppm, 1 to 900 ppm, 1 to 800 ppm, 1 to 700 ppm. 1 to 600 ppm, 1 to 500 ppm, 1 to 400 ppm, 1 to 350 ppm, 1 to 300 ppm, 1 to 250 ppm, 1 to 200 ppm, 1 to 150 ppm, 1 to 100 ppm; 1 to 60 ppm; 2 to 5000 ppm; 2 to 1000 ppm, 2 to 900 ppm, 2 to 800 ppm, 2 to 700 ppm. 2 to 600 ppm, 2 to 500 ppm, 2 to 400 ppm, 2 to 350 ppm, 2 to 300 ppm, 2 to 250 ppm, 2 to 200 ppm, 2 to 150 ppm, 2 to 100 ppm; 2 to 60 ppm; 2 to 20 ppm; 3 to 5000 ppm; 3 to 1000 ppm, 3 to 900 ppm, 3 to 800 ppm, 3 to 700 ppm. 3 to 600 ppm, 3 to 500 ppm, 3 to 400 ppm, 3 to 350 ppm, 3 to 300 ppm, 3 to 250 ppm, 3 to 200 ppm, 3 to 150 ppm, 3 to 100 ppm; 3 to 60 ppm; 3 to 20 ppm; 4 to 5000 ppm; 4 to 1000 ppm, 4 to 900 ppm, 4 to 800 ppm, 4 to 700 ppm, 4 to 600 ppm, 4 to 500 ppm, 4 to 400 ppm, 4 to 350 ppm, 4 to 300 ppm, 4 to 250 ppm, 4 to 200 ppm, 4 to 150 ppm, 4 to 100 ppm; 4 to 60 ppm; 4 to 20 ppm; 5 to 5000 ppm; 5 to 1000 ppm, 5 to 900 ppm, 5 to 800 ppm, 5 to 700 ppm, 5 to 600 ppm, 5 to 500 ppm, 5 to 400 ppm, 5 to 350 ppm, 5 to 300 ppm, 5 to 250 ppm, 5 to 200 ppm, 5 to 150 ppm, 5 to 100 ppm; 5 to 60 ppm; 5 to 20 ppm; 6 to 5000 ppm; 6 to 1000 ppm, 6 to 900 ppm, 6 to 800 ppm, 6 to 700 ppm, 6 to 600 ppm, 6 to 500 ppm, 6 to 400 ppm, 6 to 350 ppm, 6 to 300 ppm, 6 to 250 ppm, 6 to 200 ppm, 6 to 150 ppm, 6 to 100 ppm; 6 to 60 ppm; 6 to 20 ppm; 7 to 5000 ppm; 7 to 1000 ppm, 7 to 900 ppm, 7 to 800 ppm, 7 to 700 ppm, 7 to 600 ppm, 7 to 500 ppm, 7 to 400 ppm, 7 to 350 ppm, 7 to 300 ppm, 7 to 250 ppm, 7 to 200 ppm, 7 to 150 ppm, 7 to 100 ppm; 7 to 60 ppm; 7 to 20 ppm; 8 to 5000 ppm; 8 to 1000 ppm, 8 to 900 ppm, 8 to 800 ppm, 8 to 700 ppm, 8 to 600 ppm, 8 to 500 ppm, 8 to 400 ppm, 8 to 350 ppm, 8 to 300 ppm, 8 to 250 ppm, 8 to 200 ppm, 8 to 150 ppm, 8 to 100 ppm; 8 to 60 ppm; 8 to 20 ppm; 9 to 5000 ppm; 9 to 1000 ppm, 9 to 900 ppm, 9 to 800 ppm, 9 to 700 ppm, 9 to 600 ppm, 9 to 500 ppm, 9 to 400 ppm, 9 to 350 ppm, 9 to 300 ppm, 9 to 250 ppm, 9 to 200 ppm, 9 to 150 ppm, 9 to 100 ppm; 9 to 60 ppm; 9 to 20 ppm; 10 to 5000 ppm; 10 to 1000 ppm, 10 to 900 ppm, 10 to 800 ppm, 10 to 700 ppm. 10 to 600 ppm, 10 to 500 ppm, 10 to 400 ppm, 10 to 350 ppm, 10 to 300 ppm, 10 to 250 ppm, 10 to 200 ppm, 10 to 150 ppm, 10 to 100 ppm, 10 to 60 ppm, 10 to 20 ppm, 50 to 5000 ppm, 50 to 1000 ppm, 50 to 900 ppm, 50 to 800 ppm, 50 to 700 ppm, 50 to 600 ppm, 50 to 500 ppm, 50 to 400 ppm, 50 to 350 ppm, 50 to 300 ppm, 50 to 250 ppm, 50 to 200 ppm, 50 to 150 ppm, 50 to 100 ppm; 50 to 80 ppm, 100 to 5000 ppm, 100 to 1000 ppm, 100 to 900 ppm, 100 to 800 ppm, 100 to 700 ppm, 100 to 600 ppm, 100 to 500 ppm, 100 to 400 ppm, 100 to 350 ppm, 100 to 300 ppm, 100 to 250 ppm, 100 to 200 ppm, 100 to 150 ppm; 150 to 5000 ppm, 150 to 1000 ppm, 150 to 900 ppm, 150 to 800 ppm, 150 to 700 ppm, 150 to 600 ppm, 150 to 500 ppm, 150 to 400 ppm, 150 to 350 ppm, 150 to 300 ppm, 150 to 250 ppm, 150 to 200 ppm, 200 to 5000 ppm, 200 to 1000 ppm, 200 to 900 ppm, 200 to 800 ppm, 200 to 700 ppm, 200 to 600 ppm, 200 to 500 ppm, 200 to 400 ppm, 200 to 350 ppm, 200 to 300 ppm, 200 to 250 ppm, 250 to 5000 ppm, 250 to 1000 ppm, 250 to 900 ppm, 250 to 800 ppm, 250 to 700 ppm, 250 to 600 ppm, 250 to 500 ppm, 250 to 400 ppm, 250 to 350 ppm, 250 to 300 ppm, 500 to 5000 ppm, 300 to 1000 ppm, 300 to 900 ppm, 300 to 800 ppm, 300 to 700 ppm, 300 to 600 ppm, 300 to 500 ppm, 300 to 400 ppm, 300 to 350 ppm, 350 to 5000 ppm, 350 to 1000 ppm, 350 to 900 ppm, 350 to 800 ppm, 350 to 700 ppm, 350 to 600 ppm, 350 to 500 ppm, 350 to 400 ppm; based on the total weight of the polyester composition and as measured in the form of phosphorus atoms in the final polyester.

Suitable catalysts for use in the processes of the invention to make the polyesters useful in the invention include at least one tin compound. The polyester compositions of the invention may also comprise at least one of the tin compounds useful in the processes of the invention. Other catalysts could possibly be used in the invention in combination with the at least one tin compound Other catalysts may include, but are not limited to, those based on titanium, gallium, zinc, antimony, cobalt, manganese, magnesium, germanium, lithium, aluminum compounds, and an aluminum compound with lithium hydroxide or sodium hydroxide. In one embodiment, the catalyst can be a combination of at least one tin compound and at least one titanium compound.

Catalyst amounts can range from 10 ppm to 20,000 ppm or 10 to 10,000 ppm, or 10 to 5000 ppm or 10 to 1000 ppm or 10 to 500 ppm, or 10 to 300 ppm or 10 to 250 ppm based on the catalyst metal and based on the weight of the final polymer. The process can be carried out in either a batch or continuous process. In one embodiment, the catalyst is a tin compound. In one embodiment, the catalyst is solely a tin compound. In one embodiment, the tin compound can be used in either the esterification reaction or the polycondensation reaction or both reactions. In another embodiment, the catalyst is solely a tin compound used in the esterification reaction. Generally, in one embodiment, the tin compound catalyst is used in amounts of from about 0.005% to about 0.2% based on the weight of the dicarboxylic acid or dicarboxylic acid ester. Generally, in one embodiment, less than about 700 ppm elemental tin based on polyester weight should be present as residue in the polyester based on the total weight of the polyester.

When tin is added to the polyesters and/or polyester compositions and/or process of making the polyesters of the invention, it is added to the process of making the polyester in the form of a tin compound. The amount of the tin compound added to the polyesters of the invention and/or polyester compositions of the invention and/or processes of the invention can be measured in the form of tin atoms present in the final polyester, for example, by weight measured in ppm.

In another embodiment, the catalyst is solely a tin compound used in the esterification reaction in the amount of 10 ppm to 20,000 ppm or 10 to 10,000 ppm, or 10 to 5000 ppm or 10 to 4500 ppm or 10 to 4000 ppm or 10 to 3500 ppm or 10 to 3000 ppm or 10 to 2500 ppm or 10 to 2000 ppm or 10 to 1500 ppm or 10 to 1000 ppm or 10 to 500 ppm, or 10 to 300 ppm or 10 to 250 ppm or 15 ppm to 20,000 ppm or 15 to 10,000 ppm, or 15 to 5000 ppm or 15 to 4500 ppm or 15 to 4000 ppm or 15 to 3500 ppm or 15 to 3000 ppm or 15 to 2500 ppm or 15 to 2000 ppm or 15 to 1500 ppm or 15 to 1000 ppm or 15 to 500 ppm or 15 to 400 ppm or 15 to 300 ppm or 15 to 250 ppm or 20 ppm to 20,000 ppm or 20 to 10,000 ppm, or 20 to 5000 ppm or 20 to 4500 ppm or 20 to 4000 ppm or 20 to 3500 ppm or 20 to 3000 ppm or 20 to 2500 ppm or 20 to 2000 ppm or 20 to 1500 ppm or 20 to 1000 ppm or 20 to 500 ppm, or 20 to 300 ppm or 20 to 250 ppm 25 ppm to 20,000 ppm or 25 to 10,000 ppm, or 25 to 5000 ppm or 25 to 4500 ppm or 25 to 4000 ppm or 25 to 3500 ppm or 25 to 3000 ppm or 25 to 2500 ppm or 25 to 2000 ppm or 25 to 1500 ppm or 25 to 1000 ppm or 25 to 500 ppm, or 25 to 400 ppm, or 25 to 300 ppm or 25 to 250 ppm or 30 ppm to 20,000 ppm or 30 to 10,000 ppm, or 30 to 5000 ppm or 30 to 4500 ppm or 30 to 4000 ppm or 30 to 3500 ppm or 30 to 3000 ppm or 30 to 2500 ppm or 30 to 2000 ppm or 30 to 1500 ppm pr 30 to 1000 ppm or 30 to 500 ppm, or 30 to 300 ppm or 30 to 250 ppm or 35 ppm to 20,000 ppm or 35 to 10,000 ppm, or 35 to 5000 ppm or 35 to 4500 ppm or 35 to 4000 ppm or 35 to 3500 ppm or 35 to 3000 ppm or 35 to 2500 ppm or 35 to 2000 ppm or 35 to 1500 ppm or 35 to 1000 ppm or 35 to 500 ppm, or 35 to 300 ppm or 35 to 250 ppm or 40 ppm to 20,000 ppm or 40 to 10,000 ppm, or 40 to 5000 ppm or 40 to 4500 ppm or 40 to 4000 ppm or 40 to 3500 ppm or 40 to 3000 ppm or 40 to 2500 ppm or 40 to 2000 ppm or 40 to 1500 ppm or 40 to 1000 ppm or 40 to 500 ppm, or 40 to 300 ppm or 40 to 250 ppm or 40 to 200 ppm or 45 ppm to 20,000 ppm or 45 to 10,000 ppm, or 45 to 5000 ppm or 45 to 4500 ppm or 45 to 4000 ppm or 45 to 3500 ppm or 45 to 3000 ppm or 45 to 2500 ppm or 45 to 2000 ppm or 45 to 1500 ppm or 45 to 1000 ppm or 45 to 500 ppm, or 45 to 300 ppm or 45 to 250 ppm or 50 ppm to 20,000 ppm or 50 to 10,000 ppm, or 50 to 5000 ppm or 50 to 4500 ppm or 50 to 4000 ppm or 50 to 3500 ppm or 50 to 3000 ppm or 50 to 2500 ppm or 50 to 2000 ppm or 50 to 1500 ppm or 50 to 1000 ppm or 50 to 500 ppm, or 50 to 300 ppm or 50 to 250 ppm or 50 to 200 ppm or 50 to 150 ppm 50 to 125 ppm, based on the weight of the final polyester, as measured in the form of tin atoms in the final polyester.

In another embodiment, the polyesters of the invention can be prepared using at least one tin compound as catalyst. For example, see U.S. Pat. No. 2,720,507, where the portion concerning tin catalysts is incorporated herein by reference. These catalysts are tin compounds containing at least one organic radical. These catalysts include compounds of both divalent or tetravalent tin which have the general formulas set forth below:

A. $M_2(Sn(OR)_4)$
B. $MH(Sn(OR)_4)$
C. $M'(Sn(OR_4)$
D. $M'(HSn(OR)_4)_2$
E. $M_2(Sn(OR)_6)$
F. $MH(Sn(OR)_6)$
G. $M'(Sn(OR)_6)$
H. $M'(HSn(OR)_6)_2$
I. $Sn(OR)_2$
J. $Sn(OR)_4$
K. $SnR'_2$
L. $SnR'_4$
M. $R'_2SnO$
N.
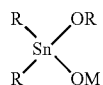
O.
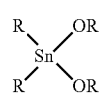
P.
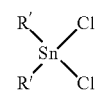
Q.
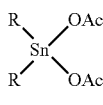

wherein M is an alkali metal, e.g. lithium, sodium, or potassium, M' is an alkaline earth metal such as Mg, Ca or Sr, each R represents an alkyl radical containing from 1 to 8 carbon atoms, each R' radical represents a substituent selected from those consisting of alkyl radicals containing from 1 to 8 carbon atoms (i.e. R radicals) and aryl radicals of the benzene series containing from 6 to 9 carbon atoms (e.g. phenyl, tolyl, benzyl, phenylethyl, etc., radicals), and Ac represents an acyl radical derived from an organic acid containing from 2 to 18 carbon atoms (e.g. acetyl, butyryl, lauroyl, benzoyl, stearoyl, etc.).

The novel bimetallic alkoxide catalysts can be made as described by Meerwein, Ann. 476, 113 (1929). As shown by Meerwein, these catalysts are not merely mixtures of the two metallic alkoxides. They are definite compounds having a salt-like structure. These are the compounds depicted above by the Formulas A through H. Those not specifically described by Meerwein can be prepared by procedures analogous to the working examples and methods set forth by Meerwein.

The other tin compounds can also be made by various methods such as those described in the following literature: For the preparation of diaryl tin dihalides (Formula P) see Ber. 62, 996 (1929); J. Am. Chem. Soc. 49, 1369 (1927). For the preparation of dialkyl tin dihalides (Formula P) see J. Am. Chem. Soc. 47, 2568 (1925); C.A. 41, 90 (1947). For the preparation of diaryl tin oxides (Formula M) see J. Am. Chem. Soc. 48, 1054 (1926). For the preparation of tetraaryl tin compounds (Formula K) see C.A. 32, 5387 (1938). For the preparation of tin alkoxides (Formula J) see C.A. 24, 586 (1930). For the preparation of alkyl tin salts (Formula Q) see C.A. 31, 4290. For the preparation of alkyl tin compounds (Formula K and L) see C.A. 35, 2470 (1941): C.A. 33, 5357 (1939). For the preparation of mixed alkyl aryl tin (Formulas K and L) see C.A. 31, 4290 (1937): C.A. 38, 331 (1944). For the preparation of other tin compounds not covered by these citations see "Die Chemie der Metal-Organischen Verbindungen." by Krause and V. Grosse, published in Berlin, 1937, by Gebroder-Borntrager.

The tin alkoxides (Formulas I and J) and the bimetallic alkoxides (Formulas A through H) contain R substituents which can represent both straight chain and branched chain alkyl radicals, e.g. diethoxide, tetramethoxide, tetrabutoxide, tetra-tert-butoxide, tetrahexoxide, etc.

The alkyl derivatives (Formulas K and L) contain one or more alkyl radicals attached to a tin atom through a direct C—Sn linkage, e.g. dibutyl tin, dihexyl tin, tetra-butyl tin, tetraethyl tin, tetramethyl tin, dioctyl tin, etc. Two of the tetraalkyl radicals can be replaced with an oxygen atom to form compounds having Formula M, e.g. dimethyl tin oxide, diethyl tin oxide, dibutyl tin oxide, diheptyl tin oxide, etc. In one embodiment, the tin catalyst comprises dimethyl tin oxide.

Complexes can be formed by reacting dialkyl tin oxides with alkali metal alkoxides in an alcohol solution to form compounds having Formula N, which compounds are especially useful catalysts, e.g. react dibutyl tin oxide with sodium ethoxide, etc. This formula is intended to represent the reaction products described. Tin compounds containing alkyl and alkoxy radicals are also useful catalysts (see Formula O), e.g. diethyl tin diethoxide, dibutyl tin dibutoxide, dihexyl tin dimethoxide, etc.

Salts derived from dialkyl tin oxides reacted with carboxylic acids or hydrochloric acid are also of particular value as catalysts; see Formulas P and Q. Examples of these catalytic condensing agents include dibutyl tin diacetate, diethyl tin dibutyrate, dibutyl tin dilauroate, dimethyl tin dibenzoate, dibutyl tin dichloride, diethyl tin dichloride, dioctyl tin dichloride, dihexyl tin distearate, etc.

The tin compounds having Formulas K, L and M can be prepared wherein one or more of the R' radicals represents an aryl radical of the benzene series, e.g. phenyl, tolyl, benzyl, etc. Examples include diphenyl tin, tetraphenyl tin, diphenyl dibutyl tin, ditolyl diethyl tin, diphenyl tin oxide, dibenzyl tin, tetrabenzyl tin, di([B-phenylethyl) tin oxide, dibenzyl tin oxide, etc.

Examples of catalysts useful in the present invention include, but are not limited to, one of more of the following: butyltin tris-2-ethylhexanoate, dibutyltin diacetate, dibutyltin oxide, and dimethyl tin oxide.

In one embodiment, catalysts useful in the present invention include, but are not limited to, one or more of the following: butyltin tris-2-ethylhexanoate, dibutyltin diacetate, dibutyltin oxide, and dimethyl tin oxide.

Processes for preparing polyesters using tin-based catalysts are well known and described in the aforementioned U.S. Pat. No. 2,720,507.

The polyester portion of the polyester compositions useful in the invention can be made by processes known from the literature such as, for example, by processes in homogenous solution, by transesterification processes in the melt, and by two phase interfacial processes. Suitable methods include, but are not limited to, the steps of reacting one or more dicarboxylic acids with one or more glycols at a temperature of 100° C. to 315° C. at a pressure of 0.1 to 760 mm Hg for a time sufficient to form a polyester. See U.S. Pat. No. 3,772, 405 for methods of producing polyesters, the disclosure regarding such methods is hereby incorporated herein by reference.

The polyester in general may be prepared by condensing the dicarboxylic acid or dicarboxylic acid ester with the glycol in the presence of the tin catalyst described herein at elevated temperatures increased gradually during the course of the condensation up to a temperature of about 225°-310° C., in an inert atmosphere, and conducting the condensation at low pressure during the latter part of the condensation, as described in further detail in U.S. Pat. No. 2,720,507 incorporated herein by reference.

In another aspect, this invention relates to a process for preparing copolyesters of the invention. In one embodiment, the process relates to preparing copolyesters comprising terephthalic acid, 2,2,4,4-tetramethyl-1,3-cyclobutanediol, and 1,4-cyclohexanedimethanol. This process comprises the steps of:
(A) heating a mixture comprising the monomers useful in the polyesters of the invention in the presence of at least one tin catalyst and at least one phosphorus compound at a temperature of 150 to 250° C. for a time sufficient to produce an initial polyester;
(B) polycondensing the product of Step (A) by heating it at a temperature of 240 to 320° C. for 1 to 6 hours; and
(C) removing any unreacted glycols.

Reaction times for the esterification Step (A) are dependent upon the selected temperatures, pressures, and feed mole ratios of glycol to dicarboxylic acid.

In one embodiment, step (A) can be carried out until 50% by weight or more of the 2,2,4,4-tetramethyl-1,3-cyclobutanediol has been reacted. Step (A) may be carried out under pressure, ranging from 0 psig to 100 psig. The term "reaction product" as used in connection with any of the catalysts useful in the invention refers to any product of a polycondensation or esterification reaction with the catalyst and any of the monomers used in making the polyester as well as the product of a polycondensation or esterification reaction between the catalyst and any other type of additive.

Typically, Step (B) and Step (C) can be conducted at the same time. These steps can be carried out by methods known in the art such as by placing the reaction mixture under a pressure ranging, from 0.002 psig to below atmospheric pressure, or by blowing hot nitrogen gas over the mixture.

In one embodiment, the invention comprises a process for making any of the polyesters useful in the invention, comprising the following steps:
(I) heating a mixture at least one temperature chosen from 150° C. to 200° C., under at least one pressure chosen from the range of 0 psig to 70 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 1 to 99 mole % of 2,2,4,4-tetramethyl-1,3-cyclobutanediol residues; and
    (ii) 1 to 99 mole % of cyclohexanedimethanol residues;
  wherein the molar ratio of glycol component/dicarboxylic acid component added in Step (I) is 1.0-1.5/1.0;
  wherein the mixture in Step (I) is heated in the presence of:
    (i) at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide;

(II) heating the product of Step (I) at a temperature of 230° C. to 320° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %; and wherein the total mole % of the glycol component of the final polyester is 100 mole %.

In one embodiment, the invention comprises a process for making any of the polyesters useful in the invention comprising the following steps:
(I) heating a mixture at least one temperature chosen from 150° C. to 200° C., under at least one pressure chosen from the range of 0 psig to 75 psig wherein said mixture comprises:
  (a) a dicarboxylic acid component comprising:
    (i) 70 to 100 mole % of terephthalic acid residues;
    (ii) 0 to 30 mole % of aromatic dicarboxylic acid residues having up to 20 carbon atoms; and
    (iii) 0 to 10 mole % of aliphatic dicarboxylic acid residues having up to 16 carbon atoms; and
  (b) a glycol component comprising:
    (i) 1 to 99 mole % of 2,2,4,4-tetramethyl-1,3-cyclobutanediol residues; and
    (ii) 1 to 99 mole % of cyclohexanedimethanol residues;
  wherein the molar ratio of glycol component/dicarboxylic acid component added in Step (I) is 1.0-1.5/1.0;
  wherein the mixture in Step (I) is heated in the presence of at least one catalyst comprising at least one tin compound, and, optionally, at least one catalyst chosen from titanium, gallium, zinc, antimony, cobalt, manganese, magnesium, germanium, lithium, aluminum compounds and an aluminum compound with lithium hydroxide or sodium hydroxide; and
(II) heating the product of Step (I) at a temperature of 230° C. to 320° C. for 1 to 6 hours, under at least one pressure chosen from the range of the final pressure of Step (I) to 0.02 torr absolute, to form a final polyester;
wherein the total mole % of the dicarboxylic acid component of the final polyester is 100 mole %;
wherein the total mole % of the glycol component of the final polyester is 100 mole %;
wherein at least one phosphorus compound, for example, at least one phosphate ester, is added to Step (I), Step (II) and/or both Steps (I) and (II); and
wherein the addition of the phosphorus compound(s), for example, at least one phosphate ester, results in a weight ratio of total tin atoms to total phosphorus atoms in the final polyester useful in the invention of 2-10:1.

For example, in the previous two paragraphs, at least one phosphorus compound can be added in Step (I), (II) and/or in both Steps (I) and (II) of the process. In one embodiment, the phosphorus compound(s) are added in Step (I). The phosphorus compounds can comprise at least one phosphate ester, for example.

In any of the processes of the invention useful in making the polyesters useful in the invention, at least one thermal stabilizer, reaction products thereof, and mixtures thereof can be added either during esterification, polycondensation, or both and/or it can be added post-polymerization. In one embodiment, the thermal stabilizer useful in any of the processes of the invention can be added during esterification. In one embodiment, if the thermal stabilizer added after both esterification and polycondensation, it is added in the amount of 1 to 2 weight % A) based on the total weight of the final polyester. In one embodiment, the thermal stabilizer can comprise at least one phosphorus compound useful in the invention. In one embodiment, the thermal stabilizer can comprise at least one phosphate ester. In one embodiment, the thermal stabilizer can comprise at least one phosphorus compound which is added during the esterification step. In one embodiment, the thermal stabilizer can comprise at least one phosphate ester, for example, which is added during the esterification step.

In one embodiment, it is believed that when at least one thermal stabilizer comprising at least one phosphorus compound described herein are used during the processes of making the polyesters according to the present invention, the polyesters can be more easily produced without at least one of the following occurring: bubbling, splay formation, color formation, foaming, off-gassing, and erratic melt levels, i.e., pulsating of the polyester or the polyester's production and processing systems. In another embodiment, it is believed that at least one process of the invention provides a means to more easily produce the polyesters useful in the invention in large quantities (for example, pilot run scale and/or commercial production) without at least one of the aforesaid difficulties occurring.

The term "large quantities" as used herein includes quantities of polyester(s) useful in the invention which are produced in quantities larger than 100 pounds. In one embodiment, the term "large quantities, as used herein, includes quantities of polyester(s) useful in the invention which are produced in quantities larger than 1000 pounds.

In one aspect, the processes of making the polyesters useful in the invention can comprise a batch or continuous process.

In one aspect, the processes of making the polyesters useful in the invention comprise a continuous process.

It is believed that any of the processes of making the polyesters useful in the invention may be used to make any of the polyesters useful in the invention.

Reaction times for the esterification Step (I) are dependent upon the selected temperatures, pressures, and feed mole ratios of glycol to dicarboxylic acid.

In one embodiment, the pressure used in Step (II) of any of the processes of the invention consists of at least one pressure chosen from 20 torr absolute to 0.02 torr absolute; in one embodiment, the pressure used in Step (II) of any of the processes of the invention consists of at least one pressure chosen from 10 torr absolute to 0.02 torr absolute; in one embodiment, the pressure used in Step (II) of any of the processes of the invention consists of at least one pressure chosen from 5 torr absolute to 0.02 torr absolute; in one embodiment, the pressure used in Step (II) of any of the processes of the invention consists of at least one pressure chosen from 3 torr absolute to 0.02 torr absolute; in one embodiment, the pressure used in Step (II) of any of the processes of the invention consists of at least one pressure chosen from 20 torr absolute to 0.1 torr absolute; in one embodiment, the pressure used in Step (II) of any of the processes of the invention consists of at least one pressure chosen from 10 torr absolute to 0.1 torr absolute; in one embodiment, the pressure used in Step (II) of any of the processes of the invention consists of at least one pressure chosen from 5 torr absolute to 0.1 torr absolute; in one embodiment, the pressure used in Step (II) of any of the processes of the invention consists of at least one pressure chosen from 3 torr absolute to 0.1 torr absolute.

In one embodiment, the molar ratio of glycol component/dicarboxylic acid component added in Step (I) of any of the processes of the invention is 1.0-1.5/1.0; in one embodiment, the molar ratio of glycol component/dicarboxylic acid component added in Step (I) of any of the processes of the invention is 1.01-1.5/1.0; in one embodiment, the molar ratio of glycol component/dicarboxylic acid component added in Step (I) of any of the processes of the invention is 1.01-1.3/1.0; in one embodiment, the molar ratio of glycol component/dicarboxylic acid component added in Step (I) of any of the processes of the invention is 1.01-1.2/1.0; in one embodiment, the molar ratio of glycol component/dicarboxylic acid component added in Step (I) of any of the processes of the invention is 1.01-1.15/1.0; in one embodiment, the molar ratio of glycol component/dicarboxylic acid component added in Step (I) of any of the processes of the invention is 1.01-1.10/1.0; in one embodiment, the molar ratio of glycol component/dicarboxylic acid component added in Step (I) of any of the processes of the invention is 1.03-1.5/1.0; in one embodiment, the molar ratio of glycol component/dicarboxylic acid component added in Step (I) of any of the processes of the invention is 1.03-1.3/1.0; in one embodiment, the molar ratio of glycol component/dicarboxylic acid component added in Step (I) of any of the processes of the invention is 1.03-1.2/1.0; in one embodiment, the molar ratio of glycol component/dicarboxylic acid component added in Step (I) of any of the processes of the invention is 1.03-1.15/1.0; in one embodiment, the molar ratio of glycol component/dicarboxylic acid component added in Step (I) of any of the processes of the invention is 1.03-1.10/1.0; in one embodiment, the molar ratio of glycol component/dicarboxylic acid component added in Step (I) of any of the processes of the invention is 1.05-1.5/1.0; in one embodiment, the molar ratio of glycol component/dicarboxylic acid component added in Step (I) of any of the processes of the invention is 1.05-1.3/1.0; in one embodiment, the molar ratio of glycol component/dicarboxylic acid component added in Step (I) of any of the processes of the invention is 1.05-1.2/1.0; in one embodiment, the molar ratio of glycol component/dicarboxylic acid component added in Step (I) of any of the processes of the invention is 1.05-1.15/1.0; and in one embodiment, the molar ratio of glycol component/dicarboxylic acid component added in Step (I) of any of the processes of the invention is 1.01-1.10/1.0.

In any of the process embodiments for making the polyesters useful in the invention, the heating time of Step (II) can be from 1 to 5 hours or 1 to 4 hours or 1 to 3 hours or 1.5 to 3 hours or 1 to 2 hours. In one embodiment, the heating time of Step (II) can be from 1.5 to 3 hours.

In one embodiment, the addition of the phosphorus compound(s) in the process(es) of the invention can result in a weight ratio of total tin atoms to total phosphorus atoms in the final polyester useful in the invention of 2-10:1. In one embodiment, the addition of the phosphorus compound(s) in the process(es) can result in a weight ratio of total tin atoms to total phosphorus atoms in the final polyester of 5-9:1. In one embodiment, the addition of the phosphorus compound(s) in the process(es) can result in a weight ratio of total tin atoms to total phosphorus atoms in the final polyester of 6-8:1. In one embodiment, the addition of the phosphorus compound(s) in the process(es) can result in a weight ratio of total tin atoms to total phosphorus atoms in the final polyester of 7:1. For example, the weight of tin atoms and phosphorus atoms present in the final polyester can be measured in ppm and can result in a weight ratio of total tin atoms to total phosphorus atoms in the final polyester of any of the aforesaid weight ratios.

In one embodiment, the amount of tin atoms in the final polyester useful in the invention can be from 15 to 400 ppm tin atoms based on the weight of the final polyester.

In one embodiment, the amount of tin atoms in the final polyester useful in the invention can be from 25 to 400 ppm tin atoms based on the weight of the final polyester.

In one embodiment, the amount of tin atoms in the final polyester useful in the invention can be from 40 to 200 ppm tin atoms based on the weight of the final polyester.

In one embodiment, the amount of tin atoms in the final polyester useful in the invention can be from 50 to 125 ppm tin atoms based on the weight of the final polyester.

In one embodiment, the amount of phosphorus atoms in the final polyester useful in the invention can be from 1 to 100 ppm phosphorus atoms based on the weight of the final polyester.

In one embodiment, the amount of phosphorus atoms in the final polyester useful in the invention can be from 4 to 60 ppm phosphorus atoms based on the weight of the final polyester.

In one embodiment, the amount of phosphorus atoms in the final polyester useful in the invention can be from 6 to 20 ppm phosphorus atoms based on the weight of the final polyester.

In one embodiment, the amount of phosphorus atoms in the final polyester useful in the invention can be from 1 to 100 ppm phosphorus atoms based on the weight of the final polyester and the amount of tin atoms in the final polyester can be from 15 to 400 ppm tin atoms based on the weight of the final polyester.

In one embodiment, the amount of phosphorus atoms in the final polyester useful in the invention can be from 1 to 100 ppm phosphorus atoms based on the weight of the final polyester and the amount of tin atoms in the final polyester can be from 25 to 400 ppm tin atoms based on the weight of the final polyester.

In one embodiment, the amount of phosphorus atoms in the final polyester useful in the invention can be from 4 to 60 ppm phosphorus atoms based on the weight of the final polyester and the amount of tin atoms in the final polyester can be from 40 to 200 ppm tin atoms based on the weight of the final polyester.

In one embodiment, the amount of phosphorus atoms in the final polyester useful in the invention can be from 6 to 20 ppm phosphorus atoms based on the weight of the final polyester and the amount of tin atoms in the final polyester can be from 50 to 125 ppm tin atoms based on the weight of the final polyester.

The invention further relates to the polyester compositions made by the process(es) described above.

The invention further relates to a polymer blend. The blend comprises:

(a) 5 to 95 wt % of at least one of the polyesters described above; and (b) 5 to 95 wt % of at least one polymeric components.

Suitable examples of the polymeric components include, but are not limited to, nylon, polyesters different from those described herein, polyamides such as ZYTEL® from DuPont; polystyrene, polystyrene copolymers, stryrene acrylonitrile copolymers, acrylonitrile butadiene styrene copolymers, poly(methylmethacrylate), acrylic copolymers, poly(ether-imides) such as ULTEM® (a poly(ether-imide) from General Electric); polyphenylene oxides such as poly(2,6-dimethylphenylene oxide) or poly(phenylene oxide)/polystyrene blends such as NORYL 1000® (a blend of poly(2,6-dimethylphenylene oxide) and polystyrene resins from General Electric); polyphenylene sulfides; polyphenylene sulfide/sulfones; poly(ester-carbonates); polycarbonates such as LEXAN® (a polycarbonate from General Electric); polysulfones; polysulfone ethers; and poly(ether-ketones) of aromatic dihydroxy compounds; or mixtures of any of the foregoing polymers. The blends can be prepared by conventional processing techniques known in the art, such as melt blending or solution blending. In one embodiment, the polycarbonate is not present in the polyester composition. If polycarbonate is used in a blend in the polyester compositions useful in the invention, the blends can be visually clear. However, the polyester compositions useful in the invention also contemplate the exclusion of polycarbonate as well as the inclusion of polycarbonate.

Polycarbonates useful in the invention may be prepared according to known procedures, for example, by reacting the dihydroxyaromatic compound with a carbonate precursor such as phosgene, a haloformate or a carbonate ester, a molecular weight regulator, an acid acceptor and a catalyst. Methods for preparing polycarbonates are known in the art and are described, for example, in U.S. Pat. No. 4,452,933, where the disclosure regarding the preparation of polycarbonates is hereby incorporated by reference herein.

Examples of suitable carbonate precursors include, but are not limited to, carbonyl bromide, carbonyl chloride, or mixtures thereof; diphenyl carbonate; a di(halophenyl)carbonate, e.g., di(trichlorophenyl)carbonate, di(tribromophenyl)carbonate, and the like; di(alkylphenyl)carbonate, e.g., di(tolyl) carbonate; di(naphthyl)carbonate; di(chloronaphthyl)carbonate, or mixtures thereof; and bis-haloformates of dihydric phenols.

Examples of suitable molecular weight regulators include, but are not limited to, phenol, cyclohexanol, methanol, alkylated phenols, such as octylphenol, para-tertiary-butyl-phenol, and the like. In one embodiment, the molecular weight regulator is phenol or an alkylated phenol.

The acid acceptor may be either an organic or an inorganic acid acceptor. A suitable organic acid acceptor can be a tertiary amine and includes, but is not limited to, such materials as pyridine, triethylamine, dimethylaniline, tributylamine, and the like. The inorganic acid acceptor can be either a hydroxide, a carbonate, a bicarbonate, or a phosphate of an alkali or alkaline earth metal.

The catalysts that can be used include, but are not limited to, those that typically aid the polymerization of the monomer with phosgene. Suitable catalysts include, but are not limited to, tertiary amines such as triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethyl ammonium chloride, tetra-methyl ammonium hydroxide, tetra-n-butyl ammonium iodide, benzyltrimethyl ammonium chloride and quaternary phosphonium compounds such as, for example, n-butyltriphenyl phosphonium bromide and methyltriphenyl phosphonium bromide.

The polycarbonates useful in the polyester compositions of the invention also may be copolyestercarbonates such as those described in U.S. Pat. Nos. 3,169,121; 3,207,814; 4,194,038; 4,156,069; 4,430,484, 4,465,820, and 4,981,898, where the disclosure regarding copolyestercarbonates from each of the U.S. patents is incorporated by reference herein.

Copolyestercarbonates useful in this invention can be available commercially and/or can prepared by known methods in the art. For example, they can be typically obtained by the reaction of at least one dihydroxyaromatic compound with a mixture of phosgene and at least one dicarboxylic acid chloride, especially isophthaloyl chloride, terephthaloyl chloride, or both.

In addition, the polyester compositions and the polymer blend compositions containing the polyesters of this invention may also contain from 0.01 to 25% by weight or 0.01 to 20% by weight or 0.01 to 15% by weight or 0.01 to 10% by weight or 0.01 to 5% by weight of the total weight of the polyester composition of common additives such as colorants, dyes, mold release agents, flame retardants, plasticizers, nucleating agents, stabilizers, including but not limited to, UV stabilizers, thermal stabilizers and/or reaction products thereof, fillers, and impact modifiers. Examples of typical commercially available impact modifiers well known in the art and useful in this invention include, but are not limited to, ethylene/propylene terpolymers; functionalized polyolefins, such as those containing methyl acrylate and/or glycidyl methacrylate; styrene-based block copolymeric impact modifiers; and various acrylic core/shell type impact modifiers. For example, UV additives can be incorporated into articles of manufacture through addition to the bulk, through application of a hard coat, or through coextrusion of a cap layer. Residues of such additives are also contemplated as part of the polyester composition.

The polyesters of the invention can comprise at least one chain extender.

Suitable chain extenders include, but are not limited to, multifunctional (including, but not limited to, bifunctional) isocyanates, multifunctional epoxides, including for example, epoxylated novolacs, and phenoxy resins. In certain embodiments, chain extenders may be added at the end of the polymerization process or after the polymerization process. If added after the polymerization process, chain extenders can be incorporated by compounding or by addition during conversion processes such as injection molding or extrusion. The amount of chain extender used can vary depending on the specific monomer composition used and the physical properties desired but is generally about 0.1 percent by weight to about 10 percent by weight, preferably about 0.1 to about 5 percent by weight based on the total weight of the polyester.

Reinforcing materials may be useful in the compositions of this invention. The reinforcing materials may include, but are not limited to, carbon filaments, silicates, mica, clay, talc, titanium dioxide, Wollastonite, glass flakes, glass beads and fibers, and polymeric fibers and combinations thereof. In one embodiment, the reinforcing materials are glass, such as fibrous glass filaments, mixtures of glass and talc, glass and mica, and glass and polymeric fibers.

In another embodiment, the invention further relates to articles of manufacture comprising any of the polyesters and blends described above.

In another embodiment, the invention further relates to articles of manufacture comprising any of the polyesters and blends described herein. extruded, calendered, and/or molded articles including but not limited to, injection molded articles, extruded articles, cast extrusion articles, profile extrusion articles, melt spun articles, thermoformed articles, extrusion molded articles, injection blow molded articles, injection stretch blow molded articles, extrusion blow molded articles, and extrusion stretch blow molded articles. These articles can include, but are not limited, to films, bottles (including, but not limited to, baby bottles), containers, sheet and/or fibers.

The present polyesters and/or polyester blend compositions can be useful in forming fibers, films, molded articles, containers, and sheeting. The methods of forming the polyesters into fibers, films, molded articles, containers, and sheeting are well known in the art. Examples of potential molded articles include without limitation: medical devices such as dialysis equipment, medical packaging, healthcare supplies, commercial food service products such as food pans, tumblers and storage boxes, baby bottles, food processors, blender and mixer bowls, utensils, water bottles, crisper trays, washing machine fronts, and vacuum cleaner parts. Other potential molded articles could include, but are not limited to, ophthalmic lenses and frames. For instance, this material can be used to make bottles, including but not limited to, baby bottles, as it is clear, tough, heat resistant, and displays good hydrolytic stability.

In another embodiment, the invention further relates to articles of manufacture comprising the film(s) and/or sheet(s) containing polyester compositions described herein.

The films and/or sheets useful in the present invention can be of any thickness which would be apparent to one of ordinary skill in the art. In one embodiment, the film(s) of the invention have a thickness of no more than 40 mils. In one embodiment, the film(s) of the invention have a thickness of no more than 35 mils. In one embodiment, the film(s) of the invention have a thickness of no more than 30 mils. In one embodiment, the film(s) of the invention have a thickness of no more than 25 mils. In one embodiment, the film(s) of the invention have a thickness of no more than 20 mils.

In one embodiment, the sheet(s) of the invention have a thickness of no less than 20 mils. In another embodiment, the sheet(s) of the invention have a thickness of no less than 25 mils. In another embodiment, the sheet(s) of the invention have a thickness of no less than 30 mils. In another embodiment, the sheet(s) of the invention have a thickness of no less than 35 mils. In another embodiment, the sheet(s) of the invention have a thickness of no less than 40 mils.

The invention further relates to the film(s) and/or sheet(s) comprising the polyester compositions of the invention. The methods of forming the polyesters into film(s) and/or sheet(s) are well known in the art. Examples of film(s) and/or sheet(s) of the invention including but not limited to extruded film(s) and/or sheet(s), calendered film(s) and/or sheet(s), compression molded film(s) and/or sheet(s), solution casted film(s) and/or sheet(s). Methods of making film and/or sheet include but are not limited to extrusion, calendering, compression molding, and solution casting.

Examples of potential articles made from film and/or sheet useful in the invention include, but are not limited, to uniaxially stretched film, biaxially stretched film, shrink film (whether or not uniaxially or biaxially stretched, liquid crystal display film (including but not limited to diffuser sheets, compensation films and protective films), thermoformed sheet, graphic arts film, outdoor signs, skylights, coating(s), coated articles, painted articles, laminates, laminated articles, and/or multiwall films or sheets.

"Graphic art film," as used herein, is a film having a thermally-curable ink (e.g., heat-curable ink or air-curable ink) or radiation-curable ink (e.g., ultra-violet-curable ink) printed thereon or therein. "Curable" refers to capable of undergoing polymerization and/or crosslinking. In addition to the ink, the graphic art film may optionally also include varnishes, coatings, laminates, and adhesives.

Exemplary thermally or air-cured inks involve pigment(s) dispersed in one or more standard carrier resins. The pigment can be 4B Toner (PR57), 2B Toner (PR48), Lake Red C (PR53), lithol red (PR49), iron oxide (PR101), Permanent Red R (PR4), Permanent Red 2G (PO5), pyrazolone orange (PO13), diaryl yellows (PY12, 13, 14), monoazo yellows (PY3,5,98), phthalocyanine green (PG7), phthalocyanine Blue, β form (PB15), ultramarine (PB62), permanent violet (PV23), titanium dioxide (PW6), carbon black (furnace/channel) (PB7), PMTA pink, green, blue, violet (PR81, PG1, PB1, PV3), copper ferrocyanide dye complexes (PR169, PG45, PB62, PV27), or the like. (Parenthetical identifications in the foregoing refer to the generic color index prepared by the Society of Dyers and Colourists.) Such pigments and combinations thereof can be used to obtain various colors including, but not limited to, white, black, blue, violet, red, green, yellow, cyan, magenta, or orange.

Other exemplary inks, including radiation-cured inks are disclosed in U.S. Pat. No. 5,382,292, where the disclosure of such inks are incorporated herein by reference.

Examples of typical carrier resins used in standard inks include those which have nitrocellulose, amide, urethane, epoxide, acrylate, and/or ester functionalities. Standard carrier resins include one or more of nitrocellulose, polyamide, polyurethane, ethyl cellulose, cellulose acetate propionate, (meth)acrylates, poly(vinyl butyral), poly(vinyl acetate), poly(vinyl chloride), and the like. Such resins can be blended, with widely used blends including nitrocellulose/polyamide and nitrocellulose/polyurethane.

Ink resin(s) normally can be solvated or dispersed in one or more solvents. Typical solvents employed include, but are not limited to, water, alcohols (e.g., ethanol, 1-propanol, isopropanol, etc.), acetates (e.g., n-propyl acetate), aliphatic hydrocarbons, aromatic hydrocarbons (e.g., toluene), and ketones. Such solvents typically can be incorporated in amounts sufficient to provide inks having viscosities, as measured on a #2 Zahn cup as known in the art, of at least 15 seconds, such as at least 20 seconds, at least 25 seconds, or from 25 to 35 seconds. In one embodiment, the polyesters have sufficient Tg values to allow thermoformability, and to allow ease of printing onto the graphic art film.

In one embodiment, the graphic art film has at least one property chosen from thermoformability, toughness, clarity, chemical resistance, Tg, and flexibility.

Graphic art films can be used in a variety of applications, such as, for example, in-mold decorated articles, embossed articles, hard-coated articles. The graphic art film can be smooth or textured.

Exemplary graphic art films include, but are not limited to, nameplates; membrane switch overlays (e.g., for an appliance); point of purchase displays; flat or in-mold decorative panels on washing machines; flat touch panels on refrigerators (e.g., capacitive touch pad arrays); flat panel on ovens; decorative interior trim for automobiles (e.g., a polyester laminate); instrument clusters for automobiles; cell phone covers; heating and ventilation control displays; automotive console panels; automotive gear shift panels; control displays or warning signals for automotive instrument panels; facings, dials or displays on household appliances; facings, dials or displays on washing machines; facings, dials or displays on dishwashers; keypads for electronic devices; keypads for mobile phones, personal digital assistants (PDAs, or hand-held computers) or remote controls; displays for electronic devices; displays for hand-held electronic devices such as phones and PDAs; panels and housings for mobile or standard phones; logos on electronic devices; and logos for hand-held phones.

Multiwall film or sheet refers to sheet extruded as a profile consisting of multiple layers that are connected to each other by means of vertical ribs. Examples of multiwall film or sheet include but are not limited to outdoor shelters (for example, greenhouses and commercial canopies).

Examples of extruded articles comprising the polyester compositions useful in this invention include, but are not limited to, thermoformed sheet, film for graphic arts applications, outdoor signs, skylights, multiwall film, plastic film for plastic glass laminates, and liquid crystal display (LCD) films, including but not limited to, diffuser sheets, compensation films, and protective films for LCDs.

Other articles within the scope of the invention comprising the polyester compositions of the invention include but are not limited to safety/sport (examples including but not limited to: safety shields, face shields, sports goggles [racquetball, ski, etc. . . . ], police riot shields); corrugated sheet articles; recreation/outdoor vehicles and devices (examples including but not limited to: lawn tractors, snow mobiles, motorcycle windshield, camper windows, golf cart windshield, jet ski); residential and commercial lighting (examples including but not limited to: diffusers, office, home and commercial fixtures; High Intensity Discharge (HID) Lighting); telecommunications/business equipment/electronics (examples including but not limited to cell phone housing, TV housing, computer housing, stereo housing, PDAs, etc); optical media; tanning beds; multiwall sheet, extruded articles; rigid medical packaging; intravenous components; dialysis filter housing; blood therapy containers; sterilization containers (for example, infant care sterilization containers); pacifiers, tool handles (examples including but not limited to screw drivers, hammer, etc.); thermoplastic articles; sound barriers; automotive exterior (headlight covers, taillight covers, side windows, sunroof); rigid consumer/industrial packaging; tubs; showers; hot tubs; machine guards; vending machine display panels; meters; sports and recreation (examples: swimming pool enclosures, stadium seats, hockey rink, open air structures, ski gondola); fish aquarium; ophthalmic products, decorative block windows; and interior automotive (instrument clusters).

The invention further relates to bottles described herein. The methods of forming the polyesters into bottles are well known in the art. Examples of bottles include but are not limited to bottles such as pharmaceutical bottles, baby bottles; water bottles; juice bottles; large commercial water bottles having a weight from 200 to 800 grams; beverage bottles which include but are not limited to two liter bottles, 20 ounce bottles, 16.9 ounce bottles; medical bottles; personal care bottles, carbonated soft drink bottles; hot fill bottles; water bottles; alcoholic beverage bottles such as beer bottles and wine bottles; and bottles comprising at least one handle. These bottles include but are not limited to injection blow molded bottles, injection stretch blow molded bottles, extrusion blow molded bottles, and extrusion stretch blow molded bottles. Methods of making bottles include but are not limited to extrusion blow molding, extrusion stretch blow molding, injection blow molding, and injection stretch blow molding. In each case, the invention further relates to the preforms (or parisons) used to make each of said bottles.

These bottles include, but are not limited to, injection blow molded bottles, injection stretch blow molded bottles, extrusion blow molded bottles, and extrusion stretch blow molded bottles. Methods of making bottles include but are not limited to extrusion blow molding, extrusion stretch blow molding, thermoforming, injection blow molding, and injection stretch blow molding.

Other examples of containers include, but are not limited to, containers for cosmetics and personal care applications including bottles, jars, vials and tubes; sterilization containers; buffet steam pans; food pans or trays; frozen food trays; microwaveable food trays; hot fill containers, amorphous lids or sheets to seal or cover food trays; food storage containers; for example, boxes; tumblers, pitchers, cups, bowls, including but not limited to those used in restaurant smallware; beverage containers; retort food containers; centrifuge bowls; vacuum cleaner canisters, and collection and treatment canisters.

"Restaurant smallware," as used herein, refers to any container used for eating or serving food. Examples of restaurant smallware include pitchers, cups, mugs optionally including handles (including decorative mugs, single- or double walled mugs, pressurized mugs, vacuum mugs), bowls (e.g.: serving bowls, soup bowls, salad bowls), and plates (e.g., eating and serving plates, such as buffet plates, saucers, dinner plates).

In one embodiment, the containers used as restaurant smallware are capable of withstanding refrigerator temperatures ranging from greater than 0° C. (e.g., 2° C.) to 5° C. In another embodiment, the restaurant smallware containers can withstand steam treatments and/or commercial dishwasher conditions. In another embodiment, the restaurant smallware containers are capable of withstanding microwave conditions. In one embodiment, restaurant smallware containers have at least one property chosen from toughness, clarity, chemical resistance, Tg, hydrolytic stability, and dishwasher stability.

In one embodiment, the medical devices comprising the polyester compositions of the invention include but are not limited to medical devices comprising an ultraviolet light (UV)-curable, silicone-based coating, on at least a portion of a surface of a medical device comprising a polyester comprising a cyclobutanediol, which improves protein resistance and biocompatibility, may be coated on various substrates, and overcomes several difficulties identified in previously disclosed methods.

In one embodiment, the present invention comprises a thermoplastic article, typically in the form of sheet material, having a decorative material embedded therein which comprise any of the compositions described herein.

"Food storage container," as used herein, are capable of storing and/or serving hot and/or cold food and/or beverages at temperatures customarily used for storing and serving foods and beverages, e.g., ranging from deep freezer temperatures to hot temperatures such as those in a low temperature oven or those used in hot beverage dispensers. In one embodiment, the food storage container can be sealed to reduce the rate of food oxidation. In another embodiment, the food storage container can be used to display and serve the food to dining customers. In one embodiment, the food storage containers are capable of being stored in a freezer, e.g., at temperatures less than 0° C., such as temperatures ranging from −20 to 0° C. (e.g., −18° C.). In another embodiment, the food storage containers are capable of storing food in the refrigerator at temperatures ranging from greater than 0° C. (e.g., 2° C.) to 5° C. In another embodiment, the food storage containers can withstand steam treatments and/or commercial dishwasher conditions. In another embodiment, the food storage containers are capable of withstanding microwave conditions.

Examples of food storage containers include buffet steam pans, buffet steam trays, food pans, hot and cold beverage dispensers (e.g. refrigerator beverage dispensers, automated hot or cold beverage dispensers), and food storage boxes.

In one embodiment, food storage containers have at least one additional property chosen from toughness, clarity, chemical resistance, Tg, and hydrolytic stability.

In one embodiment of the invention, there is provided a thermoplastic article which is obtained by applying heat and pressure to one or more laminates or "sandwiches", wherein at least one of said laminates comprises, in order, (1) at least one upper sheet material, (2) at least one decorative material, and (3) at least one lower sheet material. Optionally, an adhesive layer may be used between (1) and (2) and/or between (2) and (3). Any of layers (1), (2) and/or (3) of the "sandwich" may comprise any of the compositions of the invention.

"Ophthalmic product" as used herein, refers to prescription eyeglass lenses, nonprescription eyeglass lenses, sunglass lenses, and eyeglass and sunglass frames.

In one embodiment, the ophthalmic product is chosen from tinted eyeglass lenses and hardcoated eyeglass lenses. In one embodiment, the eyeglass lenses, such as the tinted eyeglass lenses or hardcoated eyeglass lenses, comprise at least one polarizing film or polarizing additive.

In one embodiment, when the product is a lens, the ophthalmic product has a refractive index ranging from 1.54 to 1.56.

In one embodiment, the ophthalmic product can have at least one property chosen from toughness, clarity, chemical resistance (e.g., for withstanding lens cleaners, oils, hair products, etc.), Tg, and hydrolytic stability.

"Outdoor sign," as used herein, refers to a surface formed from the polyester described herein, or containing symbols (e.g., numbers, letters, words, pictures, etc.), patterns, or designs coated with the polyester or polyester film described herein. In one embodiment, the outdoor sign comprises a polyester containing printed symbols, patterns, or designs. In one embodiment, the sign is capable of withstanding typical weather conditions, such as rain, snow, ice, sleet, high humidity, heat, wind, sunlight, or combinations thereof, for a sufficient period of time, e.g., ranging from one day to several years or more.

Exemplary outdoor signs include, but are not limited to, billboards, neon signs, electroluminescent signs, electric signs, fluorescent signs, and light emitting diode (LED) displays. Other exemplary signs include, but are not limited to, painted signs, vinyl decorated signs, thermoformed signs, and hardcoated signs.

In one embodiment, the outdoor sign has at least one property chosen from thermoformability, toughness, clarity, chemical resistance, and Tg.

A "vending machine display panel," as used herein, refers to a front or side panel on a vending machine that allows a customer to view the items for sale, or advertisement regarding such items. In one embodiment, the vending machine display panel can be a visually clear panel of a vending machine through which a consumer can view the items on sale. In other embodiments, the vending machine display panel can have sufficient rigidity to contain the contents within the machine and/or to discourage vandalism and/or theft.

In one embodiment, the vending machine display panel can have dimensions well known in the art, such as planar display panels in snack, beverage, popcorn, or sticker/ticket vending machines, and capsule display panels as in, e.g., gumball machines or bulk candy machines.

In one embodiment, the vending machine display panel can optionally contain advertising media or product identification indicia. Such information can be applied by methods well known in the art, e.g., silk screening.

In one embodiment, the vending machine display panel can be resistant to temperatures ranging from −100 to 120° C. In another embodiment, the vending machine display panel can be UV resistant by the addition of, e.g., at least one UV additive, as disclosed herein.

In one embodiment, the vending machine display panel has at least one property chosen from thermoformability, toughness, clarity, chemical resistance, and Tg.

"Point of purchase display," as used herein, refers to a wholly or partially enclosed casing having at least one visually clear panel for displaying an item. Point of purchase displays are often used in retail stores to for the purpose of catching the eye of the customer. Exemplary point of purchase displays include enclosed wall mounts, countertops, enclosed poster stands, display cases (e.g., trophy display cases), sign frames, and cases for computer disks such as CDs and DVDs. The point of purchase display can include shelves, and additional containers, such as holders for magazines or pamphlets. One of ordinary skill in the art can readily envision the shape and dimensions for the point of purchase display depending on the item to be displayed. For example, the display can be as small as a case for jewelry, or a larger enclosed cabinet for displaying multiple trophies.

In one embodiment, the point of purchase display has at least one property chosen from toughness, clarity, chemical resistance, Tg, and hydrolytic stability.

"Intravenous component," as used herein, refers to components made from a polymeric material used for administering fluids (e.g., medicaments, nutrients) to the bloodstream of a patient. In one embodiment, the intravenous component is a rigid component.

Exemplary intravenous components include y-site connector assemblies, luer components, filters, stopcocks, manifolds, and valves. A y-site connector has a "Y" shape including a first arm having a first passage, a second arm having a second passage, and a third arm connected with said first and second arms and having a third passage communicating with said first and second passages. Luer components can include luer locks, connections, and valves.

In one embodiment, the intravenous component can withstand sterilization treatments, such as high pressure steam sterilization, ethylene oxide gas sterilization, radiation sterilization, and dry-heating sterilization. In one embodiment, the intravenous component has at least one property chosen from toughness, clarity, chemical resistance, Tg, and hydrolytic stability.

A "dialysis filter housing," as used herein, refers to a protective casing having a plurality of openings for holding a plurality of hollow fibers or tubing, which can be used for introducing and discharging a dialyzate to a patient. In one embodiment, a cross-sectional area of one opening in the protective casing ranges from 0.001 $cm^2$ to less than 50 $cm^2$.

In one embodiment, the dialysis filter housing has at least one property chosen from toughness, clarity, chemical resistance, Tg, and hydrolytic stability.

"Blood therapy containers," as used herein, refers to those containers used in administering and withdrawing blood to and from a patient. Exemplary blood therapy containers include oxygenators, cassettes, centrifuge bowls, collection and treatment canisters, pump cartridges, venal port housings, and dialyzer housings. Oxygenators can remove carbon dioxide from the venous blood of the patient, introduce oxygen to the withdrawn blood to convert it into arterial blood, and introduce the oxygenated blood to the patient. Other containers can be used to temporarily house the withdrawn or stored blood prior to its administration to the patient.

In one embodiment, the blood therapy container can withstand sterilization treatments, such as high pressure steam sterilization, ethylene oxide gas sterilization, radiation sterilization, and dry-heating sterilization. In one embodiment, the blood therapy container has at least one property chosen from toughness, clarity, chemical resistance, Tg, and hydrolytic stability.

"Appliance parts," as used herein, refers to a rigid piece used in conjunction with an appliance. In one embodiment, the appliance part is partly or wholly separable from the appliance. In another embodiment, the appliance part is one that is typically made from a polymer. In one embodiment, the appliance part is visually clear.

Exemplary appliance parts include those requiring toughness and durabilty, such as cups and bowls used with food processors, mixers, blenders, and choppers; parts that can withstand refrigerator and freezer temperatures (e.g., refrigerator temperatures ranging from greater than 0° C. (e.g., 2° C.) to 5° C., or freezer temperatures, e.g., at temperatures less than 0° C., such as temperatures ranging from −20 to 0° C., e.g., −18° C.), such as refrigerator and freezer trays, bins, and shelves; parts having sufficient hydrolytic stability at temperatures up to 90° C., such as washing machine doors, steam cleaner canisters, tea kettles, and coffee pots; and vacuum cleaner canisters and dirt cups.

In one embodiment, these appliance parts have at least one property chosen from toughness, clarity, chemical resistance, Tg, hydrolytic stability, and dishwasher stability. The appliance part can also be chosen from steam cleaner canisters, which, in one embodiment, can have at least one property chosen from toughness, clarity, chemical resistance, Tg, and hydrolytic stability.

In one embodiment, the polyester useful in the appliance part has a Tg of 105 to 140° C. and the appliance part is chosen from vacuum cleaner canisters and dirt cups. In another embodiment, the polyester useful in the appliance part has a Tg of 120 to 150° C. and the appliance part is chosen from steam cleaner canisters, tea kettles and coffee pots.

"Skylight," as used herein, refers to a light permeable panel secured to a roof surface such that the panel forms a portion of the ceiling. In one embodiment, the panel is rigid, e.g., has dimensions sufficient to achieve stability and durability, and such dimensions can readily be determined by one skilled in the art. In one embodiment, the skylight panel has a thickness greater than 3/16 inches, such as a thickness of at least 1/2 inches.

In one embodiment, the skylight panel is visually clear. In one embodiment, the skylight panel can transmit at least 35% visible light, at least 50%, at least 75%, at least 80%, at least 90%, or even at least 95% visible light. In another embodiment, the skylight panel comprises at least one UV additive that allows the skylight panel to block up to 80%, 90%, or up to 95% UV light.

In one embodiment, the skylight has at least one property chosen from thermoformability, toughness, clarity, chemical resistance, and Tg.

"Outdoor shelters," as used herein, refer to a roofed and/or walled structure capable of affording at least some protection from the elements, e.g., sunlight, rain, snow, wind, cold, etc., having at least one rigid panel. In one embodiment, the outdoor shelter has at least a roof and/or one or more walls. In one embodiment, the outdoor shelter has dimensions sufficient to achieve stability and durability, and such dimensions can readily be determined by one skilled in the art. In one embodiment, the outdoor shelter panel has a thickness greater than 3/16 inches.

In one embodiment, the outdoor shelter panel is visually clear. In one embodiment, the outdoor shelter panel can transmit at least 35% visible light, at least 50%, at least 75%, at least 80%, at least 90%, or even at least 95% visible light. In another embodiment, the outdoor shelter panel comprises at least one UV additive that allows the outdoor shelter to block up to 80%, 90%, or up to 95% UV light.

Exemplary outdoor shelters include security glazings, transportation shelters (e.g., bus shelters), telephone kiosks, and smoking shelters. In one embodiment, where the shelter is a transportation shelter, telephone kiosk, or smoking shelter, the shelter has at least one property chosen from thermoformability, toughness, clarity, chemical resistance, and Tg. In one embodiment, where the shelter is a security glazing, the shelter has at least one property chosen from toughness, clarity, chemical resistance, and Tg.

A "canopy," as used herein, refers to a roofed structure capable of affording at least some protection from the elements, e.g., sunlight, rain, snow, wind, cold, etc. In one embodiment, the roofed structure comprises, either in whole or in part, at least one rigid panel, e.g., has dimensions sufficient to achieve stability and durability, and such dimensions can readily be determined by one skilled in the art. In one embodiment, the canopy panel has a thickness greater than 3/16 inches, such as a thickness of at least 1/2 inches.

In one embodiment, the canopy panel is visually clear. In one embodiment, the canopy panel can transmit at least 35% visible light, at least 50%, at least 75%, at least 80%, at least 90%, or even at least 95% visible light. In another embodiment, the canopy panel comprises at least one UV additive that allows the canopy to block up to 80%, 90%, or up to 95% UV light.

Exemplary canopies include covered walkways, roof lights, sun rooms, airplane canopies, and awnings. In one embodiment, the canopy has at least one property chosen from toughness, clarity, chemical resistance, Tg, and flexibility.

A "sound barrier," as used herein, refers to a rigid structure capable of reducing the amount of sound transmission from one point on a side of the structure to another point on the other side when compared to sound transmission between two points of the same distance without the sound barrier. The effectiveness in reducing sound transmission can be assessed by methods known in the art. In one embodiment, the amount of sound transmission that is reduced ranges from 25% to 90%.

In another embodiment, the sound barrier can be rated as a sound transmission class value, as described in, for example, ASTM E90, "Standard Test Method for Laboratory Measurement of Airborne Sound Transmission Loss of Building Partitions and Elements," and ASTM E413, "Classification of Rating Sound Insulation." An STC 55 barrier can reduce the sound of a jet engine, ~130 dBA, to 60 dBA, which is the sound level within a typical office. A sound proof room can have a sound level ranging from 0-20 dBA. One of ordinary skill in the art can construct and arrange the sound barrier to achieve a desired STC rating. In one embodiment, the sound barrier has an STC rating of at least 20, such as a rating ranging from 20 to 60.

In one embodiment, the sound barrier comprises a plurality of panels connected and arranged to achieve the desired barrier outline. The sound barriers can be used along streets and highways to dampen automotive noises. Alternatively, the sound barriers can be used in the home or office, either as a discrete panel or panels, or inserted within the architecture of the walls, floors, ceilings, doors, and/or windows.

In one embodiment, the sound barrier is visually clear. In one embodiment, the sound barrier can transmit at least 35% visible light, at least 50%, at least 75%, at least 80%, at least 90%, or even at least 95% visible light. In another embodiment, the sound barrier comprises at least one UV additive that allows the sound barrier to block up to 80%, 90%, or up to 95% UV light.

In one embodiment, the sound barrier has at least one property chosen from toughness, clarity, chemical resistance, and Tg.

A "greenhouse," as used herein, refers to an enclosed structure used for the cultivation and/or protection of plants. In one embodiment, the greenhouse is capable of maintaining a humidity and/or gas (oxygen, carbon dioxide, nitrogen, etc.) content desirable for cultivating plants while being capable of affording at least some protection from the elements, e.g., sunlight, rain, snow, wind, cold, etc. In one embodiment, the roof of the greenhouse comprises, either in whole or in part, at least one rigid panel, e.g., has dimensions sufficient to achieve stability and durability, and such dimensions can readily be determined by one skilled in the art. In one embodiment, the greenhouse panel has a thickness greater than 3/16 inches, such as a thickness of at least ½ inches.

In one embodiment, the greenhouse panel is visually clear. In another embodiment, substantially all of the roof and walls of the greenhouse are visually clear. In one embodiment, the greenhouse panel can transmit at least 35% visible light, at least 50%, at least 75%, at least 80%, at least 90%, or even at least 95% visible light. In another embodiment, the greenhouse panel comprises at least one UV additive that allows the greenhouse panel to block up to 80%, 90%, or up to 95% UV light.

In one embodiment, the greenhouse panel has at least one property chosen from toughness, clarity, chemical resistance, and Tg.

An "optical medium," as used herein, refers to an information storage medium in which information is recorded by irradiation with a laser beam, e.g., light in the visible wavelength region, such as light having a wavelength ranging from 600 to 700 nm. By the irradiation of the laser beam, the irradiated area of the recording layer is locally heated to change its physical or chemical characteristics, and pits are formed in the irradiated area of the recording layer. Since the optical characteristics of the formed pits are different from those of the area having been not irradiated, the digital information is optically recorded. The recorded information can be read by reproducing procedure generally comprising the steps of irradiating the recording layer with the laser beam having the same wavelength as that employed in the recording procedure, and detecting the light-reflection difference between the pits and their periphery.

In one embodiment, the optical medium comprises a transparent disc having a spiral pregroove, a recording dye layer placed in the pregroove on which information is recorded by irradiation with a laser beam, and a light-reflecting layer. The optical medium is optionally recordable by the consumer. In one embodiment, the optical medium is chosen from compact discs (CDs) and digital video discs (DVDs). The optical medium can be sold with prerecorded information, or as a recordable disc.

In one embodiment, at least one of the following comprises the polyester of the invention: the substrate, at least one protective layer of the optical medium, and the recording layer of the optical medium.

In one embodiment, the optical medium has at least one property chosen from toughness, clarity, chemical resistance, Tg, and hydrolytic stability.

"Infant-care sterilization container," as used herein, refers to a container configured to hold infant-care products for use in in-home sterilization of the infant-care products. In one embodiment, the infant-care sterilization container is a baby bottle sterilization container.

In one embodiment, infant-care sterilization containers have at least one additional property chosen from toughness, clarity, chemical resistance, Tg, hydrolytic stability, and dishwasher stability.

"Pacifiers" as used herein, comprise a flexible nipple (e.g., for an infant to suck and/or bite) surrounded by a rigid mouth shield, where the rigid mouth shield is optionally connected to a handle, allowing the infant or supervising adult a convenient structure for gripping and/or holding the pacifier. The handle may be rigid or flexible.

In one embodiment, the pacifier can be made of multiple components. For example, the nipple can pass through an aperture in the center of the mouth shield. The handle may or may not be integrally connected to the mouth shield. The handle can be rigid or flexible.

In another embodiment, the nipple and mouth shield of the pacifier is formed as an integral unit. Generally, the selection of plastic is governed by the need to provide a relatively rigid mount shield and handle. In this embodiment, the nipple of the pacifier may be more rigid yet still be desirable for an infant to suck or bite.

In one embodiment, pacifiers have at least one property chosen from toughness, clarity, chemical resistance, Tg, hydrolytic stability, and dishwasher stability.

A "retort food container," as used herein, refers to flexible container or pouch for storing food and/or beverages, in which the food and/or beverage is hermetically sealed for long-term unrefrigerated storage. The food can be sealed under vacuum or an inert gas. The retort food container can comprise at least one polyester layer, e.g., a single layer or multi-layer container. In one embodiment, a multi-layer container includes a light reflecting inner layer, e.g., a metallized film.

In one embodiment, at least one foodstuff chosen from vegetables, fruit, grain, soups, meat, meat products, dairy products, sauces, dressings, and baking supplies is contained in the retort food container.

In one embodiment, the retort food container has at least one property chosen from toughness, clarity, chemical resistance, Tg, and hydrolytic stability.

A "glass laminate," as used herein, refers to at least one coating on a glass, where at least one of the coatings comprises the polyester. The coating can be a film or a sheet. The glass can be clear, tinted, or reflective. In one embodiment, the laminate is permanently bonded to the glass, e.g., applying the laminate under heat and pressure to form a single, solid laminated glass product. One or both faces of the glass can be laminated. In certain embodiments, the glass laminate contains more than one coating comprising the polyester compositions of the present invention. In other embodiments, the glass laminate comprises multiple glass substrates, and more than one coating comprising the polyester compositions of the present invention.

Exemplary glass laminates include windows (e.g., windows for high rise buildings, building entrances), safety glass, windshields for transportation applications (e.g., automotive, buses, jets, armored vehicles), bullet proof or resistant glass, security glass (e.g., for banks), hurricane proof or resistant glass, airplane canopies, mirrors, solar glass panels, flat panel displays, and blast resistant windows. The glass laminate can be visually clear, be frosted, etched, or patterned.

In one embodiment the glass laminate can be resistant to temperatures ranging from −100 to 120° C. In another embodiment, the glass laminate can be UV resistant by the addition of, e.g., at least one UV additive, as disclosed herein.

Methods for laminating the films and/or sheets of the present invention to the glass are well known to one of ordinary skill in the art. Lamination without the use of an adhesive layer may be performed by vacuum lamination. To obtain an effective bond between the glass layer and the laminate, in one embodiment, the glass has a low surface roughness.

Alternatively, a double-sided adhesive tape, an adhesive layer, or a gelatin layer, obtained by applying, for example, a hotmelt, a pressure- or thermo-sensitive adhesive, or a UV or electron-beam curable adhesive, can be used to bond the laminate of the present invention to the glass. The adhesive layer may be applied to the glass sheet, to the laminate, or to both, and may be protected by a stripping layer, which can be removed just before lamination.

In one embodiment, the glass laminate has at least one property chosen from toughness, clarity, chemical resistance, hydrolytic stability, and Tg.

As used herein, the abbreviation "wt" means "weight".

The following examples further illustrate how the compositions of matter of the invention can be made and evaluated, and are intended to be purely exemplary of the invention and are not intended to limit the scope thereof. Unless indicated otherwise, parts are parts by weight, temperature is in degrees C. or is at room temperature, and pressure is at or near atmospheric.

EXAMPLES

The following examples illustrate in general how a polyester is prepared and the effect of using 2,2,4,4-tetramethyl-1,3-cyclobutanediol (and various cis/trans mixtures) on various polyester properties such as toughness, glass transition temperature, inherent viscosity, etc., compared to polyesters comprising 1,4-cyclohexanedimethanol and/or ethylene glycol residues, but lacking 2,2,4,4-tetramethyl-1,3-cyclobutanediol. Additionally, based on the following examples, the skilled artisan will understand how the thermal stabilizers of the invention can be used in the preparation of polyesters containing them.

Measurement Methods

The inherent viscosity of the polyesters was determined in 60/40 (wt/wt) phenol/tetrachloroethane at a concentration of 0.25 g/50 ml at 25° C., and is reported in dL/g.

Unless stated otherwise, the glass transition temperature ($T_g$) was determined using a TA DSC 2920 instrument from Thermal Analyst Instruments at a scan rate of 20° C./min according to ASTM D3418.

The glycol content and the cis/trans ratio of the compositions were determined by proton nuclear magnetic resonance (NMR) spectroscopy. All NMR spectra were recorded on a JEOL Eclipse Plus 600 MHz nuclear magnetic resonance spectrometer using either chloroform-trifluoroacetic acid (70-30 volume/volume) for polymers or, for oligomeric samples, 60/40(wt/wt) phenol/tetrachloroethane with deuterated chloroform added for lock. Peak assignments for 2,2,4,4-tetramethyl-1,3-cyclobutanediol resonances were made by comparison to model mono- and dibenzoate esters of 2,2,4,4-tetramethyl-1,3-cyclobutanediol. These model compounds closely approximate the resonance positions found in the polymers and oligomers.

The crystallization half-time, $t_{1/2}$, was determined by measuring the light transmission of a sample via a laser and photo detector as a function of time on a temperature controlled hot stage. This measurement was done by exposing the polymers to a temperature, $T_{max}$, and then cooling it to the desired temperature. The sample was then held at the desired temperature by a hot stage while transmission measurements were made as a function of time. Initially, the sample was visually clear with high light transmission and became opaque as the sample crystallized. The crystallization half-time was recorded as the time at which the light transmission was halfway between the initial transmission and the final transmission. $T_{max}$ is defined as the temperature required to melt the crystalline domains of the sample (if crystalline domains are present). The $T_{max}$ reported in the examples below represents the temperature at which each sample was heated to condition the sample prior to crystallization half time measurement. The $T_{max}$ temperature is dependant on composition and is typically different for each polyester. For example, PCT may need to be heated to some temperature greater than 290° C. to melt the crystalline domains.

Density was determined using a gradient density column at 23° C.

The melt viscosity reported herein was measured by using a Rheometrics Dynamic Analyzer (RDA II). The melt viscosity was measured as a function of shear rate, at frequencies ranging from 1 to 400 rad/sec, at the temperatures reported. The zero shear melt viscosity ($\eta_o$) is the melt viscosity at zero shear rate estimated by extrapolating the data by known models in the art. This step is automatically performed by the Rheometrics Dynamic Analyzer (RDA II) software.

The polymers were dried at a temperature ranging from 80 to 100° C. in a vacuum oven for 24 hours and injection molded on a Boy 22S molding machine to give ⅛×½×5-inch and ¼×½×5-inch flexure bars. These bars were cut to a length of 2.5 inch and notched down the ½ inch width with a 10-mil notch in accordance with ASTM D256. The average Izod impact strength at 23° C. was determined from measurements on 5 specimens.

In addition, 5 specimens were tested at various temperatures using 5° C. increments in order to determine the brittle-to-ductile transition temperature. The brittle-to-ductile transition temperature is defined as the temperature at which 50% of the specimens fail in a brittle manner as denoted by ASTM D256.

Color values reported herein are CIELAB L*, a*, and b* values measured following ASTM D 6290-98 and ASTM E308-99, using measurements from a Hunter Lab Ultrascan XE Spectrophotometer (Hunter Associates Laboratory Inc., Reston, Va.) with the following parameters: (1) D65 illuminant, (2) 10 degree observer, (3) reflectance mode with specular angle included, (4) large area view, (5) 1" port size. The measurements were performed on polymer granules ground to pass a 6 mm sieve.

The percent foam in the polyesters of the invention was measured as follows. A 20 mL Headspace Vial supplied by MicroLiter Analytical Supplies, Suwanee, Ga. was placed on laboratory scale, 5 grams of dried polymer was added and the weight was recorded. Water was then carefully added until the vial was full and this weight was then recorded. The difference in weight (wt1) was recorded and used to estimate the vial volume with polymer containing no foam. This value was used for all subsequent runs. For each test, 5 grams of dried polymer sample was added to a clean Headspace Vial. A septum cap was attached to the top of the vial and the vial purged with dry nitrogen gas for approximately one minute. The purge line was removed and a dry nitrogen line equipped with a bubbler was inserted into the septum cap to ensure inert gas at atmospheric (ambient) pressure was maintained in the vial during the heating time. The vial was then placed into a pre-heated 300° C. heating block (drilled out for a loose but close fit for vial) and held in the block for 15 minutes. The vial was then removed and air-cooled on a laboratory bench. After the vial was cooled, the vial top was removed and the vial was placed on a laboratory scale and weighed. Once the weight was recorded, water was carefully added to completely fill the vial. In this context, to completely fill the vial means to add water to the top of vial as judged to be the same height as when determining wt1) and the weight recorded. The difference in these weights (wt2) was calculated. By subtracting wt2 from wt1, the amount of "displaced water" by the foaming of the polymer is determined (wt3=wt1−wt2). It was assumed that for this test the density of water is one, which allows these weights to be converted into volumes, V1=wt1, V2=wt2, and V3=wt3. The "% foam in the polyester" is calculated by the following formula: "% foam in the polymer"=V3/[(5 g polymer/Density of dry polyester in g/mL)+V3]. In this formula, the density of the dry polyesters of the invention comprising about 45 mole % 2,2,4,4-tetramethyl-1,3-cyclobutanediol was 1.17 g/mL. This 1.17 g/mL value did not change significantly for the polyesters tested with a composition in the range from 40% to 50% mol TMCD. The density value for dry polyesters of about 20 mole % TMCD was 1.18 g/mL. The % Foam is a volume % of void volume in the after-test polymer. A visual grade of the final polymer sample after heating and cooling can also be determined.

The amount of tin (Sn) in the examples below is reported in part per million (ppm) of metal and was measured by x-ray fluorescence (xrf) using a PANanalytical Axios Advanced wavelength dispersive x-ray fluorescence spectrometer. The amount of phosphorous is similarly reported as ppm of elemental phosphorus and was also measured by xrf using the same instrument.

10-mil films of selected polyester samples were compression molded using a Carver press at 240° C. Inherent viscosity was measured on these films as described above.

Unless otherwise specified, the cis/trans ratio of the 1,4-cyclohexanedimethanol used in the following examples was approximately 30/70, and could range from 35/65 to 25/75. Unless otherwise specified, the cis/trans ratio of the 2,2,4,4-tetramethyl-1,3-cyclobutanediol used in the following examples was approximately 50/50.

The following abbreviations apply throughout the working examples and figures:

| | |
|---|---|
| TPA | Terephthalic acid |
| DMT | Dimethyl terephthalate |
| TMCD | 2,2,4,4-tetramethyl-1,3-cyclobutanediol |
| CHDM | 1,4-cyclohexanedimethanol |
| IV | Inherent viscosity |
| TPP | Triphenyl phosphate |
| DBTO | Dibutyl tin oxide |
| DMTO | Dimethyl tin oxide |
| $\eta_o$ | Zero shear melt viscosity |
| $T_g$ | Glass transition temperature |
| $T_{bd}$ | Brittle-to-ductile transition temperature |
| $T_{max}$ | Conditioning temperature for crystallization half time measurements |

Example 1

This example illustrates that 2,2,4,4-tetramethyl-1,3-cyclobutanediol is more effective at reducing the crystallization rate of PCT than ethylene glycol or isophthalic acid. In addition, this example illustrates the benefits of 2,2,4,4-tetramethyl-1,3-cyclobutanediol on the glass transition temperature and density.

A variety of copolyesters were prepared as described below. These copolyesters were all made with 200 ppm dibutyl tin oxide as the catalyst in order to minimize the effect of catalyst type and concentration on nucleation during crystallization studies. The cis/trans ratio of the 1,4-cyclohexanedimethanol was 31/69 while the cis/trans ratio of the 2,2,4,4-tetramethyl-1,3-cyclobutanediol is reported in Table 1.

For purposes of this example, the samples had sufficiently similar inherent viscosities thereby effectively eliminating this as a variable in the crystallization rate measurements.

Crystallization half-time measurements from the melt were made at temperatures from 140 to 200° C. at 10° C. increments and are reported in Table 1. The fastest crystallization half-time for each sample was taken as the minimum value of crystallization half-time as a function of temperature, typically occurring around 170 to 180° C. The fastest crystallization half-times for the samples are plotted in FIG. 1 as a function of mole % comonomer modification to PCT.

The data shows that 2,2,4,4-tetramethyl-1,3-cyclobutanediol is more effective than ethylene glycol and isophthalic acid at decreasing the crystallization rate (i.e., increasing the crystallization half-time). In addition, 2,2,4,4-tetramethyl-1,3-cyclobutanediol increases $T_g$ and lowers density.

TABLE 1

Crystallization Half-times (min)

| Example | Comonomer (mol %)[1] | IV (dl/g) | Density (g/ml) | $T_g$ (° C.) | $T_{max}$ (° C.) | at 140° C. (min) | at 150° C. (min) | at 160° C. (min) | at 170° C. (min) | at 180° C. (min) | at 190° C. (min) | at 200° C. (min) |
|---|---|---|---|---|---|---|---|---|---|---|---|---|
| 1A | 20.2% A[2] | 0.630 | 1.198 | 87.5 | 290 | 2.7 | 2.1 | 1.3 | 1.2 | 0.9 | 1.1 | 1.5 |
| 1B | 19.8% B | 0.713 | 1.219 | 87.7 | 290 | 2.3 | 2.5 | 1.7 | 1.4 | 1.3 | 1.4 | 1.7 |
| 1C | 20.0% C | 0.731 | 1.188 | 100.5 | 290 | >180 | >60 | 35.0 | 23.3 | 21.7 | 23.3 | 25.2 |
| 1D | 40.2% A[2] | 0.674 | 1.198 | 81.2 | 260 | 18.7 | 20.0 | 21.3 | 25.0 | 34.0 | 59.9 | 96.1 |
| 1E | 34.5% B | 0.644 | 1.234 | 82.1 | 260 | 8.5 | 8.2 | 7.3 | 7.3 | 8.3 | 10.0 | 11.4 |
| 1F | 40.1% C | 0.653 | 1.172 | 122.0 | 260 | >10 days | >5 days | >5 days | 19204 | >5 days | >5 days | >5 days |
| 1G | 14.3% D | 0.646[3] | 1.188 | 103.0 | 290 | 55.0 | 28.8 | 11.6 | 6.8 | 4.8 | 5.0 | 5.5 |
| 1H | 15.0% E | 0.728[4] | 1.189 | 99.0 | 290 | 25.4 | 17.1 | 8.1 | 5.9 | 4.3 | 2.7 | 5.1 |

[1]The balance of the diol component of the polyesters in Table 1 is 1,4-cyclohexanedimethanol; and the balance of the dicarboxylic acid component of the polyesters in Table 1 is dimethyl terephthalate; if the dicarboxylic acid is not described, it is 100 mole % dimethyl terephthalate.
[2]100 mole % 1,4-cyclohexanedimethanol.
[3]A film was pressed from the ground polyester of Example 1G at 240° C. The resulting film had an inherent viscosity value of 0.575 dL/g.
[4]A film was pressed from the ground polyester of Example 1H at 240° C. The resulting film had an inherent viscosity value of 0.0.652 dL/g.

where:

A is Isophthalic Acid

B is Ethylene Glycol

C is 2,2,4,4-Tetramethyl-1,3-cyclobutanediol (approx. 50/50 cis/trans)

D is 2,2,4,4-Tetramethyl-1,3-cyclobutanediol (98/2 cis/trans)

E is 2,2,4,4-Tetramethyl-1,3-cyclobutanediol (5/95 cis/trans)

As shown in Table 1 and FIG. 1, 2,2,4,4-tetramethyl-1,3-cyclobutanediol is more effective than other comonomers, such ethylene glycol and isophthalic acid, at increasing the crystallization half-time, i.e., the time required for a polymer to reach half of its maximum crystallinity. By decreasing the crystallization rate of PCT (increasing the crystallization half-time), amorphous articles based on 2,2,4,4-tetramethyl-1,3-cyclobutanediol-modified PCT as described herein may be fabricated by methods known in the art. As shown in Table 1, these materials can exhibit higher glass transition temperatures and lower densities than other modified PCT copolyesters.

Preparation of the polyesters shown on Table 1 is described below.

Example 1A

This example illustrates the preparation of a copolyester with a target composition of 80 mol % dimethyl terephthalate residues, 20 mol % dimethyl isophthalate residues, and 100 mol % 1,4-cyclohexanedimethanol residues (28/72 cis/trans).

A mixture of 56.63 g of dimethyl terephthalate, 55.2 g of 1,4-cyclohexanedimethanol, 14.16 g of dimethyl isophthalate, and 0.0419 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 5 minutes and then the temperature was gradually increased to 290° C. over 30 minutes. The reaction mixture was held at 290° C. for 60 minutes and then vacuum was gradually applied over the next 5 minutes until the pressure inside the flask reached 100 mm of Hg. The pressure inside the flask was further reduced to 0.3 mm of Hg over the next 5 minutes. A pressure of 0.3 mm of Hg was maintained for a total time of 90 minutes to remove excess unreacted diols. A high melt viscosity, visually clear and colorless polymer was obtained with a glass transition temperature of 87.5° C. and an inherent viscosity of 0.63 dl/g. NMR analysis showed that the polymer was composed of 100 mol % 1,4-cyclohexanedimethanol residues and 20.2 mol % dimethyl isophthalate residues.

Example 1B

This example illustrates the preparation of a copolyester with a target composition of 100 mol % dimethyl terephthalate residues, 20 mol % ethylene glycol residues, and 80 mol % 1,4-cyclohexanedimethanol residues (32/68 cis/trans).

A mixture of 77.68 g of dimethyl terephthalate, 50.77 g of 1,4-cyclohexanedimethanol, 27.81 g of ethylene glycol, and 0.0433 g of dibutyl tin oxide was placed in a 500-milliliter flask equipped with an inlet for nitrogen, a metal stirrer, and a short distillation column. The flask was placed in a Wood's metal bath already heated to 200° C. The stirring speed was set to 200 RPM throughout the experiment. The contents of the flask were heated at 200° C. for 60 minutes and then the temperature was gradually increased to 210° C. over 5 minutes. The reaction mixture was held at 210° C. for 120 minutes and then heated up to 280° C. in 30 minutes. Once at 280° C., vacuum was gradually applied over the next 5 minutes until the pressure inside the flask reached 100 mm of Hg. The pressure inside the flask was further reduced to 0.3 mm of Hg over the next 10 minutes. A pressure of 0.3 mm of Hg was maintained for a total time of 90 minutes to remove excess unreacted diols. A high melt viscosity, visually clear and colorless polymer was obtained with a glass transition temperature of 87.7° C. and an inherent viscosity of 0.71 dl/g. NMR analysis showed that the polymer was composed of 19.8 mol % ethylene glycol residues.

Example 1C

This example illustrates the preparation of a copolyester with a target composition of 100 mol % dimethyl terephthalate residues, 20 mol % 2,2,4,4-tetramethyl-1,3-cyclobutanediol residues, and 80 mol % 1,4-cyclohexanedimethanol residues (31/69 cis/trans).

A mixture of 77.68 g of dimethyl terephthalate, 48.46 g of 1,4-cyclohexanedimethanol, 17.86 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. This polyester was prepared in a manner similar to that described in Example 1A. A high melt viscosity, visually clear and colorless polymer was obtained with a glass transition temperature of 100.5° C. and an inherent viscosity of 0.73 dl/g. NMR analysis showed that the polymer was composed of 80.5 mol % 1,4-cyclohexanedimethanol residues and 19.5 mol % 2,2,4,4-tetramethyl-1,3-cyclobutanediol residues.

Example 1D

This example illustrates the preparation of a copolyester with a target composition of 100 mol % dimethyl terephthalate residues, 40 mol % dimethyl isophthalate residues, and 100 mol % 1,4-cyclohexanedimethanol residues (28/72 cis/trans).

A mixture of 42.83 g of dimethyl terephthalate, 55.26 g of 1,4-cyclohexanedimethanol, 28.45 g of dimethyl isophthalate, and 0.0419 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 5 minutes and then the temperature was gradually increased to 290° C. over 30 minutes. The reaction mixture was held at 290° C. for 60 minutes and then vacuum was gradually applied over the next 5 minutes until the pressure inside the flask reached 100 mm of Hg. The pressure inside the flask was further reduced to 0.3 mm of Hg over the next 5 minutes. A pressure of 0.3 mm of Hg was maintained for a total time of 90 minutes to remove excess unreacted diols. A high melt viscosity, visually clear and colorless polymer was obtained with a glass transition temperature of 81.2° C. and an inherent viscosity of 0.67 dl/g. NMR analysis showed that the polymer was composed of 100 mol % 1,4-cyclohexanedimethanol residues and 40.2 mol % dimethyl isophthalate residues.

Example 1E

This example illustrates the preparation of a copolyester with a target composition of 100 mol % dimethyl terephthalate residues, 40 mol % ethylene glycol residues, and 60 mol % 1,4-cyclohexanedimethanol residues (31/69 cis/trans).

A mixture of 81.3 g of dimethyl terephthalate, 42.85 g of 1,4-cyclohexanedimethanol, 34.44 g of ethylene glycol, and 0.0419 g of dibutyl tin oxide was placed in a 500-milliliter flask equipped with an inlet for nitrogen, a metal stirrer, and a short distillation column. The flask was placed in a Wood's metal bath already heated to 200° C. The stirring speed was set to 200 RPM throughout the experiment. The contents of the flask were heated at 200° C. for 60 minutes and then the temperature was gradually increased to 210° C. over 5 minutes. The reaction mixture was held at 210° C. for 120 minutes and then heated up to 280° C. in 30 minutes. Once at 280° C., vacuum was gradually applied over the next 5 minutes until the pressure inside the flask reached 100 mm of Hg. The pressure inside the flask was further reduced to 0.3 mm of Hg over the next 10 minutes. A pressure of 0.3 mm of Hg was maintained for a total time of 90 minutes to remove excess unreacted diols. A high melt viscosity, visually clear and colorless polymer was obtained with a glass transition temperature of 82.1° C. and an inherent viscosity of 0.64 dl/g. NMR analysis showed that the polymer was composed of 34.5 mol % ethylene glycol residues.

Example 1F

This example illustrates the preparation of a copolyester with a target composition of 100 mol % dimethyl terephthalate residues, 40 mol % 2,2,4,4-tetramethyl-1,3-cyclobutanediol residues, and 60 mol % 1,4-cyclohexanedimethanol residues (31/69 cis/trans).

A mixture of 77.4 g of dimethyl terephthalate, 36.9 g of 1,4-cyclohexanedimethanol, 32.5 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 3 minutes and then the temperature was gradually increased to 260° C. over 30 minutes. The reaction mixture was held at 260° C. for 120 minutes and then heated up to 290° C. in 30 minutes. Once at 290° C., vacuum was gradually applied over the next 5 minutes until the pressure inside the flask reached 100 mm of Hg. The pressure inside the flask was further reduced to 0.3 mm of Hg over the next 5 minutes. A pressure of 0.3 mm of Hg was maintained for a total time of 90 minutes to remove excess unreacted diols. A high melt viscosity, visually clear and colorless polymer was obtained with a glass transition temperature of 122° C. and an inherent viscosity of 0.65 dl/g. NMR analysis showed that the polymer was composed of 59.9 mol % 1,4-cyclohexanedimethanol residues and 40.1 mol % 2,2,4,4-tetramethyl-1,3-cyclobutanediol residues.

Example 1G

This example illustrates the preparation of a copolyester with a target composition of 100 mol % dimethyl terephthalate residues, 20 mol % 2,2,4,4-tetramethyl-1,3-cyclobutanediol residues (98/2 cis/trans), and 80 mol % 1,4-cyclohexanedimethanol residues (31/69 cis/trans).

A mixture of 77.68 g of dimethyl terephthalate, 48.46 g of 1,4-cyclohexanedimethanol, 20.77 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 3 minutes and then the temperature was gradually increased to 260° C. over 30 minutes. The reaction mixture was held at 260° C. for 120 minutes and then heated up to 290° C. in 30 minutes. Once at 290° C., vacuum was gradually applied over the next 5 minutes until the pressure inside the flask reached 100 mm of Hg and the stirring speed was also reduced to 100 RPM. The pressure inside the flask was further reduced to 0.3 mm of Hg over the next 5 minutes and the stirring speed was reduced to 50 RPM. A pressure of 0.3 mm of Hg was maintained for a total time of 60 minutes to remove excess unreacted diols. A high melt viscosity, visually clear and colorless polymer was obtained with a glass transition temperature of 103° C. and an inherent viscosity of 0.65 dl/g. NMR analysis showed that the polymer was composed of 85.7 mol % 1,4-cyclohexanedimethanol residues and 14.3 mol % 2,2,4,4-tetramethyl-1,3-cyclobutanediol residues.

Example 1H

This example illustrates the preparation of a copolyester with a target composition of 100 mol % dimethyl terephthalate residues, 20 mol % 2,2,4,4-tetramethyl-1,3-cyclobutanediol residues (5/95 cis/trans), and 80 mol % 1,4-cyclohexanedimethanol residues (31/69 cis/trans).

A mixture of 77.68 g of dimethyl terephthalate, 48.46 g of 1,4-cyclohexanedimethanol, 20.77 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM at the beginning of the experiment. The contents of the flask were heated at 210° C. for 3 minutes and then the temperature was gradually increased to 260° C. over 30 minutes. The reaction mixture was held at 260° C. for 120 minutes and then heated up to 290° C. in 30 minutes. Once at 290° C., vacuum was gradually applied over the next 5 minutes with a set point of 100 mm of Hg and the stirring speed was also reduced to 100 RPM. The pressure inside the flask was further reduced to a set point of 0.3 mm of Hg over the next 5 minutes and the stirring speed was reduced to 50 RPM. This pressure was maintained for a total time of 60 minutes to remove excess unreacted diols. It was noted that the vacuum system failed to reach the set point mentioned above, but produced enough vacuum to produce a high melt viscosity, visually clear and colorless polymer with a glass transition temperature of 99° C. and an inherent viscosity of 0.73 dl/g. NMR analysis showed that the polymer was composed of 85 mol % 1,4-cyclohexanedimethanol residues and 15 mol % 2,2,4,4-tetramethyl-1,3-cyclobutanediol residues.

Example 2

This example illustrates that 2,2,4,4-tetramethyl-1,3-cyclobutanediol improves the toughness of PCT-based copolyesters (polyesters containing terephthalic acid and 1,4-cyclohexanedimethanol).

Copolyesters based on 2,2,4,4-tetramethyl-1,3-cyclobutanediol were prepared as described below. The cis/trans ratio of the 1,4-cyclohexanedimethanol was approximately 31/69 for all samples. Copolyesters based on ethylene glycol and 1,4-cyclohexanedimethanol were commercial polyesters. The copolyester of Example 2A (Eastar PCTG 5445) was obtained from Eastman Chemical Co. The copolyester of Example 2B was obtained from Eastman Chemical Co. under the trade name Spectar. Example 2C and Example 2D were prepared on a pilot plant scale (each a 15-lb batch) following an adaptation of the procedure described in Example 1A and having the inherent viscosities and glass transition temperatures described in Table 2 below. Example 2C was prepared with a target tin amount of 300 ppm (Dibutyltin Oxide). The final product contained 295 ppm tin. The color values for the polyester of Example 2C were L*=77.11; a*=−1.50; and b*=5.79. Example 2D was prepared with a target tin amount of 300 ppm (Dibutyltin Oxide). The final product contained 307 ppm tin. The color values for the polyester of Example 2D were L*=66.72; a*=−1.22; and b*=16.28.

Materials were injection molded into bars and subsequently notched for Izod testing. The notched Izod impact strengths were obtained as a function of temperature and are also reported in Table 2.

For a given sample, the Izod impact strength undergoes a major transition in a short temperature span. For instance, the Izod impact strength of a copolyester based on 38 mol % ethylene glycol undergoes this transition between 15 and 20° C. This transition temperature is associated with a change in failure mode; brittle/low energy failures at lower temperatures and ductile/high energy failures at higher temperatures. The transition temperature is denoted as the brittle-to-ductile transition temperature, $T_{bd}$, and is a measure of toughness. $T_{bd}$ is reported in Table 2 and plotted against mol % comonomer in FIG. 2.

The data shows that adding 2,2,4,4-tetramethyl-1,3-cyclobutanediol to PCT lowers $T_{bd}$ and improves the toughness, as compared to ethylene glycol, which increases $T_{bd}$ of PCT.

TABLE 2

Notched Izod Impact Energy (ft-lb/in)

| Example | Comonomer (mol %)[1] | IV (dl/g) | $T_g$ (° C.) | $T_{bd}$ (° C.) | at −20° C. | at −15° C. | at −10° C. | at −5° C. | at 0° C. | at 5° C. | at 10° C. | at 15° C. | at 20° C. | at 25° C. | at 30° C. |
|---|---|---|---|---|---|---|---|---|---|---|---|---|---|---|---|
| 2A | 38.0% B | 0.68 | 86 | 18 | NA | NA | NA | 1.5 | NA | NA | 1.5 | 1.5 | 32 | 32 | NA |
| 2B | 69.0% B | 0.69 | 82 | 26 | NA | NA | NA | NA | NA | NA | 2.1 | NA | 2.4 | 13.7 | 28.7 |
| 2C | 22.0% C | 0.66 | 106 | −5 | 1.5 | NA | 12 | 23 | 23 | NA | 23 | NA | NA | NA | NA |
| 2D | 42.8% C | 0.60 | 133 | −12 | 2.5 | 2.5 | 11 | NA | 14 | NA | NA | NA | NA | NA | NA |

[1]The balance of the glycol component of the polyesters in the Table is 1,4-cyclohexanedimethanol. All polymers were prepared from 100 mole % dimethyl terephthalate.
NA = Not available.
where:
B is Ethylene glycol
C is 2,2,4,4-Tetramethyl-1,3-cyclobutanediol (50/50 cis/trans)

Example 3

This example illustrates that 2,2,4,4-tetramethyl-1,3-cyclobutanediol can improve the toughness of PCT-based copolyesters (polyesters containing terephthalic acid and 1,4-cyclohexanedimethanol). Polyesters prepared in this example comprise from 15 to 25 mol % of 2,2,4,4-tetramethyl-1,3-cyclobutanediol residues.

Copolyesters based on dimethyl terephthalate, 2,2,4,4-tetramethyl-1,3-cyclobutanediol, and 1,4-cyclohexanedimethanol were prepared as described below, having the composition and properties shown on Table 3. The balance up to 100 mol % of the diol component of the polyesters in Table 3 was 1,4-cyclohexanedimethanol (31/69 cis/trans).

Materials were injection molded into both 3.2 mm and 6.4 mm thick bars and subsequently notched for Izod impact testing. The notched Izod impact strengths were obtained at 23° C. and are reported in Table 3. Density, Tg, and crystallization halftime were measured on the molded bars. Melt viscosity was measured on pellets at 290° C.

TABLE 3

Compilation of various properties for certain polyesters useful in the invention

| Example | TMCD mole % | % cis TMCD | Pellet IV (dl/g) | Molded Bar IV (dl/g) | Notched Izod of 3.2 mm thick bars at 23° C. (J/m) | Notched Izod of 6.4 mm thick bars at 23° C. (J/m) | Specific Gravity (g/mL) | Tg (° C.) | Crystallization Halftime from melt at 170° C. (min) | Melt Viscosity at 1 rad/sec at 290° C. (Poise) |
|---|---|---|---|---|---|---|---|---|---|---|
| A | 15 | 48.8 | 0.736 | 0.707 | 1069 | 878 | 1.184 | 104 | 15 | 5649 |
| B | 18 | NA | 0.728 | 0.715 | 980 | 1039 | 1.183 | 108 | 22 | 6621 |
| C | 20 | NA | 0.706 | 0.696 | 1006 | 1130 | 1.182 | 106 | 52 | 6321 |

TABLE 3-continued

Compilation of various properties for certain polyesters useful in the invention

| Example | TMCD mole % | % cis TMCD | Pellet IV (dl/g) | Molded Bar IV (dl/g) | Notched Izod of 3.2 mm thick bars at 23° C. (J/m) | Notched Izod of 6.4 mm thick bars at 23° C. (J/m) | Specific Gravity (g/mL) | Tg (° C.) | Crystallization Halftime from melt at 170° C. (min) | Melt Viscosity at 1 rad/sec at 290° C. (Poise) |
|---|---|---|---|---|---|---|---|---|---|---|
| D | 22 | NA | 0.732 | 0.703 | 959 | 988 | 1.178 | 108 | 63 | 7161 |
| E | 21 | NA | 0.715 | 0.692 | 932 | 482 | 1.179 | 110 | 56 | 6162 |
| F | 24 | NA | 0.708 | 0.677 | 976 | 812 | 1.180 | 109 | 58 | 6282 |
| G | 23 | NA | 0.650 | 0.610 | 647 | 270 | 1.182 | 107 | 46 | 3172 |
| H | 23 | 47.9 | 0.590 | 0.549 | 769 | 274 | 1.181 | 106 | 47 | 1736 |
| I | 23 | 48.1 | 0.531 | 0.516 | 696 | 352 | 1.182 | 105 | 19 | 1292 |
| J | 23 | 47.8 | 0.364 | NA | NA | NA | NA | 98 | NA | 167 |

NA = Not available.

Example 3A 21.24 lb (49.71 gram-mol) dimethyl terephthalate, 14.34 lb (45.21 gram-mol) 1,4-cyclohexanedimethanol, and 4.58 lb (14.44 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and at a pressure of 20 psig. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to <1 mm of Hg. The reaction mixture was held at 290° C. and at a pressure of <1 mm of Hg until the power draw to the agitator no longer increased (70 minutes). The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.736 dL/g and a Tg of 104° C. NMR analysis showed that the polymer was composed of 85.4 mol % 1,4-cyclohexanedimethanol residues and 14.6 mol % 2,2,4,4-tetramethyl-1,3-cyclobutanediol residues. The polymer had color values of: V=78.20, a*=−1.62, and b*=6.23.

Example 3B to Example 3D

The polyesters described in Example 3B to Example 3D were prepared following a procedure similar to the one described for Example 3A. The composition and properties of these polyesters are shown in Table 3.

Example 3E 21.24 lb (49.71 gram-mol) dimethyl terephthalate, 12.61 lb (39.77 gram-mol) 1,4-cyclohexanedimethanol, and 6.30 lb (19.88 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to <1 mm of Hg. The reaction mixture was held at 290° C. and at a pressure of <1 mm of Hg for 60 minutes. The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.715 dL/g and a Tg of 110° C. X-ray analysis showed that the polyester had 223 ppm tin. NMR analysis showed that the polymer was composed of 78.6 mol % 1,4-cyclohexanedimethanol residues and 21.4 mol % 2,2,4,4-tetramethyl-1,3-cyclobutanediol residues. The polymer had color values of: V=76.45, a*=−1.65, and b*=6.47.

Example 3F

The polyester described in Example 3F was prepared following a procedure similar to the one described for Example 3A. The composition and properties of this polyester are shown in Table 3.

Example 3H 21.24 lb (49.71 gram-mol) dimethyl terephthalate, 12.61 lb (39.77 gram-mol) 1,4-cyclohexanedimethanol, and 6.30 lb (19.88 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to <1 mm of Hg. The reaction mixture was held at 290° C. and at a pressure of <1 mm of Hg for 12 minutes. The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.590 dL/g and a Tg of 106° C. NMR analysis showed that the polymer was composed of 77.1 mol % 1,4-cyclohexanedimethanol residues and 22.9 mol % 2,2,4,4-tetramethyl-1,3-cyclobutanediol residues. The polymer had color values of: V=83.27, a*=−1.34, and b*=5.08.

Example 3I 21.24 lb (49.71 gram-mol) dimethyl terephthalate, 12.61 lb (39.77 gram-mol) 1,4-cyclohexanedimethanol, and 6.30 lb (19.88 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to 4 mm of Hg. The reaction mixture was held at 290° C. and at a pressure of 4 mm of Hg for 30 minutes. The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.531 dL/g and a Tg of 105° C. NMR analysis showed that the polymer was composed of 76.9 mol % 1,4-cyclohexanedimethanol residues and 23.1 mol % 2,2,4,4-tetramethyl-1,3-cyclobutanediol residues. The polymer had color values of: L*=80.42, a*=−1.28, and b*=5.13.

20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to 4 mm of Hg. When the reaction mixture temperature was 290° C. and the pressure was 4 mm of Hg, the pressure of the pressure vessel was immediately increased to 1 atmosphere using nitrogen gas. The molten polymer was then extruded from the pressure vessel. The cooled, extruded polymer was ground to pass a 6-mm screen. The polymer had an inherent viscosity of 0.364 dL/g and a Tg of 98° C. NMR analysis showed that the polymer was composed of 77.5 mol % 1,4-cyclohexanedimethanol residues and 22.5 mol % 2,2,4,4-tetramethyl-1,3-cyclobutanediol residues. The polymer had color values of: V=77.20, a*=−1.47, and b*=4.62.

Example 4

This example illustrates that 2,2,4,4-tetramethyl-1,3-cyclobutanediol can improve the toughness of PCT-based copolyesters(polyesters containing terephthalic acid and 1,4-cyclohexanedimethanol). Polyesters prepared in this example fall comprise more than 25 to less than 40 mol % of 2,2,4,4-tetramethyl-1,3-cyclobutanediol residues.

Copolyesters based on dimethyl terephthalate, 2,2,4,4-tetramethyl-1,3-cyclobutanediol, and 1,4-cyclohexanedimethanol (31/69 cis/trans) were prepared as described below, having the composition and properties shown on Table 4. The balance up to 100 mol % of the diol component of the polyesters in Table 4 was 1,4-cyclohexanedimethanol (31/69 cis/trans).

Materials were injection molded into both 3.2 mm and 6.4 mm thick bars and subsequently notched for Izod impact testing. The notched Izod impact strengths were obtained at 23° C. and are reported in Table 4. Density, Tg, and crystallization halftime were measured on the molded bars. Melt viscosity was measured on pellets at 290° C.

TABLE 4

Compilation of various properties for certain polyesters useful in the invention

| Example | TMCD mole % | % cis TMCD | Pellet IV (dl/g) | Molded Bar IV (dl/g) | Notched Izod of 3.2 mm thick bars at 23° C. (J/m) | Notched Izod of 6.4 mm thick bars at 23° C. (J/m) | Specific Gravity (g/mL) | Tg (° C.) | Crystallization Halftime from melt at 170° C. (min) | Melt Viscosity at 1 rad/sec at 290° C. (Poise) |
|---|---|---|---|---|---|---|---|---|---|---|
| A | 27 | 47.8 | 0.714 | 0.678 | 877 | 878 | 1.178 | 113 | 280 | 8312 |
| B | 31 | NA | 0.667 | 0.641 | 807 | 789 | 1.174 | 116 | 600 | 6592 |

NA = Not available.

Example 3J 21.24 lb (49.71 gram-mol) dimethyl terephthalate, 12.61 lb (39.77 gram-mol) 1,4-cyclohexanedimethanol, and 6.30 lb (19.88 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and Example 4A 21.24 lb (49.71 gram-mol) dimethyl terephthalate, 11.82 lb (37.28 gram-mol) 1,4-cyclohexanedimethanol, and 6.90 lb (21.77 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The temperature of the reaction mixture was then increased to 270° C. and the pressure was decreased to 90 mm of Hg. After a 1 hour hold time at 270° C. and 90 mm of Hg, the agitator speed was decreased to 15 RPM, the reaction mixture temperature was increased to 290° C., and the pressure was decreased to <1 mm of Hg. The reaction mixture was held at 290° C. and at a pressure of <1 mm of Hg until the power draw to the agitator no longer increased (50 minutes). The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.714 dL/g and a Tg of 113° C. NMR analysis showed that the polymer was composed of 73.3 mol % 1,4-cyclohexanedimethanol residues and 26.7 mol % 2,2,4,4-tetramethyl-1,3-cyclobutanediol residues.

Example 4B

The polyester of Example 4B was prepared following a procedure similar to the one described for Example 4A. The composition and properties of this polyester are shown in Table 4.

Example 5

This example illustrates that 2,2,4,4-tetramethyl-1,3-cyclobutanediol can improve the toughness of PCT-based copolyesters(polyesters containing terephthalic acid and 1,4-cyclohexanedimethanol).

A copolyester based on dimethyl terephthalate, 2,2,4,4-tetramethyl-1,3-cyclobutanediol, and 1,4-cyclohexanedimethanol was prepared as described below, having the composition and properties shown on Table 5. The balance up to 100 mol % of the diol component of the polyesters in Table 5 was 1,4-cyclohexanedimethanol (31/69 cis/trans).

The polyester was injection molded into both 3.2 mm and 6.4 mm thick bars and subsequently notched for Izod impact testing. The notched Izod impact strengths were obtained at 23° C. and are reported in Table 5. Density, Tg, and crystallization halftime were measured on the molded bars. Melt viscosity was measured on pellets at 290° C.

was increased to 250° C. and the pressure was increased to 20 psig. The reaction mixture was held for 2 hours at 250° C. and 20 psig pressure. The pressure was then decreased to 0 psig at a rate of 3 psig/minute. Then the agitator speed was decreased to 15 RPM, the temperature of the reaction mixture was then increased to 290° C. and the pressure was decreased to 2 mm of Hg. The reaction mixture was held at 290° C. and at a pressure of 2 mm of Hg until the power draw to the agitator no longer increased (80 minutes). The pressure of the pressure vessel was then increased to 1 atmosphere using nitrogen gas. The molten polymer was then extruded from the pressure vessel. The cooled, extruded polymer was ground to pass a 6-mm screen. The polymer had an inherent viscosity of 0.657 dL/g and a Tg of 119° C. NMR analysis showed that the polymer was composed of 56.3 mol % 1,4-cyclohexanedimethanol residues and 43.7 mol % 2,2,4,4-tetramethyl-1,3-cyclobutanediol residues. The polymer had color values of: V=75.04, a*=−1.82, and b*=6.72.

Example 6

Comparative Example

This example shows data for comparative materials are shown in Table 6. The PC was Makrolon 2608 from Bayer, with a nominal composition of 100 mole % bisphenol A residues and 100 mole % diphenyl carbonate residues. Makrolon 2608 has a nominal melt flow rate of 20 grams/10 minutes measured at 300 C using a 1.2 kg weight. The PET was Eastar 9921 from Eastman Chemical Company, with a nominal composition of 100 mole % terephthalic acid, 3.5 mole % cyclohexanedimethanol (CHDM) and 96.5 mole % ethylene glycol. The PETG was Eastar 6763 from Eastman Chemical Company, with a nominal composition of 100 mole % terephthalic acid, 31 mole % cyclohexanedimethanol (CHDM) and 69 mole % ethylene glycol. The PCTG was Eastar DN001 from Eastman Chemical Company, with a nominal composition of 100 mole % terephthalic acid, 62 mole % cyclohexanedimethanol (CHDM) and 38 mole % ethylene glycol. The PCTA was Eastar AN001 from Eastman Chemical Company, with a nominal composition of 65 mole % terephthalic acid, 35 mole % isophthalic acid and 100 mole % cyclohexanedimethanol (CHDM). The Polysul-

TABLE 5

Compilation of various properties for certain polyesters useful in the invention

| Example | TMCD mole % | % cis TMCD | Pellet IV (dl/g) | Molded Bar IV (dl/g) | Notched Izod of 3.2 mm thick bars at 23° C. (J/m) | Notched Izod of 6.4 mm thick bars at 23° C. (J/m) | Specific Gravity (g/mL) | Tg (° C.) | Crystallization Halftime from melt at 170° C. (min) | Melt Viscosity at 1 rad/sec at 290° C. (Poise) |
|---|---|---|---|---|---|---|---|---|---|---|
| A | 44 | 46.2 | 0.657 | 0.626 | 727 | 734 | 1.172 | 119 | NA | 9751 |

NA = Not available.

Example 5A 21.24 lb (49.71 gram-mol) dimethyl terephthalate, 8.84 lb (27.88 gram-mol) 1,4-cyclohexanedimethanol, and 10.08 lb (31.77 gram-mol) 2,2,4,4-tetramethyl-1,3-cyclobutanediol were reacted together in the presence of 200 ppm of the catalyst butyltin tris(2-ethylhexanoate). The reaction was carried out under a nitrogen gas purge in an 18-gallon stainless steel pressure vessel fitted with a condensing column, a vacuum system, and a HELICONE-type agitator. With the agitator running at 25 RPM, the reaction mixture temperature fone was Udel 1700 from Solvay, with a nominal composition of 100 mole % bisphenol A residues and 100 mole % 4,4-dichlorosulfonyl sulfone residues. Udel 1700 has a nominal melt flow rate of 6.5 grams/10 minutes measured at 343 C using a 2.16 kg weight. The SAN was Lustran 31 from Lanxess, with a nominal composition of 76 weight % styrene and 24 weight % acrylonitrile. Lustran 31 has a nominal melt flow rate of 7.5 grams/10 minutes measured at 230 C using a 3.8 kg weight. The examples of the invention show improved toughness in 6.4 mm thickness bars compared to all of the other resins.

TABLE 6

| | | | Notched Izod of | Notched Izod of | | | Crystallization |
| | | Pellet | Molded | 3.2 mm thick | 6.4 mm thick | Specific | | Halftime from |
| | Polymer | IV | Bar IV | bars at 23° C. | bars at 23° C. | Gravity | Tg | melt |
| Example | name | (dl/g) | (dl/g) | (J/m) | (J/m) | (g/mL) | (° C.) | (min) |
|---|---|---|---|---|---|---|---|---|
| A | PC | 12 MFR | NA | 929 | 108 | 1.20 | 146 | NA |
| B | PCTG | 0.73 | 0.696 | NB | 70 | 1.23 | 87 | 30 at 170° C. |
| C | PCTA | 0.72 | 0.702 | 98 | 59 | 1.20 | 87 | 15 at 150° C. |
| D | PETG | 0.75 | 0.692 | 83 | 59 | 1.27 | 80 | 2500 at 130° C. |
| E | PET | 0.76 | 0.726 | 45 | 48 | 1.33 | 78 | 1.5 at 170° C. |
| F | SAN | 7.5 MFR | NA | 21 | NA | 1.07 | ~110 | NA |
| G | PSU | 6.5 MFR | NA | 69 | NA | 1.24 | ~190 | NA |

NA = Not available

Example 7

This example illustrates the effect of the amount of 2,2,4,4-tetramethyl-1,3-cyclobutanediol used for the preparation of the polyesters of the invention on the glass transition temperature of the polyesters. Polyesters prepared in this example comprise from 15 to 25 mol % of 2,2,4,4-tetramethyl-1,3-cyclobutanediol residues.

Example 7A to Example 7G

Dimethyl terephthalate, 1,4-cyclohexanedimethanol, and 2,2,4,4-tetramethyl-1,3-cyclobutanediol were weighed into a 500-ml single neck round bottom flask. NMR analysis on the 2,2,4,4-tetramethyl-1,3-cyclobutanediol starting material showed a cis/trans ratio of 53/47. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 20 mol %.

Inherent viscosities were measured as described in the "Measurement Methods" section above. The compositions of the polyesters were determined by $^1$H NMR as explained before in the Measurement Methods section. The glass transition temperatures were determined by DSC, using the second heat after quench at a rate of 20° C./min.

Example 7H to Example 7Q

These polyesters were prepared by carrying out the ester exchange and polycondensation reactions in separate stages. The ester exchange experiments were conducted in a continuous temperature rise (CTR) reactor. The CTR was a 3000 ml glass reactor equipped with a single shaft impeller blade agitator, covered with an electric heating mantle and fitted with a heated packed reflux condenser column. The reactor was charged with 777 g (4 moles) of dimethyl terephthalate, 230 g (1.6 moles) of 2,2,4,4-tetramethyl-1,3,-cyclobutanediol, 460.8 g (3.2 moles) of cyclohexane dimethanol and 1.12 g of butyltin tris-2-ethylhexanoate (such that there will be 200 ppm tin metal in the final polymer). The heating mantle was set manually to 100% output. The set points and data collection were facilitated by a Camile process control system. Once the reactants were melted, stirring was initiated and slowly increased to 250 rpm. The temperature of the reactor gradually increased with run time. The weight of methanol collected was recorded via balance. The reaction was stopped when methanol evolution stopped or at a pre-selected lower temperature of 260° C. The oligomer was discharged with a nitrogen purge and cooled to room temperature. The oligomer was frozen with liquid nitrogen and broken into pieces small enough to be weighed into a 500 ml round bottom flask.

In the polycondensation reactions, a 500 ml round bottom flask was charged with approximately 150 g of the oligomer prepared above. The flask was equipped with a stainless steel stirrer and polymer head. The glassware was set up on a half mole polymer rig and the Camile sequence was initiated. The stirrer was positioned one full turn from the flask bottom once the oligomer melted. The temperature/pressure/stir rate sequence controlled by the Camile software for each example is reported in the following tables.

Camile Sequence for Example 7H and Example 7I

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 290 | 6 | 25 |

Camile Sequence for Example 7N to Example 7Q

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 3 | 25 |
| 7 | 110 | 290 | 3 | 25 |

Camile Sequence for Example 7K and Example 7L

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 2 | 25 |
| 7 | 110 | 290 | 2 | 25 |

Camile Sequence for Example 7J and Example 7M

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 1 | 25 |
| 7 | 110 | 290 | 1 | 25 |

The resulting polymers were recovered from the flask, chopped using a hydraulic chopper, and ground to a 6 mm screen size. Samples of each ground polymer were submitted for inherent viscosity in 60/40 (wt/wt) phenol/tetrachloroethane at a concentration of 0.5 g/100 ml at 25° C., catalyst level (Sn) by x-ray fluorescence, and color (L*, a*, b*) by transmission spectroscopy. Polymer composition was obtained by $^1$H NMR. Samples were submitted for thermal stability and melt viscosity testing using a Rheometrics Mechanical Spectrometer (RMS-800).

Figure 3:
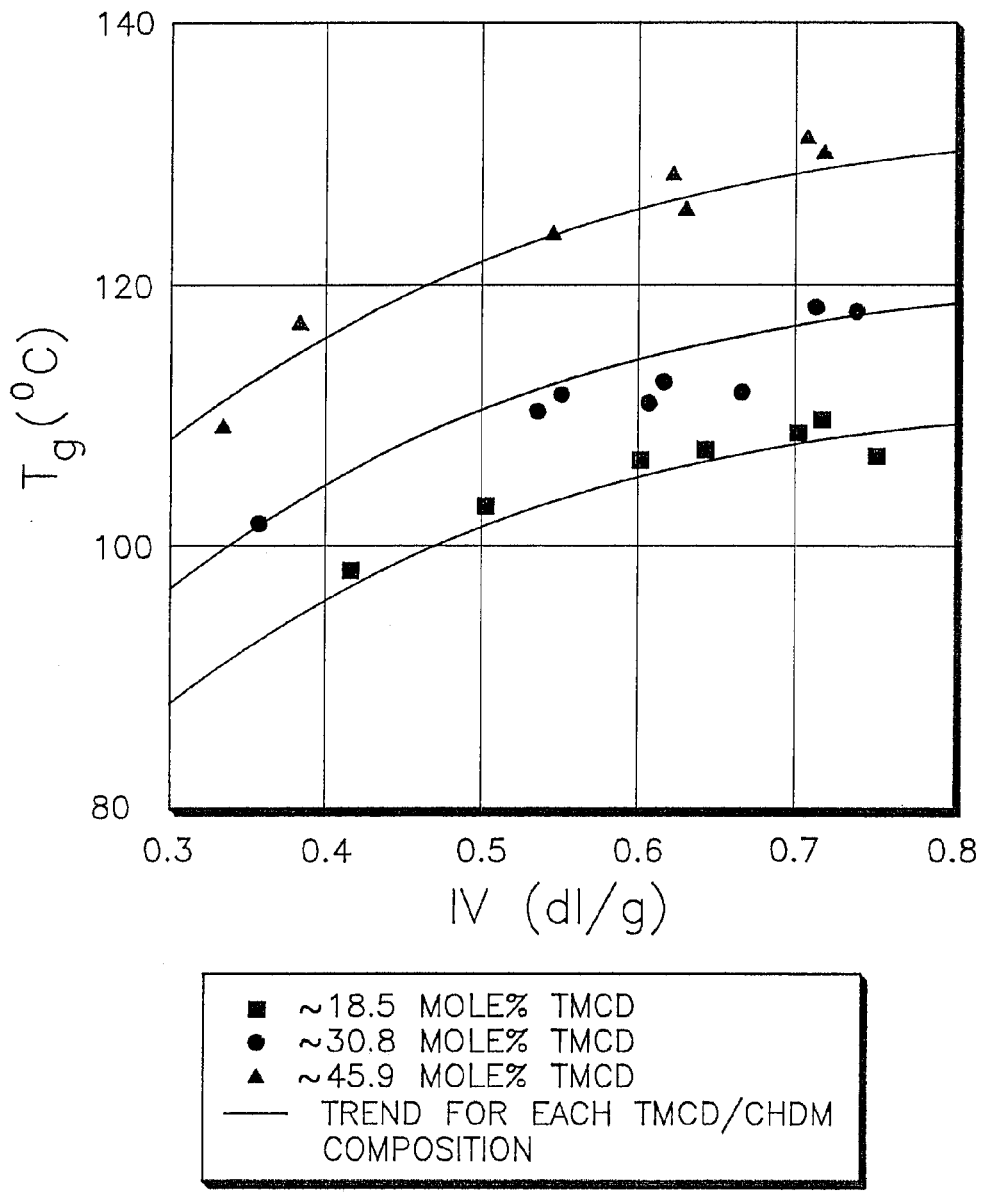
FIG. 3 is a graph showing the effect of 2,2,4,4-tetramethyl-1,3-cyclobutanediol composition on the glass transition temperature (Tg) of the copolyester.

The table below shows the experimental data for the polyesters of this example. The data shows that an increase in the level of 2,2,4,4-tetramethyl-1,3-cyclobutanediol raises the glass transition temperature in an almost linear fashion, for a constant inherent viscosity. FIG. 3 also shows the dependence of Tg on composition and inherent viscosity.

TABLE 7

Glass transition temperature as a function of inherent viscosity and composition

| Example | mol % TMCD | % cis TMCD | IV (dL/g) | $T_g$ (° C.) | $\eta_o$ at 260° C. (Poise) | $\eta_o$ at 275° C. (Poise) | $\eta_o$ at 290° C. (Poise) |
|---|---|---|---|---|---|---|---|
| A | 20 | 51.4 | 0.72 | 109 | 11356 | 19503 | 5527 |
| B | 19.1 | 51.4 | 0.60 | 106 | 6891 | 3937 | 2051 |
| C | 19 | 53.2 | 0.64 | 107 | 8072 | 4745 | 2686 |
| D | 18.8 | 54.4 | 0.70 | 108 | 14937 | 8774 | 4610 |
| E | 17.8 | 52.4 | 0.50 | 103 | 3563 | 1225 | 883 |
| F | 17.5 | 51.9 | 0.75 | 107 | 21160 | 10877 | 5256 |
| G | 17.5 | 52 | 0.42 | 98 | NA | NA | NA |
| H | 22.8 | 53.5 | 0.69 | 109 | NA | NA | NA |
| I | 22.7 | 52.2 | 0.68 | 108 | NA | NA | NA |
| J | 23.4 | 52.4 | 0.73 | 111 | NA | NA | NA |
| K | 23.3 | 52.9 | 0.71 | 111 | NA | NA | NA |
| L | 23.3 | 52.4 | 0.74 | 112 | NA | NA | NA |
| M | 23.2 | 52.5 | 0.74 | 112 | NA | NA | NA |
| N | 23.1 | 52.5 | 0.71 | 111 | NA | NA | NA |
| O | 22.8 | 52.4 | 0.73 | 112 | NA | NA | NA |
| P | 22.7 | 53 | 0.69 | 112 | NA | NA | NA |
| Q | 22.7 | 52 | 0.70 | 111 | NA | NA | NA |

NA = Not available

Example 8

This example illustrates the effect of the amount of 2,2,4,4-tetramethyl-1,3-cyclobutanediol used for the preparation of the polyesters of the invention on the glass transition temperature of the polyesters. Polyesters prepared in this example fall comprise more than 25 to less than 40 mol % of 2,2,4,4-tetramethyl-1,3-cyclobutanediol residues.

Dimethyl terephthalate, 1,4-cyclohexanedimethanol, and 2,2,4,4-tetramethyl-1,3-cyclobutanediol were weighed into a 500-ml single neck round bottom flask. NMR analysis on the 2,2,4,4-tetramethyl-1,3-cyclobutanediol starting material showed a cis/trans ratio of 53/47. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 32 mol %.

Inherent viscosities were measured as described in the "Measurement Methods" section above. The compositions of the polyesters were determined by $^1$H NMR as explained before in the Measurement Methods section. The glass transition temperatures were determined by DSC, using the second heat after quench at a rate of 20° C./min.

The table below shows the experimental data for the polyesters of this example. FIG. 3 also shows the dependence of Tg on composition and inherent viscosity. The data shows that an increase in the level of 2,2,4,4-tetramethyl-1,3-cyclobutanediol raises the glass transition temperature in an almost linear fashion, for a constant inherent viscosity.

TABLE 8

Glass transition temperature as a function of inherent viscosity and composition

| Example | mol % TMCD | % cis TMCD | IV (dL/g) | $T_g$ (°C.) | $\eta_o$ at 260° C. (Poise) | $\eta_o$ at 275° C. (Poise) | $\eta_o$ at 290° C. (Poise) |
|---|---|---|---|---|---|---|---|
| A | 32.2 | 51.9 | 0.71 | 118 | 29685 | 16074 | 8522 |
| B | 31.6 | 51.5 | 0.55 | 112 | 5195 | 2899 | 2088 |
| C | 31.5 | 50.8 | 0.62 | 112 | 8192 | 4133 | 2258 |
| D | 30.7 | 50.7 | 0.54 | 111 | 4345 | 2434 | 1154 |
| E | 30.3 | 51.2 | 0.61 | 111 | 7929 | 4383 | 2261 |
| F | 30.0 | 51.4 | 0.74 | 117 | 31476 | 17864 | 8630 |
| G | 29.0 | 51.5 | 0.67 | 112 | 16322 | 8787 | 4355 |
| H | 31.1 | 51.4 | 0.35 | 102 | NA | NA | NA |

NA = Not available

Example 9

This example illustrates the effect of the amount of 2,2,4,4-tetramethyl-1,3-cyclobutanediol used for the preparation of the polyesters of the invention on the glass transition temperature of the polyesters. Polyesters prepared in this example comprise 2,2,4,4-tetramethyl-1,3-cyclobutanediol residues in an amount of 40 mol % or greater.

Examples A to C

These polyesters were prepared by carrying out the ester exchange and polycondensation reactions in separate stages. The ester exchange experiments were conducted in a continuous temperature rise (CTR) reactor. The CTR was a 3000 ml glass reactor equipped with a single shaft impeller blade agitator, covered with an electric heating mantle and fitted with a heated packed reflux condenser column. The reactor was charged with 777 g of dimethyl terephthalate, 375 g of 2,2,4,4-tetramethyl-1,3,-cyclobutanediol, 317 g of cyclohexane dimethanol and 1.12 g of butyltin tris-2-ethylhexanoate (such that there will be 200 ppm tin metal in the final polymer). The heating mantle was set manually to 100% output. The set points and data collection were facilitated by a Camile process control system. Once the reactants were melted, stirring was initiated and slowly increased to 250 rpm. The temperature of the reactor gradually increased with run time. The weight of methanol collected was recorded via balance. The reaction was stopped when methanol evolution stopped or at a pre-selected lower temperature of 260° C. The oligomer was discharged with a nitrogen purge and cooled to room temperature. The oligomer was frozen with liquid nitrogen and broken into pieces small enough to be weighed into a 500 ml round bottom flask.

In the polycondensation reactions, a 500 ml round bottom flask was charged with 150 g of the oligomer prepared above. The flask was equipped with a stainless steel stirrer and polymer head. The glassware was set up on a half mole polymer rig and the Camile sequence was initiated. The stirrer was positioned one full turn from the flask bottom once the oligomer melted. The temperature/pressure/stir rate sequence controlled by the Camile software for these examples is reported in the following table, unless otherwise specified below.

Camile Sequence for Polycondensation Reactions

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 290 | 6 | 25 |

Camile Sequence for Examples A and B

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 80 | 290 | 6 | 25 |

For Example C, the same sequence in the preceding table was used, except the time was 50 min in Stage 7.

The resulting polymers were recovered from the flask, chopped using a hydraulic chopper, and ground to a 6 mm screen size. Samples of each ground polymer were submitted for inherent viscosity in 60/40 (wt/wt) phenol/tetrachloroethane at a concentration of 0.5 g/100 ml at 25° C., catalyst level (Sn) by x-ray fluorescence, and color (L*, a*, b*) by transmission spectroscopy. Polymer composition was obtained by $^1$H NMR. Samples were submitted for thermal stability and melt viscosity testing using a Rheometrics Mechanical Spectrometer (RMS-800).

Examples D to K and M

The polyesters of these examples were prepared as described above for Examples A to C, except that the target tin amount in the final polymer was 150 ppm for examples AD to K and M. The following tables describe the temperature/pressure/stir rate sequences controlled by the Camile software for these examples.

Camile Sequence for Examples D, F, and H

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 400 | 50 |
| 5 | 110 | 290 | 400 | 50 |
| 6 | 5 | 290 | 8 | 50 |
| 7 | 110 | 295 | 8 | 50 |

For Example D, the stirrer was turned to 25 rpm with 95 min left in Stage 7.

Camile Sequence for Example E

| Stage | Time (min) | Temp (° C.) | Vacuum (torr) | Stir (rpm) |
|---|---|---|---|---|
| 1 | 10 | 245 | 760 | 0 |
| 2 | 5 | 245 | 760 | 50 |
| 3 | 30 | 283 | 760 | 50 |
| 4 | 3 | 283 | 175 | 50 |
| 5 | 5 | 283 | 5 | 50 |
| 6 | 5 | 283 | 1.2 | 50 |
| 7 | 71 | 285 | 1.2 | 50 |

For Example K, the same sequence in the preceding table was used, except the time was 75 min in Stage 7.

Camile Sequence for Example G

| Stage | Time (min) | Temp (° C.) | Vacuum (torr) | Stir (rpm) |
|---|---|---|---|---|
| 1 | 10 | 245 | 760 | 0 |
| 2 | 5 | 245 | 760 | 50 |
| 3 | 30 | 285 | 760 | 50 |
| 4 | 3 | 285 | 175 | 50 |
| 5 | 5 | 285 | 5 | 50 |
| 6 | 5 | 285 | 4 | 50 |
| 7 | 220 | 290 | 4 | 50 |

Camile Sequence for Example I

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 285 | 90 | 50 |
| 6 | 5 | 285 | 6 | 50 |
| 7 | 70 | 290 | 6 | 50 |

Camile Sequence for Example J

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 295 | 6 | 25 |

Examples L and K

Dimethyl terephthalate, 1,4-cyclohexanedimethanol, and 2,2,4,4-tetramethyl-1,3-cyclobutanediol were weighed into a 500-ml single neck round bottom flask. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 45 mol %.

Inherent viscosities were measured as described in the "Measurement Methods" section above. The compositions of the polyesters were determined by $^1$H NMR as explained before in the Measurement Methods section. The glass transition temperatures were determined by DSC, using the second heat after quench at a rate of 20° C./min.

The table below shows the experimental data for the polyesters of this example. The data shows that an increase in the level of 2,2,4,4-tetramethyl-1,3-cyclobutanediol raises the glass transition temperature in an almost linear fashion, for a constant inherent viscosity. FIG. 3 also shows the dependence of Tg on composition and inherent viscosity.

TABLE 9

Glass transition temperature as a function of inherent viscosity and composition

| Example | mol % TMCD | % cis TMCD | IV (dL/g) | $T_g$ (° C.) | $\eta_o$ at 260° C. (Poise) | $\eta_o$ at 275° C. (Poise) | $\eta_o$ at 290° C. (Poise) |
|---|---|---|---|---|---|---|---|
| A | 44.2 | 36.4 | 0.49 | 118 | NA | NA | NA |
| B | 44.3 | 36.3 | 0.51 | 119 | NA | NA | NA |
| C | 44.4 | 35.6 | 0.55 | 118 | NA | NA | NA |
| D | 46.3 | 52.4 | 0.52 | NA | NA | NA | NA |
| E | 45.7 | 50.9 | 0.54 | NA | NA | NA | NA |
| F | 46.3 | 52.6 | 0.56 | NA | NA | NA | NA |
| G | 46 | 50.6 | 0.56 | NA | NA | NA | NA |
| H | 46.5 | 51.8 | 0.57 | NA | NA | NA | NA |
| I | 45.6 | 51.2 | 0.58 | NA | NA | NA | NA |
| J | 46 | 51.9 | 0.58 | NA | NA | NA | NA |
| K | 45.5 | 51.2 | 0.59 | NA | NA | NA | NA |
| L | 46.1 | 49.6 | 0.383 | 117 | NA | NA | 387 |
| K | 45.6 | 50.5 | 0.325 | 108 | NA | NA | NA |
| M | 47.2 | NA | 0.48 | NA | NA | NA | NA |

NA = Not available

Example 10

This example illustrates the effect of the predominance of the type of 2,2,4,4-tetramethyl-1,3-cyclobutanediol isomer (cis or trans) on the glass transition temperature of the polyester.

Dimethyl terephthalate, 1,4-cyclohexanedimethanol, and 2,2,4,4-tetramethyl-1,3-cyclobutanediol were weighed into a 500-ml single neck round bottom flask. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 45 mol %.

Inherent viscosities were measured as described in the "Measurement Methods" section above. The compositions of the polyesters were determined by $^1$H NMR as explained before in the Measurement Methods section. The glass transition temperatures were determined by DSC, using the second heat after quench at a rate of 20° C./min.

The table below shows the experimental data for the polyesters of this Example. The data shows that cis 2,2,4,4-tetramethyl-1,3-cyclobutanediol is approximately twice as effective as trans 2,2,4,4-tetramethyl-1,3-cyclobutanediol at increasing the glass transition temperature for a constant inherent viscosity.

TABLE 10

Effect of 2,2,4,4-tetramethyl-1,3-cyclobutanediol cis/trans composition on $T_g$

| Example | mol % TMCD | IV (dL/g) | $T_g$ (° C.) | $\eta_o$ at 260° C. (Poise) | $\eta_o$ at 275° C. (Poise) | $\eta_o$ at 290° C. (Poise) | % cis TMCD |
|---|---|---|---|---|---|---|---|
| A | 45.8 | 0.71 | 119 | N.A. | N.A. | N.A. | 4.1 |
| B | 43.2 | 0.72 | 122 | N.A. | N.A. | N.A. | 22.0 |
| C | 46.8 | 0.57 | 119 | 26306 | 16941 | 6601 | 22.8 |
| D | 43.0 | 0.67 | 125 | 55060 | 36747 | 14410 | 23.8 |
| E | 43.8 | 0.72 | 127 | 101000 | 62750 | 25330 | 24.5 |
| F | 45.9 | 0.533 | 119 | 11474 | 6864 | 2806 | 26.4 |
| G | 45.0 | 0.35 | 107 | N.A. | N.A. | N.A. | 27.2 |
| H | 41.2 | 0.38 | 106 | 1214 | 757 | N.A. | 29.0 |
| I | 44.7 | 0.59 | 123 | N.A. | N.A. | N.A. | 35.4 |
| J | 44.4 | 0.55 | 118 | N.A. | N.A. | N.A. | 35.6 |
| K | 44.3 | 0.51 | 119 | N.A. | N.A. | N.A. | 36.3 |
| L | 44.0 | 0.49 | 128 | N.A. | N.A. | N.A. | 71.7 |
| M | 43.6 | 0.52 | 128 | N.A. | N.A. | N.A. | 72.1 |
| N | 43.6 | 0.54 | 127 | N.A. | N.A. | N.A. | 72.3 |
| O | 41.5 | 0.58 | 133 | 15419 | 10253 | 4252 | 88.7 |
| P | 43.8 | 0.57 | 135 | 16219 | 10226 | 4235 | 89.6 |
| Q | 41.0 | 0.33 | 120 | 521 | 351 | 2261 | 90.4 |
| R | 43.0 | 0.56 | 134 | N.A. | N.A. | N.A. | 90.6 |
| S | 43.0 | 0.49 | 132 | 7055 | 4620 | 2120 | 90.6 |
| T | 43.1 | 0.55 | 134 | 12970 | 8443 | 3531 | 91.2 |
| U | 45.9 | 0.52 | 137 | N.A. | N.A. | N.A. | 98.1 |

NA = not available

Example 11

Comparative Example

This example illustrates that a polyester based on 100% 2,2,4,4-tetramethyl-1,3-cyclobutanediol has a slow crystallization half-time.

A polyester based solely on terephthalic acid and 2,2,4,4-tetramethyl-1,3-cyclobutanediol was prepared in a method similar to the method described in Example 1A with the properties shown on Table 11. This polyester was made with 300 ppm dibutyl tin oxide. The trans/cis ratio of the 2,2,4,4-tetramethyl-1,3-cyclobutanediol was 65/35.

Films were pressed from the ground polymer at 320° C. Crystallization half-time measurements from the melt were made at temperatures from 220 to 250° C. at 10° C. increments and are reported in Table 11. The fastest crystallization half-time for the sample was taken as the minimum value of crystallization half-time as a function of temperature. The fastest crystallization half-time of this polyester is around 1300 minutes. This value contrasts with the fact that the polyester (PCT) based solely on terephthalic acid and 1,4-cyclohexanedimethanol (no comonomer modification) has an extremely short crystallization half-time (<1 min) as shown in FIG. 1.

TABLE 11

| Comonomer (mol %) | IV (dl/g) | $T_g$ (° C.) | $T_{max}$ (° C.) | at 220° C. (min) | at 230° C. (min) | at 240° C. (min) | at 250° C. (min) |
|---|---|---|---|---|---|---|---|
| | | | | Crystallization Half-times (min) | | | |
| 100 mol % F | 0.63 | 170.0 | 330 | 3291 | 3066 | 1303 | 1888 | where:
F is 2,2,4,4-Tetramethyl-1,3-cyclobutanediol (65/35 Trans/Cis)

Example 12

Sheets comprising a polyester that had been prepared with a target composition of 100 mole % terephthalic acid residues, 80 mole % 1,4-cyclohexanedimethanol residues, and 20 mole % 2,2,4,4-tetramethyl-1,3-cyclobutanediol residues were produced using a 3.5 inch single screw extruder. A sheet was extruded continuously, gauged to a thickness of 177 mil and then various sheets were sheared to size. Inherent viscosity and glass transition temperature were measured on one sheet. The sheet inherent viscosity was measured to be 0.69 dl/g. The glass transition temperature of the sheet was measured to be 106° C. Sheets were then conditioned at 50% relative humidity and 60° C. for 2 weeks. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example G). The thermoformed part was visually inspected for any blisters and the degree of blistering rated as none (N), low (L), or high (H). The results below demonstrate that these thermoplastic sheets with a glass transition temperature of 106° C. can be thermoformed under the conditions shown below, as evidenced by these sheets having at least 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 86 | 145 | 501 | 64 | N |
| B | 100 | 150 | 500 | 63 | N |
| C | 118 | 156 | 672 | 85 | N |
| D | 135 | 163 | 736 | 94 | N |
| E | 143 | 166 | 760 | 97 | N |
| F | 150 | 168 | 740 | 94 | L |
| G | 159 | 172 | 787 | 100 | L |

Example 13

Sheets comprising a polyester that had been prepared with a target composition of 100 mole % terephthalic acid residues, 80 mole % 1,4-cyclohexanedimethanol residues, and 20 mole % 2,2,4,4-tetramethyl-1,3-cyclobutanediol residues were produced using a 3.5 inch single screw. A sheet was extruded continuously, gauged to a thickness of 177 mil and then various sheets were sheared to size. Inherent viscosity and glass transition temperature were measured on one sheet. The sheet inherent viscosity was measured to be 0.69 dl/g. The glass transition temperature of the sheet was measured to be 106° C. Sheets were then conditioned at 100% relative humidity and 25° C. for 2 weeks. Sheets were subsequently thermoformed into a female mold having a draw ratio of 2.5:1 using a Brown thermoforming machine. The thermoforming oven heaters were set to 60/40/40% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example G). The thermoformed part was visually inspected for any blisters and the degree of blistering rated as none (N), low (L), or high (H). The results below demonstrate that these thermoplastic sheets with a glass transition temperature of 106° C. can be thermoformed under the conditions shown below, as evidenced by the production of sheets having at least 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 141 | 154 | 394 | 53 | N |
| B | 163 | 157 | 606 | 82 | N |
| C | 185 | 160 | 702 | 95 | N |
| D | 195 | 161 | 698 | 95 | N |
| E | 215 | 163 | 699 | 95 | L |
| F | 230 | 168 | 705 | 96 | L |
| G | 274 | 174 | 737 | 100 | H |
| H | 275 | 181 | 726 | 99 | H |

Example 14

Comparative Example

Sheets consisting of Kelvx 201 were produced using a 3.5 inch single screw extruder. Kelvx is a blend consisting of 69.85% PCTG (Eastar from Eastman Chemical Co. having 100 mole % terephthalic acid residues, 62 mole % 1,4-cyclohexanedimethanol residues, and 38 mole % ethylene glycol residues); 30% PC (bisphenol A polycarbonate); and 0.15% Weston 619 (stabilizer sold by Crompton Corporation). A sheet was extruded continuously, gauged to a thickness of 177 mil and then various sheets were sheared to size. The glass transition temperature was measured on one sheet and was 100° C. Sheets were then conditioned at 50% relative humidity and 60° C. for 2 weeks. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example E). The thermoformed part was visually inspected for any blisters and the degree of blistering rated as none (N), low (L), or high (H). The results below demonstrate that these thermoplastic sheets with a glass transition temperature of 100° C. can be thermoformed under the conditions shown below, as evidenced by the production of sheets having at least 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 90 | 146 | 582 | 75 | N |
| B | 101 | 150 | 644 | 83 | N |
| C | 111 | 154 | 763 | 98 | N |
| D | 126 | 159 | 733 | 95 | N |
| E | 126 | 159 | 775 | 100 | N |
| F | 141 | 165 | 757 | 98 | N |
| G | 148 | 168 | 760 | 98 | L |

Example 15

Comparative Example

Sheets consisting of Kelvx 201 were produced using a 3.5 inch single screw extruder. A sheet was extruded continuously, gauged to a thickness of 177 mil and then various sheets were sheared to size. The glass transition temperature was measured on one sheet and was 100° C. Sheets were then conditioned at 100% relative humidity and 25° C. for 2 weeks. Sheets were subsequently thermoformed into a female mold having a draw ratio of 2.5:1 using a Brown thermoforming machine. The thermoforming oven heaters were set to 60/40/40% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example H). The thermoformed part was visually inspected for any blisters and the degree of blistering rated as none (N), low (L), or high (H). The results below demonstrate that these thermoplastic sheets with a glass transition temperature of 100° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 110 | 143 | 185 | 25 | N |
| B | 145 | 149 | 529 | 70 | N |
| C | 170 | 154 | 721 | 95 | N |
| D | 175 | 156 | 725 | 96 | N |
| E | 185 | 157 | 728 | 96 | N |
| F | 206 | 160 | 743 | 98 | L |
| G | 253 | NR | 742 | 98 | H |
| H | 261 | 166 | 756 | 100 | H |

NR = Not recorded

Example 16

Comparative Example

Sheets consisting of PCTG 25976 (100 mole % terephthalic acid residues, 62 mole % 1,4-cyclohexanedimethanol residues, and 38 mole % ethylene glycol residues) were produced using a 3.5 inch single screw extruder. A sheet was extruded continuously, gauged to a thickness of 118 mil and then various sheets were sheared to size. The glass transition temperature was measured on one sheet and was 87° C. Sheets were then conditioned at 50% relative humidity and 60° C. for 4 weeks. The moisture level was measured to be 0.17 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 87° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 102 | 183 | 816 | 100 | N |
| B | 92 | 171 | 811 | 99 | N |
| C | 77 | 160 | 805 | 99 | N |
| D | 68 | 149 | 804 | 99 | N |
| E | 55 | 143 | 790 | 97 | N |
| F | 57 | 138 | 697 | 85 | N |

Example 17

Comparative Example

A miscible blend consisting of 20 wt % Teijin L-1250 polycarbonate (a bisphenol-A polycarbonate), 79.85 wt %

PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 94° C. Sheets were then conditioned at 50% relative humidity and 60° C. for 4 weeks. The moisture level was measured to be 0.25 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 94° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 92 | 184 | 844 | 100 | H |
| B | 86 | 171 | 838 | 99 | N |
| C | 73 | 160 | 834 | 99 | N |
| D | 58 | 143 | 787 | 93 | N |
| E | 55 | 143 | 665 | 79 | N |

Example 18

Comparative Example

A miscible blend consisting of 30 wt % Teijin L-1250 polycarbonate, 69.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 99° C. Sheets were then conditioned at 50% relative humidity and 60° C. for 4 weeks. The moisture level was measured to be 0.25 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 99° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 128 | 194 | 854 | 100 | H |
| B | 98 | 182 | 831 | 97 | L |
| C | 79 | 160 | 821 | 96 | N |
| D | 71 | 149 | 819 | 96 | N |
| E | 55 | 145 | 785 | 92 | N |
| F | 46 | 143 | 0 | 0 | NA |
| G | 36 | 132 | 0 | 0 | NA |

NA = not applicable. A value of zero indicates that the sheet was not formed because it did not pull into the mold (likely because it was too cold).

Example 19

Comparative Example

A miscible blend consisting of 40 wt % Teijin L-1250 polycarbonate, 59.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 105° C. Sheets were then conditioned at 50% relative humidity and 60° C. for 4 weeks. The moisture level was measured to be 0.265 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Examples 8A to 8E). The thermoformed part was visually inspected for any blisters and the degree of blistering rated as none (N), low (L), or high (H). The results below demonstrate that these thermoplastic sheets with a glass transition temperature of 105° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 111 | 191 | 828 | 100 | H |
| B | 104 | 182 | 828 | 100 | H |

-continued

| Example | Thermoforming Conditions | | Part Quality | | |
|---|---|---|---|---|---|
| | Heat Time (s) | Sheet Temperature (° C.) | Part Volume (mL) | Draw (%) | Blisters (N, L, H) |
| C | 99 | 179 | 827 | 100 | N |
| D | 97 | 177 | 827 | 100 | N |
| E | 78 | 160 | 826 | 100 | N |
| F | 68 | 149 | 759 | 92 | N |
| G | 65 | 143 | 606 | 73 | N |

Example 20

Comparative Example

A miscible blend consisting of 50 wt % Teijin L-1250 polycarbonate, 49.85 wt % PCTG 25976, and 0.15 wt % Weston 619 was produced using a 1.25 inch single screw extruder. A sheet was extruded continuously, gauged to a thickness of 118 mil and then various sheets were sheared to size. The glass transition temperature was measured on one sheet and was 111° C. Sheets were then conditioned at 50% relative humidity and 60° C. for 4 weeks. The moisture level was measured to be 0.225 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Examples A to D). The thermoformed part was visually inspected for any blisters and the degree of blistering rated as none (N), low (L), or high (H). The results below demonstrate that these thermoplastic sheets with a glass transition temperature of 111° C. can be thermoformed under the conditions shown below, as evidenced by the production of sheets having greater than 95% draw and no blistering, without predrying the sheets prior to thermoforming.

| Example | Thermoforming Conditions | | Part Quality | | |
|---|---|---|---|---|---|
| | Heat Time (s) | Sheet Temperature (° C.) | Part Volume (mL) | Draw (%) | Blisters (N, L, H) |
| A | 118 | 192 | 815 | 100 | H |
| B | 99 | 182 | 815 | 100 | H |
| C | 97 | 177 | 814 | 100 | L |
| D | 87 | 171 | 813 | 100 | N |
| E | 80 | 160 | 802 | 98 | N |
| F | 64 | 154 | 739 | 91 | N |
| G | 60 | 149 | 0 | 0 | NA |

NA = not applicable. A value of zero indicates that the sheet was not formed because it did not pull into the mold (likely because it was too cold).

Example 21

Comparative Example

A miscible blend consisting of 60 wt % Teijin L-1250 polycarbonate, 39.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 117° C. Sheets were then conditioned at 50% relative humidity and 60° C. for 4 weeks. The moisture level was measured to be 0.215 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 117° C. cannot be thermoformed under the conditions shown below, as evidenced by the inability to produce sheets having greater than 95% draw and no blistering, without predrying the sheets prior to thermoforming.

| Example | Thermoforming Conditions | | Part Quality | | |
|---|---|---|---|---|---|
| | Heat Time (s) | Sheet Temperature (° C.) | Part Volume (mL) | Draw (%) | Blisters (N, L, H) |
| A | 114 | 196 | 813 | 100 | H |
| B | 100 | 182 | 804 | 99 | H |
| C | 99 | 177 | 801 | 98 | L |
| D | 92 | 171 | 784 | 96 | L |
| E | 82 | 168 | 727 | 89 | L |
| F | 87 | 166 | 597 | 73 | N |

Example 22

Comparative Example

A miscible blend consisting of 65 wt % Teijin L-1250 polycarbonate, 34.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 120° C. Sheets were then conditioned at 50% relative humidity and 60° C. for 4 weeks. The moisture level was measured to be 0.23 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 120° C. cannot be thermoformed under the conditions shown below, as evidenced by the inability to produce sheets having greater than 95% draw and no blistering, without predrying the sheets prior to thermoforming.

| Example | Thermoforming Conditions | | Part Quality | | |
|---|---|---|---|---|---|
| | Heat Time (s) | Sheet Temperature (° C.) | Part Volume (mL) | Draw (%) | Blisters (N, L, H) |
| A | 120 | 197 | 825 | 100 | H |
| B | 101 | 177 | 820 | 99 | H |
| C | 95 | 174 | 781 | 95 | L |
| D | 85 | 171 | 727 | 88 | L |
| E | 83 | 166 | 558 | 68 | L |

Example 23

Comparative Example

A miscible blend consisting of 70 wt % Teijin L-1250 polycarbonate, 29.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 123° C. Sheets were then conditioned at 50% relative humidity and 60° C. for 4 weeks. The moisture level was measured to be 0.205 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Examples A and B). The thermoformed part was visually inspected for any blisters and the degree of blistering rated as none (N), low (L), or high (H). The results below demonstrate that these thermoplastic sheets with a glass transition temperature of 123° C. cannot be thermoformed under the conditions shown below, as evidenced by the inability to produce sheets having greater than 95% draw and no blistering, without predrying the sheets prior to thermoforming.

| Example | Thermoforming Conditions | | Part Quality | | |
|---|---|---|---|---|---|
| | Heat Time (s) | Sheet Temperature (° C.) | Part Volume (mL) | Draw (%) | Blisters (N, L, H) |
| A | 126 | 198 | 826 | 100 | H |
| B | 111 | 188 | 822 | 100 | H |
| C | 97 | 177 | 787 | 95 | L |
| D | 74 | 166 | 161 | 19 | L |
| E | 58 | 154 | 0 | 0 | NA |
| F | 48 | 149 | 0 | 0 | NA |

NA = not applicable. A value of zero indicates that the sheet was not formed because it did not pull into the mold (likely because it was too cold).

Example 24

Comparative Example

Sheets consisting of Teijin L-1250 polycarbonate were produced using a 3.5 inch single screw extruder. A sheet was extruded continuously, gauged to a thickness of 118 mil and then various sheets were sheared to size. The glass transition temperature was measured on one sheet and was 149° C. Sheets were then conditioned at 50% relative humidity and 60° C. for 4 weeks. The moisture level was measured to be 0.16 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 149° C. cannot be thermoformed under the conditions shown below, as evidenced by the inability to produce sheets having greater than 95% draw and no blistering, without predrying the sheets prior to thermoforming.

| Example | Thermoforming Conditions | | Part Quality | | |
|---|---|---|---|---|---|
| | Heat Time (s) | Sheet Temperature (° C.) | Part Volume (mL) | Draw (%) | Blisters (N, L, H) |
| A | 152 | 216 | 820 | 100 | H |
| B | 123 | 193 | 805 | 98 | H |
| C | 113 | 191 | 179 | 22 | H |
| D | 106 | 188 | 0 | 0 | H |
| E | 95 | 182 | 0 | 0 | NA |
| F | 90 | 171 | 0 | 0 | NA |

NA = not applicable. A value of zero indicates that the sheet was not formed because it did not pull into the mold (likely because it was too cold).

Example 25

This example illustrates the preparation of polyesters comprising at least one thermal stabilizer, reaction products thereof, and mixtures thereof, resulting in improved stability of the polyester melts during processing.

A variety of polyesters were prepared as described below from 100 mole % dimethyl terephthalate (DMT), 1,4-cyclohexanedimethanol (CHDM), and 2,2,4,4-tetramethyl-1,3-cyclobutanediol (TMCD). The mole % of TMCD for the experiments of this example is reported in Table 12 below, with the glycol balance being CHDM. The DMT was purchased from Cape Industries, the CHDM (min. 98%) and the TMCD (min. 98%) were from Eastman Chemical Company. The tin compound was either dimethyltin oxide (from Strem Chemical Co. or Gelest, Inc.) or butyltin-tris-2-ethylhexonate (from Aldrich or Arkema). The phosphorus compound was triphenyl phosphate (TPP, from Aldrich (98%) or FERRO, Corp.). Unless otherwise indicated below, the source of phosphorous was added upfront, with the rest of the polyester reagents. The cis/trans ratio of the CHDM was as described above while the cis/trans ratio of the TMCD is reported in Table 12.

TABLE 12

Composition and inherent viscosity for the polyesters of Example 25

| Example | Melt IV (dL/g) | TMCD (mole %) | TMCD % cis | Sn (ppm) | P (ppm) theo/meas | Sn/P actual wt ratio | Final Pz Temp (° C.) |
|---|---|---|---|---|---|---|---|
| A | 0.605 | 44.8 | 50.0 | 205[1] | none | * | 290 |
| B | 0.583 | 44.4 | 51.9 | 201[1] | none | * | 290 |
| C | 0.578 | 43.9 | 50.7 | 199[1] | none | * | 290 |
| D | 0.607 | 44.9 | 50.5 | 199[2] | none | * | 290 |
| E | 0.437 | 44.5 | 52.0 | 200[2] | none | * | 290 |
| F | 0.585 | 45.1 | 50.2 | 191[2] | 10/11 | 17.4 | 290 |
| G | 0.580 | 45.1 | 50.5 | 192[1] | 10/11 | 17.5 | 290 |
| H | 0.541 | 44.0 | 52.3 | 202[2] | 19/20 | 10.1 | 290 |
| I | 0.595 | 45.3 | 50.6 | 198[2] | 20/20 | 9.9 | 290 |
| J | 0.632 | 45.6 | 49.0 | 203[2] | 20/22 | 9.2 | 265 |
| K | 0.577 | 46.2 | 50.1 | 196[2] | 30/26 | 7.5 | 265 |
| L | 0.608 | 46.0 | 49.6 | 190[1] | 20/19 | 10.0 | 265 |
| M | 0.517 | 45.2 | 49.4 | 100[2] | 10/10 | 10.0 | 265 |
| N | 0.602 | 46.1 | 49.2 | 102[2] | 10/10 | 10.2 | 265 |

[1] butyltin tris-2-ethylhexanoate was used as the source of tin
[2] dimethyl tin oxide was used as the source of tin The data in Table 13 shows that the stability of polymer melts for Comparative Examples A to D was not deemed acceptable if the same conditions were to be used at a pilot-pant or commercial scale. In contrast, experiments having appropriate ratios of tin/phosphorous produced stable melts, suitable for scale up processes.

TABLE 13

Properties of the polyesters of Example 25

| Example | L* | a* | b* | Melt level stability | Polymer color observations | % foam in polyester | Visual grading of polyester |
|---|---|---|---|---|---|---|---|
| A | 82.50 | −0.89 | 4.66 | 4 | Yellow tint | 34% | 4 |
| B | 79.74 | −0.75 | 4.89 | 4 | Yellow tint | 21% | 4 |
| C | 78.64 | −0.39 | 6.83 | 4 | Brownish-yellow tint | 37% | 4 |
| D | 85.44 | −1.45 | 4.07 | 3 | Slight yellow tint | 27% | 4 |
| E | 86.19 | −1.04 | 3.94 | 3 | Good color: No yellow tint | 35% | 4 |
| F | 80.92 | −1.02 | 3.22 | 2 | Good color: No yellow tint | 20% | 3 |
| G | 82.10 | −1.67 | 3.69 | 2 | Good color: No yellow tint | 22% | 3 |
| H | 85.74 | −0.81 | 2.46 | 1 | NM | NM | NM |
| I | 82.51 | −1.03 | 2.56 | 1 | Good color: No yellow tint | 15% | 2 |
| J | 85.54 | −1.07 | 2.06 | 1 | Good color: No yellow tint | 22% | 3 |
| K | 84.54 | −0.71 | 1.07 | 1 | Good color: No yellow tint | 14% | 2 |
| L | 85.03 | −0.82 | 1.17 | 1 | Slight yellow tint | 14% | 3 |
| M | 85.02 | −0.87 | 1.59 | 1 | Slight yellow tint | 17% | 2 |
| N | 82.49 | −0.86 | 1.09 | 1 | Good color: No yellow tint | 17% | 2 |
| O | NA | NA | NA | NA | NA | 35% | NA |
| P | NA | NA | NA | NA | NA | 9% | NA |

NM = not measured

The melt level stability reported in Table 13 is based on the following scale:

| | |
|---|---|
| 1 | Stable melt levels, limited off-gassing, similar to conventional polyesters where excess glycols slowly boil off |
| 2 | Relatively stable melt levels but some additional void/bubbles compared to 1 above. |
| 3 | Unstable melt levels during vacuum levels, heavy foaming and frothing leading to high void volumes (bubbles that increase melt overall volume), unstable off-gassing, melt level surges that were kept from overflowing flask only with adjustment of stirring rate or |

-continued

| Grading | Explanation |
|---|---|
| 4 | by having stirrer above level of melt to push down and break up the foam. Too unstable to scale up dependably. |
| 5 | Very unstable melt levels during vacuum levels, excessive foaming and frothing leading to high void volumes (bubbles that increase melt overall volume), unstable off-gassing, melt level surges that overflowed out of flask and frequently pushed melt/foam into the gas space in vacuum system. Frequently, it was not possible to complete run (greater than 50% of duplicate runs could not be completed for this level of stability). |

The visual grading reported in Table 13 is based on the following scale:

| Grading | Explanation |
|---|---|
| 1 | Few bubbles: can see through molten polymer |
| 2 | Sparse bubbles: enough bubbles to obstruct view through polymer but not enough to drastically increase the polymer volume |
| 3 | Numerous bubbles: volume of polymer is affected by the bubbles |
| 4 | Very dense foam: volume of polymer is drastically affected by the numerous bubbles |

Example 25O and Example 25P are comparative examples. Example 25O represents a polyester prepared in a similar manner to pilot plant examples described below with no phosphorus thermal stabilizer, having an IV of 0.54 dL/g and containing 100 mole % terephthalic acid residues, 43.8 mole % TMCD residues and 56.2 mole % CHDM acid residues. This polyester was prepared using butyltin tris-2-ethylhexanoate was used as the source of tin catalyst (Sn=216 ppm) at 290° C. final finisher temperature and having color values V=60.97, b*=9.02, and a*=−0.89. Example 25P represents a commercial Kelvx polymer containing 65 mole % terephthalic acid residues, 35 mole % isophthalic acid residues, and 100 mole % 1,4-cyclohexanedimethanol residues.

The polyesters of this example were prepared in a 500 ml round bottom flask fitted with a stirrer and a polymer head that allowed both a nitrogen purge and vacuum when necessary. Raw materials were weighed into the flask for a 0.4 mole run (polymer repeat unit=274 grams/mole): 0.400 moles of DMT (77.6 grams), 0.224 moles of CHDM (32.3 grams) and 0.256 moles of TMCD (36.8 grams) and 0.112 g butyltin tris-2-ethylhexanoate or 0.0314 g dimethyl tin oxide (as reported in Table 12), such that there was approximately 200 ppm tin metal in the final polymer, but were modified accordingly for other target concentrations, such as 100 ppm Sn.

The glycol/acid ratio was 1.2/1 with the excess being 2% CHDM and the rest of the 20% excess being TMCD. The catalyst was weighed into the flask, either as a solid or liquid. Triphenyl phosphate was weighed into the flask as a solid in the amount recited in Table 12 for each experiment. 100 ppm (0.0109 g as a liquid) of tetramethyl ammonium hydroxide (TMAH) was used in the preparation of Example 25K.

The set points and data collection were facilitated by a Camile process control system. Once the reactants were melted, stirring was initiated and slowly increased as indicated below in the corresponding Camile sequences. The temperature of the reactor also gradually increased with run time.

The ester exchange and polycondensation reactions were carried out in the same 500 ml flask. The blade of the stirrer was moved up to the top of the melt during the processing of the polyesters of Example 25A and Example 25B to beat down the foam layer. The temperature/pressure/stir rate sequence controlled by the Camile software for each example is reported in the following tables. The final polymerization temperature (Pz Temp.) for the experiments of this Example ranged from 265° C. to 290° C. and is reported in Table 12.

Camile Sequence for Example 25A to Example 25I

| Stage | Time (minutes) | Temperature (° C.) | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 5 | 245 | 760 | 50 |
| 11 | 5 | 245 | 760 | 50 |
| 12 | 30 | 265 | 760 | 50 |
| 13 | 3 | 265 | 90 | 50 |
| 14 | 110 | 290 | 90 | 50 |
| 15 | 5 | 290 | 6 | 25 |
| 16 | 110 | 290 | 6 | 25 |
| 17 | 2 | 290 | 400 | 0 |
| 18 | 1 | 300 | 760 | 0 |

Camile Sequence for Example 25J to Example 25L

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 5 | 245 | 760 | 50 |
| 11 | 3 | 245 | 375 | 50 |
| 12 | 30 | 245 | 375 | 50 |
| 13 | 3 | 250 | 20 | 50 |
| 14 | 30 | 250 | 20 | 50 |
| 15 | 3 | 255 | 5 | 25 |
| 16 | 110 | 255 | 5 | 25 |
| 17 | 3 | 265 | 1 | 25 |
| 18 | 110 | 265 | 1 | 25 |
| 19 | 2 | 265 | 400 | 0 |
| 20 | 1 | 265 | 760 | 0 |

Camile Sequence for Example 25M

Viscosity Constrained Sequence, Low Vacuum

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 5 | 245 | 760 | 50 |
| 11 | 3 | 245 | 375 | 50 |
| 12 | 30 | 245 | 375 | 50 |
| 13 | 3 | 250 | 20 | 50 |
| 14 | 30 | 250 | 20 | 50 |
| 15 | 3 | 255 | 5 | 25 |
| 16 | 110 | 255 | 5 | 25 |
| 17 | 3 | 265 | 0.2 | 25 |
| 18 | 110 | 265 | 0.2 | 25 |
| 19 | 2 | 265 | 400 | 0 |
| 20 | 1 | 265 | 760 | 0 |

Camile Sequence for Example 25N

Viscosity Constrained Sequence, Low Vacuum

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 5 | 245 | 760 | 50 |
| 11 | 3 | 245 | 375 | 50 |
| 12 | 30 | 245 | 375 | 50 |
| 13 | 3 | 250 | 20 | 50 |
| 14 | 30 | 250 | 20 | 50 |
| 15 | 3 | 255 | 3 | 25 |
| 16 | 110 | 255 | 3 | 25 |
| 17 | 3 | 265 | 0.2 | 25 |
| 18 | 110 | 265 | 0.2 | 25 |
| 19 | 2 | 265 | 400 | 0 |
| 20 | 1 | 265 | 760 | 0 |

Example 26

This example illustrates the preparation of polyesters comprising at least one thermal stabilizer, reaction products thereof, and mixtures thereof, employing different process conditions from Example 25, resulting in improved stability of the polyester melts during processing.

A variety of polyesters were prepared as described below from 100 mole % DMT, CHDM, and TMCD. The mole % of TMCD for the experiments of this example is reported in Table 14 below, with the glycol balance being CHDM. The DMT, CHDM, and TMCD were of the same origin as in Example 25. The catalyst was dimethyltin oxide (Strem Chemical Co., Batch B4058112), butyltin-tris-2-ethylhexonate (Aldrich, Batch 06423CD, or Arkema), or dibutyl tin oxide (Arkema). The thermal stabilizer was triphenyl phosphate, also with the same origin as in Example 25. Unless otherwise indicated below, the source of phosphorous was added upfront, with the rest of the polyester reagents. The cis/trans ratio of the CHDM was as described above while the cis/trans ratio of the TMCD is reported in Table 14. The polyesters of Example 26A and Example 26E were not prepared with TPP.

TABLE 14

Composition and inherent viscosity for the polyesters of Example 26

| Example | Melt IV (dL/g) | TMCD (mole %) | TMCD % cis | Sn (ppm) | P (ppm) theo/meas | Sn/P actual wt ratio | Final Pz Temp (° C.) |
|---|---|---|---|---|---|---|---|
| A | 0.548 | 46.3 | 50.1 | 190[3] | none | * | 290 |
| B | 0.696 | 45.3 | 49.3 | 193[2] | 10/9 | 21.4 | 275 |
| C | 0.597 | 45.1 | 50.4 | 199[2] | 20/18 | 11.1 | 275 |
| D | 0.547 | 45.6 | 50.4 | 195[2] | 30/27 | 7.2 | 275 |
| E | 0.714 | 45.4 | 49.9 | 198[2] | none | * | 265 |
| F | 0.731 | 44.5 | 48.0 | 188[2] | 30/25 | 7.5 | 265 |
| G | 0.727 | 44.7 | 48.5 | 203[2] | 30/26 | 7.8 | 265 |
| H | 0.645 | 44.0 | 51.0 | 55[2] | 7.5/8 | 6.9 | 265 |
| I | 0.605 | 43.3 | 48.6 | 55[2] | 7.5/8 | 6.9 | 265 |
| J | 0.711 | 46.1 | 48.6 | 196[2] | 20/17 | 11.5 | 275 |
| K | 0.721 | 45.8 | 48.8 | 193[2] | 20/17 | 11.4 | 275 |

[1] butyltin tris-2-ethylhexanoate was used as the source of tin
[2] dimethyl tin oxide was used as the source of tin
[3] dibutyl tin oxide was used as the source of tin The data in Table 15 shows that the stability of polymer melts can be enhanced by modifying process conditions such as final polymerization temperature, rate of vacuum being created in the reaction vessel, the time under vacuum, among other, as reported below. The melt level stability and the visual grading reported in Table 15 are based on the scales disclosed in Example 25.

TABLE 15

Properties of the polyesters of Example 26

| Example | L* | a* | b* | Melt level stability | Polymer color observations | % foam in polyester | Visual grading of polyester |
|---|---|---|---|---|---|---|---|
| A | 83.55 | −0.93 | 2.44 | 2 | Slight yellow tint | 30% | 4 |
| B | 84.39 | −1.48 | 3.89 | 1 | Good color: No yellow tint | 29% | 4 |
| C | 84.46 | −0.98 | 1.82 | 1 | Slight yellow tint | 21% | 2 |
| D | 86.30 | −0.75 | 1.27 | 1 | Good color: No yellow tint | 17% | 2 |
| E | 85.60 | −1.20 | 2.68 | 3 | Yellow tint | 38% | 4 |
| F | 83.88 | −0.97 | 1.64 | 1 | Slight yellow tint | 12% | 1 |
| G | 85.76 | −0.92 | 2.03 | 1 | Slight yellow tint | 12% | 2 |
| H | 84.40 | −0.98 | 1.61 | 1 | Good color: No yellow tint | NM | 1 |
| I | 84.88 | −0.63 | 0.99 | 1 | Slight yellow tint | 11% | 1 |
| J | 85.01 | −1.02 | 1.77 | 1 | Slight yellow tint | 18% | 3 |
| K | 84.13 | −0.93 | 1.56 | 1 | Slight yellow tint | 25% | 4 |

NM = not measured

20% excess being TMCD. The glycol/acid ratio for Example 26H was 1.1/1, with the excess being TMCD. The glycol/acid ratio for Example 26I was 1.05/1, with the excess being TMCD. The catalyst was weighed into the flask, either as a solid or liquid. Triphenyl phosphate was weighed into the flask as a solid in the amounts recited in Table 14. The TPP in Example 26K was added late from a methanol solution.

Example 26A

A 500 ml round bottom flask was charged with 0.4 moles of DMT (77.6 grams), 0.224 moles of CHDM (32.3 grams), 0.256 moles of TMCD (36.8 grams), and 0.0460 grams of dibutyl tin oxide. The flask was equipped with a stainless steel stirrer and polymer head that allowed both nitrogen purge and vacuum capabilities. The flask was immersed in a Belmont metal bath at 200° C. and stirred at 25 RPM until the contents melted. The stirring was increased to 200 RPM and these conditions were held for 3 hours and 15 minutes. The temperature was increased to 220° C. and these conditions held for an additional 30 minutes. The temperature was increased to 290° C. over 20 minutes. After 290° C. was obtained, the pressure was reduced from atmosphere to a set point (SP) of 0.3 over 15 minutes. Stirring was decreased as the viscosity increased to a minimum of 15 RPM. The lowest vacuum reading measured was 0.70 (even though the SP was 0.3) and the total time under vacuum was 30 minutes.

The rest of the polyesters of this example were prepared in a 500 ml round bottom flask fitted with a stirrer and a polymer head that allowed both a nitrogen purge and vacuum when necessary. Raw materials were weighed into the flask for a 0.4 mole run (polymer repeat unit=274 grams/mole): 0.400 moles of DMT (77.6 grams), 0.224 moles of CHDM (32.3 grams) and 0.256 moles of TMCD (36.8 grams) and 0.112 g butyltin tris-2-ethylhexanoate, 0.0314 g dimethyl tin oxide, or 0.0460 g dibutyl tin oxide (as reported in Table 14). These values assume a target concentration of 200 ppm Sn in the final polymer and were adjusted accordingly for other target concentrations. The actual tin concentration for each polyester in this example is reported in Table 14

The glycol/acid ratio for all but two runs in this example was 1.2/1 with the excess being 2% CHDM and the rest of the The set points and data collection were facilitated by a Camile process control system. Once the reactants were melted, stirring was initiated and slowly increased as indicated below in the corresponding Camile sequences. The temperature of the reactor also gradually increased with run time.

The ester exchange and polycondensation reactions were carried out in the same 500 ml flask. The temperature/pressure/stir rate sequence controlled by the Camile software for each example is reported in the following tables. The final polymerization temperature (Pz Temp.) for the experiments of this Example ranged from 265° C. to 290° C. and is reported in Table 14.

Camile Sequence for Example 26B to Example 26D

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 5 | 245 | 760 | 50 |
| 11 | 32 | 250 | 375 | 50 |
| 12 | 30 | 255 | 375 | 50 |
| 13 | 3 | 255 | 50 | 50 |
| 14 | 30 | 260 | 50 | 50 |
| 15 | 3 | 265 | 15 | 25 |
| 16 | 110 | 265 | 15 | 25 |
| 17 | 3 | 270 | 2 | 25 |
| 18 | 110 | 275 | 2 | 25 |

-continued

| Stage | Time (minutes) | Temperature, C. | Vacuum (torr) | Stirring (RPM) |
|---|---|---|---|---|
| 19 | 2 | 275 | 400 | 0 |
| 20 | 1 | 275 | 760 | 0 |

Camile Sequence for Example 26E

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 5 | 245 | 760 | 50 |
| 11 | 3 | 245 | 375 | 50 |
| 12 | 30 | 245 | 375 | 50 |
| 13 | 3 | 250 | 20 | 50 |
| 14 | 30 | 250 | 20 | 50 |
| 15 | 3 | 255 | 5 | 25 |
| 16 | 110 | 255 | 5 | 25 |
| 17 | 3 | 265 | 1 | 25 |
| 18 | 110 | 265 | 1 | 25 |
| 19 | 2 | 265 | 400 | 0 |
| 20 | 1 | 265 | 760 | 0 |

Camile Sequence for Example 26F and Example 26G

Viscosity Constrained Sequence, Low Vacuum

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 5 | 245 | 760 | 50 |
| 11 | 3 | 245 | 375 | 50 |
| 12 | 30 | 245 | 375 | 50 |
| 13 | 3 | 250 | 20 | 50 |
| 14 | 30 | 250 | 20 | 50 |
| 15 | 3 | 255 | 5 | 25 |
| 16 | 110 | 255 | 5 | 25 |
| 17 | 3 | 265 | 0.2 | 25 |
| 18 | 110 | 265 | 0.2 | 25 |
| 19 | 2 | 265 | 400 | 0 |
| 20 | 1 | 265 | 760 | 0 |

Camile Sequence for Example 26H and Example 26I

Viscosity Constrained Sequence, Low Vacuum

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 5 | 245 | 760 | 50 |
| 11 | 3 | 245 | 375 | 50 |
| 12 | 30 | 245 | 375 | 50 |
| 13 | 3 | 250 | 20 | 50 |
| 14 | 30 | 250 | 20 | 50 |
| 15 | 3 | 255 | 3 | 25 |
| 16 | 110 | 255 | 3 | 25 |
| 17 | 3 | 265 | 1 | 25 |
| 18 | 110 | 265 | 1 | 25 |
| 19 | 2 | 265 | 400 | 0 |
| 20 | 1 | 265 | 760 | 0 |

Camile Sequence for Example 26J and Example 26K

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 100 |
| 10 | 5 | 245 | 760 | 50 |
| 11 | 3 | 245 | 375 | 50 |
| 12 | 30 | 245 | 375 | 50 |
| 13 | 3 | 250 | 20 | 50 |
| 14 | 30 | 250 | 20 | 50 |
| 15 | 3 | 260 | 5 | 25 |
| 16 | 110 | 260 | 5 | 25 |
| 17 | 3 | 275 | 1 | 25 |
| 18 | 110 | 275 | 1 | 25 |
| 19 | 2 | 275 | 400 | 0 |
| 20 | 1 | 275 | 760 | 0 |

Example 27

This example illustrates the preparation of polyesters utilizing different thermal stabilizers and showing their effect on the stability of the polyester melts during processing.

A variety of polyesters were prepared as described below from 100 mole % DMT, and different concentrations of CHDM, and TMCD. The mole % of TMCD for the experiments of this example is reported in Table 16 below, with the glycol balance being CHDM. The DMT, CHDM, and TMCD were of the same origin as in Example 25. The catalyst was either dimethyltin oxide (Strem Chemical Co., Batch B4058112) or butyltin-tris-2-ethylhexonate (Aldrich, Batch 06423CD). The thermal stabilizer is indicated in Table 16 and was chosen from Merpol A (an octyl alcohol phosphate ester mixture from DuPont), triethylphosphate (Aldrich), Irgafos 168 (tris(2,4-di-tert-butylphenyl)phosphate, Ciba Specialty Chemicals), Doverphos 9228 (CAS#154862-43-8, bis(2,4-dicumylphenyl)pentaerythritol diphosphite, Dover), Weston 619 g (CAS#85190-63-2,2-propanol, 1,1',1"-nitrilotris-, mixt. with 3,9-bis(octadecyloxy)-2,4,8,10-tetraoxa-3,9-diphosphaspiro[5.5]undecane, GE SC), triphenylphosphine oxide (Aldrich), triphenylphosphate (Aldrich or FERRO), NaH$_2$PO$_4$ (Aldrich), Zn$_3$(PO$_4$)$_2$ (Aldrich), and H$_3$PO$_4$ (Aldrich). Unless otherwise indicated in Table 16, the source of phosphorous was added upfront, with the rest of the polyester reagents. The cis/trans ratio of the CHDM was as described above while the cis/trans ratio of the TMCD is reported in Table 16.

Example 27B, while outside the scope of the originally-filed claims with respect to mole % TMCD, is included here to show the use of phosphoric acid as a thermal stabilizer. The data shows that phosphate esters and phosphorous compounds that can be hydrolyzed to phosphate esters provide stable melt and acceptable polyester products. The melt level

TABLE 16

Composition and inherent viscosity for the polyesters of Example 27

| Example | Melt IV (dL/g) | TMCD (mole %) | TMCD % cis | Sn (ppm) | P (ppm) theo/meas | Sn/P actual wt ratio | Final Pz Temp (° C.) |
|---|---|---|---|---|---|---|---|
| A | 0.564 | 45.7 | 49.7 | 211[2] | 28/26 | 8.1 | 265 |
| B | 0.167 | 29.2 | 58.2 | 218[2] | 28/39 | 5.6 | 265 |
| C | 0.647 | 45.2 | 49.2 | 195[2] | 20/19 | 10.3 | 265 |
| D | 0.674 | 46.3 | 48.7 | 196[2] | 20/18 | 10.9 | 265 |
| E | 0.700 | 45.6 | 49.4 | 195[2] | 20/0 | * | 265 |
| F | 0.738 | 45.9 | 49.0 | 214[2] | 20/8 | 26.8 | 265 |
| G | 0.672 | 46.4 | 49.7 | 192[2] | 20/11 | 17.5 | 265 |
| H | 0.714 | 46.0 | 48.5 | 189[2] | 20/7 | 27.0 | 265 |
| I | 0.73 | 42.3 | 45.1 | 212[1] | 0 | * | 265 |
| J | 0.58 | 44.4 | 44.5 | 209[1] | 28/27 | 7.7 | 265 |
| K | 0.53 | 43.4 | 45.0 | 213[1] | 28/28 | 7.6 | 265 |
| L | 0.69 | 44.3 | 44.4 | 209[1] | 28/20 | 10.5 | 265 |
| M | 0.61 | 43.7 | 45.4 | 211[1] | 28/25 | 8.4 | 265 |
| N | 0.76 | 43.9 | 44.4 | 200[1] | 28/20 | 10.0 | 265 |
| O | 0.66 | 44.6 | 44.3 | 58[1] | 0 | * | 265 |
| P | 0.6 | 42.4 | 44.7 | 60[1] | 7/7 | 8.6 | 265 |
| Q | 0.5 | 42.9 | 45.4 | 57[1] | 7/7 | 8.1 | 265 |
| R | 0.51 | 43.8 | 45.1 | 52[1] | 200/55[4] | 0.9 | 265 |
| S | 0.64 | 44.0 | 44.4 | 58[1] | 200/71[4] | 0.8 | 265 |

[1] butyltin tris-2-ethylhexanoate was used as the source of tin
[2] dimethyl tin oxide was used as the source of tin
[3] dibutyl tin oxide was used as the source of tin
[4] polymer was hazy due to insolubles The data in Table 17 shows the stability of polymer melts using different sources of phosphorous as thermal stabilizers. stability and the visual grading reported in Table 17 are based on the scales disclosed in Example 25.

TABLE 17

Properties of the polyesters of Example 27

| Example | L* | a* | b* | Phosphorus source | Melt level stability | Polymer color observations | % foam in polyester | Visual grading of polyester |
|---|---|---|---|---|---|---|---|---|
| A | 83.87 | −1.09 | 1.61 | Merpol A | 1 | NM | NM | NM |
| B | NM | NM | NM | H$_3$PO$_4$ | 1 | Good color: No yellow tint | 7% | 1 |
| C | 84.84 | −0.94 | 1.40 | Merpol A | 1 | Good color: No yellow tint | 22% | 3 |
| D | 85.86 | −0.69 | 1.07 | Merpol A added after EE | 1 | Slight yellow tint | 21% | 3 |
| E | 83.77 | −1.12 | 1.91 | Triethyl phosphate | 2 | Slight yellow tint | 25% | 4 |
| F | 84.05 | −2.06 | 8.66 | Triethyl phosphate | 2 | Brownish-yellow tint | 22% | 4 |
| G | 77.63 | −0.82 | 3.33 | Irgafos 168 | 3 | NM | NM | NM |
| H | 78.68 | −0.83 | 3.34 | Irgafos 168 added after EE | 3 | Brownish-yellow tint | 24% | 4 |
| I | NM | NM | NM | none | NN | Slight yellow tint | 26% | 4 |
| J | NM | NM | NM | Doverphos 9228 | NN | Good color: No yellow tint | 21% | 3 |
| K | NM | NM | NM | Doverphos 9228 | NN | NM | NM | NM |
| L | NM | NM | NM | Weston 619g | NN | Good color: No yellow tint | 21% | 4 |

TABLE 17-continued

Properties of the polyesters of Example 27

| Example | L* | a* | b* | Phosphorus source | Melt level stability | Polymer color observations | % foam in polyester | Visual grading of polyester |
|---|---|---|---|---|---|---|---|---|
| M | NM | NM | NM | Triphenyl phosphate | NN | Slight yellow tint | 14% | 2 |
| N | NM | NM | NM | Triphenyl phosphine oxide | NN | Slight yellow tint | 23% | 3 |
| O | NM | NM | NM | none | NN | Slight yellow tint | 19% | 2 |
| P | NM | NM | NM | Triphenyl phosphate | NN | NM | NM | NM |
| Q | NM | NM | NM | Triphenyl phosphate | NN | Good color: No yellow tint | 10% | 1 |
| R | NM | NM | NM | NaH$_2$PO$_4$ | NN | Good color: No yellow tint | 17% | 1 |
| S | NM | NM | NM | Zn$_3$(PO$_4$)$_2$ | NN | Good color: No yellow tint | 16% | 2 |

EE = ester exchange; NM = not measured; NN = nor noted
The sample of Example R was hazy so visual grading may have been impaired

Example 27A to Example 27H

These polyesters were prepared as follows. A mixture of 77.6 g (0.4 mol) dimethyl terephthalate, 32.3 g (0.224 mol) 1,4-cyclohexanedimethanol, 36.8 g (0.256 mol) 2,2,4,4-tetramethyl-1,3-cyclobutanediol was placed in a 500-ml flask equipped with an inlet for nitrogen, a metal stirrer, and a short distillation column. The catalyst was also added to the reaction flask. The amount and type of catalyst are in detailed in Table 16. The phosphorus compounds were also added to the reaction flask. The theoretical and measured amount of phosphorus compound for each experiment in this example is detailed in Table 16. The flask was placed in a Wood's metal bath already heated to 200° C. The temperature/pressure/stir rate sequence were controlled by the Camile software for each experiment and is reported below. In some cases, where noted (Example 27D and Example 27H), the phosphorus additive was added after ester exchange. This corresponds to the end of stage 9 in the corresponding Camile sequence.

Example 27I to Example 27S

These polyesters were prepared as follows. A mixture of 77.6 g (0.4 mol) dimethyl terephthalate, 33.31 g (0.231 mol) 1,4-cyclohexanedimethanol, 35.91 g (0.249 mol) 2,2,4,4-tetramethyl-1,3-cyclobutanediol was placed in a 500-ml flask equipped with an inlet for nitrogen, a metal stirrer, and a short distillation column. The catalyst was also added to the reaction flask. The amount and type of catalyst are in detailed in Table 16. The source of phosphorous was weighed into the flask in the amounts recited in Table 16, which includes the theoretical and measured amount of phosphorus compound for each experiment. The flask was placed in a Wood's metal bath already heated to 200° C. The temperature/pressure/stir rate sequence controlled by the Camile software for each example is reported below.

The glycol/acid ratio for all experiments in this example was 1.2/1 with the excess being 2% CHDM and the rest of the 20% excess being TMCD. The catalyst was weighed into the flask, either as a solid or liquid.

The set points and data collection were facilitated by a Camile process control system. Once the reactants were melted, stirring was initiated and slowly increased as indicated below in the corresponding Camile sequences. The temperature of the reactor also gradually increased with run time.

The temperature/pressure/stir rate sequence controlled by the Camile software for each example is reported in the following tables. The final polymerization temperature (Pz Temp.) for the experiments of this example was 265° C.

Camile Sequence for Example 27A and Example 27B

Viscosity Constrained Sequence

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 0.1 | 220 | 760 | 200 |
| 11 | 30 | 220 | 760 | 200 |
| 12 | 5 | 245 | 760 | 50 |
| 13 | 3 | 245 | 375 | 50 |
| 14 | 30 | 245 | 375 | 50 |
| 15 | 3 | 250 | 20 | 50 |
| 16 | 30 | 250 | 20 | 50 |
| 17 | 3 | 255 | 3 | 25 |
| 18 | 110 | 255 | 3 | 25 |
| 19 | 3 | 265 | 1 | 25 |
| 20 | 110 | 265 | 1 | 25 |

Camile Sequence for Example 27C to Example 27S

Viscosity Constrained Sequence, Low Vacuum

| Stage | Time (minutes) | Temperature, C. | Vacuum (torr) | Stirring (RPM) |
|---|---|---|---|---|
| 1 | 3 | 200 | 760 | 0 |
| 2 | 0.1 | 200 | 760 | 25 |
| 3 | 2 | 200 | 760 | 25 |
| 4 | 0.1 | 200 | 760 | 100 |

-continued

| Stage | Time (minutes) | Temperature, C. | Vacuum (torr) | Stirring (RPM) |
|---|---|---|---|---|
| 5 | 1 | 200 | 760 | 100 |
| 6 | 0.1 | 200 | 760 | 200 |
| 7 | 90 | 200 | 760 | 200 |
| 8 | 0.1 | 210 | 760 | 200 |
| 9 | 120 | 210 | 760 | 200 |
| 10 | 5 | 245 | 760 | 50 |
| 11 | 3 | 245 | 375 | 50 |
| 12 | 30 | 245 | 375 | 50 |
| 13 | 3 | 250 | 20 | 50 |
| 14 | 30 | 250 | 20 | 50 |
| 15 | 3 | 255 | 3 | 25 |
| 16 | 110 | 255 | 3 | 25 |
| 17 | 3 | 265 | 1 | 25 |
| 18 | 110 | 265 | 1 | 25 |
| 19 | 2 | 265 | 400 | 0 |
| 20 | 1 | 265 | 760 | 0 |

Example 28

This example illustrates the preparation of polyesters at a pilot plant scale comprising at least one thermal stabilizer, reaction products thereof, and mixtures thereof, resulting in improved stability of the polyester melts during processing.

A variety of polyesters were prepared as described below from 100 mole % DMT, CHDM, and TMCD. The mole % of TMCD for the experiments of this example is reported in Table 18 below, with the glycol balance being CHDM. The DMT, CHDM, and TMCD were of the same origin as in Example 25. The catalyst was either dimethyltin oxide (Strem Chemical Co., Batch B4058112) or butyltin-tris-2-ethylhexonate (Aldrich, Batch 06423CD). The thermal stabilizer was triphenyl phosphate (TPP) (Aldrich). Unless otherwise indicated below, the source of phosphorous was added upfront, with the rest of the polyester reagents. The cis/trans ratio of the CHDM was as described above while the cis/trans ratio of the TMCD is reported in Table 18.

TABLE 18

Composition and inherent viscosity for the polyesters of Example 28

| Example | Melt IV (dL/g) | TMCD (mole %) | TMCD % cis | Sn (ppm) | P (ppm) theo | L* | a* | b* |
|---|---|---|---|---|---|---|---|---|
| A | 0.553 | 46.1 | 45.8 | 228[2] | 300 | 80.50 | −1.51 | 4.27 |
| B | 0.620 | 46.0 | 46.0 | 204[1] | 100 | 83.42 | −1.18 | 4.92 |
| C | 0.613 | 45.1 | 46.3 | 193[1] | 100 | 77.60 | −1.80 | 4.85 |
| D | 0.624 | 45.4 | 46.2 | 209[2] | 100 | 79.69 | −1.71 | 6.45 |

[1]butyltin tris-2-ethylhexanoate was used as the source of tin
[2]dimethyl tin oxide was used as the source of tin Example 28A 84.96 lbs (198.83 gram-mol) dimethyl terephthalate, 35.38 lbs (111.54 gram-mol) 1,4-cyclohexanedimethanol, 40.30 lbs (127.06 gram-mol) 2,2,4,4-tetramethyl-1,3-cyclobutanediol were reacted together in the presence of 200 ppm of dimethyltin oxide as tin catalyst and 300 ppm triphenylphosphate (16.35 grams). The reaction was carried out under a nitrogen gas purge in an 74-gallon stainless steel pressure vessel which was fitted with a condensing column, a vacuum system, and a HELICONE-type agitator. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The agitator speed was then decreased to 15 RPM, the temperature of the reaction mixture was then increased to 270° C., and the pressure was decreased to ≦1-mm. The reaction mixture was held at 270° C. and a pressure of ≦1 mm of Hg for 3.75 hours. The pressure of the vessel was then increased to 1 atmosphere using nitrogen gas. The molten polymer was then extruded from the pressure vessel using an extrusion die. The extruded polymer strands were then pulled through a cold water bath to cool them after which the strands were pelletized. The pelletized polymer had an inherent viscosity of 0.553. NMR analysis showed that the polymer was composed of 53.9 mol % 1,4-cyclohexanedimethanol moiety and 46.1 mol % 2,2,4,4-tetramethyl-1,3-cyclobutanediol moiety. The polymer had color values of: L*=80.50, a*=−1.51, and b*=4.27.

Example 28B to Example 28D were prepared in a similar manner to Example 28A, having the composition disclosed in Table 18.

Example 28E represents PCTG Eastar DN001 from Eastman Chemical Company, having an IV of 0.73 dL/g with a nominal composition of 100 mole % terephthalic acid residues, 62 mole % CHDM residues and 38 mole % ethylene glycol residues. Example 28F represents the polycarbonate Makrolon 2608 from Bayer, with a nominal composition of 100 mole % bisphenol A residues and 100 mole % diphenyl carbonate residues. Example 28G represents an Eastman Chemical Company polyester, with a nominal composition of 100 mole % terephthalic acid residues, 55 mole % CHDM residues and 45 mole % TMCD residues. Example 28H represents PETG Eastar 6763 from Eastman Chemical Company, with a nominal composition of 100 mole % terephthalic acid, 31 mole % cyclohexanedimethanol (CHDM) and 69 mole % ethylene glycol.

Example 28I

The polyester of Example 28I is a blend of 10 different polyesters, each prepared in the following manner. 84.96 lbs (198.83 gram-mol) dimethyl terephthalate were reacted in the presence of 200 ppm of tin catalyst (as butyltin-tris-ethylhexanoate) with 50.45 to 51.46-lbs (159.06 162.24 gram-mol, depending on the batch) 1,4-cyclohexanedimethanol and 24.22 to 31.53-lbs (76.36 to 99.41 gram-mol, also depending on the batch) 2,2,4,4-tetramethyl-1,3-cyclobutanediol. The reaction was carried out under a nitrogen gas purge in an 74-gallon stainless steel pressure vessel fitted with a condensing column, a vacuum system, and a HELICONE-type agitator, to provide glycol/dimethyl terephthalate molar ratios of 1.2/1 to 1.3/1. With the agitator running at 25 RPM, the reaction mixture temperature was increased to 250° C. and the pressure was increased to 20 psig. The reaction mixture was held for 2 hours at 250° C. and 20 psig pressure. The pressure was then decreased to 0 psig at a rate of 3 psig/minute. The agitator speed was then decreased to 15 RPM, the temperature of the reaction mixture was then increased to 260-270° C., and the pressure was decreased to 90 mm of Hg. The reaction mixture was held at 260-270° C. and 90-mm pressure for 1 hour. The temperature of the reaction mixture was then increased to 275-290° C. and the pressure was decreased to ≦1 mm of Hg. The reaction mixture was held at 275-290° C. and ≦1 mm of Hg for 1.5-3 hours to complete the polycondensation stage. The pressure of the pressure vessel was then increased to 1 atmosphere using nitrogen gas. The molten polymer was then extruded from the pressure vessel into a cold water bath. The cooled, extruded polymer was ground to pass a 6-mm screen.

Ten separate batches were prepared using the above procedure. The following table contains the NMR compositions, IV values, and color values that were obtained on the 10 batches. The final polyester blend had an IV of 0.63 dL/g, 100 mole % terephthalic acid residues and a target of 20 mole % TMCD residues and 80 mole % CHDM residues.

| Batch | Target Composition | % TMCD by NMR | IV (dL/g) | Color L* | a* | b* |
|---|---|---|---|---|---|---|
| 1 | 20% TMCD; 80% CHDM | 16.8 | 0.665 | 73.95 | −0.61 | 10.31 |
| 2 | 20% TMCD; 80% CHDM | 17.5 | 0.691 | 70.48 | −0.49 | 10.68 |
| 3 | 20% TMCD; 80% CHDM | 16.4 | 0.650 | 71.14 | −0.68 | 10.16 |
| 4 | 20% TMCD; 80% CHDM | 22.2 | 0.685 | 79.80 | −1.80 | 7.43 |
| 5 | 20% TMCD; 80% CHDM | 24.9 | 0.668 | 74.47 | −1.11 | 7.83 |
| 6 | 20% TMCD; 80% CHDM | 22.6 | 0.705 | 67.94 | 1.28 | 26.91 |
| 7 | 20% TMCD; 80% CHDM | 22.1 | 0.627 | 72.43 | 0.41 | 22.68 |
| 8 | 20% TMCD; 80% CHDM | 25.3 | 0.712 | 76.70 | 0.41 | 10.73 |
| 9 | 20% TMCD; 80% CHDM | 23.5 | 0.697 | 74.21 | 0.79 | 15.23 |
| 10 | 20% TMCD; 80% CHDM | 25.3 | 0.724 | 73.55 | −0.61 | 9.52 |

Plaques (4 inch×4 inch×⅛ inch thick) were prepared in a Toyo 110 injection molding press from the polyesters of Table 18. Pellets of each polyester were feed into the press and heated to the temperatures reported in Table 19. The residence time of the molten polymer in the barrel before injection is also reported in Table 19. Once the part had cooled sufficiently, it was visually analyzed and the splay generated during the injection molding process was recorded.

The data in Table 19 shows the effect of molding conditions on splay generation in injection-molded plaques made out of the polyesters in Table 18.

TABLE 19

Splay generation in molded parts made out of the polyesters of Example 28

| Temp Setpoint, ° F. | Residence Time, min | Splay in part made out of polyester in Table 18 | | | | | | |
|---|---|---|---|---|---|---|---|---|
| | | A | B | C | D | E | F | G |
| 520 (271° C.) | 0.47 | 0 | 0 | 0 | 0 | 0 | 0 | 0 |
| | 1.02 | 0 | 0 | 0 | 0 | 0 | 0 | 0 |
| | 1.59 | 0 | 0 | 0 | 0 | 0 | 0 | 0 |
| | 2.7 | 0 | 0 | 0 | 0 | 0 | 0 | 0 |
| | 4.94 | 0 | 0 | 0 | 0 | 0 | 0 | 0 |
| | 9.4 | 0 | 0 | 0 | 0 | 0 | 0 | 1 |
| 550 (288° C.) | 0.47 | 0 | 0 | 0 | 0 | 0 | 0 | 0 |
| | 1.02 | 0 | 0 | 0 | 0 | 0 | 0 | 0 |
| | 1.59 | 0 | 0 | 0 | 0 | 0 | 0 | 0 |
| | 2.7 | 0 | 0 | 0 | 0 | 0 | 0 | 0 |
| | 4.94 | 0 | 0 | 0 | 0 | 0 | 0 | 1 |
| | 9.4 | 0 | 1 | 1 | 1 | 0 | 0 | 2-3 |
| 580 (304° C.) | 0.47 | 0 | 0 | 0 | 0 | 0 | 0 | 0 |
| | 1.02 | 0 | 0 | 0 | 0 | 0 | 0 | 0 |
| | 1.59 | 0 | 0 | 0 | 0 | 0 | 0 | 1 |
| | 2.7 | 0 | 0 | 1 | 0 | 0 | 0 | 1-2 |
| | 4.94 | 0 | 1-2 | 1-2 | 1-2 | 0 | 0 | 2-3 |
| | 9.4 | 1-2 | 2-3 | 2-3 | 2-3 | 1-2 | 0 | 3 |
| 610 (321° C.) | 0.47 | 0 | 0 | 0 | 0 | NA | NA | NA |
| | 1.02 | 0 | 0 | 0 | 0 | NA | NA | NA |
| | 1.59 | 0 | 0 | 0 | 0 | NA | NA | NA |
| | 2.7 | 0 | 1-2 | 1-2 | 1-2 | NA | NA | NA |
| | 4.94 | 1-3 | 2-3 | 2-3 | 2-3 | NA | NA | NA |
| | 9.4 | 3 | 3 | 3 | 3 | NA | NA | NA |

Splay Ratings: none (0), light (1), moderate (2), heavy (3); NA = not available

The data in Table 20 shows the quality of films made out of the polyesters in Table 18.

The polymers were extruded on a 1.5" Killion extruder using a General Purpose screw. The polymers were extruded at temperatures of 572° F. (300° C.) and 527° F. (275° C.). The following extruder conditions were used for each polymer in the 572° F. extrusions:

| Sample | Zone Temp | Die Temp | Adapter Temp | Clamp Ring Temp | Melt Temp | Pressure (PSI) | Screw Speed (RPM) | Chill Roll Speed (RPM) |
|---|---|---|---|---|---|---|---|---|
| 1 | 572 | 572 | 572 | 572 | 612 | 1200 | 70 | 4.3 |
| 2 | 572 | 572 | 572 | 572 | 619 | 1450 | 35 | 2.2 |
| 3 | 572 | 572 | 572 | 572 | 618 | 2500 | 105 | 7.2 |

The following extruder conditions were used for each polymer in the 527° F. extrusions:

| Sample | Zone Temp | Die Temp | Adapter Temp | Clamp Ring Temp | Melt Temp | Pressure (PSI) | Screw Speed (RPM) | Chill Roll Speed (RPM) |
|---|---|---|---|---|---|---|---|---|
| 1 | 527 | 527 | 527 | 527 | 569 | 1600 | 70 | 4.2 |
| 2 | 527 | 527 | 527 | 527 | 565 | 900 | 35 | 2.3 |
| 3 | 527 | 527 | 527 | 527 | 571 | 2200 | 105 | 7.2 |

TABLE 20

Quality of films made out of the polyesters of Example 28

| Extrusion Conditions | A | B | C | D | H | I |
|---|---|---|---|---|---|---|
| 275° C.: 35 RPM | 1 | 2 | 2 | 2 | 1 | 4 |
| 275° C.: 70 RPM | 1 | 2 | 2 | 2 | 1 | 3 |
| 275° C.: 105 RPM | 1 | 1 | 2 | 2 | 1 | 3 |
| 300° C.: 35 RPM | 2 | 3 | 3 | 3 | 1 | 4 |
| 300° C.: 70 RPM | 1 | 2 | 3 | 2 | 1 | 4 |
| 300° C.: 105 RPM | 1 | 2 | 2 | 1 | 1 | 4 |

| Rating Key | Rating |
|---|---|
| Good film quality; no visual bubbles were observed exiting the die or in melt bank: nice film, very difficult to visually detect bubbles. | 1 |
| Good film quality; occasional bubbles observed leaving the die; bubbles in the film are visually easier to detect but sparse. | 2 |
| Mediocre film quality; bubbles are easily seen leaving the die lips and are very evident in the finished film. | 3 |
| Very poor film quality; bubbles evident in the melt bank and exiting the die lips; very poor color. | 4 |

It can be clearly seen from a comparison of the data in the above relevant working examples that the polyesters of the present invention offer an advantage over the commercially available polyesters with regard to at least one of bubbling, splaying, color formation, foaming, off-gassing, and erratic melt levels in the polyester's production and processing systems.

The invention has been described in detail with reference to the embodiments disclosed herein, but it will be understood that variations and modifications can be effected within the spirit and scope of the invention.

We claim:

1. A polyester composition comprising at least one polyester which comprises:
   (a) a dicarboxylic acid component comprising:
      i) 80 to 100 mole % of terephthalic acid residues;
      ii) 0 to 20 mole % of aromatic dicarboxylic acid residues having up to 20 carbon atoms; and
      iii) 0 to 10 mole % of aliphatic dicarboxylic acid residues having up to 16 carbon atoms; and
   (b) a glycol component comprising:
      i) 1 to 5 mole % of 2,2,4,4-tetramethyl-1,3-cyclobutanediol residues; and
      ii) 95 to 99 mole % of 1,4-cyclohexanedimethanol residues, wherein the total mole % of the dicarboxylic acid component is 100 mole %, and the total mole % of the glycol component is 100 mole %;
   wherein the inherent viscosity of said polyester is from 0.35 to 1.2 dL/g as determined in 60/40 (wt/wt) phenol/tetrachloroethane at a concentration of 0.5 g/100 ml at 25° C.;
   wherein said polyester has a Tg of 85 to 115° C.

2. The polyester composition of claim 1, wherein the inherent viscosity of the polyester is from 0.35 to 1.0 dL/g.

3. The polyester composition of claim 1, wherein the polyester has a Tg of 90 to 115° C.

4. The polyester composition of claim 1, wherein the dicarboxylic acid component of the polyester comprises 90 to 100 mole % of terephthalic acid residues.

5. The polyester composition of claim 1, wherein the polyester comprises 1,3-propanediol residues, 1,4-butanediol residues, or mixtures thereof.

6. The polyester composition of claim 1, wherein the polyester comprises from 0.01 to 10 mole % of ethylene glycol residues.

7. The polyester composition of claim 1, wherein the 2,2,4,4-tetramethyl-1,3-cyclobutanediol residues are a mixture comprising greater than 50 mole % of cis-2,2,4,4-tetramethyl-1,3-cyclobutanediol residues and less than 50 mole % to trans-2,2,4,4-tetramethyl-1,3-cyclobutanediol residues.

8. The polyester composition of claim 1, wherein the 2,2,4,4-tetramethyl-1,3-cyclobutanediol residues are a mixture comprising from 30 to 70 mole % of cis-2,2,4,4-tetramethyl-1,3-cyclobutanediol residues and from 70 to 30 mole % of trans-2,2,4,4-tetramethyl-1,3-cyclobutanediol residues.

9. The polyester composition of claim 1, wherein said 2,2,4,4-tetramethyl-1,3-cyclobutanediol residues are a mixture comprising from 40 to 60 mole % of cis-2,2,4,4-tetramethyl-1,3-cyclobutanediol residues and from 60 to 40 mole % of trans-2,2,4,4-tetramethyl-1,3-cyclobutanediol residues.

10. The polyester composition of claim 1, comprising at least one polymer chosen from at least one of the following: poly(etherimides), polyphenylene oxides, polycarbonates, polyestercarbonates, poly(phenylene oxide)/polystyrene blends, polystyrene resins, polyphenylene sulfides, polyphenylene sulfide/sulfones, polysulfones; polysulfone ethers, or poly(ether-ketones).

11. The polyester composition of claim 1, wherein said polyester comprises residues of at least one branching agent.

12. The polyester composition of claim 1, wherein said polyester comprises residues of at least one branching agent in the amount of 0.01 to 10 mole % based on the total mole percentage of the diacid or diol residues.

13. The polyester composition of claim 1, wherein said polyester has a crystallization half-time of greater than 5 minutes at 170° C.

14. The polyester composition of claim 1, wherein said polyester composition has a density of less than 1.2 g/ml at 23° C.

15. The polyester composition of claim 1, wherein said polyester composition comprises at least one thermal stabilizer or reaction products thereof.

16. The polyester composition of claim 1, having a b* value of from −10 to less than 10 and a L* value from 50 to 90 according to the L*, a* and b* color system of the CIE (International Commission on Illumination).

17. The polyester composition of claim 1, wherein said polyester has a notched Izod impact strength of at least 10 ft-lbs/in at 23° C. according to ASTM D256 with a 10-mil notch in a ⅛-inch thick bar.

18. The polyester composition of claim 1, wherein the polyester comprises the residue of at least one catalyst comprising a tin compound or a reaction product thereof.

19. The polyester composition of claim 1, comprising at least one additive chosen from colorants, dyes, mold release agents, flame retardants, plasticizers, nucleating agents, UV stabilizers, glass fiber, carbon filaments, fillers, impact modifiers, or mixtures thereof.

20. A clear, semicrystalline article of manufacture comprising a polyester composition comprising at least one polyester which comprises:
  (a) a dicarboxylic acid component comprising:
    i) 80 to 100 mole % of terephthalic acid residues;
    ii) 0 to 20 mole % of aromatic dicarboxylic acid residues having up to 20 carbon atoms; and
    iii) 0 to 10 mole % of aliphatic dicarboxylic acid residues having up to 16 carbon atoms and
  (b) a glycol component comprising:
    i) 1 to 5 mole % of 2,2,4,4-tetramethyl-1,3-cyclobutanediol residues; and
    ii) 95 to 99 mole % of 1,4-cyclohexanedimethanol residues,
  wherein the total mole % of the dicarboxylic acid component is 100 mole %, and the total mole % of the glycol component is 100 mole %;
  wherein the inherent viscosity of said polyester is from 0.35 to 1.2 dL/g as determined in 60/40 (wt/wt) phenol/tetrachloroethane at a concentration of 0.5 g/100 ml at 25° C.;
  wherein said polyester has a Tg of 85 to 115° C.

21. The article of claim 20, wherein said polyester has a Tg of 90 to 115° C.

22. The article of claim 20 wherein said polyester comprises ethylene glycol.

23. The article of claim 20 wherein said polyester comprises residues of at least one branching agent in the amount of 0.01 to 10 mole % based on the total mole percentage of the diacid residues or diol residues.

24. The article of claim 20, wherein the polyester composition comprises at least one additive chosen from colorants, dyes, mold release agents, flame retardants, plasticizers, nucleating agents, UV stabilizers, glass fiber, carbon filaments, fillers, impact modifiers, and mixtures thereof.

25. The article of claim 20, wherein the polyester composition comprises at least one polymer chosen from at least one of the following: poly(etherimides), polyphenylene oxides, polycarbonates, polyestercarbonates, poly(phenylene oxide)/polystyrene blends, polystyrene resins, polyphenylene sulfides, polyphenylene sulfide/sulfones, polysulfones; polysulfone ethers, or poly(ether-ketones).

26. The article of claim 20, having a b* value of from −10 to less than 10 and a L* value from 50 to 90 according to the L*, a* and b* color system of the CIE (International Commission on Illumination).

27. The polyester composition of claim 1, wherein said polyester composition does not contain polycarbonate.

28. The polyester composition of claim 27, wherein said polyester has a notched Izod impact strength of at east 7.5 ft-lbs/in at 23° C. according to ASTM D256 with a 10-mil notch in a ⅛-inch thick bar.

29. The polyester composition of claim 27, wherein the melt viscosity of said polyester is less than 10,000 poise as measured at 1 radian/second on a rotary melt rheometer at 290° C.

30. The article of claim 20, wherein said polyester composition does not contain polycarbonate.

31. The article of claim 30, wherein said polyester has a notched Izod impact strength of at least 7.5 ft-lbs/in at 23° C. according to ASTM D256 with a 10-mil notch in a ⅛-inch thick bar.

32. The article of claim 30, wherein the melt viscosity of said polyester is less than 10,000 poise as measured at 1 radian/second on a rotary melt rheometer at 290° C.

* * * * *